US009840553B2

(12) United States Patent
Perlroth et al.

(10) Patent No.: US 9,840,553 B2
(45) Date of Patent: Dec. 12, 2017

(54) DUAL PDGF/VEGF ANTAGONISTS

(71) Applicant: KODIAK SCIENCES INC., Palo Alto, CA (US)

(72) Inventors: D. Victor Perlroth, Palo Alto, CA (US); Stephen A. Charles, Ravenna, OH (US); James Aggen, Westwood, MA (US); Didler Benoit, San Jose, CA (US); Wayne To, San Mateo, CA (US); Lidia Mosyak, Newton, MA (US); Laura Lin, Weston, MA (US); Justin Cohen, Quincy, MA (US); Tetsuya Ishino, Boston, MA (US); William Somers, Lexington, MA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 0 days.

(21) Appl. No.: 14/753,824

(22) Filed: Jun. 29, 2015

(65) Prior Publication Data
US 2015/0376271 A1 Dec. 31, 2015

Related U.S. Application Data

(63) Continuation of application No. PCT/US2015/038203, filed on Jun. 28, 2015.

(60) Provisional application No. 62/018,579, filed on Jun. 28, 2014.

(51) Int. Cl.
| A61K 39/395 | (2006.01) |
| C07K 16/46 | (2006.01) |
| C07K 16/22 | (2006.01) |
| C07K 14/71 | (2006.01) |
| C07K 16/28 | (2006.01) |
| A61K 38/17 | (2006.01) |
| A61K 38/18 | (2006.01) |
| A61K 39/00 | (2006.01) |

(52) U.S. Cl.
CPC ............ *C07K 16/22* (2013.01); *A61K 38/179* (2013.01); *A61K 38/1858* (2013.01); *A61K 38/1866* (2013.01); *C07K 14/71* (2013.01); *C07K 16/28* (2013.01); *C07K 16/2863* (2013.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/71* (2013.01); *C07K 2317/72* (2013.01); *C07K 2317/76* (2013.01); *C07K 2317/92* (2013.01); *C07K 2318/10* (2013.01); *C07K 2319/036* (2013.01); *C07K 2319/30* (2013.01)

(58) Field of Classification Search
None
See application file for complete search history.

(56) References Cited

U.S. PATENT DOCUMENTS

| 4,634,664 A | 1/1987 | Oestberg |
| 4,634,666 A | 1/1987 | Engleman et al. |
| 5,225,539 A | 7/1993 | Winter |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,661,016 A | 8/1997 | Lonberg et al. |
| 5,663,425 A | 9/1997 | Detroit et al. |
| 5,733,743 A | 3/1998 | Johnson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,837,242 A | 11/1998 | Holliger et al. |
| 5,858,657 A | 1/1999 | Winter et al. |

(Continued)

FOREIGN PATENT DOCUMENTS

| WO | WO 1991/010741 A1 | 7/1991 |
| WO | WO 1991/017271 A1 | 11/1991 |

(Continued)

OTHER PUBLICATIONS

Lafaut, et al., "Clinicopathological correlation in exudative age related macular degeneration: histological differentiation between classic and occult choroidal neovascularisation," *Br J Ophthalmol*, 84:239-243 (2000).

Uutela, et al., "PDGF-D induces macrophage recruitment, increased interstitial pressure, and blood vessel maturation during angiogenesis," *Blood*, vol. 104 10:3198-3204 (Nov. 15, 2004).

Ferrara, et al., "Development of Ranibizumab, An Anti-Vascular Endothelial Growth Factor Antigen Binding Fragment, As Therapy for Neovascular Age-Related Macular Degeneration," *Retina, The Journal of Retinal and Vitreous Diseases*, vol. 26 8:859-870 (2006).

(Continued)

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

The invention provides a dual VEGF/PDGF antagonist comprising a VEGF antagonist linked to a PDGF antagonist. The VEGF antagonist is an antibody to a VEGF or VEGFR or is a VEGFR extracellular trap segment (i.e., a segment from the extracellular region of one or more VEGFR receptors that inhibits binding of at least one VEGFR to at least one VEGF). The PDGF antagonist is an antibody to a PDGF or PDGFR or is a PDGFR extracellular trap segment (i.e., segment from the extracellular region of one or more PDGFRs, which inhibits binding of at least one PDGFR and at least one PDGF). The dual antagonist is preferably conjugated to a half-life extending moiety, such as a HEMA-PC polymer. The dual antagonist is particularly useful for treating wet aged related macular degeneration.

34 Claims, 41 Drawing Sheets

(56) References Cited

U.S. PATENT DOCUMENTS

| | | | |
|---|---|---|---|
| 5,859,205 A | 1/1999 | Adair et al. | |
| 5,871,907 A | 2/1999 | Winter et al. | |
| 5,872,218 A | 2/1999 | Wolf et al. | |
| 5,874,299 A | 2/1999 | Lonberg et al. | |
| 5,877,218 A | 3/1999 | Herzig et al. | |
| 5,877,397 A | 3/1999 | Lonberg et al. | |
| 5,882,644 A | 3/1999 | Chang et al. | |
| 6,407,213 B1 | 6/2002 | Carter et al. | |
| 6,881,557 B2 | 4/2005 | Foote | |
| 7,060,271 B2 | 6/2006 | Ramakrishnan et al. | |
| 7,169,901 B2 | 1/2007 | Baca et al. | |
| 7,306,799 B2 | 12/2007 | Wiegand et al. | |
| 7,374,757 B2 | 5/2008 | Papadopoulos et al. | |
| 7,375,193 B2 | 5/2008 | Baca et al. | |
| 7,521,541 B2 | 4/2009 | Eigenbrot et al. | |
| 7,740,850 B2 | 6/2010 | Zhu et al. | |
| 7,759,472 B2 | 7/2010 | Shima et al. | |
| 7,855,178 B2 | 12/2010 | Alitalo et al. | |
| 8,008,453 B2 | 8/2011 | Gegg et al. | |
| 8,187,597 B2 | 5/2012 | Shima et al. | |
| 8,206,707 B2 | 6/2012 | Shima et al. | |
| 8,273,353 B2 | 9/2012 | Davis-Smyth et al. | |
| 8,455,622 B2 | 6/2013 | McDonagh et al. | |
| 8,486,397 B2 | 7/2013 | Bagri et al. | |
| 8,492,527 B2 | 7/2013 | Fuh et al. | |
| 8,512,699 B2 | 8/2013 | Fuh et al. | |
| 8,765,432 B2 | 7/2014 | Charles et al. | |
| 8,815,236 B2 | 8/2014 | Burke et al. | |
| 8,846,021 B2 | 9/2014 | Charles | |
| 2008/0199464 A1 | 8/2008 | Plowman et al. | |
| 2009/0117103 A1 | 5/2009 | Devalaraja et al. | |
| 2010/0111942 A1 | 5/2010 | Shima et al. | |
| 2010/0166700 A1* | 7/2010 | Charles | C08F 293/005 424/85.2 |
| 2012/0100136 A1 | 4/2012 | Patel et al. | |
| 2012/0213705 A1 | 8/2012 | Dimasi et al. | |
| 2013/0259881 A1 | 10/2013 | Fandl et al. | |
| 2014/0170140 A1 | 2/2014 | Bennett et al. | |
| 2014/0242082 A1 | 8/2014 | Shima et al. | |

FOREIGN PATENT DOCUMENTS

| | | |
|---|---|---|
| WO | WO 1992/001047 A1 | 1/1992 |
| WO | WO 1993/012227 A1 | 6/1993 |
| WO | WO 98/45331 | 10/1998 |
| WO | WO 2007/100902 A2 | 9/2007 |
| WO | WO 2008/020827 A2 | 2/2008 |
| WO | WO 2011/075185 A1 | 6/2011 |
| WO | WO 2011/075736 A1 | 6/2011 |
| WO | WO 2013/059137 A1 | 4/2013 |
| WO | 2013093809 A1 | 6/2013 |
| WO | WO 2013/093809 A1 | 6/2013 |
| WO | WO 2014/060401 A1 | 4/2014 |
| WO | 2014160507 A1 | 10/2014 |
| WO | WO 2015/035342 A2 | 3/2015 |
| WO | 2015200905 A3 | 12/2015 |

OTHER PUBLICATIONS

Magalhaes, et al., "Methods of Endotoxin Removal from Biological Preparations: a Review," *J. Pharm Pharmaceut Sci.*, 10(3): 388-404 (2007).

Raica, et al., "Platelet-Derived Growth Factor (PDGF)/PDGF Receptors (PDGFR) Axis as Target for Antitumor and Antiangiogenic Therapy," *Pharmaceuticals*, 3:572-599 (2010).

Ishikawa, et al., "Molecular mechanisms of subretinal fibrosis in age-related macular degeneration," *Experimental Eye Research*, pp. 1-7 (2015).

Papadopoulos, et al., "Binding and neutralization of vascular endothelial growth factor (VEGF) and related ligands by VEGF Trap, ranibizumab and bevacizumab," *Angiogenesis*, 15:171-185 (2012).

Ferrara, et al., "The biology of VEGF and its receptors," *Nature Medicine*, 9(6):669-676 (2003).

Zetter, "Angiogenesis and Tumor Metastasis," *Annu. Rev. Med.*, 49:407-424 (1998).

Presta, et al., "Humanization of an Anti-Vascular Endothelial Growth Factor Monoclonal Antibody for the Therapy of Solid Tumors and Other Disorders," *Cancer Research*, 57:4593-4599 (1997).

Carmeliet, "Angiogenesis in health and disease," *Nature Medicine*, 9(6):653-660 (2006).

Humphreys, et al., "Alternative antibody FAB' fragment PEGylation strategies: combination of strong reducing agents, disruption of the interchain disulphide bond and disulphide engineering," *Protein Engineering, Design & Selection*, 20(5):227-234 (2007).

Chen, et al., "Factors affecting endotoxin removal from recombinant therapeutic proteins by anion exchange chromatography," *Protein Expression and Purification*, 64:76-81 (2009).

Ferrara, et al., "Discovery and Development of Bevacizumab, an anti-VEGF Antibody for Treating Cancer," *Nature Reviews*, 3:391-400 (2004).

Andrae, et al., "Role of platelet-derived growth factors in physiology and medicine," *Genes & Development*, 22:1276-1312 (2008).

Bowen-Pope, et al., "History of Discovery: Platelet-derived Growth Factor," *Arterioscler Thromb Vasc Biol.* 31(11):2397-2401 (Nov. 2011).

Mones, "Inhibiting VEGF and PDGF to Treat AMD," *Review of Ophthalmology*, retrived from <http://www.reviewofophthalmology.com/content/d/retinal_insider/c/29979/#> (Sep. 9, 2011).

Kumar, et al., "PDGF-DD targeting arrests pathological angiogenesis by modulating GSK3β phosphorylation," *JBC Papers in Press*, published on Mar. 15, 2010 as Manuscript M110.113787, retrieved on Jun. 18, 2015 from <http://www.jbc.org>.

Fontaine, et al., "Long-Term Stabilization of Maleimide-Thiol Conjugates," *Bioconjugate Chem.*, 26:145-152 (2015).

Declaration of Harvey N. Masonson, M.D. Jul. 6, 2011.

Carmeliet, "Mechanisms of angiogenesis and arteriogenesis," *Nature Medicine*, 6(3):389-395 (2000).

Ambati, et al., "Mechanisms of age-related macular degeneration," *Neuron*, 75(1): 26-39 (2012).

Mabry, et al., "A dual-targeting PDGFRβ/VEGF—A molecule assembled from stable antibody fragments demonstrates anti-angiogenic activity in vitro and in vivo," *mAbs*, 2(1):20-34 (2010).

Shim, et al., "Structures of a platelet-derived growth factor/propeptide complex and a platelet-derived growth factor/receptor complex," *PNAS*, 107(25):11307-11312 (2010).

*Regeneron Pharmceuticals Inc* vs *Bayer Pharma AG* Approved Judgment dated Feb. 21, 2013.

Stuttfeld, et al., "Structure and Function of VEGF Receptors," *Life*, 61(9): 915-922 (2009).

Lucentis ramibizumab (reb) Product Information Sheet most recent amendment Oct. 23, 2013.

Dillon et al., "Structural and Functional Characterization of Disulfide Isoforms of the Human IgG2 Subclass" The Journal of Biological Chemistry, 283(23):16206-16215 (2008).

Ferrara et al., "Development of Ranibizumab, an Anti-Vascular Endothelial Growth Factor Antigen Binding Fragment, as Therapy for Neovascular Age-Related Macular Degeneration" Retina, 26(8):859-70 (2006).

International Search Report and Written Opinion for PCT/US2015/038203, dated Dec. 8, 2015 (13 pages).

Kuhnert et al., "Soluble Receptor Mediated Selective Inhibition of VEGFR and PDGFRβ Signaling During Physiologic and Tumor Angiogenesis" Proceedings of the National Academy of Science of the United State of America, 105(29):10185-10190 (2008).

Mabry et al., "A dual-targeting PDGFRβ/VEGF—A molecule assembled from stable antibody fragments demonstrates anti-angiogenic activity in vitro and in vivo" mAbs, 2(1): 20-34 (2010).

Edelman, et al. "The Covalent Structure of an Entire gammaG Immunoglobulin Molecule," Proc Natl Acad Sci U S A, 63(1), pp. 78-85, (1969).

Armulik, A. et al., "Endothelial/Pericyte Interactions," Circulation Research, vol. 97, Issue 6, pp. 512-523, Sep. 16, 2005.

(56) References Cited

OTHER PUBLICATIONS

Baluk, P. et al., "Cellular abnormalities of blood vessels as targets in cancer," Current Opinion in Genetics & Development, vol. 15, Issue 1, pp. 102-111, Feb. 2005.
Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.
Berthold, W. et al., "Protein Purification: Aspects of processes for pharmaceutical products," Biologicals, vol. 22, Issue 2, pp. 135-150, Jun. 1994.
Brown, D. et al., "Ranibizumab versus Verteporfin for Neovascular Age-Related Macular Degeneration," The New England Journal of Medicine, vol. 355, No. 14, pp. 1432-1444, Oct. 5, 2006.
Carmeliet, P., "Angiogenesis in healt and disease," Nature Medicine, vol. 9, pp. 653-660, (2003).
Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.
Chothia, C. et al., "Canonical structures for the hypervariable regions of immunoglobulins," Journal of Molecular Biology, vol. 196, Issue 4, pp. 901-917, Aug. 20, 1987.
Christy, N.E. et al., "Antibiotic prophylaxis of postoperative endophthalmitis," Annals of Ophthalmology, vol. 11, No. 8, pp. 1261-1265, Aug. 1, 1979.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
De Pascalis, R. et al., "Grafting of "abbreviated" complementarity-determining regions containing specificity-determining residues essential for ligand contact to engineer a less immunogenic humanized monoclonal antibody," The Journal of Immunology, vol. 169, Issue 6, pp. 3076-3084, Sep. 15, 2002.
Ferrara, N. et al., "Discovery and development of bevacizumab, an anti-VEGF antibody for treating cancer," Nature Reviews Drug Discovery, vol. 3, No. 5, pp. 391-400, (May 2004).
Ferrara, N. et al., "The biology of vascular endothelial growth factor," Endocrine Reviews, vol. 18, No. 1, pp. 4-25, (1997).
Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.
Folkman, J., "Angiogenesis: an organizing principle for drug discover?" Nature Reviews, Drug Discovery, vol. 6, pp. 273-286, Apr. 2007.
Friedman, D.S. et al., "Prevalence of age-related macular degeneration in the United States," Arch. Ophthalmol., vol. 122, No. 4, pp. 564-572, Apr. 2004.
Greene et al., "Protective Groups in Organic Synthesis," 3rd Edition, John Wiley and Sons, Inc., New York, (1999).
Haishima, Y. et al., "Estimation of uncertainty in kinetic-colorimetric assay of bacterial endotoxins," Journal of Pharmaceutical and Biomedical Analysis, vol. 32, Issue 3, pp. 495-503, Jul. 14, 2003.
Hirayama, C. et al., "Chromatographic removal of endotoxin from protein solutions by polymer particles," Journal of Chromatography B, vol. 781, Issues 1-2, pp. 419-432, Dec. 5, 2002.
International Search Report dated Jun. 4, 2013, in International Application No. PCT/IB2012/057491, 9 pages.
International Preliminary Report on Patentability (IPRP) dated Jun. 24, 2014, in International Application No. PCT/IB2012/057491, 10 pages.
International Preliminary Report on Patentability (IPRP) dated Jul. 5, 2016, in International Application No. PCT/US2015/038203, 29 pages.
Ishikawa, K. et al., "Molecular mechanisms of subretinal fibrosis in age-related macular degeneration," Experimental Eye Research, vol. 142, pp. 19-25, Jan. 2016.
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.
Junghans, R.P. et al., "Anti-Tac-H, a humanized antibody to the interlekin 2 receptor with new features for immunotherapy in malignant and immune disorders," Cancer Research, vol. 50, pp. 1495-1502, Mar. 1, 1990.
Kostelny, S.A. et al., "Formation of a bispecific antibody by the use of leucine zippers," J. Immunol., vol. 148, No. 5, pp. 1547-1553, Mar. 1, 1992.
Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.
Marticorena, J. et al., "Sterile endophthalmitis after intravitreal injections," Mediators of Inflammation, vol. 2012, 6 pages, (2012).
Morris, Glenn E. (editor), "Epitope Mapping Protocols," Methods in Molecular Biology, vol. 66, (1996).
Neuberger, M., "Generating high-avidity human Mabs in mice," Nature Biotechnology, vol. 14, pp. 826, (1996).
Ong, K. et al., "A rapid highly-sensitive endotoxin detection system," Biosensors and Bioelectronics, vol. 21, Issue 12, pp. 2270-2274, Jun. 15, 2006.
Ostberg, L. et al., "Human X (mouse x human) hybridomas stably producing human antibodies," Hybridoma, vol. 2, Issue 2, pp. 361-367, Apr. 24, 2009.
Padlan, Eduardo, "A possible procedure for reducing the immunogenicity of antibody variable domains while preserving their ligand-binding properties," Molecular Immunology, vol. 28, Issues 4-5, pp. 489-498, Apr.-May 1991.
Paul, W., Fundamental Immunology, 2nd ed. Raven Press, N.Y., (1989).
Petsch, D. et al., "Endotoxin removal from protein solutions," Journal of Biotechnology, vol. 76, Issues 2-3, pp. 97-119, Jan. 21, 2000.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Rycroft, B.W., "Penicillin and the control of deep intra-ocular infection," The British Journal of Ophthalmology, vol. 29, No. 2, pp. 57-87, (1945).
Songsivilai, S., "Bispecific antibody: a tool for diagnosis and treatment of disease," Clinical & Experimental Immunology, vol. 79, Issue 3, pp. 315-321, Mar. 1990.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Zebrowski, B. et al., "Vascular endothelial growth factor levels and induction of permeability in malignant pleural effusions," Clinical Cancer Research, vol. 5, pp. 3364-3368, Nov. 1999.
Mabry, R. et al., "A dual-targeting PDGFRβ/VEGF—A molecule assembled from stable antibody fragments demonstrates anti-angiogenic activity In vitro and in vivo", Landes Bioscience, vol. 2, Issue 2, pp. 20-34 (2010).
Kuhnert, F. et al. "Soluble receptor-mediated selective inhibition of VEGFR and PDGFR_signaling during physiologic and tumor angiogenesis", PNAS, vol. 105, No. 29, pp. 10185-10190, (2008).
Office Action in U.S. Appl. No. 14/932,913, dated Aug. 16, 2017.

\* cited by examiner

```
   1 MRLPGAMPAL ALKGELLLLS LLLLLEPQIS QGLVVTPPGP ELVLNVSSTF VLTCSGSAPV
  61 VWERMSQEPP QEMAKAQDGT FSSVLTLTNL TGLDTGEYFC THNDSRGLET DERKRLYIFV
 121 PDPTVGFLPN DAEELFIFLT EITEITIPCR VTDPQLVVTL HEKKGDVALP VPYDHQRGFS
 181 GIFEDRSYIC KTTIGDREVD SDAYYVYRLQ VSSINVSVNA VQTVVRQGEN ITLMCIVIGN
 241 EVVNFEWTYP RKESGRLVEP VTDFLLDMPY HIRSILHIPS AELEDSGTYT CNVTESVNDH
 301 QDEKAINITV VESGYVRLLG EVGTLQFAEL HRSRTLQVVF EAYPPPTVLW FKDNRTLGDS
 361 SAGEIALSTR NVSETRYVSE LTLVRVKVAE AGHYTMRAFH EDAEVQLSFQ LQINVPVRVL
 421 ELSESHPDSG EQTVRCRGRG MPQPNIIWSA CRDLKRCPRE LPPTLLGNSS EEESQLETNV
 481 TYWEEEQEFE VVSTLRLQHV DRPLSVRCTL RNAVGQDTQE VIVVPHSLPF KVVVISAILA
 541 LVVLTIISLI ILIMLWQKKP RYEIRWKVIE SVSSDGHEYI YVDPMQLPYD STWELPRDQL
 601 VLGRTLGSGA FGQVVEATAH GLSHSQATMK VAVKMLKSTA RSSEKQALMS ELKIMSHLGP
 661 HLNVVNLLGA CTKGGPIYII TEYCRYGDLV DYLHRNKHTF LQHHSDKRRP PSAELYSNAL
 721 PVGLPLPSHV SLTGESDGGY MDMSKDESVD YVPMLDMKGD VKYADIESSN YMAPYDNYVP
 781 SAPERTCRAT LINESPVLSY MDLVGFSYQV ANGMEFLASK NCVHRDLAAR NVLICEGKLV
 841 KICDFGLARD IMRDSNYISK GSTFLPLKWM APESIFNSLY TTLSDVWSFG ILLWEIFTLG
 901 GTPYPELPMN EQFYNAIKRG YRMAQPAHAS DEIYEIMQKC WEEKFEIRPP FSQLVLLLER
 961 LLGEGYKKKY QQVDEEFLRS DHPAILRSQA RLPGFHGLRS PLDTSSVLYT AVQPNEGDND
1021 YIIPLPDPKP EVADEGPLEG SPSLASSTLN EVNTSSTISC DSPLEPQDEP EPEPQLELQV
1081 EPEPELEQLP DSGCPAPRAE AEDSFL      (SEQ. ID No.: 33)
```

FIG. 1

```
   1 MVSYNDTGVL LCALLSCLIL TGSSSGSKLK DPELSLKGTQ HTMQAGQTLH LQCRGEAAHK WSLPEMVSKE SERLSITKSA
  81 CGRNGKQFCS TLTLNTAQAN HTGFYSCKYL AVPTSKKKET ESAIYIFISD TGRPFVEMYS EIPEITHMTE GRELVIPCRV
 161 TSPNITVTLK KFPLDTLIPD GKRIIWDSRK GFIISNATYK EIGLLTCEAT VNGHLYKTNY LTHRQTNTII DVQISTPRPV
 241 KLLRGHTLVL NCTATTPLNT RVQMTWSYPD EKNKRASVRR RIDQSNSHAN IFYSVLTIDK MQNKDKGLYT CRVRSGPSFK
 321 SVNTSVHTYD KAPITVKHRK QQVLETVAGK RSYRLSMKVK AFPSPEVVWL KDGLPATEKS ARYLTRGYSL IIKDVTEEDA
 401 GNYTILLSIK QSNVFKNLTA TLIVNVKPQI YEKAVSSFPD PALYPLGSRQ ILLCTAYGIP QPTTKWFWHP CNHNBSEARC
 481 DFCSNNEESF ILDADSNMGN RIESITQRMA IIEGKNKMAS TLIVADSRIS GIYICTASNK VGTVGRNISF YITDVPNGFH
 561 VNLEKMPTEG EDIKLSCTVN KFLYRDVTWI LLRTVNMRTM HYSISKQKMA ITKEHSITLN LTIMNVSLQD SGTYACRARN
 641 VTTGEEILQK KETITRDQEA PYLLRNLSDH TVAISSSTTL ESSAYLTVQG QITWFKMNEK IQQEPGIILG PGSSTLFIER
 721 VTEEDEGVTH CKATNQKGSV ESSAYLMVQG EFARERLKLG TDSKSNLELI TLTCTCVAAT LFWLLLTLFI RKMKRSSSEI KTDYLSTTMD
 801 PDEVPLDEQC ERLPYDASKW QGGPLMVIVE YCKYGNLSNY LKSKRDLFFL KSPTCRTVAV VVQASAEGTK KMLKEGATAS EYKALMTELK
 881 ILTHIGHHLN VVNLLGACTK EEEEDSDGFY KEPITMEDLI IFDKIYSTKS DVWSYGVLLW NVQDGKDYI NDAALHMEP KKEKMEPGLE QGKKPRLDSV
 961 TSSESFASSG FQEDKSLSDV PKERPRFAEL VEKLGDLLQA NVQQDGKDYI PINAILTGNS GFTYSTPAFS EDFFKESISA
1041 FGLARDIYKN PDYVRKGDTR LPLKWMAPES LLPNATSMPD DYQGDSSTLL ASPMLKRFTW TDSKPKASLK IDLRVTSKSK
1121 APEYSTPEIY QIMLDCWHRD PKERPRFAEL VEKLGDLLQA NVQQDGKDYI PINAILTGNS EIPSLGGSPY PGVQMDEDFC SRLREGMRMR
1201 PKFNSGSSDD VRYVNAFKFM SLERIKTEEE LLPNATSMPD DYQGDSSTLL ASPMLKRFTW TDSKPKASLK IDLRVTSKSK
1281 ESGLSDVSRP SFCHSSCGHV SEGKRRFTYD HAELERKIAC CSPPPDYNSV VLYSTPPI (SEQ ID NO.34)
```

FIG. 2

```
   1 MQSKVLLAVA LWLCVETRAA SVGLPSVSLD LPRLSIQKDI LTIKANTRLQ ITCRGQRDLD WLWPNMQSGS EQRVEVTECS
  81 DGLFCKTLTI PKVIGNDTGA YKCFYRETDL ASVIYVYVQD YRSPFIASVS DQHGVVYITE NKNKTVVIPC LGSISNLNVS
 161 LCARYPEKRF VPDGNRISWD SKKGFTIPSY MISYAGMVFC EAKINDESYQ SIMYIYVVG YRIYDVVLSP SHGIELSVGE
 241 KLVLNCTART ELNVGIDFNW EYPSSKHQHK KLVNRDLKTQ SGSEMKKFLS TLTIDGVTRS DQGLYTCAAS SGLMTKKNST
 321 FVRVHEKPFV APGSGMESLV EANVGERVRI PAKYLGYPPP EIKWYKNGIP LESNHTIKAG HVLTIMEVSE RDTGNYTVIL
 401 TNPISKEKQS HVVSLVVYVP PQIGEKSLIS PVDSYQYGTT QTLTCTVYAI PPPHIHWYW QLEEECANEP SQAVSVTNPY
 481 PCHEWRSVED FQGGNKIEVN KNQFALTECK NKTVSTLVIQ AANVSALYKC EAVNKVGRGE RVISFHVTRG PEITLQPDMQ
 561 PTEQESVSLW CTADRSTFEN LTWYKLGPQP LPIHVGELPT PVCKNLDTLW KLNATMFSNS TNDILIMELX NASLQDQGDY
 641 VCLAQDRKTK KRHCVRQLT VLERVAPTIT GNLENQTTSI GESIEVSCTA SGNPPPQIMW FKDNETLVED SGIVLKDGNR
 721 NLTIRRVRKE DEGLYTCQAC SVLGCAKVEA FFIEGAQEK TNLETILVG TAVIANFFWL LLVILRTVK RANGELKTG
 801 YLSIVMDPDE LPLDEHCERL PYDASKWFP RDRLKLGKPL PLMVTVEPCK TLEHLICYSF ADAFGIDKTA TCRTVAVKML KEGATHSEHR
 881 ALMSELKILI HIGHHLMVUN LLGACTKPGG KSLSDVHEEE APEDLYKDFL VYTIQSDVWS KRNEFPYKT QVAKGMERTLA SRKCTHRDLA ARNILLSEKN
 961 RRLDSITSSQ SSASSGFVEE KSLSDVHEEE APEDLYKDFL TLEHLICYSF ADAFGIDKTA PGVLMEIFS LGASPYPGVK IDEEFCRRLK
1041 VVKICDFGLA RDIYKDPDYV RKGBARLPLK WMAPETIFDR VYTIQSDVWS FGVTLVPLI SETLSMEEDS GLSPTSPVS
1121 EGTRMRAPDY TTPEMYQTRL DCWHGEPSQR PTFSELVEHL GNLLQANAQ DGKDYIVLPI SETLSMEEDS GLSPTSPVS
1201 CMREEEVCDP KFHYDNTAGI SQTLQWSKRK SRPVSKTPE DIPLEEPEVK VIPDDNQTDS GMVLASEELK TLEDRTKLSP
1281 SFGGMVPSKS RESVASEGSN QTSGYQSGH SDDTDTTVYS SERAELLKLI EIGVQTGSTA QILQPDSGTT LSSPPV (SEQ. ID No.: 35)
```

FIG. 3

```
   1 MQRGAALCLR LWLCLGLLDG LVSGYSMTPP TLNITEESHV IDYGDSLSIS CRGQHPLEWA WPGAQEAPAT GDKDSEDTGV
  81 VRDCEGTDAR PVCKVLLHE VHANDTGSYV CYTKYIKARI EGTAASSYV FVRDEQFFI NKPDTLLVNR KDAMWPCLV
 161 SIPGLNVTLR SQESVLNPDG QEVVWDDRRG MLVSTPLLHD ALYLQCETTW GDQDFLSNPF LVHITGNELY DIQLLPRKSL
 241 ELLVGEKLVL NCTVWAEFNS GVTFDWDYPG KQAERGKWVP ERRSQQTHTE LSSILTIHNV SQHDLGSTVC KANNGIQRFR
 321 ESTEVIVHEN PFISVEWLKG PILEATAGDE LVKLPVKLAA YPPPEFQWYK DGKALSGRHS PHALVLKEVT EASTGTTTLA
 401 LWNSAAGLRR NISLELVVNV PPQIHEKEAS SPSIYSRHSR QALICTAYGV PLPLSIQWHW RPWTPCKMFA QRSLRRRQQQ
 481 DLMPQCRDMR AVTTQDAVNP IESLDTWTEF VEGKNKTVSK LVIQNANVSA MYKCVVSNKV GQDERLIYFY VTTIPDGFTI
 561 ESKPSEELIE GQPVLLSCQA DSYKYEHLRW YRLNLSTLHD AHGNPLLLDC KNVHLFATPL AASLEEVAPG ARHATLSLSI
 641 PRVAPEHEGH TVCEVQDRRS HDKHCHKKYL SVQALEAPRL TQNLIDILVN VSDSLEMQCL VAGAHAPSIV WYKDERLLEE
 721 KSGVDLADSN QKLSIQRVRE EDAGRYLCSV CNAKGCVNSS ASVAVEGSED KGSMEIVILV GTGVIAVFFW VLLLIFCNM
 801 RRPAHADIKT GYLSIMDPG EVPLEEQCEY LSVDASQWEF PRERLHGRV LGYGAFGKVV EASAFGTHKG SSCDTVAVRM
 881 LKEGATASEH RALMSELKIL IHIGNHLNVV NLLGACTKPQ GPLMVTVEEC KYGNLSNFLR AKRDAFSPCA EKSPEQRGRF
 961 RAMVELARLD RRRPGSSDRV LFARPSKTEG GARRASPDQE AEDLWLSPLT MEDIVCYSFQ VARGMEFLAS RKCIHRDLAA
1041 RNILLSESDV VKICDFGLAR DIYKDPDYVR KGSARLPLKW MAPESIFDKV YTTQSDVWSF GVLLWEIFSL GASPYPGVQI
1121 NEEFCQRLRD GTRMRAPELA TPAIRRIMLN CWSGDPKARP AFSELVEILG DLLQGRGLQE EEEVCMAPRS SQSSEEGSFS
1201 QVSTMALHIA QADAEDSPPS LQRHSLAARY YNWVSFPGCL ARGAETRGSS RMKTFEEFPM TPTTYKGSVD NQTDSGMVLA
1281 SEEFEQIESR HRQESGPSCK GPGQNVAVTR AHPDSQGRRR RPERGARGGQ VPYNSEYGEL SEPSEEDHCS PSARVTFFTD
1361 NSY (SEQ ID No.: 36)
```

FIG. 4

A. LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

B. HEAVY CHAIN

```
  1 EVQLVESGGG LVQPGGSLRL SCAASGYTFT NYGMNWVRQA PGKGLEWVGW INTYTGEPTY AADFKRRFTI SLDTSKSTAY
 81 LQMNSLRAED TAVYYCAKYP HYVSSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK (SEQ. ID No.: 2)
```

FIG. 5

A. Light Chain Sequence

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHG LSSPVTKSFN RGEC (SEQ. ID No.: 12)
```

B. Heavy Chain Sequence

```
  1 EVQLVESGGG LVQPGGSLRL SCAASGYDFT HYGMNWVRQA PGKGLEWVGW INTYTGEPTY AADFKRRFTI SLDTSKSTAY
 81 LQMNSLRAED TAVYYCAKYP YYYGTSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTICNVNH KPSNTKVDKK VEPKSCDKTH L (SEQ. ID No.: 13)
```

FIG. 6

PDGFR-GS10-ANTI-VEGF-A LIGHT CHAIN:

```
  1 LVTTPPGPEL VLNVSSTFVL TCSGSAPVVW ERMSQEPPQE MAKAQDGTFS SVIJLTNLTG LDTGEYFCTH NDSRGLETDE
 81 RKRLYIFVPD PTVGFLPNDA EELFIFLTEI TEITIPCRVT DPQLVTLHE KKGDVALPVP VDHQRGFSGI FEDRSYICKT
161 TIGDREVDSD AYYYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSDIQMTQSP SSLSASVGDR VTITCSASQD
321 ISNYLNWYQQ KPGKAPKVLI YFTSSLHSGV PSRFSGSGSG TDFTLTISSL QPEDFATYYC QQYSTVPWTF GQGTKVEIKR
401 TVAAPSVFIF PPSDEQLKSG TASVVCLLNN FYPREAKVQW KVDNALQSGN SQESVTEQDS KDSTYSLSST LTLSKADYEK
481 HKVYACEVTH QGLSSPVTKS FNRGEC (SEQ ID No.: 19)
```

FIG. 7A

ANTI-VEGF-A HEAVY CHAIN (WILD TYPE Fc):

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK (SEQ ID No.: 2)
```

FIG. 7B

PDGFR-GG-ANTI-VEGF-A LIGHT CHAIN:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDBQD EKAINITVVE SGGGDIQMTQ SPSSLSASVG DRVTICSAS QDISNYLNWY
321 QQKPGKAPKV LIYFTSSLHS GVPSRFSGSG SGTDFTLTIS SLQPEDFATY YCQQYSTVPW TPGQGTKVEI KRTVAAPSVF
401 IFPPSDEQLK SGTASVVCLL NNFYPREAKV QWKVDNALQS GNSQESVTEQ DSKDSTYSLS SSTLTLSKADY EKHKVYACEV
481 THQGLSSPVT KSFNRGEC   (SEQ. ID No.: 3)
```

FIG. 8A

ANTI-VEGF-A HEAVY CHAIN (WILD TYPE Fc):

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYP DWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCRTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK  (SEQ. ID No.: 2)
```

FIG. 8B

PDGFR-GS10-ANTI-VEGF-A HEAVY CHAIN (WILD TYPE Fc):

```
  1 LVVTPPGPEL VLNVSSTFVL TCSGSAPVVW ERKSQEPQQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFENTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYT
321 FTNYGMNWVR QAPGKGLEWV GWINTYTGEP TYAADFKRRF TFSLDTSKST AYLQMNSLRA EDTAVYYCAK YPHYYGSSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KRVEPKSCDK THTCPPCPAP ELLGGPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPQVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS LSPGK  (SEQ. ID No.: 4)
```

FIG. 9A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC  (SEQ. ID No.: 5)
```

FIG. 9B

PDGFR-GG-ANTI-VEGF-A HEAVY CHAIN (WILD TYPE Fc):

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITTPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGEVQLVE SGGGLVQPGG SLRLSCAASG YTFTNYGMNW
321 VRQAPGKGLE WVGWINTYTG EPTYAADFKR RFTFSLDTSK STAYLQMNSL RAEDTAVYYC AKYPHYYGSS HWYFDVWGQG
401 TLVTVSSAST KGPSVFPLAP SSKSTSGGTA ALGCLVKDYF PEPVTVSWNS GALTSGVHTF PAVLQSSGLY SLSSVVTVPS
481 SSLGTQTYIC NVNHKPSNTK VDKKVEPKSC DKTHTCPPCP APELLGGPSV FLFPPKPKDT LMISRTPEVT CVVVDVSHED
561 PEVKFNWYVD GVEVHNAKTK PREEQYNSTY RVVSVLTVLH QDWLNGKEYK CKVSNKALPA PIEKTISKAK GQPREPQVYT
641 LPPSREEMTK NQVSLTCLVK GFYPSDIAVE WESNGQPENN YKTTPPVLDS DGSFFLYSKL TVDKSRWQQG NVFSCSVMHE
721 ALHNHYTQKS LSLSPGK    (SEQ. ID No.: 6)
```

FIG. 10A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC    (SEQ. ID No.: 5)
```

FIG. 10B

ANTI-VEGF-A HEAVY CHAIN (WILD TYPE Fc)-GS21-PDGFR-β TRAP:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGGGGSGGGG SGGGGSGGGG GSGLVTPPPG
481 PELVLNVSST FVLTCSGSAP VVWERMSQEP PQEMAKAQDG TPSSVTLTIEN HYTQKSLSLS LPGLDTGEYF CTHNDSRGLE TDERKRLYIF
561 VPDPTVGFLP NDAEELFIFL TEITEITIPC RVTDPQLVVT LHEKKGDVAL PVPYDHQRGF SGIFEDRSYI CKTTIGDREV
641 DSDAYYVYRL QVSSINVSVN AVQTVRGEE NITLMCIVIG NEVVNFEWTY PRKESGRLVE PVTDFLLDMP YHIRSILHIP
721 SAELEDSGTY TCNVTESVND HQDEKAINIT VVESG (SEQ. ID No.: 7)
```

FIG. 11A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 11B

PDGFR-β-GS10-ANTI-VEGF-A HEAVY CHAIN (Q347C):

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THTCPPCPAP ELAAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPQVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS LSPGK    (SEQ. ID No.: 8)
```

FIG. 12A

ANTI-VEGF LIGHT CHAIN:

```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC    (SEQ. ID No.: 12)
```

FIG. 12B

PDGFR-GS10-ANTI-VEGF-A HEAVY CHAIN (L443C):

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSTNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THTCPPCPAP EAAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPQVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS CSPGK  (SEQ ID No.: 9)
```

FIG. 13A

ANTI-VEGF LIGHT CHAIN:

```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC  (SEQ ID No.: 12)
```

FIG. 13B

PDGFR-GS10-ANTI-VEGF-A LIGHT CHAIN:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI THTIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSDIQMTQSP SSLSASVGDR VTITCSASQD
321 ISNYLNWYQQ KPGKAPKVLI YFTSSLHSGV PSRFSGSGSG TDFTLTISSL QPEDFATYYC QQYSTVPWTF GQGTKVEIKR
401 TVAAPSVFIF PPSDEQLKSG TASVVCLLNN FYPREAKVQW KVDNALQSGN SQESVTEQDS KDSTYSLSST LTLSKADYEK
481 HKVYACEVTH QGLSSPVTKS FNRGEC (SEQ ID No.: 1)
```

FIG. 14A

ANTI-VEGF-A FAB:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH T (SEQ ID No.: 21)
```

FIG. 14B

PDGFR-GG-ANTI-VEGF-A LIGHT CHAIN:

```
  1 LVTTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENLT LMCIVIGNEV VNFEWTYPRK ESGRLVEPVT DFLLDMPYHI
241 RSILHIPSAE LEDSGTYTCN VTESVNDHQD EKAINITVVE SGGDIQMTQ SPSSLSASVG DRVTITCSAS QDISNYLNWY
321 QQKPGKAPKV LIYFTSSLHS GVPSRFSGSG SGTDFTLTIS SLQPEDFATY YCQQYSTVPW TFGQGTKVEI KRTVAAPSVF
401 IFPPSDEQLK SGTASVVCLL NNFYPREAKV QWKVDNALQS GNSQESVTEQ DSKDSTYSLS STLTLSKADY EKHKVYACEV
481 THQGLSSPVT KSFNRGEC   (SEQ ID No.: 3)
```

FIG. 15A

ANTI-VEGF-A FAB:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH T   (SEQ ID No.: 21)
```

FIG. 15B

PDGFR-GS10-ANTI-VEGF-A FAB:

```
  1 LVVTPGEPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSTLHIPSAE LEDSGTYTCN VTESVNDHQD EKAINITVVE SGGGGSGGGG GSEVQLVESG GGLVQPGGSL RLSCAASGYT
321 FTNYGMNWVR QAPGKGLEWV GWINTYTGEP TYAADFKRRF TFSLDTSKST AYLQMNSLRA EDTAVYYCAK YPHYYGSSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THT (SEQ. ID No.: 22)
```

FIG. 16A

ANTI-VEGF LIGHT CHAIN:

```
  1 DIQMTQSPSS LSASVGDRVT ITCSASQDIS NYLNWYQQKP GKAPKVLIYF TSSLHSGVPS RPSGSGSGTD FTLTISSLQP
 81 EDFATYYCQQ YSTYPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 16B

PDGFR-GG-ANTI-VEGF-A FAB:

```
  1 LVVTPQGEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSTLHIPSAE LEDSGTYTCN VTESVNDHQD EKAINITVVE SGGEVQLVE SGGGLVQPGG SLRLSCAASG YTFTNYGMNW
321 VRQAPGKGLE WVGWINTYTG EPTYAADFKR RFTFSLDTSK STAYLQMNSL RAEDTAVYYC AKYPHYYGSS HWYFDVWGQG
401 TLVTVSSAST KGPSVFPLAP SSKSTSGGTA ALGCLVKDYF PEPVTVSWNS GALTSGVHTF PAVLQSSGLY SLSSVVTVPS
481 SSLGTQTYIC NVNHKPSNTK VDKKVEPKSC DKTHT (SEQ ID No.: 23)
```

FIG. 17A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLP LSKADYEKHK VYACEVTHQG LSSPVTKSFN RGEC (SEQ ID No.: 5)
```

FIG. 17B

ANTI-VEGF-A FAB-GS21-PDGFR-β TRAP:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGGSGGGG
241 GSGGGGSGGG GSGLVTPPG PELVLNVSST FVLTCSGSAP VVWERMSQEP PQEMAKAQDG TFSSVLTLTN LTGLDTGEYF
321 CTHNDSRGLE TDERKRLYIF VPDPTVGFLP NDAEELFIFL TEITEITIPC RVTDPQLVVT LHEKKGDVAL PVPYDHQRGF
401 SGIFEDRSVI CKTTIGDREV DSDAYYVYRL QVSSINVSVN AVQTVVRQGE NITLMCIVIG NEVVNFEWTY PRKESGRLVE
481 PVTDFLLDMP YHIRSILHIP SAELEDSGTY TCNVTESVND HQDEKAINIT VVESG  (SEQ. ID No.: 24)
```

FIG. 18A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC  (SEQ. ID No.: 5)
```

FIG. 18B

PDGFR-β-GS10-ANTI-VEGF-A FAB:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THL (SEQ ID No.: 25)
```

FIG. 19A

ANTI-VEGF LIGHT CHAIN:

```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ ID No.: 12)
```

FIG. 19B

PDGFR-β-ANTI-VEGF-A HEAVY CHAIN:

```
  1 LVTPPGPE LVLNVSSTPV LTCSGSAPVV WERMSQEPPQ EMAKAQDGTF SSVLTLTNLT GLDTGEYFCT HNDSRGLETD
 80 ERKRLYIFVP DPTVGFLPND AEELFIFLTE ITEITIPCRV TDPQLVTLH EKKGDVALPV PYDHQRGFSG IFEDRSYICK
160 TTIGDREVDS DAYYVTRLQV SSINVSVNAV QTVVRQGENI TLMCIVIGNE VVNFEWTYPR KESGRLVEPV TDFLLDMPYH
240 IRSILHIPSA ELEDSGTYTC NVTESVNDHQ DEKAINITVV ESGEVQLVES GGGLVQPGGS LRLSCAASGY TFTNYGMNWV
320 RQAPGKGLEW VGWINTYTGE PTYAADFKRR PTFSLDTSKS TAYLQMNSLR AEDTAVYYCA KYPHYGSSH WYPDVWGQGT
400 LVTVSSASTK GPSVFPLAPS SKSTSGGTAA LGCLVKDYFP EPVTVSWNSG ALTSGVHTFP AVLQSSGLYS LSSVVTVPSS
480 SLGTQTYICN VNHKPSNTKV DKKVEPKSCD KTHTCPPCPA PELLGGPSVF LFPPKPKDTL MISRTPEVTC VVVDVSHEDP
560 EVKFNWYVDG VEVHNAKTKP REEQYNSTYR VVSVLTVLHQ DWLNGKEYKC KVSNKALPAP IEKTISKAKG QPREPQVYTL
640 PPSREEMTKN QVSLTCLVKG FYPSDIAVEW ESNGQPENNY KTTPPVLDSD GSFFLYSKLT VDKSRWQQGN VFSCSVMHEA
720 LHNHYTQKSL SLSPGK          (SEQ. ID No.: 26)
```

FIG. 20A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC        (SEQ. ID No.: 5)
```

FIG. 20B

PDGFR-β-ANTI-VEGF-A HEAVY CHAIN:

```
  1 VGFLPNDAEE LFIFLTEIIR IITPCRVTDP QLVVTLHEKK GDVALPVPYD HQRGFSGIFE DRSYICKTTI GDREVDSDAY
 81 YVVRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPS

PDGFR-β-ANTI-VEGF-A FAB:

```
  1 VGFLPNDAEE LPIFLTEITE ITIPCRVTDP QLVVTLHEKK GDVALPVPYD HQRGFSGIFE DRSYICKTTI GDREVDSDAY
 81 YVVRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTI SLDTSKSTAY LQMNSLRAED TAVYYCAKYP HYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH T (SEQ. ID No.: 28)
```

FIG. 22A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 22B

PDGFR-β-ANTI-VEGF-A FAB:

```
  1 VGFLPNDAEE LFIFLTEITE ITTPCRVTDP QLVVTLHEKK GDVALPVPYD HQRGFSGIFE DRSTCKTTI GDREVDSDAY
 81 YVVRLQVSSI NVSVNAVQTY VRQGENTILM CIVIGNEVVN FEWTYPRKES GRLVEPVTDF LLDMPYHIRS ILHIPSAELE
161 DSGTYTCNVT ESVNDHQDEK AINITVVESG GGGSGGGGSG GGGSGGGGSE GGGSGGGGSL VQLVESGGGL VQPGGSLRLS
241 CAASGYTFTN YGMNWVRQAP GKGLEWVGWI NTYTGEPTYA ADFKRRFTFS LDTSKSTAYL QMNSLRAEDT AVYYCAKYPH
321 YYGSSHWYFD VWGQGTLVTV SSASTKGPSV FPLAPSSKST SGGTAALGCL VKDYFPEPVT VSWNSGALTS GVHTFPAVLQ
401 SSGLYSLSSV VTVPSSSLGT QTYICNVNHK PSNTKVDKKV EPKSCDKTHT (SEQ. ID No.: 29)
```

FIG. 23A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 23B

PDGFR-β-6XGS-ANTI-VEGF-A FAB:

```
  1 VGFLPNDAEE LPTLTHTTE ITTPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDP LLDMPYHIRS TLHIPSAELE
161 DSGTYTCNVT ESVNDEQDEK AINITVVESG GGGSGGGGSG GGGSGGGGSE VQLVESGGGL VQPGGSLRLS
241 CAASGYTFTN YGMNWVRQAP GKGLEWVGWI NTYTGEPTYA ADFKRRFTFS LDTSKSTAYL QMNSLRAEDT AVYYCAKYPH
321 YYGSSHWYFD VWGQGTLVTV SSASTKGPSV FPLAPSSKST SGGTAALGCL VKDYFPEPVT VSWNSGALTS GVHTFPAVLQ
401 SSGLYSLSSV VTVPSSSLGT QTYICNVNHK PSNTKVDKKV EPKSCDKTHT       (SEQ. ID No.: 29)
```

FIG. 24A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 24B

ANTI-VEGF-A FAB-6XGS-PDGFR-β

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGSGGGGS
241 GGGGSGGGGS GGGGSGGGGS VGELPNDAEE LFIFLTEITE ITIPCRVTDP QLVTLHEKK GDVALPVPYD HQRGFSGIFE
321 DRSYICKTTI GDREVDSDAY YVYRLQVSSI NVSVNAVQTV VRQGENITLM CIVIGNEVVN (SEQ ID No.: 30)
401 LLDMPYHIRS ILHIPSAELE DSGTYTCNVT ESVNDHQDEK AINITVVESG
```

FIG. 25A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ ID No.: 5)
```

FIG. 25B

COMPOUND L

COMPOUND K

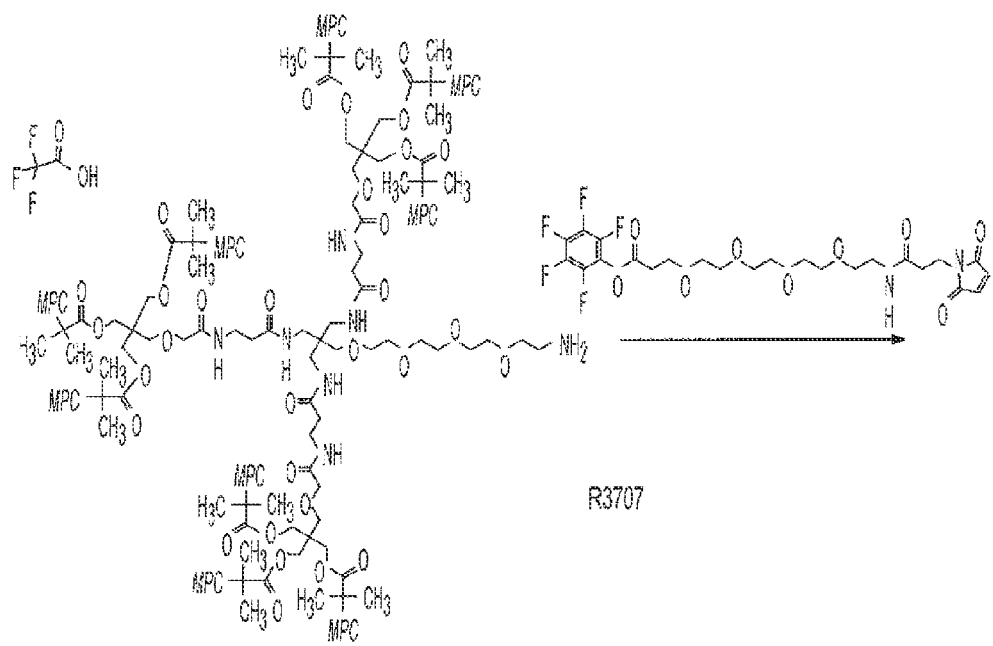
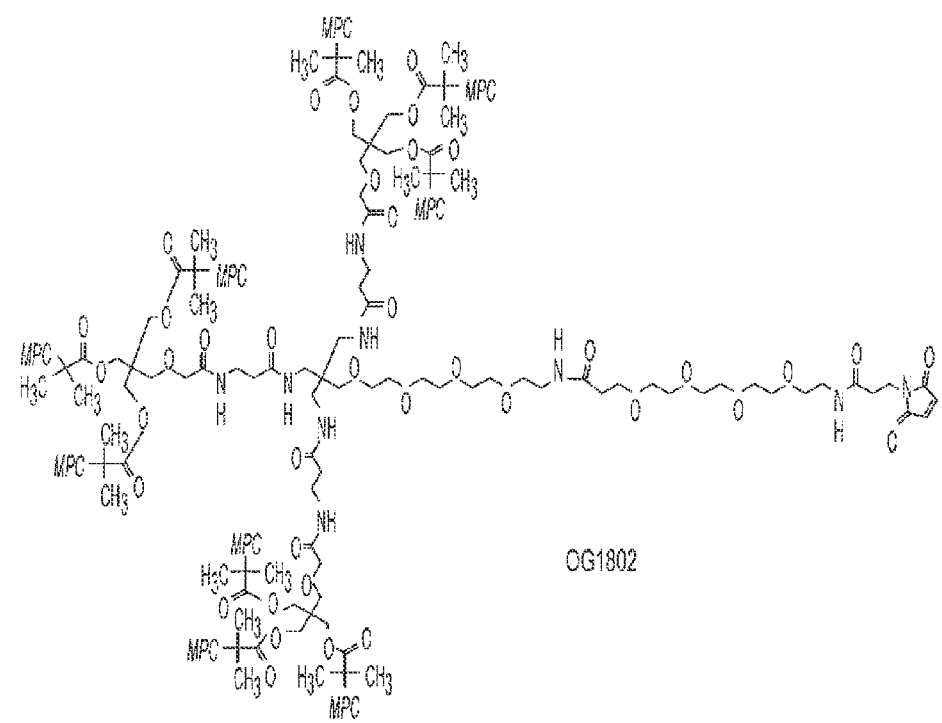
FIG. 29

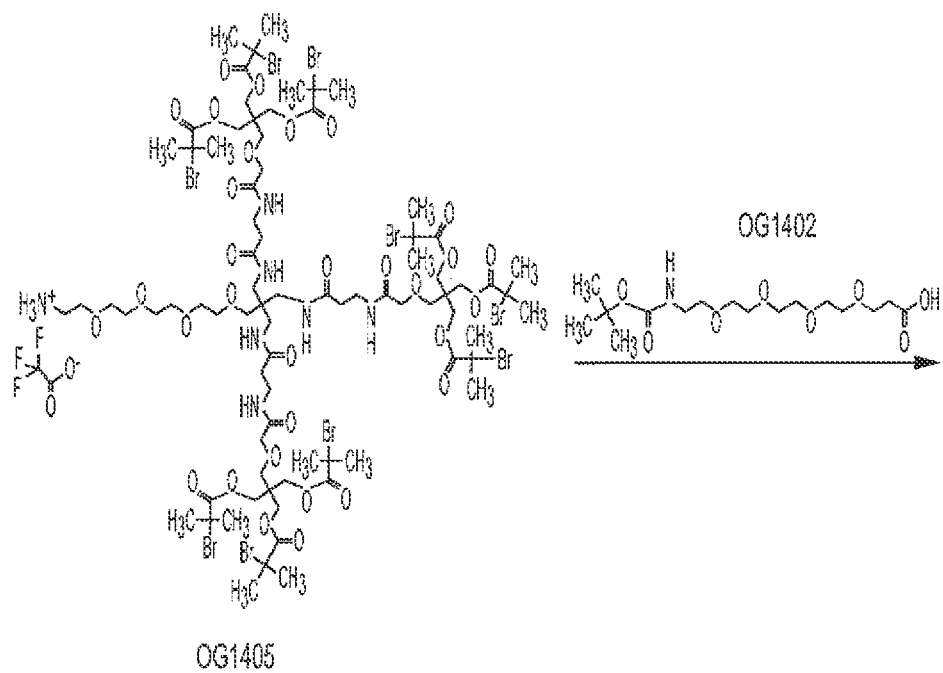
OG1405
OG1402
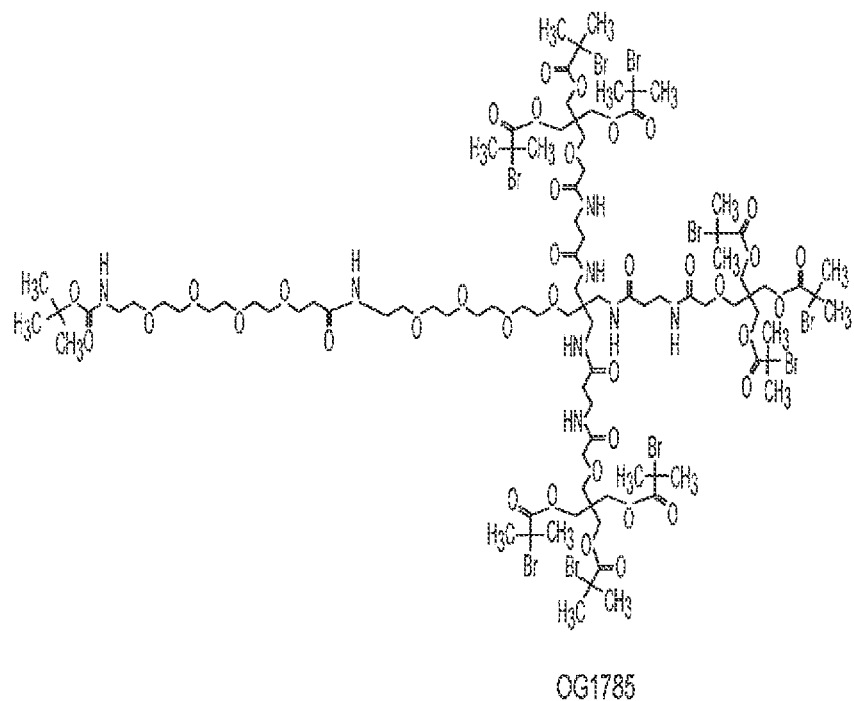
OG1785
FIG. 34

DUAL PDGF/VEGF ANTAGONISTS

CROSS-REFERENCE TO RELATED APPLICATION

The present application is a continuation of International Application No. PCT/US2015/038203, filed Jun. 28, 2015, which claims the benefit of U.S. Provisional Application No. 62/018,579, filed Jun. 28, 2014, incorporated by reference in its entirety for all purposes. The present application also claims the benefit of U.S. Provisional Application No. 62/018,579, filed Jun. 28, 2014.

REFERENCE TO A SEQUENCE LISTING

This application includes an electronic sequence listing in a file named 464337_SEQLIST.TXT, created on Aug. 25, 2015 and containing 224,345 bytes, which is hereby incorporated by reference in its entirety for all purposes.

BACKGROUND

Angiogenesis (the formation of blood vessels) occurs throughout an organism's development. Indeed, the first organ in an embryo is a blood vessel. Angiogenesis is also crucial for wound healing, restoring blood flow to damaged tissue. However, improper or dysregulated angiogenesis contributes to or causes many diseases including cancer, psoriasis, arthritis and blindness. Carmeliet P. 2003. Angiogenesis in health and disease. Nature Med 9(6):653-660.

Age related macular degeneration (AMD) is a leading cause of vision loss and blindness in the elderly. About ten million Americans are afflicted with AMD. The prevalence of AMD in the population increases steadily with age: at 40 years of age only about 2% of the population is affected by AMD but by the age of 80 it is about 25%. Friedman, D. S. et al. 2004. Arch. Ophthalmol. 122:564-572. There are generally two types of AMD: dry and wet.

Dry AMD is the most common form of the disease. In dry AMD, there is a depletion of the layer of the retinal pigment epithelial cells in the macula. Dry AMD is chronic and generally causes some loss of vision. In severe cases of dry AMD, patients can develop near total blindness. Wet AMD develops in some 10-15% of patients with dry AMD. Wet AMD is characterized by angiogenesis, specifically choroidal neovascularization (CNV). CNV is characterized by the presence of new immature blood vessels which grow towards the outer retina from the choroid. These immature blood vessels leak fluid below and in the retina, causing vision loss and blindness. Wet AMD blindness is typically acute.

Angiogenesis also plays a crucial role in cancer and tumor formation and maintenance. The recruitment of new blood vessels is an essential component of the metastatic pathway. For many tumors, the vascular density can provide a prognostic indicator of metastatic potential: highly vascular tumors have a higher incidence of metastasis than less vascular tumors.

Angiogenesis is the result of a complex interplay between growth factors, vascular endothelial cells, extracellular matrix molecules, chemokines and cell signaling molecules. Factors identified as mediators of angiogenesis include: basic and acidic fibroblast growth factor, transforming growth factors α and β, platelet-derived growth factor (PDGF), angiogenin, platelet-derived endothelial cell growth factor, IL8, and vascular endothelial growth factor (VEGF). The role of VEGF in angiogenesis has been extensively reported on.

It has been shown that VEGF signaling presents a crucial rate limiting step in physiological angiogenesis. VEGF also plays a central role in pathological angiogenesis (e.g., tumor growth). Ferrara N and Davis-Smyth T. 1997. The biology of vascular endothelial growth factor. Endocr. Rev. 18: 4-25. VEGF is also known to induce vascular leakage. Bates D O and Curry F E. 1997. Vascular endothelial growth factor increases microvascular permeability via a Ca (2+)-dependent pathway. Am J Physiol. 273: H687-H694; Roberts W G and Palade G E. 1995. Increased microvascular permeability and endothelial fenestration induced by vascular endothelial growth factor. J Cell Sci. 108:2369-2379.

Anti-VEGF therapeutics have been successfully used to treat wet AMD and cancer. Genentech's anti-VEGF monoclonal antibody bevacizumab (Avastin®) received FDA approval in 2004 for the treatment of cancer. Anti-VEGF agents have been approved for the treatment of wet AMD. In 2004, the FDA approved Eyetech/Pfizer Macugen®. Genentech's Lucentis® was approved in 2006 for wet AMD. Bevacizumab is also used off label for the treatment of wet AMD. In 2011, Regeneron's Eylea® was approved for treatment of wet AMD.

Despite the success of anti-VEGF therapeutics, none of them causes regression in the pathological neovascular (NV) tissue. Hence, NV tissue remains despite continued anti-VEGF treatment and can prevent significant vision gain for treated patients. The NV tissue consists of endothelial cells, pericytes and inflammatory cells (i.e., occasional macrophages). The presence of pericytes on capillaries not only leads to NV support and stabilization but promotes endothelial cell survival through chemical signaling and physical interactions including pericyte production of VEGF. This endothelial survival signaling by integrated pericytes is critical and may explain the resistance of the NV tissue to VEGF withdrawal, i.e., lack of NV regression to monotherapy anti-VEGF treatment. In addition, over time the pathological NV tissue can lead to fibrosis and scarring.

Subretinal scarring develops in nearly half of treated eyes within two years of anti-VEGF therapy. Daniel E, Toth C A, Grunwald J E. 2014. Risk of scar in the comparison of age-related macular degeneration in clinical settings. Retina 32:1480-1485. Subretinal fibrosis formation can cause permanent dysfunction of the macular system; it causes destruction of photoreceptors, retinal pigment epithelium and choroidal vessels. Ishikawa K, Ram K, Hinton D R. 2015. Molecular mechanisms of subretinal fibrosis in age-related macular degeneration. Eye Res. xxx:1-7. While anti-VEGF therapy generally stabilizes or improves visual acuity, scar formation has been identified as one of the causes of loss of visual acuity after treatment. Cohen S Y, Oubraham H, Uzzan J, et al. 2012. Causes of unsuccessful ranibizumab treatment in exudative age-related macular degeneration in clinical settings. Retina 32:1480-1485.

PDGF has been reported to play a role in pericyte recruitment, maturation and resistance to anti-VEGF mediated regression. Corneal and choroidal neovascularization animal models have been reported to have demonstrated that administration of agents that block the PDGF-B/PDGFR-β interaction leads to pericyte stripping from the pathological neovasculature. Jo N, Mailhos C, Ju M, et al. 2006. Inhibition of Platelet-Derived Growth Factor B Signaling Enhances the Efficacy of Anti-Vascular Endothelial Growth Factor Therapy in Multiple Models of Ocular Neovascularization. American J Path. 168(6):2036-2053.

To target both pathways, clinical trials are currently underway in which patients receive two medications: Lucentis® (an anti-VEGF Fab) and Fovista™ a PEGYlated aptamer directed against PDGF by Ophthotech. Fovista is directed against only a single PDGF ligand: PDGF-BB. However, there are many other PDGF ligands: PDGF-AA, PDGF-CC and PDGF-DD. PDGF-DD, for example, has been shown to play a crucial role in ocular angiogenesis. Kumar A, Hou X, Chunsik L, et al. 2010. Platelet-derived Growth Factor-DD Targeting Arrests Pathological Angiogenesis by Modulating Glycogen Synthase Kinase-3β Phosphorylation. J Biol Chem 285(20):15500-15510. Yet Fovista does not interact with PDGF-DD. There is a need in the art for broader based anti-PDGF therapies.

In addition, aptamer based therapeutics in general have poor pharmacokinetic properties in that aptamers are subject to renal filtration and to serum digestion. While these problems can be somewhat overcome with PEGylation, PEGylation tends to reduce binding to target. Aptamers typically bind with much lower affinity to targets than their antibody counterparts. PEGylation will tend to reduce binding even further. There is, thus, a need in the art for non-aptamer based anti-PDGF therapeutics.

Current clinical plans for Fovista double the number of injections patients must receive for treatment relative to the currently approved anti-VEGF therapies. Fovista is formulated separately from the anti-VEGF agent so patients must be given two injections instead of one. Moreover the injections cannot be at the same time because of build-up in intraocular pressure caused by a single injection.

From the view point of both patients and treating physicians, intravitreal injections are not trivial. Many patients experience pain and discomfort from the injection and patient compliance is a serious issue. Common side effects of intravitreal injections include conjunctival hemorrhage, eye pain, vitreous floaters, increased intraocular pressure, and intraocular inflammation. Intravitreal injections are associated with relatively rare serious adverse events, including endophthalmitis, retinal detachment and traumatic cataracts.

There is thus a need in the art for therapies that do not increase the number of intravitreal injections that patients must endure. In addition, current anti-VEGF therapies often require once a month injections. There is also a need for therapies which are needed less frequently than once a month.

SUMMARY OF THE CLAIMED INVENTION

The invention provides a dual VEGF/PDGF antagonist comprising a VEGF antagonist linked to a PDGF antagonist, wherein the VEGF antagonist (a) is an antibody to a VEGF or VEGFR or (b) is a VEGFR extracellular trap segment and the PDGF antagonist (a) is an antibody to a PDGF or PDGFR or (b) is a PDGFR extracellular trap segment, provided that the VEGF and PDGF antagonists are not both antibodies. Optionally, the VEGF antagonist is an antibody comprising a heavy chain and a light chain and the PDGF antagonist is the PDGFR extracellular trap segment, and the heavy chain of the antibody is fused via a linker to the C-terminus of the PDGFR extracellular trap segment, and the light chain is complexed with the heavy chain. Optionally, the antibody is a Fab fragment. Optionally, the antibody is an intact antibody. Optionally, the PDGF antagonist is an extracellular trap segment of a PDGFR-α or PDGFR-β receptor and the VEGF antagonist is an antibody to a VEGF. Optionally, the PDGFR extracellular trap segment comprises one or more of domains D1-D5 of PDGFR-β. Optionally, the PDGFR extracellular trap segment comprises domains D1-D3 of PDGFR-β. Optionally, the PDGFR extracellular trap segment comprises amino acids 33 to 314 of SEQ ID NO. 11. Optionally, the VEGF antagonist comprises an anti-VEGF antibody. Optionally, the anti-VEGF antibody is an anti-VEGF-A antibody. Optionally, the PDGFR extracellular trap segment is located C-terminal of the heavy or light chain. Optionally, the PDGFR extracellular trap segment is located N-terminal of the heavy or light chain.

Optionally, the dual VEGF/PDGF antagonist of further comprising a linker which is located between the PDGFR trap and the anti-VEGF antibody heavy chain. Optionally the linker is GGGGSGGGGS, GG, or GGGGSGGGGSGGGGSGGGGSG.

Optionally, the anti-VEGF antibody heavy chain comprises $CDR_H1$: GYDFTHYGMN, $CDR_H2$: WINTYTGEPTYAADFKR, and $CDR_H3$: YPYYYGTSHWYFDV.

Optionally, the anti-VEGF light chain comprises $CDR_L1$: SASQDISNYLN, $CDR_L2$: FTSSLHS and $CDR_L3$: QQYSTVPWT.

Optionally, the anti-VEGF heavy chain isotype is IgG1 comprising a $CH_1$, hinge, $CH_2$ and $CH_3$ domains and the light chain isotype is kappa. Optionally the IgG1 constant domain has the sequence set forth in SEQ ID NO. 17 and the light chain constant region has the sequence set forth in SEQ ID NO. 18.

Optionally, the IgG1 constant domain has one or more mutations to reduce effector function. Optionally the mutations are to one or more of the following amino acid positions (EU numbering): E233, L234, L235, G236, G237, A327, A330, and P331. Optionally, the mutations are selected from the group consisting of: E233P, L234V, L234A, L235A, G237A, A327G, A330S and P331S. Optionally, mutations are L234A, L235A and G237A.

Optionally, the dual VEGF/PDGF antagonist comprises a heavy chain further comprising a cysteine residue added by recombinant DNA technology. Optionally, the cysteine residue is selected from the group consisting of (EU numbering) Q347C and L443C.

Optionally, the dual VEGF/PDGF antagonist has a heavy chain comprising the amino acid sequence off SEQ ID NO. 9 and the light chain has an amino acid sequence of SEQ ID NO. 10.

Optionally, the dual VEGF/PDGF antagonist comprises a PDGFR trap extracellular segment comprising one or more of domains D1-D5 of PDGFR-β. Optionally, the PDGFR trap extracellular segment comprises domains D1-D3 of PDGFR-β. Optionally, the PDGFR trap extracellular segment comprises amino acids 33 to 314 of SEQ ID NO. 11.

Optionally, the dual VEGF/PDGF antagonist comprises a VEGF antagonist, which is an anti-VEGF antibody. Optionally, the antibody is an anti-VEGF-A Fab fragment. Optionally, the PDGFR extracellular trap segment is located C-terminal of the Fab heavy or light chain. Optionally, the PDGFR extracellular trap segment is located N-terminal of the Fab heavy or light chain.

Optionally, the dual VEGF/PDGF comprises a heavy chain comprising an anti-VEGF-A Fab fragment heavy chain and a light chain comprising an anti-VEGF-A light chain. Optionally, the dual antagonist further comprises a linker which is located between the PDGFR trap and the anti-VEGF Fab fragment heavy chain. Optionally, the linker is selected from group consisting of GGGGSGGGGS, GG, and GGGGSGGGGSGGGGSGGGGSG. Optionally, the anti-VEGF Fab fragment heavy chain comprises $CDR_H1$: GYDFTHYGMN, $CDR_H2$: WINTYTGEPTYAADFKR, and CDR$_H$3: YPYYYGTSHWYFDV. Optionally, the anti-VEGF light chain comprises CDR$_L$1: SASQDISNYLN, CDR$_L$2: FTSSLHS and CDR$_L$3: QQYSTVPWT. Optionally, the anti-VEGF heavy chain isotype is IgG1 comprising a CH$_1$ domain and the light chain isotype is kappa.

Any of the dual VEGF/PDGF antagonists can further comprise a half-life extending moiety. Optionally, the half-life extending moiety comprises a polymer, which is PEG or a zwitterionic polymer. Optionally, the zwitterionic polymer comprises a monomer comprising phosphorylcholine. Optionally, the monomer comprises 2-(acryloyloxyethyl)-2'-(trimethylammoniumethyl) phosphate. Optionally, the monomer comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer has 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da. Optionally, the dual VEGF/PDGF antagonist is covalently bonded to the polymer. Optionally, the polymer is covalently bonded to at least one of an amino group, a hydroxyl group, a sulfhydryl group and a carboxyl group. Optionally, the sulfhydryl group is from a naturally occurring cysteine residue. Optionally, the sulfhydryl group is from a cysteine residue added by recombinant DNA technology. Optionally, the polymer is covalently bonded to the cysteine residue at position 741 of SEQ ID NO. 9.

Optionally, the VEGF antagonist comprises a VEGFR extracellular trap segment comprising one or more extracellular segments of VEGFR-1, VEGFR-2 and VEGFR-3 and the PDGF antagonist is an anti-PDGF antibody. Optionally, the extracellular segment of VEGFR comprises one or more of domains D1-D7. Optionally, the extracellular segment comprises D2 from VEGFR-1 and D3 from VEGFR-2. Optionally, the D2 is N-terminal to the D3 and further comprises a linker between the domains. Optionally, the PDGF antagonist is an intact antibody. Optionally, the PDGF antagonist is a Fab fragment. Optionally, the anti-PDGFR antibody is humanized 2A1E2, HuM4 Ts.22, humanized 1B3, humanized 2C5, anti-PDGF-BB, anti-PDGF-DD, anti-PDGF-BB or anti-PDGF-AB. Optionally, the heavy chain is IgG1 and the light chain is kappa. Optionally, the heavy chain sequence has a cysteine added via recombinant DNA technology the cysteine selected from the groups consisting of Q347C or a L443C. Optionally, the dual VEGF/PDGF antagonist further comprises a half-life extending moiety conjugated to the cysteine. Optionally, the dual VEGF/PDGF antagonist protein has a half-life extending moiety comprising a zwitterionic polymer, the polymer comprising one or more monomer units and wherein at least one monomer unit comprises a zwitterionic group, such as phosphorylcholine. Optionally, the monomer comprises 2-(acryloyloxyethyl)-2'-(trimethylammoniumethyl)phosphate. Optionally, the monomer comprises 2-(methacryloyloxyethyl)-2'-(trimethylammoniumethyl)phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer has 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da.

In some dual VEGF/PDGF antagonists the PDGF antagonist comprises a PDGF extracellular trap segment comprising one or more extracellular segments of a PDGFR selected from the group consisting of PDGFR-α and PDGFR-β and the VEGF antagonist is a VEGF extracellular trap segment comprising one or more extracellular segments of a VEGFR selected from the group consisting of VEGFR-1, VEGFR-2 and VEGFR-3. Optionally, the extracellular trap segment of VEGFR comprises one or more of domains D1-D7. Optionally, the extracellular trap segment comprises D2 from VEGFR-1 and D3 from VEGFR-2. Optionally, the D2 is N-terminal to the D3 and further comprises a linker between the domains. Optionally, the PDGFR trap comprises one or more of domains D1-D5 of PDGFR-β. Optionally, the PDGFR trap comprises domains D1-D3 of PDGFR-β. Optionally, the PDGFR trap comprises amino acids 33 to 314 of SEQ ID NO. 11. Optionally, the dual VEGF/PDGF antagonist further comprises a linker sequence between the VEGF antagonist and the PDGF antagonist. Optionally, the dual VEGF/PDGF antagonist further comprises a half-life extending moiety. Optionally, the half-life extending moiety comprises a polymer selected from the group consisting of PEG and a zwitterionic polymer. Optionally, the half-life extending moiety comprises a zwitterionic polymer. Optionally, the zwitterionic polymer comprises a monomer comprising phosphorylcholine. Optionally, the monomer comprises 2-(acryloyloxyethyl)-2'-(trimethylammoniumethyl) phosphate. Optionally, the monomer comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da. Optionally, the polymer has 9 arms. Optionally, the dual VEGF/PDGF antagonist is covalently bonded to the polymer. Optionally, the polymer is covalently bonded to at least one of an amino group, a hydroxyl group, a sulfhydryl group and a carboxyl group. Optionally, the sulfhydryl group is from a naturally occurring cysteine residue. Optionally, the sulfhydryl group is from a cysteine residue added by recombinant DNA technology.

Any dual VEGF/PDGF antagonist as described above can be used in treatment or prophylaxis of disease, particularly a neovascular disorder, optionally an ocular neovascular disorder, such as wet age related macular degeneration.

BRIEF DESCRIPTION OF THE DRAWINGS

FIG. 1: Protein Sequence of human PDGFR-β
FIG. 2: Protein Sequence of VEGFR-1
FIG. 3: Protein Sequence of VEGFR-2
FIG. 4: Protein Sequence of VEGFR-3
FIG. 5: bevacizumab sequence (DrugBank DB00112)
FIG. 6: ranibizumab (published by Novartis).
FIGS. 7A, B: Protein Sequence of A. PDGFRβ-GS10-anti-VEGF-A light chain and B. anti-VEGF-A heavy chain.
FIGS. 8A, B: A. Protein Sequence of PDGFRβ-GG-anti-VEGF-A light chain and B. anti-VEGF-A heavy chain.

FIGS. 9A, B. Protein Sequence of A. PDGFRβ-GS10-anti-VEGF-A heavy chain (wild type Fc) and B. anti-VEGF-A light chain.

FIGS. 10A, B. Protein Sequence of A. PDGFRβ-GG-anti-VEGF-A heavy chain (wild type Fc) and B. anti-VEGF-A light chain.

FIGS. 11A, B. Protein Sequence of A. anti-VEGF-A heavy chain (wild type Fc)-GS21-PDGFRβ and B. anti-VEGF-A light chain.

FIGS. 12A, B. Protein Sequence of A. PDGFR-β-GS21-anti-VEGF-A heavy chain (Q347C) and B. anti-VEGF-A light chain (TAF347).

FIGS. 13A, B. Protein Sequence of A. PDGFR-β-GS21-anti-VEGF-A heavy chain (L443C) and B. anti-VEGF-A light chain (TAF443).

FIGS. 14A, B. Protein Sequence of A. PDGFRβ-GS10-anti-VEGF-A light chain and B. anti-VEGF-A Fab.

FIGS. 15A, B. Protein Sequence of A. PDGFRβ-GG-anti-VEGF-A light chain and B. anti-VEGF-A Fab.

FIGS. 16A, B. Protein Sequence of A. PDGFRβ-GS10-anti-VEGF-A Fab and B. anti-VEGF-A light chain.

FIGS. 17A, B. Protein Sequence of A. PDGFRβ-GG-anti-VEGF-A Fab and B. anti-VEGF-A light chain.

FIGS. 18A, B. Protein Sequence of A. anti-VEGF-A Fab-G521-PDGFRβ and B. anti-VEGF-A light chain.

FIGS. 19A, B. Protein Sequence of A. PDGFRβ-GS10-anti-VEGF-A Fab with certain mutations and B. anti-VEGF-A light chain.

FIGS. 20A, B. Protein Sequence of A. PDGFRβ-anti-VEGF-A heavy chain and B. anti-VEGF-A light chain (1a).

FIGS. 21A, B. Protein Sequence of A. PDGFR-β (D2-D3)-anti-VEGF-A heavy chain and B. anti-VEGF-A light chain (1b).

FIGS. 22A, B. Protein Sequence of A. PDGFR-β (D1-D3)-anti-VEGF-A Fab and B. anti-VEGF-A light chain (2b).

FIGS. 23A, B. Protein Sequence of A. PDGFR-β (D2-D3)-6×GS-anti-VEGF-A Fab and B. anti-VEGF-A light chain (2b').

FIGS. 24A, B. Protein sequence of A. PDGFR-β-6×GS-anti-VEGF-A Fab and B. anti-VEGF-A light chain.

FIGS. 25A, B: Protein Sequence of A. anti-VEGF-A Fab-6×GS-PDGFR-β (D2-D3) and B. anti-VEGF-A light chain (3).

FIG. 29 shows the synthesis of OG1802 from R3707.

FIG. 34 shows the synthesis of OG 1785 from OG1405.

BRIEF DESCRIPTION OF SEQ ID NOS

Figure 26:
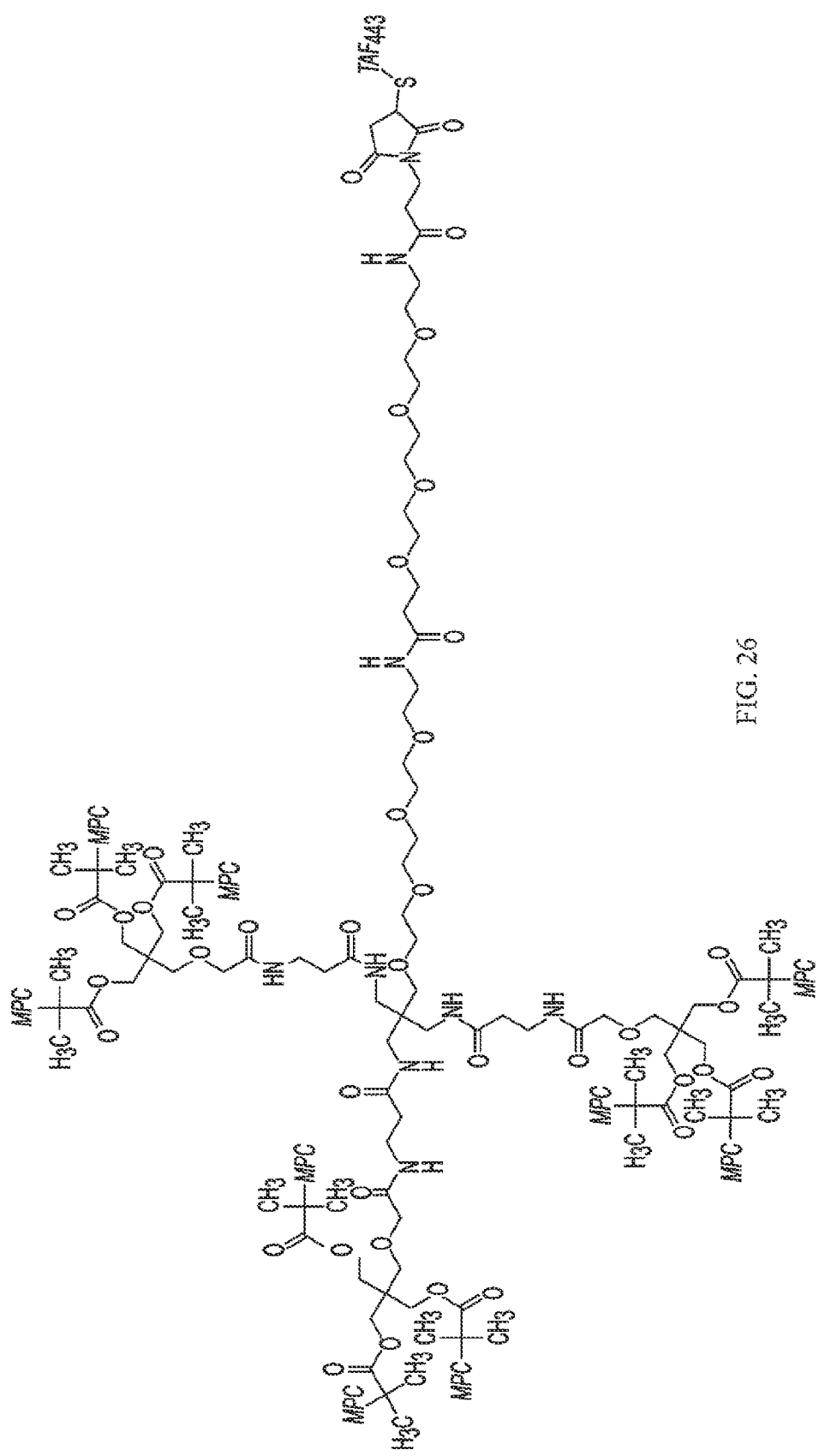
FIG. 26 shows the chemical structure of OG1448.

SEQ ID NO. 1 is the protein sequence of PDGFRb-GS10-LightChain anti-VEGF-A (Bevacizumab).

SEQ ID NO. 2 is the anti-VEGF-A Bevacizumab heavy chain.

SEQ ID NO. 3 is protein sequence of PDGFRb-GG-Light Chain anti-VEGF-A (Bevacizumab).

SEQ ID NO. 4 is PDGFRβ-GS10-Heavy Chain-anti-VEGF-A (Bevacizumab).

SEQ ID NO. 5 is the anti-VEGF-A Bevacizumab light chain.

SEQ ID NO. 6 is PDGFRβ-GG-Heavy Chain-anti-VEGF-A (Bevacizumab).

SEQ ID NO. 7 is anti-VEGF-A Heavy Chain (Bevacizumab)-G521-PDGFRβ.

SEQ ID NO. 8 is the amino acid sequence of the heavy chain trap extracellular segment of TAF347: PDGFR-β trap-anti-VEGF-A heavy chain (Q347C).

SEQ ID NO. 9 is the amino acid sequence of the heavy chain trap extracellular segment of TAF443: PDGFR-β trap-anti-VEGF-A heavy chain (L443C) and SEQ ID NO:10 is the amino acid sequence of the light chain of anti-VEGF-A.

SEQ ID NO. 11 is human PDGFR-β.

SEQ ID NO. 12 is the ranibizumab light chain.

SEQ ID NO. 13 is the ranibizumab heavy chain.

SEQ ID NO. 14 is human VEGFR-1.

SEQ ID NO. 15 is human VEGFR-2.

SEQ ID NO. 16 is human VEGFR-3.

SEQ ID NO. 17 is a human IgG1 constant region.

SEQ ID NO. 18 is a human kappa light constant region.

SEQ ID NO. 19 is FIG. 7. PDGFR-GS10-anti-VEGF-A light chain.

SEQ ID NO. 20 is FIG. 8. PDGFR-GG-anti-VEGF-A light chain.

SEQ ID NO. 21 is a Bevacizumab Fab.

SEQ ID NO. 22 is a PDGFR-β-GS10-anti-VEGF-A Fab.

SEQ ID NO. 23 is a PDGFR-β-GG-anti-VEGF-A Fab.

SEQ ID NO. 24 is an anti-VEGF-A Fab-G521-PDGFR-β.

SEQ ID NO. 25 is a PDGFR-β-GS10-anti-VEGF-A Fab with certain mutations.

SEQ ID NO. 26 is a protein sequence of PDGFRβ-anti-VEGF-A heavy chain (1a).

SEQ ID NO. 27 is a protein sequence of PDGFR-β (D2-D3)-anti-VEGF-A heavy chain (1b).

SEQ ID NO. 28 is a protein sequence of PDGFR-β (D2-D3)-anti-VEGF-A Fab (2b).

SEQ ID NO. 29 is a protein sequence of PDGFR-β (D2-D3)-6×GS-anti-VEGF-A Fab.

SEQ ID NO. 30 is a protein sequence of anti-VEGF-A Fab-6×GS-PDGFR-β (D2-D3).

SEQ ID NO. 31 is a nucleic acid encoding a heavy chain anti-VEGF-PDGFR fusion.

SEQ ID NO. 32 is a nucleic acid encoding a light chain anti-VEGF.

GGGGS (SEQ ID NO. 37), GGGS (SEQ ID NO. 38), GGGES (SEQ ID NO. 39), GGGGSGGGGS (SEQ ID NO. 40) and GGGGSGGGGSGGGGSGGGGSG) (SEQ ID NO. 41).

Ranibizumab CDRs are: $CDR_H1$: GYDFTHYGMN, $CDR_H2$: WINTYTGEPTYAADFKR, and $CDR_H3$: YPYYYGTSHWYFDV (SEQ ID NOS. 42-44), $CDR_L1$: SASQDISNYLN, $CDR_L2$: FTSSLHS and $CDR_L3$: QQYST-VPWT (SEQ ID NOS. 45-47). Bevacizumab $CDR_H1$ is GYTFTNYGMN (SEQ ID NO. 48) and $CDR_H3$ is YPHYYGSSHWYFDV (SEQ ID NO:49).

Definitions

A "neovascular disorder" is a disorder or disease state characterized by altered, dysregulated or unregulated angiogenesis. Examples of neovascular disorders include neoplastic transformation (e.g. cancer) and ocular neovascular disorders including diabetic retinopathy and age-related macular degeneration.

An "ocular neovascular" disorder is a disorder characterized by altered, dysregulated or unregulated angiogenesis in the eye of a patient. Such disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

A "polypeptide linker" is a polypeptide comprising two or more amino acid residues joined by peptide bonds that are used to link two polypeptides (e.g., a VH and VL domain or a VH domain and an extracellular trap segment). Examples of such linker polypeptides are well known in the art (see, e.g., Holliger P, Prospero T, Winter G. 1993. PNAS USA. 90:6444-6448; Poljak R J. 1994. Production and Structure of Diabodies. Structure 2:1121-1123). Exemplary linkers include G, GG, GGGGS, GGGS, and GGGES, and oligomers of such linkers (e.g., GGGGSGGGGS and GGGGSGGGGSGGGGSGGGGSG).

Dual antagonists or other biologics described herein are typically provided in isolated form. This means that an antagonist is typically at least 50% w/w pure of interfering proteins and other contaminants arising from its production or purification but does not exclude the possibility that the antagonist is combined with an excess of pharmaceutical acceptable excipient intended to facilitate its use. Sometimes antagonists are at least 60, 70, 80, 90, 95 or 99% w/w pure of interfering proteins and contaminants from production or purification. Often an antagonist is the predominant macromolecular species remaining after its purification.

The term antibody includes intact antibodies and binding fragments thereof. A binding fragment refers to a molecule other than an intact antibody that comprises a portion of an intact antibody that binds the antigen to which the intact antibody binds. Examples of binding fragments include Fv, Fab', Fab'-SH, F(ab')2; diabodies; linear antibodies; single-chain antibody molecules (e.g. scFv); and multispecific antibodies formed from antibody fragments. scFv antibodies are described in Houston J S. 1991. Methods in Enzymol. 203:46-96. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

Specific binding of an antibody, extracellular trap segment or dual antagonist to its target antigen(s) means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcR binding.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai S, Lachmann P C. 1990. Bispecific antibody: a tool for diagnosis and treatment of disease. Clin Exp Immunol. 79:315-321; Kostelny S A, Cole M S, Tso J Y. 1992. Formation of bispecific antibody by the use of leucine zippers. J Immunol. 148: 1547-1553). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. For convenience, the variable heavy CDRs can be referred to as $CDR_H1$, $CDR_H2$ and $CDR_H3$; the variable light chain CDRs can be referred to as $CDR_L1$, $CDR_L2$ and $CDR_L3$. The assignment of amino acids to each domain is in accordance with the definitions of Kabat E A, et al. 1987 and 1991. Sequences of Proteins of Immunological Interest (National Institutes of Health, Bethesda, Md.) or Chothia C, Lesk A M. 1987. Canonical Structures for the Hypervariable Regions of Immunoglobulins. J Mol Biol 196:901-917; Chothia C, et al. 1989. Conformations of Immunoglobulin Hypervariable Regions. Nature 342:877-883. Kabat also provides a widely used numbering convention (Kabat numbering) in which corresponding residues between different heavy chain variable regions or between different light chain variable regions are assigned the same number. Although Kabat numbering can be used for antibody constant regions, EU numbering is more commonly used, as is the case in this application. Although specific sequences are provided for exemplary dual antagonists, it will be appreciated that after expression of protein chains one to several amino acids at the amino or carboxy terminus of the light and/or heavy chain, particularly a heavy chain C-terminal lysine residue, may be missing or derivatized in a proportion or all of the molecules.

The term "epitope" refers to a site on an antigen to which an antibody or extracellular trap segment binds. An epitope on a protein can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody (or Fab fragment) bound to its antigen to identify contact residues.

Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50: 1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., De Pascalis R, Iwahashi M, Tamura M, et al. 2002. Grafting "Abbreviated" Complementary-Determining Regions Containing Specificity-Determining Residues Essential for Ligand Contact to Engineer a Less Immunogenic Humanized Monoclonal Antibody. J Immunol. 169:3076-3084; Vajdos F F, Adams C W, Breece T N, Presta L G, de Vos A M, Sidhu, S S. 2002. Comprehensive functional maps of the antigen-binding site of an anti-ErbB2 antibody obtained with shotgun scanning mutagenesis. J Mol Biol. 320: 415-428; Iwahashi M, Milenic D E, Padlan E A, et al. 1999. CDR substitutions of a humanized monoclonal antibody (CC49): Contributions of individual CDRs to antigen binding and immunogenicity. Mol Immunol. 36:1079-1091; Tamura M, Milenic D E, Iwahashi M, et al. 2000. Structural correlates of an anticarcinoma antibody: Identification of specificity-determining regions (SDRs) and development of a minimally immunogenic antibody variant by retention of SDRs only. J Immunol. 164:1432-1441).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan E A. 1991. A possible procedure for reducing the immunogenicity of antibody variable domains while preserving their ligand-binding properties. Mol Immunol. 28:489-98) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Östberg L, Pursch E. 1983. Human×(mouse×human) hybridomas stably producing human antibodies. Hybridoma 2:361-367; Östberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332.

"Polymer" refers to a series of monomer groups linked together. A polymer is composed of multiple units of a single monomer (a homopolymer) or different monomers (a heteropolymer). High MW polymers are prepared from monomers that include, but are not limited to, acrylates, methacrylates, acrylamides, methacrylamides, styrenes, vinylpyridine, vinyl-pyrrolidone and vinyl esters such as vinyl acetate. Additional monomers are useful in the high MW polymers of the present invention. When two different monomers are used, the two monomers are called "comonomers," meaning that the different monomers are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using the monomers or comonomers of the present invention. The polymerization can be a conventional free radical polymerization or preferably a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments of the present invention, the initiator contains one of more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

"Phosphorylcholine," also denoted as "PC," refers to the following:

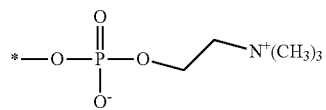

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate (HEA-PC shown below in Example 51) as monomer.

Poly(methacryloyloxyethyl phosphorylcholine) containing polymer refers to a polymer containing 2-(methacryloyloxy)ethyl-2-(trimethylammonium)ethyl phosphate (HEMA-PC) as monomer.

"Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography—multi angle light scattering). The polymeric reagents of the invention are typically polydisperse (i.e., number average molecular weight and weight average molecular weight of the polymers are not equal), preferably possessing low polydispersity values of, for example, less than about 1.5, as judged, for example, by the PDI value derived from the SEC-MALS measurement. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

The phrase "a" or "an" entity refers to one or more of that entity; for example, a compound refers to one or more compounds or at least one compound. As such, the terms "a" (or "an"), "one or more", and "at least one" can be used interchangeably herein.

"About" means variation one might see in measurements taken among different instruments, samples, and sample preparations.

"Protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," 3$^{rd}$ Edition, John Wiley and Sons, Inc., New York, 1999.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=N H, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. The term "alkyl" is include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR'"', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R'"' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'"' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means a cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached to but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

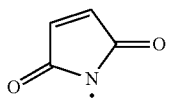

which upon reaction with a sulfhydryl (e.g., a thio alkyl) forms an —S-maleimido group having the structure

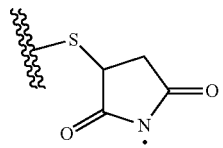

where "•" indicates the point of attachment for the maleimido group and "⚡" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as N-alpha-methyl amino acids (e.g. sarcosine), 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

"Pharmaceutically acceptable excipient" refers to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Dual antagonists are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a pre-clinical or clinical trial in a population of treated patients relative to a control population of untreated patients.

The "biological half-life" of a substance is a pharmacokinetic parameter which specifies the time required for one half of the substance to be removed from a tissue or an organism following introduction of the substance.

"HEMA-PC" is 2-(methacryloyloxyethyl)-2'-(trimethylammoniumethyl)phosphate.

"TAF" means a PDGFRβ-GS10-anti-VEGF-A heavy chain/anti-VEGF-A light chain wherein amino acids 1-282 of the heavy chain correspond to amino acids 33 to 314 of human PDGFR-β (UniProtKB/Swiss-Prot: P09619.1), fused as a single open reading frame via a glycine-serine linker (GGGGSGGGGS) linked to the N terminus of a bevacizumab heavy chain sequence having the following mutations in the variable region: T28D, N31H, H97Y, S100aT (Ferrara N, Damico L, Shams N, et al. 2006. Development of Ranibizumab, an anti-vascular endothelial growth factor antigen binding fragment, as therapy for neovascular age-related macular degeneration. Retina 26(8):859-870); and the following in the Fc region: L234A, L235A, and G237A (EU numbering) (Strohl W R. 2009. Optimization of Fc-mediated effector functions of monoclonal antibodies. Curr Opin in Biotech. 20: 685-691). The light chain is the bevacizumab light chain having an M4L mutation. TAF normally exists as a dimer having two heavy chains and two light chains. TAF may or may not have carbohydrate or other post-translational modifications after being expressed from cells. TAF is also sometimes called TAFwt or TAFWT, which indicates that the molecule in question does not have either the Q347C or L443C mutations in the heavy chain (Fc region) as do TAF347 or TAF443, defined infra.

"TAF347" is the same as TAF except that it has the Q347C mutation.

"TAF443" is the same as TAF except that it has the L443C mutation. TAF443 is sometimes referred to herein as OG1321.

Figure 35:
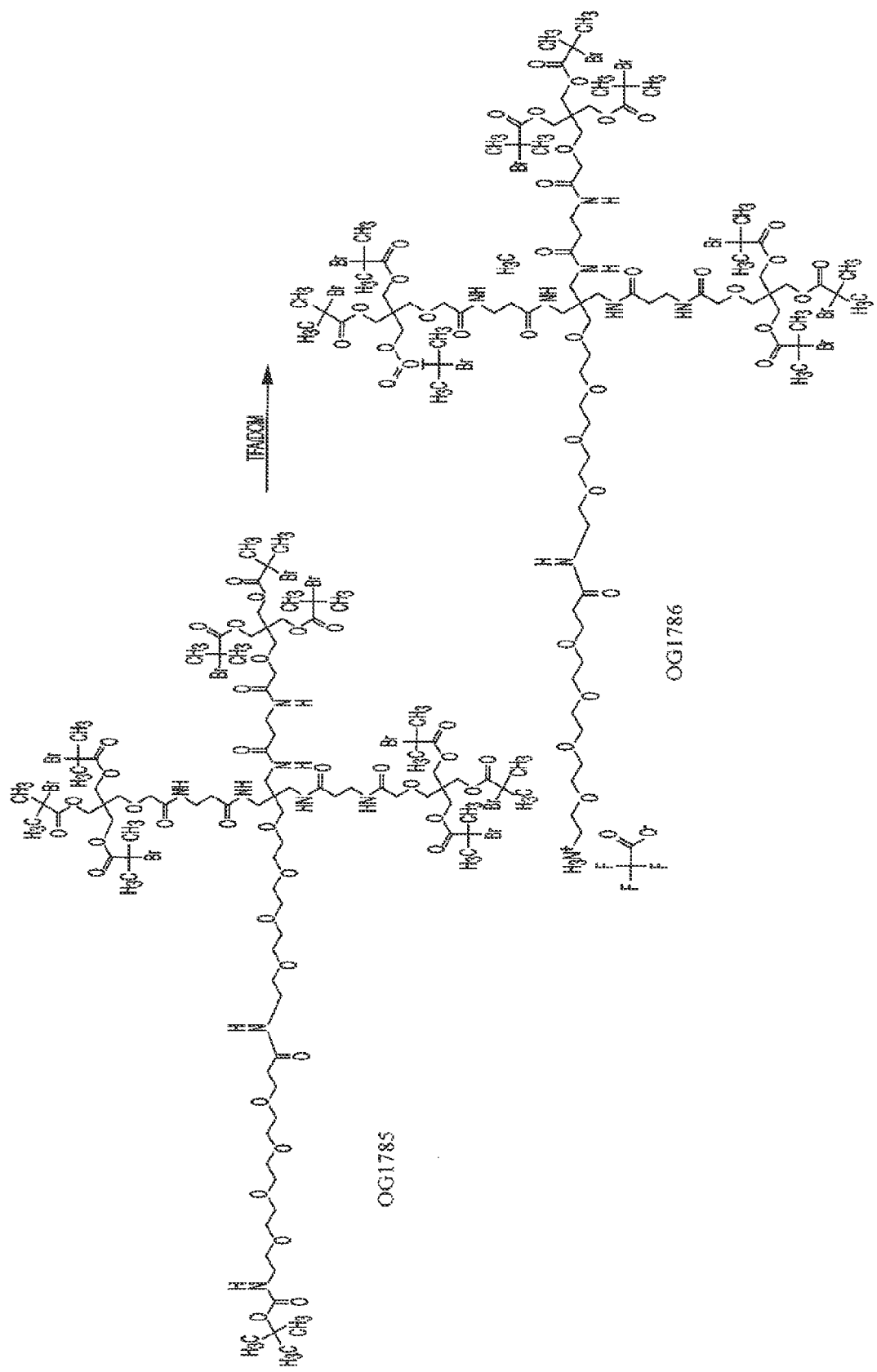
FIG. 35 shows the synthesis of OG1786 from OG1785.

"OG1786" is a 9-arm initiator used for polymer synthesis with the structure shown in FIG. 35, which depicts that salt form of OG1786 with trifluororacetic acid. OG1786 may be used in accordance with the present invention as other salts or as the free base.

"OG1801" is an approximately (+/−15%) 750 kDa polymer (either by Mn or Mp) made using OG1786 as an intiator for ATRP synthesis using the monomer HEMA-PC.

Figure 36:
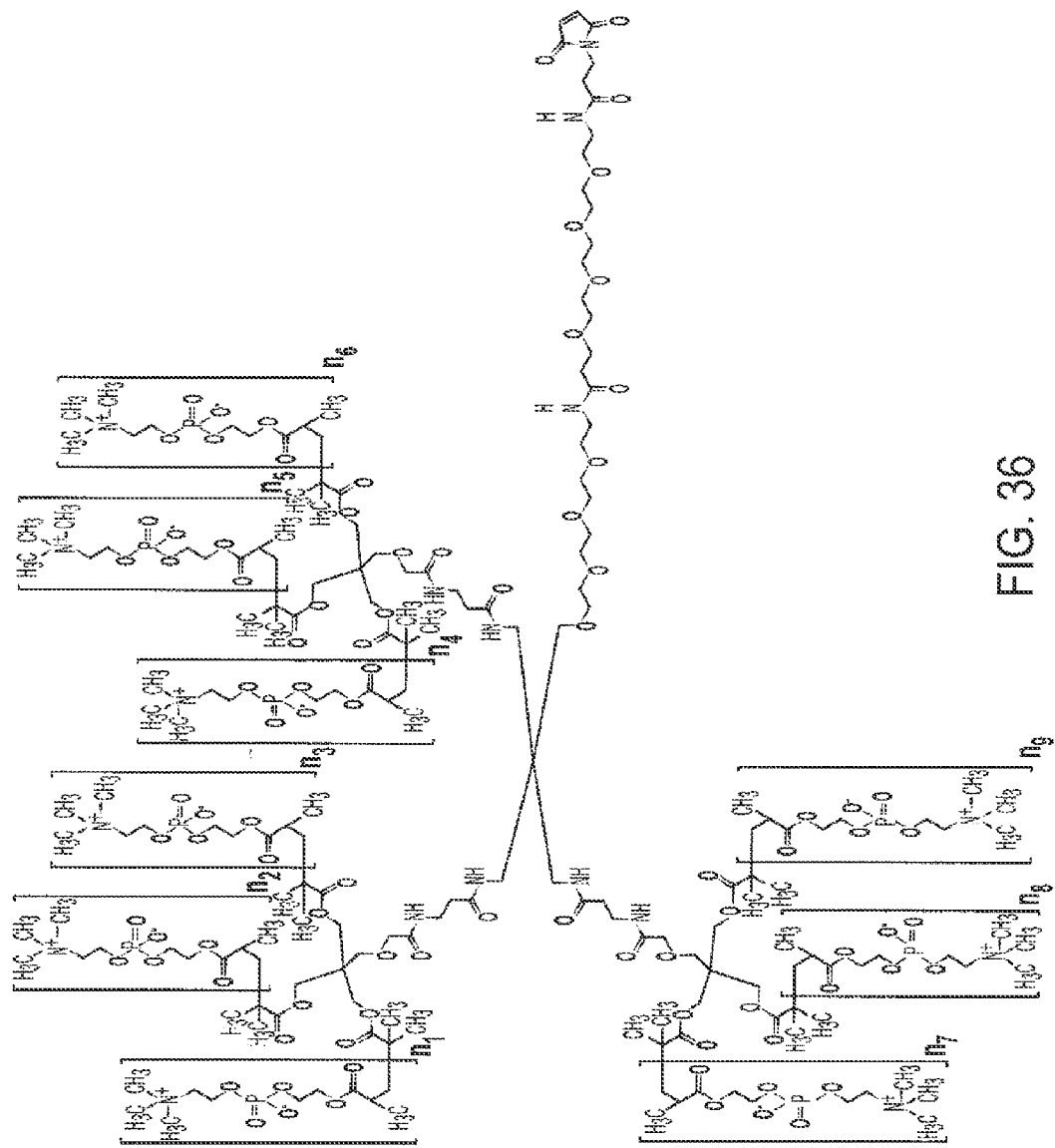
FIG. 36 shows OG1802.
Figure 37:
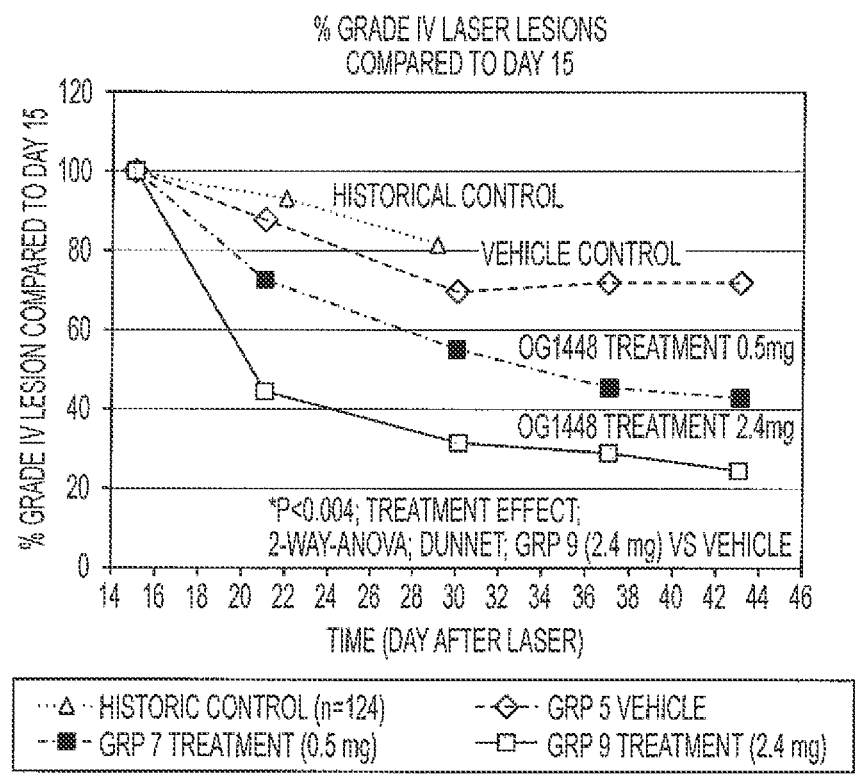
FIG. 37 shows a graph of percent Grade IV laser lesions.

"OG1802" is OG1801 with a maleimide functionality added and is shown in FIG. 36 wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% daltons.

"OG1448" is TAF443 conjugated to the OG1802 biopolymer.

DETAILED DESCRIPTION

I. General

The present invention provides a dual VEGF/PDGF antagonist comprising a VEGF antagonist linked to a PDGF antagonist. The VEGF antagonist is an antibody to a VEGF or VEGFR or is a VEGFR extracellular trap segment (i.e., a segment from the extracellular region of one or more VEGFR receptors that inhibits binding of at least one VEGFR to at least one VEGF). The PDGF antagonist is an antibody to a PDGF or PDGFR or is a PDGFR extracellular trap segment (i.e., segment from the extracellular region of one or more PDGFRs, which inhibits binding of at least one PDGFR and at least one PDGF). At least one of the antagonists is not an antibody, or put another way, at least one of the antagonists is an extracellular trap segment. Preferably, the dual antagonist includes an antibody antagonist and one extracellular trap segment antagonist. In such a dual antagonist the extracellular trap segment is preferably fused, optionally via a linker to the N-terminus of the antibody heavy chain. The antibody light chain is complexed with the antibody heavy chain in similar manner to that in a natural antibody. Such dual antagonists are preferably provided in the form of conjugates with a half-life extending moiety conjugated to the dual antagonist. Preferably, a cysteine residue is used for conjugation which has been introduced into the antagonist. More preferably, the cysteine residue is at positions 347 or 443 of an IgG1 heavy chain. It is preferred that the half-life extending moiety is a zwitterionic polymer. Most preferably the zwitterionic polymer is a phosphorylcholine containing polymer.

Angiogenesis is the process by which new blood vessels are created and plays a crucial role in development (going from embryo to adult) and in wound healing (restoring blood flow to damaged or injured tissue). However, when angiogenesis is dysregulated, it contributes to the pathologies of many disorders, including cancer, psoriasis, arthritis and blindness. Carmeliet P. 2003. Angiogenesis in health and disease. Nature Med 9(6):653-660.

Abnormal angiogenesis is associated with wet age related macular degeneration (a leading cause of blindness in the elderly) and with cancer. Angiogenesis is characterized by an increase in proliferating endothelial and stromal cells and vasculature with altered morphology. See, generally, Folkman J. 2007. Angiogenesis: an organizing principle for drug discovery?. Nat Rev Drug 6:273-286 and Baluk P, Hashizume H, McDonald D M. 2005. Cellular abnormalities of blood vessels as targets in cancer. Curr Opin Genet Dev. 15:102-111.

As mentioned above, neovascularization (NV) is a normal process occurring both in development and in wound healing but can become pathological when angiogenesis is dysregulated and occurs in tissues associated with tumors (cancer), avascular cornea or the subretinal space (wet AMD). The proliferation, invastion and migration of NV vessels is controlled by a complex interplay between growth factors, vascular endothelial cells, extracellular matrix molecules, chemokines and cell signaling molecules.

NV tissue is composed of endothelial cells (EC), pericytes and inflammatory cells (e.g. macrophages). Pericytes are derived via differentiation from mast cells. The process of neovascularization first involves the formation of angiogenic sprouts composed of EC from existing capillaries into the avascular space. VEGF signaling is understood to be the master switch for this NV process. In this regard, VEGF has been localized in the tip cell fiopodia which leads the angiogenic sprout.

Following sprout formation, the newly formed vessels are coated by pericytes, leading to maturation of the NV. Pericyte coating of NV leads to stabilization and support of NV both physically and through signaling, including pericyte production of VEGF. Armulik A, Abramsson A, Betsholtz C. 2005. Endothelial/Pericyte Interactions. Circ Res. 97:512-523.

Approved wet AMD therapies are all directed at the suppression of VEGF signaling. These therapies include pegaptanib (Macugen®), approved in 2004, Genentech's bevacizumab (Avastin®), approved in 2004 for cancer, used off label for AMD, Genentech's ranibizumab (Lucentis®), approved in 2006, and Regeneron's aflibercept (Eylea®) approved in 2011. Pegaptanib is an aptamer based therapeutic, but with a limited market compared with protein based therapeutics likely due to the limited gains in visual acuity for patients. Bevacizumab is an anti-VEGFA IgG1 antibody approved for cancer treatment, but is widely used off label for treatment of AMD. Ranibizumab is a Fab which was affinity matured from bevacizumab and is approved for AMD. However, the market for Ranibizumab is substantially undercut by use of the much cheaper bevacizumab. Finally, aflibercept is a VEGF trap, employing a soluble receptor fragment decoy.

Anti-VEGF monotherapy has not lead to disease-modifying regression of pathological NV. Brown D M, Kaiser P K, Michels M, et al. 2006. ANCHOR Study Group. Ranibizumab versus verteporfin for neovascular age-related macular degeneration. N Engl J Med 355(14):1432-1444; Rosenfeld P J, Brown D M, Heier J S, et al. 2006. MARINA study group. Ranibizumab for neovascular age-related macular degeneration. N Engl J Med 355(14):1419-1431; Regillo C D, Brown D M, Abraham P, et al. 2008. Randomized, double-masked, sham0controlloed trial of ranibizumab for neovacular age-related macular degeneration: PIER study year 1. Am J Ophthalmol. 145:239-248. Instead the majority of the efficacy or therapeutic benefit of anti-VEGF therapies is due to their anti-permeability property. Zebrowski B K, Yano S, Liu W, et al. 1999. Vascular endothelial growth factor levels and induction of permeability in malignant pleural effusions. Clin Cancer Res 5:3364-3368.

Because conventional anti-VEGF therapies do not cause regression of pathological NV, visual acuity gains for many patients have been quite limited. Moreover, neovasculature can also lead to subretinal fibrosis which is a cause of blindness in wet AMD patients.

Subretinal scarring develops in nearly half of treated eyes within two years of anti-VEGF therapy. Daniel E, Toth C A, Grunwald J E. 2014. Risk of scar in the comparison of age-related macular degeneration in clinical settings. Retina 32:1480-1485. Subretinal fibrosis formation can cause permanent dysfunction of the macular system; it causes destruction of photoreceptors, retinal pigment epithelium and choroidal vessels. Ishikawa K, Ram K, Hinton D R. 2015. Molecular mechanisms of subretinal fibrosis in age-related macular degeneration. Eye Res. Mar. 13, 2015 Epub 1-7. Although anti-VEGF therapy generally stabilizes or improves visual acuity, scar formation has been identified as one of the causes of loss of visual acuity after treatment. Cohen S Y, Oubraham H, Uzzan J, et al. 2012. Causes of unsuccessful ranibizumab treatment in exudative age-related macular degeneration in clinical settings. Retina 32:1480-1485.

Proangiogenic factors are generally upregulated in pathological angiogenesis, including two members of the vascular endothelial growth factor (VEGF) family: VEGF-A and placental growth factor (PGF). VEGF-A and PGF activate quiescent endothelial cells, promote cell proliferation and vascular permeability. VEGF-A has been identified as a major factor in vascular leak in wet AMD. Dvorak H F, Nagy J A, Feng D, Brown L F, Dvorak A M. 1999. Vascular permeability factor/vascular endothelial growth factor and the significance of microvascular hyperpermeability in angiogenesis. Curr Top Microbiol Immunol. 237:97-132.

Platelet derived growth factor "PDGF" signaling plays an important role in NV maturation and in particular to the coating of NV by pericytes. The coating of NV endothelial cells by pericytes begins with EC expression of the paracrine platelet-derived growth factor B, which forms the homodimer PDGF-BB. PDGF-BB is highly retained in the tip cells of the angiogenic sprouts by heparin sulfate proteoglycan. This PDGF-BB is then recognized by the pericyte bound receptor PDGFR-β, which initiates the proliferation and migration of pericytes along the growing neovascularization.

PDGF-DD had also been discovered to play a central role in pathological angiogenesis. Kumar A, Hou X, Chunsik L, et al. 2010. Platelet-derived Growth Factor-DD Targeting Arrests Pathological Angiogenesis by Modulating Glycogen Synthase Kinase-3β Phosphorylation. J Biol Chem 285(20): 15500-15510. PDGF-DD overexpression induces blood vessel maturation during angiogenesis. Kong D, Wang Z, Sarkar F H, et al. 2008. Platelet-Derived Growth Factor-D Overexpression Contributes to Epithelial-Mesenchymal Transition of PC3 Prostate Cancer Cells. Stem Cells 26:1425-1435. PDGF-DD is highly expressed in the eye. Ray S, Gao C, Wyatt K, et al. 2005. Platelet-derived Frowth Factor D, Tissue-specific Expression in the Eye, and a Key Role in Control of Lens Epithelial Cell Proliferation. J Biol Chem. 280:8494-8502. Kumar et al. (2010) found that PDGF-DD expression was upregulated during pathological angiogenesis and that inhibition of PDGF-DD signaling decreased choroidal and retinal neovascularization.

The term "PDGF" as used herein means any member of the class of growth factors that (i) bind to a PDGF receptor such as PDGFR-β, or PDGFR-α; (ii) activates a tyrosine kinase activity associated with the PDGF receptor; and (iii) thereby affects angiogenesis or an angiogenic process. The term "PDGF" generally refers to those members of the class of growth factors that induce DNA synthesis and mitogenesis through the binding and activation of a platelet-derived growth factor cell surface receptor (i.e., PDGFR) on a responsive cell type. PDGFs effect specific biological effects including, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; fibrosis and potent vasoconstrictor activity. The term "PDGF" is meant to include both a "PDGF" polypeptide and its corresponding "PDGF" encoding gene or nucleic acid.

The PDGF family consists of disulfide bonded homoffdimers of PDGF-A (Swiss Protein P04085), -B (P01127), -C (Q9NRA1) and -D (Q9GZP0) and the hetero dimer PDGF-AB. The various PDGF isoforms exert their effect by binding to α and β-tyrosine kinase receptors (PDGFR-α (P16234) and PDGFR-β (P09619) respectively). See generally U.S. Pat. No. 5,872,218 which is incorporated herein by reference for all purposes. The α and β receptors are structurally similar: both have extracellular domains with five immunoglobulin (Ig) like domains and intracellular domains with a kinase function. PDGF binding occurs mainly through domains 2 and 3 of the receptors and causes dimerization of the receptors. Ig like domain 4 is involved in receptor dimerization. Receptor dimerization is a key component of PDGF signaling: receptor dimerization leads to receptor auto-phosphorylation. Auto-phosphorylation in turns causes a conformational change in the receptor and activates the receptor kinase. PDGF-A, -B, -C and -D bind to the two different receptors with different affinities and effects. PDGF-AA, -AB, -BB and -CC induce αα receptor homodimers, PDGF-BB and -DD induced ββ homodimers and PDGF-AB, -BB, -CC and -DD produce αβ receptor heterodimers.

In terms of function, PDGFR-α and PDGFR-β appear to have substantially different roles. PDGFR-α signaling is involved in gastrulation and in development of the cranial and cardiac neural crest, gonads, lung, intestine, skin, CNS and skeleton. PDGFR-β signaling is involved in blood vessel formation and early hematopoiesis. Andrae J, Radiosa G, Betsholtz C. 2008. Role of platelet-derived growth factors in physiology and medicine. Genes Develop 22:1276-1312. In terms of interaction of the various PDGF ligands with the receptors, PDGF-AA and PDGF-CC exclusively bind to and interact with PDGFR-α. PDGF-BB and PDGF-AB bind with α and β receptors. PDGF-DD exclusively interacts with PDGFR-β. Raica M, Cimpean A M. 2010. Platelet-Derived Growth Factor (PDGF)/PDGF Receptors (PDGFR) Axis as Target for Antitumor and Antiangiogenic Therapy. Pharmaceut. 3:572-599.

Unless otherwise apparent from the context reference to a PDGF means any of PDGF-A, -B, -C and -D in any of the natural isoforms or natural variants or induced variants having at least 90, 95, 98 or 99% sequence identity to a natural form. Preferably, such PDGFs are human PDGFs. Likewise reference to a PDGFR means PDGFR-A (P16234) or PDGFR-B including any natural isoform or natural variant, or an induced variant having at least 90, 95, 98 or 99% or 100% sequence identity to a natural sequences.

The amino acid sequence of human PDGFR-β (UniProtKB/Swiss-Prot: P09619.1) is set forth in FIG. 1, which shows a full-length human PDGFR-β (including the leader sequence), a 1106 amino acid protein. Amino acids 1-32 are part of the leader peptide which is cleaved off in the mature protein. PDGFR-β has five extracellular Ig-like domains D1-D5. Williams A F, Barclay A N. 1988. The immunoglobulin superfamily—domains for cell surface recognition. Annu Rev Immunol. 6:381-405. The full-length extracellular region runs from about amino acid 33 to 532, the transmembrane domain from about residue 533 to 553 and the cytoplasmic domain from about residue 554 to 1106. The extracellular region includes five immunoglobulin-like domains, D1-D5. The D1 domain is typically considered to be from about amino acid 33 (Leu) to about 123 (Pro). In accordance with the present invention, D1 may also be from 33 to 122 (Val). D2 is typically considered to be from about 124 (Thr) to about 213 (Ser). In accordance with the present invention, D2 may be 129 (Pro) to 210 (Gln). D3 is typically considered to be from about amino acid 214 (Ile) to 314 (Gly). In accordance with the present invention, D3 may be from 214 (Ile) to 309 (Thr). D4 is typically considered to be from about amino acid 315 (Tyr) to 416 (Pro). D5 is typically considered to be from about amino acid 417 (Val) to 531 (Lys).

The exact boundaries of the D1-D5 domains can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid. The essential characteristic of each domain is its ability to bind to its cognate ligands.

A "PDGF antagonist" or a molecule that "antagonizes PDGF" is an agent that reduces, or inhibits, either partially or fully, at least one activity of a PDGF including its ability to specifically bind to a PDGFR, and consequent cellular responses, such as proliferation. PDGF antagonists include antibodies that specifically bind to a PDGF or PDGFR and extracellular trap segments from a PDGFR.

One or more portions of a PDGFR-β extracellular receptor sequence can be used as an antagonist for PDGF-PDGFR-β signaling. The term extracellular trap segment refers to a full length extracellular region or any portion thereof, or combination of portions from different PDGF receptors that can antagonize PDGF-PDGFR-beta signaling. Such portions are typically used free of the transmembrane and intracellular sequence of the PDGFR and are consequently referred to as being soluble. The portions antagonize by acting as a trap or decoy for a cognate PDGF. PDGF binds to the soluble PDGFR-β segment trap and is unable to bind to the corresponding membrane bound receptor. Preferably, such traps include one of more of PDGFR-β domains D1-D5. Preferably, the trap contains at least one of D2 and D3. More preferably, the trap contains D1, D2 and D3. More preferably the trap is a contiguous segment corresponding to amino acids 33 to 314 of FIG. 8 which contains D1-D3. PDGFR-alpha likewise includes domains D1 through D5 and extracellular trap segments incorporating corresponding domains of PDGFR-alpha can likewise be used instead of PDGFR-beta.

Antibodies can also be used as antagonists of PDGFR-β, including antibodies which bind to the receptor (e.g., 2A1E2 [U.S. Pat. No. 7,060,271]; HuM4 Ts.22 [U.S. Pat. No. 5,882,644]; or 1B3 or 2C5 [U.S. Pat. No. 7,740,850]), and anti-PDGF antibodies such as anti-PDGF BB, anti-PDGF-DD, anti-PDGF-BB and anti-PDGF-AB.

"VEGF" or "vascular endothelial growth factor" is a human vascular endothelial growth factor that affects angiogenesis or an angiogenic process. In particular, the term VEGF means any member of the class of growth factors that (i) bind to a VEGF receptor such as VEGFR-1 (Flt-1), VEGFR-2 (KDR/Flk-1), or VEGFR-3 (FLT-4); (ii) activates a tyrosine kinase activity associated with the VEGF receptor; and (iii) thereby affects angiogenesis or an angiogenic process.

The VEGF family of factors is made up of five related glycoproteins: VEGF-A (also known as VPE), -B, -C, -D and PGF (placental growth factor). Of these, VEGF-A is the most well studied and is the target of anti-angiogenic therapy. Ferrara et al, (2003) Nat. Med. 9:669-676. VEGF-A exists as a number of different isotypes which are generated both by alternative splicing and proteolysis: VEGF-$A_{206}$, VEGF-$A_{189}$, VEGF-$A_{165}$, and VEGF-$A_{121}$. The isoforms differ in their ability to bind heparin and non-signaling binding proteins called neuropilins. The isoforms are all biologically active as dimers.

The various effects of VEGF are mediated by the binding of a VEGF, e.g., VEGF-A (P15692), -B (P49766), -C (P49767) and -D (Q43915), to receptor tyrosine kinases (RTKs). The VEGF family receptors belong to class V RTKs and each carry seven Ig-like domains in the extracellular domain (ECD). In humans, VEGF binds to three types of RTKs: VEGFR-1 (Flt-1) (P17948), VEGFR-2 (KDR, Flk-1) (P935968) and VEGFR-3 (Flt-4) (P35916). A sequence of VEGFR-1 is shown in FIG. 2. Unless otherwise apparent from the context reference to a VEGF means any of VEGF-A, -B, -C, -D, and PGF, in any of the natural isoforms or natural variants or induced variants having at least 90, 95, 98 or 99% or 100% sequence identity to a natural form. Preferably, such VEGFs are human VEGFs. Likewise reference to a VEGFR means any of VEGR-1, R-2 or R-3, including any natural isoform or natural variant, or an induced variant having at least 90, 95, 98 or 99% or 100% sequence identity to a natural sequences.

The extracellular region runs from about amino acid 27-758, the transmembrane domain from about amino acid 759 to 780 and the intracellular region from about 781-1338. The extracellular region includes seven immunoglobulin-like domains, D1-D7. Domain 1 of VEGFR-1 is from 32 (P) to 128 (I), Domain 2 from 134 (P) to 125 (Q), Domain 3 from 232 (V) to 331 (K), Domain 4 from 333 (F) to 428 (P), Domain 5 is from 431 (Y) to 553 (T), Domain 6 from 558 (G) to 656 (R) and Domain 7 from 662 (Y) to 751 (T). See generally U.S. Pat. No. 8,273,353, incorporated herein by reference for all purposes. The exact boundaries of the domains D1-D7 of VEGFR-1 can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid.

The protein sequence of VEGFR-2 is shown below in FIG. 3.

The extracellular region runs from about residues 20-764, the transmembrane domain from about residues 765-785 and the intracellular domain from about residues 786 to 1356. The extracellular region includes seven immunoglobulin-like domains, D1-D7. Domain 1 of VEGFR-2 is from 32 (P) to 118 (V), Domain 2 is from 124 (P) to 220 (G), Domain 3 is from 226 (V) to 327 (K), Domain 4 is from 329 (F) to 421 (P), Domain 5 is from 424 (G) to 548 (T), Domain 6 is from 553 (I) to 662 (L), and Domain 7 is from 668 (T) to 757 (A). See generally U.S. Pat. No. 8,273,353, incorporated herein by reference for all purposes. The exact boundaries of the domains D1-D7 of VEGFR-2 can vary depending on how the analysis is done. Preferably, the boundaries vary by 9 amino acids or less. Typically they vary by 7 amino acids of less, more typically by 5 amino acids or less. Usually, boundary variance be by 3 amino acids or less. Most typically the boundaries 1 vary by only an amino acid.

The protein sequence of VEGFR-3 is shown below in FIG. 4. The extracellular region runs from about residues 25-775, the transmembrane domain from about residues 776-796 and the intracellular domain from about residues 797-1363. The extracellular domain includes seven immunoglobulin-like domains D1-D7. Domain 1 of VEGFR-3 is from 30 (P) to 132 (V), Domain 2 is from 138 (P) to 226 (G), Domain 3 is from 232 (I) to 330 (N), Domain 4 is from 332 (F) to 422 (P), Domain 5 is from 425 (H) to 552 (T), Domain 6 is from 557 (G) to 673 (Q), and Domain 7 is from 679 (R) to 768 (S). See generally U.S. Pat. No. 8,273,353, incorporated herein by reference for all purposes. The exact boundaries of the domains D1-D7 of VEGFR-3 can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid.

VEGFR-2 is expressed predominately on vascular endothelial cells. VEGFR-1 is also expressed on the vascular endothelium, but in addition is also expressed by a number of other cell types: neutrophils, monocytes, macrophages, mural cells and endothelial progenitor cells. VEGFR-1 has a higher affinity for VEGF-A than does VEGFR-2. However, when VEGFR-1 is bound to VEGF-A in endothelial cells, VEGFR-1 exhibits only very weak tyrosine phosphorylation. Hence, it is believed that the effects of VEGF-A (including its various isoforms) on the vascular endothelium are mediated by the binding of VEGF-A to VEGFR-2.

PGF and VEGF-B bind only to VEGFR-1. PGF and VEGF-B have been implicated in pathogenic vascular remodeling. Carmeliet P, Moons L, Lutten A, et al. 2001. Synergism between vascular endothelial growth factor and placental growth factor contributes to angiogenesis and plasma extravasation in pathological conditions. Nat Med. 7(5); 575-583. VEGF-C and -D bind with high affinity to VEGFR-3, which is primarily found on lymphatic endothelial cells in the adult. VEGF-C and -D are thought to play a role in regard to Lymphangiogenesis.

A "VEGF antagonist" or a molecule that "antagonizes VEGF" is an agent that reduces, or inhibits, either partially or fully, an activity of a VEGF including its ability to specifically bind to its receptor a VEGFR and consequent cellular responses, such as angiogenesis and cellular proliferation. VEGF antagonists include antibodies specifically binding to a VEGF or a VEGFR or a VEGFR extracellular trap segment.

The term extracellular trap segment refers to a full length extracellular region or any portion thereof, or combination of portions from different VEGFR receptors that can antagonize signaling between at least one VEGF and VEGFR. Preferably, the extracellular trap segment includes at least one domain from one of VEGFR-1, -2 or -3 defined above, and more preferably at least two contiguous domains, such as D2 and D3. Optionally, an extracellular domain includes at least one domain as defined above from at least two different VEGFRs. A preferred extracellular domain comprises or consists essentially of D2 of VEGFR-1 and D3 of VEGFR-2.

VEGF antagonist therapies have been approved for the treatment of certain cancers and wet AMD. Bevacizumab (AVASTIN®, Genentech/Roche) is a humanized mouse monoclonal antibody that binds to and neutralizes human VEGF, in particular to all isoforms of VEGF-A and to bioactive proteolytic fragments of VEGF-A. See, e.g., Ferrara N, Hillan K J, Gerber H P, Novotny W. 2004. Discovery and development of bevacizumab, an anti-VEGF antibody for treating cancer. Nat Rev Drug Discov. 3(5):391-400. Bevacizumab has been approved for the treatment of certain cancers. The protein sequence of the heavy and light chains of bevacizumab (DrugBank DB00112) is shown below in FIG. 5 with CDRs underlined (see also SEQ ID NOs. 2 and 5).

Bevacizumab variable light chain CDRs are $CDR_L1$: SASQDISNYLN, $CDR_L2$: FTSSLHS and $CDR_L3$: QQYSTVPWT. Bevacizumab variable heavy chain CDRs are $CDR_H1$: GYTFTNYGMN, $CDR_H2$: WINTYTGEPTYAADFKR, and $CDR_H3$: YPHYYGSSHWYFDV. CDRs are defined by Kabat except CDRH1 is the composite Kabat/Chothia definition.

Another anti-VEGF molecule, derived from the same mouse monoclonal antibody as bevacizumab has been approved as a treatment for wet AMD: ranibizumab (LUCENTIS®, Genentech/Roche). Ranibizumab is an antibody fragment or Fab. Ranibizumab was produced by affinity maturation of the variable heavy and light chains of bevacizumab. The sequence of the heavy and light chains of ranibizumab is shown below (as published by Novartis) in FIG. 6 (see also SEQ ID NOs. 12 and 13):

Ranibizumab variable light chain CDRs are $CDR_L1$: SASQDISNYLN, $CDR_L2$: FTSSLHS and $CDR_L3$: QQYSTVPWT. Ranibizumab variable heavy chain CDRs are $CDR_H1$: GYDFTHYGMN, $CDR_H2$: WINTYTGEPTYAADFKR, and $CDR_H3$: YPYYYGTSHWYFDV.

Antibodies competing with bevacizumab for binding to VEGF-A or binding to the same epitope on VEGF-A as bevacizumab can also be used.

Another anti-VEGF therapy is a VEGF Trap. For example, aflibercept (Eylea®, Regeneron), consists of the second Ig like domain of VEGFR-1 and the third Ig like domain of VEGFR-2 expressed as an in line fusion with the constant region (Fc) of human IgG1. Papadopoulos N, et al. 2012. Binding and neutralization of vascular endothelial growth factor (VEGF) and related ligands by VEGF Trap, ranibizumab and bevacizumab. Angiogenesis 15:171-185. In theory, aflibercept binds not only VEGF-A, but also VEGF-B and PGF thereby antagonizing their interaction with VEGFR-1.

In accordance with the present invention, a dual VEGF/PDGF antagonist is provided comprising a VEGF antagonist linked to a PDGF antagonist. The linkage preferably includes a fusion of protein chains to form a hybrid chain formed from components of both antagonists. Alternatively, the components can be joined by chemical cross linking. As an example, of linkage by fusion, if the dual antagonist is formed from an antibody and an extracellular trap segment, then a heavy or light chain of the antibody can be fused to the extracellular trap segment. Preferably, the extracellular trap segment is fused directly or indirectly via a linker to the N-terminus of the antibody heavy or light chain. Whichever chain is not fused to the extracellular trap segment can associate with the chain that is in similar fashion to heavy light chain association in a natural antibody. For example, an exemplary format has an extracellular trap segment fused to the N-terminus of an antibody heavy chain via a linker and the antibody light chain complexed with the antibody heavy chain. The antibody in such a dual antagonist can be an intact antibody or any of the binding fragments described above, such as a Fab fragment. Preferably, in such dual antagonists, the VEGF antagonist is an antibody to VEGF-A, such as bevacizumab or ranibizumab, and the PDGF antagonist is an extracellular trap segment from PDGR-1.

In an alternative format, the VEGF antagonist and PDGF antagonist are both extracellular trap segments. The two segments can be fused in either orientation with respect to one another, directly or via a linker. That is the VEGFR extracellular trap region can be joined to the N-terminus or the C-terminus of the PDGFR extracellular trap region. The C-terminus of such a fusion protein can be linked to an Fc region of an antibody forming an Fc fusion proteins.

In preferred embodiments, the PDGFR is PDGFR-β and the extracellular trap segment comprises one or more of domains D1-D5 of PDGFR-β. More preferably, the extracellular trap segment comprises domains D1-D3 of PDGFR-β. Still more preferably, the extracellular trap segment comprises or consists of amino acids 33 to 314 of SEQ ID NO. 11. In preferred embodiments, the VEGF antagonist is an anti-VEGF antibody, preferably an anti-VEGF-A antibody.

In dual antagonists having antibody and extracellular trap components fused to one another, the respective components, typically the antibody heavy chain and the extracellular trap segment are separated by a linker sequence. The linker is preferably GGGGSGGGGS, GG, or GGGGSGGGGSGGGGSGGGGSG or an oligomers of any of these. More preferably, the linker is GGGGSGGGGS.

In accordance with an aspect of the present invention, the anti-VEGF-A antibody heavy chain has at least the following CDR sequences: $CDR_H1$: GYDFTHYGMN, $CDR_H2$: WINTYTGEPTYAADFKR, and $CDR_H3$: YPYYYGTSHWYFDV. Preferably, the anti-VEGF-A light chain has at least the following CDRs: $CDR_L1$: SASQDISNYLN, $CDR_L2$: FTSSLHS and $CDR_L3$: QQYSTVPWT. In the case of the anti-VEGF-A antibody heavy chain, it is preferred that its isotype is IgG1 and has a $CH_1$, hinge, $CH_2$ and $CH_3$ domains. It is also preferred that the light chain isotype is kappa. The constant region of the preferred IgG1 sequence is set forth in SEQ ID NO. 17. The sequence of the light chain constant region is preferably set forth in SEQ ID NO. 18.

The IgG1 domain of the anti-VEGF-A antibody preferably has one or more mutations to reduce or lower effector function. Preferred amino acids to use for effector function reducing mutations include (EU numbering) E233P, L234V, L235, G236, G237, delG236, D270A, K322A, A327G, P329A, A330, A330S, P331S, and P331A, in which the second mentioned amino acid is the mutation. Preferably, the mutations include one or more of the following: E233P, L234V, L234A, L235A, G237A, A327G, A330S and P331S (EU numbering). More preferably, the anti-VEGF-A heavy chain has the following mutations: L234A, L235A and G237A. The number of such mutations relative to a natural human IgG1 sequence is no more than 10, and preferably no more than 5, 4, 3, 2 or 1.

Alternatively, the IgG domain can be IgG2, IgG3 or IgG4, preferably, human IgG2, IgG3 or IgG4, or a composite in which a constant regions is formed from more than one of these isotypes (e.g., CH1 region from IgG2 or IgG4, hinge, CH2 and CH3 regions from IgG1). Such domains can contain mutations to reduce effector function at one or more of the EU position mentioned for IgG1. Human IgG2 and IgG4 have reduced effector functions relative to human IgG1 and IgG3.

The anti-VEGF-A heavy chain can also contain a cysteine residue added as a mutation by recombinant DNA technology which can be used to conjugate a half-life extending moiety. Preferably, the mutation is (EU numbering) Q347C and/or L443C. More preferably, the mutation is L443C. Preferably, the stoichiometry of dual antagonist to polymer is 1:1; in other words, a conjugate consists essentially of molecules each comprising one molecule of dual antagonist conjugated to one molecule of polymer.

A preferred dual antagonist including an antibody to VEGF-A and a PDGFR extracellular trap segment comprises a fusion protein of the antibody heavy chain and the PDGFR extracellular trap segment having the amino acid sequence of SEQ ID NO. 9 and the antibody light chain having the amino acid sequence of SEQ ID NO. 10, or variants thereof including sequences differing each of from SEQ ID NO: 9 and 10 by no more than 10, 9, 8, 7, 6, 5, 4, 3, 2 or 1 amino acids.

In another aspect of the present invention, a dual VEGF/PDGF antagonist is presented having a PDGF antagonist constituting one or more segments of a PDGFR as described above and a VEGF antagonist constituting an anti-VEGF Fab fragment. For this aspect of the present invention, the PDGFR extracellular trap comprises one or more of domains D1-D5 of PDGFR-β. More preferably, the PDGFR trap constitutes domains D1-D3 of PDGFR-β. More preferably, the PDGFR trap is amino acids 33 to 314 of SEQ ID NO. 11.

The PDGFR trap is preferably located C-terminal of the Fab heavy or light chain. The PDGFR trap is also preferentially located N-terminal of the Fab heavy or light chain. Preferably, the dual antagonist includes an anti-VEGF-A Fab fragment heavy chain fused via a linker to a PDGFR extracellular trap segment and an anti-VEGF-A light chain.

In another aspect of the invention, a dual VEGF/PDGF antagonist is presented wherein the extracellular trap segment binds to one or more of PDGF-AA, PDGF-BB, PDGF-AB, PDGF-CC and PDGF-DD. Preferably, the extracellular trap binds PDGF-AB, PDGF-BB and PDGF-DD. Still more preferably, the extracellular trap inhibits PDGF-AB, PDGF-BB and PDGF-DD from binding to any one of PDGFR-αα, PDGFR-αβ, and PDGFR-ββ receptors.

A linker is preferably located between the PDGFR trap and the anti-VEGF Fab fragment heavy chain. Preferably, the linker is selected from group consisting of GGGGSGGGGS, GG, and GGGGSGGGGSGGGGSGGGGSG, and oligomers of any of these. More preferably, the linker is GGGGSGGGGS.

The anti-VEGF Fab fragment heavy chain preferably has at least the following CDRs: $CDR_H1$: GYDFTHYGMN, $CDR_H2$: WINTYTGEPTYAADFKR, and $CDR_H3$: YPYYYGTSHWYFDV. The anti-VEGF-A light chain preferably has at least the following CDRs: $CDR_L1$: SASQDISNYLN, $CDR_L2$: FTSSLHS and $CDR_L3$: QQYSTVPWT.

A preferred anti-VEGF Fab fragment heavy chain isotype is IgG1 and comprises a $CH_1$ domain and the light chain isotype is kappa.

The dual VEGF/PDGF antagonist can have a half-life extending moiety attached. Preferably the half-life extending moiety is a zwitterionic polymer but PEG or other half-life extenders discussed below can alternatively be used. More preferably, the zwitterionic polymer is formed of monomers having a phosphorylcholine group. Preferably the monomer is 2-(acryloyloxyethyl)-2'-(trimethylammoniumethyl)phosphate. More preferably, the monomer is 2-(methacryloyloxyethyl)-2'-(trimethylammoniumethyl)phosphate (HEMA-PC).

A polymer conjugated to a dual antagonist preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. Preferably, the polymer peak molecular weight is between 300,000 and 1,750,000 Da. More preferably, the polymer has a peak molecular weight between 500,000 and 1,000,000 Da. Still more preferably, the polymer has a peak molecular weight between 600,000 to 800,000 Da.

The polymer can be covalently bonded to the dual antagonist via conjugation. Preferably, the polymer is conjugated to the dual VEGF/PDGF antagonist via a group such as an amino group, a hydroxyl group, a sulfhydryl group or a carboxyl group. The sulfhydryl group can be from a naturally occurring cysteine residue. The sulfhydryl group can also be from a cysteine residue added by recombinant DNA technology.

In a preferred aspect of the present invention, the polymer is conjugated to the cysteine residue at position 741 of SEQ ID NO. 9, or aligned position of any variants of SEQ ID NO. 9 disclosed herein.

In another aspect of the present invention, a dual VEGF/PDGF antagonist having a VEGFR trap containing one or more extracellular segments of a VEGFR, such as VEGFR-1, VEGFR-2 or VEGFR-3, fused to an anti-PDGF antibody or Fab fragment heavy or light chain and an anti-PDGF antibody or Fab fragment heavy or light chain not included in fusion.

In accordance with an aspect of the present invention, the extracellular segment of VEGFR is preferably one or more of domains D1-D7. More preferably, the extracellular segment comprises D2 from VEGFR-1 and D3 from VEGFR-2. Still more preferably, the D2 is N-terminal to the D3 and further comprises a linker between the domains.

In preferred embodiments of this aspect of the present invention, the PDGF antagonist is an antibody. More preferably, the antibody is selected from the group consisting of humanized 2A1E2, HuM4 Ts.22, humanized 1B3, humanized 2C5, anti-PDGF-BB, anti-PDGF-DD, anti-PDGF-BB and anti-PDGF-AB. The PDGF antagonist is also preferably a Fab fragment.

In accordance with this aspect of the present invention, the antibody heavy chain is preferably IgG1, more preferably human IgG1 and the light chain is preferably kappa, human kappa. The heavy chain can have a cysteine added via recombinant DNA technology. Preferably, the cysteine is selected from the group consisting of Q347C and L443C. Preferably, there is a half-life extending moiety conjugated to the cysteine.

Preferably, the half-life extending moiety is a zwitterionic polymer having one or more monomer units and wherein at least one monomer unit has a zwitterionic group. Preferably, the zwitterionic group is phosphorylcholine. The monomer is preferably 2-(acryloyloxyethyl)-2'-(trimethylammoniumethyl)phosphate. More preferably, the monomer is 2-(methacryloyloxyethyl)-2'-(trimethylammoniumethyl)phosphate (HEMA-PC).

In accordance with this aspect of the present invention, the polymer preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. In accordance with an aspect of the present invention, the polymer peak molecular weight of between 300,000 and 1,750,000 Da. More preferably, the polymer has a peak molecular weight between 500,000 and 1,000,000 Da. Still more preferably, the polymer has a peak molecular weight between 600,000 to 800,000 Da.

In accordance with an aspect of the present invention, the polymer is covalently bound to the polymer via conjugation. Preferably, the polymer is conjugated to the dual VEGF/PDGF antagonist via a group selected from the group consisting of an amino group, a hydroxyl group, a sulfhydryl group and a carboxyl group. Preferably, the sulfhydryl group is from a naturally occurring cysteine residue. In other preferred embodiments, the sulfhydryl group is from a cysteine residue added by recombinant DNA technology.

In preferred aspects of the present invention, the PDGF trap-VEGF trap is conjugated to a half-life extending moiety as discussed with other dual antagonists.

Preferably, the half-life extending moiety is a zwitterionic polymer having one or more monomer units and wherein at least one monomer unit has a zwitterionic group. Preferably, the zwitterionic group is phosphorylcholine. The monomer is preferably 2-(acryloyloxyethyl)-2'-(trimethylammoniumethyl)phosphate. More preferably, the monomer is 2-(methacryloyloxyethyl)-2'-(trimethylammoniumethyl)phosphate (HEMA-PC).

In accordance with this aspect of the present invention, the polymer preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. In accordance with an aspect of the present invention, the polymer peak molecular weight of between 300,000 and 1,750,000 Da. More preferably, the polymer has a peak molecular weight between 500,000 and 1,000,000 Da. Still more preferably, the polymer has a peak molecular weight between 600,000 to 800,000 Da.

In accordance with an aspect of the present invention, the polymer is covalently bound to the polymer via conjugation. Preferably, the polymer is conjugated to the dual VEGF/PDGF antagonist via a group such as an amino group, a hydroxyl group, a sulfhydryl group or a carboxyl group. In some conjugates, the sulfhydryl group is from a naturally occurring cysteine residue. In some conjugates, the sulfhydryl group is from a cysteine residue added by recombinant DNA technology.

Dual PDGF/VEGF antagonists can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing dual antagonists, e.g. constitutively or on induction, and (v) isolating the dual antagonist, e.g. from the culture medium or by harvesting the transformed cells, in order to (vi) obtain purified dual antagonist.

Dual antagonists can be produced by expression in a suitable prokaryotic or eukaryotic host system characterized by producing a pharmacologically acceptable dual antagonist molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the dual antagonist and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

The half-life of dual antagonists can be extended by attachment of a "half-life extending moieties" or "half-life extending groups," which terms are herein used interchangeably to refer to one or more chemical groups attached to one or more amino acid site chain functionalities such as —SH, —OH, —COOH, —CONH2, —NH2, or one or more N- and/or O-glycan structures and that can increase in vivo circulatory half-life of proteins/peptides when conjugated to these proteins/peptides. Examples of half-life extending moieties include polymers described herein, particularly those of zwitterionic monomers, such as HEMA-phosphorylcholine, PEG, biocompatible fatty acids and derivatives thereof, Hydroxy Alkyl Starch (HAS) e.g. Hydroxy Ethyl Starch (HES), Poly Ethylene Glycol (PEG), Poly (Glyx-Sery) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, FcRn binding peptides and any combination thereof.

In one embodiment a half-life extending moiety can be conjugated to a dual antagonist via free amino groups of the protein using N-hydroxysuccinimide (NHS) esters. Reagents targeting conjugation to amine groups can randomly react to ε-amine group of lysines, α-amine group of N-terminal amino acids, and δ-amine group of histidines.

However, dual antagonists of the present have many amine groups available for polymer conjugation. Conjugation of polymers to free amino groups, thus, might negatively impact the ability of the dual antagonist proteins to bind to VEGF and/or PDGF.

In another embodiment, a half-life extending moiety is coupled to one or more free SH groups using any appropriate thiol-reactive chemistry including, without limitation, maleimide chemistry, or the coupling of polymer hydrazides or polymer amines to carbohydrate moieties of the dual antagonist after prior oxidation. The use of maleimide coupling is a particularly preferred embodiment of the present invention. Coupling preferably occurs at cysteines naturally present or introduced via genetic engineering.

Polymers are preferably covalently attached to cysteine residues introduced into dual antagonist by site directed mutagenesis. It is particularly preferred to employ cysteine residues in the Fc portion of the dual antagonist. For preferred sites to introduce cysteine residues into an Fc region see WO 2013/093809, U.S. Pat. No. 7,521,541, WO 2008/020827, U.S. Pat. No. 8,008,453, U.S. Pat. No. 8,455,622 and US2012/0213705, incorporated herein by reference for all purposes. Particularly preferred cysteine mutations are Q347C and L443C referring to the human IgG heavy chain by EU numbering.

The invention provides conjugates of dual antagonist and high MW polymers serving as half-life extenders. A preferred conjugate comprises a dual antagonist is coupled to a zwitterionic polymer wherein the polymer is formed from one or more monomer units and wherein at least one monomer unit has a zwitterionic group. Preferably, the zwitterionic group is phosphorylcholine.

Preferably, one of the monomer units is 2-(acryloyloxyethyl)-2'-(trimethylammoniumethyl)phosphate or 2-(methacryloyloxyethyl)-2'-(trimethylammoniumethyl)phosphate (HEMA-PC). In other preferred embodiments, polymer is synthesized from a single monomer which is preferably 2-(acryloyloxyethyl)-2'-(trimethylammoniumethyl)phosphate or 2-(methacryloyloxyethyl)-2'-(trimethylammoniumethyl)phosphate.

Some dual antagonist conjugates have 2 or more preferably 3 or more polymer arms wherein the monomer is HEMA-PC. Preferably, the conjugates have 2, 3, 4, 5, 6, 7, 8, 9, 10, 11, or 12 polymer arms wherein the monomer is HEMA-PC. More preferably, the conjugates have 3, 6 or 9 arms. Most preferably, the conjugate has 9 arms.

Polymer-dual antagonist conjugates preferably have a polymer portion with a molecular weight of between 100,000 and 1,500,000 Da. More preferably the conjugate has a polymer portion with a molecular weight between 500,000 and 1,000,000 Da. Still more preferably the conjugate has a polymer portion with a molecular weight between 600,000 to 800,000 Da. Most preferably the conjugate has a polymer portion with a molecular weight between 600,000 and 850,000 Da and has 9 arms. When a molecular weight is given for a dual VEGF/PDGF antagonist conjugated to a polymer, the molecular weight will be the addition of the molecular weight of the protein, including any carbohydrate moieties associated therewith, and the molecular weight of the polymer.

In accordance with an aspect of the present invention, a dual VEGF/PDGF antagonist having a HEMA-PC polymer which has a molecular weight measured by Mw of between about 100 kDa and 1500 kDa. More preferably, the molecular weight of the polymer as measured by Mw is between about 500 kDa and 1000 kDa. Still more preferably, the molecular weight of the polymer as measured by Mw is between about 600 kDa to about 900 kDa. Most preferably, the polymer molecular weight as measured by Mw is 750 kDa plus or minus 15%.

In this aspect of the present invention, the polymer is preferably made from an initiator suitable for ATRP having one or more polymer initiation sites. Preferably, the polymer initiation site has a 2-bromoisobutyrate site. Preferably, the initiator has 3 or more polymer initiation sites. More preferably, the initiator has 3, 4, 5, 6, 7, 8, 9, 10, 11 or 12 polymer initiation sites. More preferably, the initiator has 3, 6 or 9 polymer initiation sites. Still more preferably, the initiator has 9 polymer initiation sites. Most preferably, the initiator is OG1786.

The invention provides methods for synthesizing a zwitterionic polymer-dual antagonist conjugate, the conjugate having one or more functional agents and one or more polymer arms wherein each of the polymer arms has one or more monomer units wherein at least one of the units has a zwitterion. The method can have the steps of
 a. providing an initiator having one or more sites for monomer polymerization and a first linker having an amine group wherein the initiator is a trifluoro acetic acid salt;
 b. providing one or more monomers suitable for polymerization wherein at least one of the monomers is zwitterionic;
 c. reacting the monomers with the initiator to form one or more polymer arms each corresponding to the sites for monomer polymerization to provide an initiator-polymer conjugate having the first linker with the amine group;
 d. providing a second linker having at least second and third reactive groups;
 e. coupling one of the second and third reactive groups of the second linker to the amine group of the first linker of the initiator-polymer conjugate to provide a linker-initiator-polymer conjugate having one or more reactive groups that were not used in the coupling step; and
 f. coupling one or more functional agents to one or more of the unreacted reactive groups of the linker-initiator-polymer moiety to provide the polymer-functional agent conjugate.

Prior to the instant invention, the initiator molecule or entity had to contain a deprotectable functional group that would allow coupling of the functional agent. An example of such an initiator having a protected maleimide is shown below:

adapted to various types of functional agents by "snapping-on" various types of linkers and functional conjugation chemistries.

For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In preferred embodiments of the methods, the initiator has 1, 2, 3, 4, 5, 6, 7, 8, 9, 10, 11 or 12 sites for polymer initiation. Preferably, the initiator has 3, 6 or 9 sites for polymer initiation.

In accordance with an aspect of the present invention, a second linker has second, third, fourth, fifth, and sixth reactive groups. More preferably, a second linker has just second and third reactive groups.

In accordance with an aspect of the present invention, each polymer arm has from about 20 to about 2000 monomer units. Preferably, each arm has from about 100 to 500 monomer units or from about 500 to 1000 monomer units or from about 1000 to 1500 monomer units or from about 1500 to 2000 monomer units.

In accordance with an aspect of the present invention, the peak molecular weight of the polymer-functional agent conjugate is about 100,000 to 1,500,000 Da. Preferably, the peak molecular weight of the polymer-functional agent conjugate is about 200,000 to about 300,000 Da, about 400,000 to about 600,000 Da or about 650,000 to about 850,000 Da.

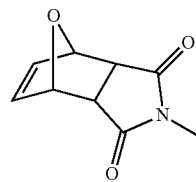

After polymer synthesis, the protected maleimide is deprotected with heat to allow for generation of maleimide which could be used to couple functional agent. If one wanted to vary the nature of the chemical entity in between the maleimide and the polymer initiation site, one would have to synthesize an entire new initiator.

Each time the initiator is changed or altered in any way, a new scaled up synthesis procedure would have to be developed. Each change in the nature of the initiator molecule can have a wide range of effects on polymer synthesis. However, in accordance with the present invention, a method is presented where the conjugation group (e.g. maleimide) is added after polymer synthesis. This is sometimes referred to as a "snap-on strategy" or "universal polymer strategy. A single initiator moiety can be used for large scale polymer and bioconjugate discovery and development. Thus, conditions can be developed for scaled up optimal polymer synthesis. Such polymer can then be In accordance with another aspect of the present invention, the first linker is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. More preferably, the first linker has the formula:

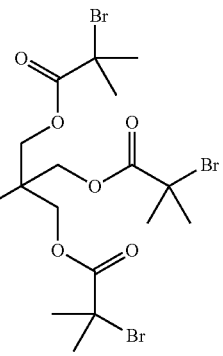

wherein m is 1 to 10. More preferably, the first linker has the above formula and m is 4.

In still other aspects of the present invention, the initiator preferably includes a structure selected from group consisting of

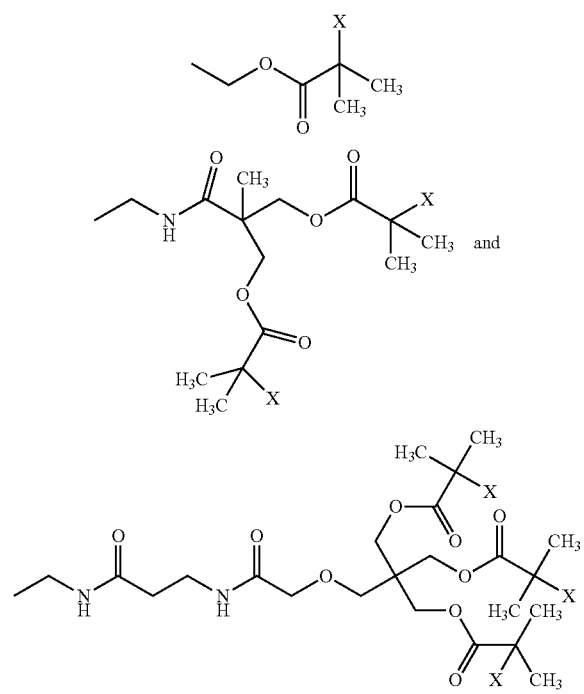

wherein X is selected from the group consisting of NCS, F, Cl, Br and I. More preferably, X is Br.

In preferred embodiments of the present invention, the monomer is selected from the group consisting of

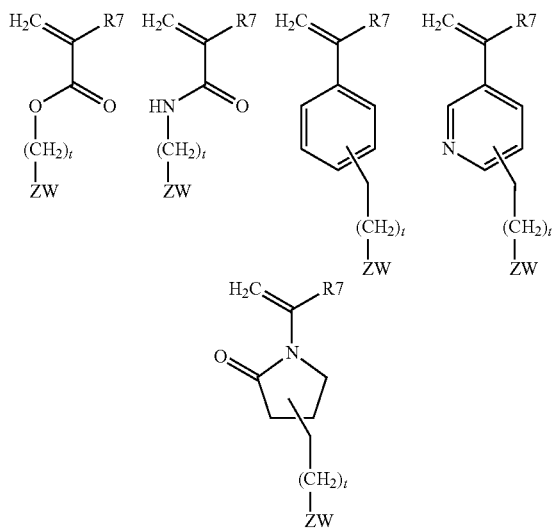

wherein R7 is H or $C_{1-6}$ alkyl and t is 1 to 6.

More preferably, the monomer is selected from the group consisting of 2-(methacryloyloxyethyl)-2'-(trimethylammoniumethyl)phosphate (HEMA-PC) and 2-(acryloyloxyethyl)-2'-(trimethylammoniumethyl)phosphate.

Most preferably, the monomer is 2-(methacryloyloxyethyl)-2'-(trimethylammoniumethyl)phosphate.

The second linker moiety preferably comprises an activated ester having the structure

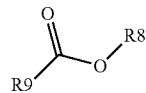

wherein R8 is selected from the group consisting of

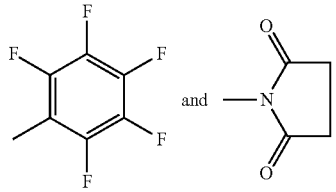

and R9 is

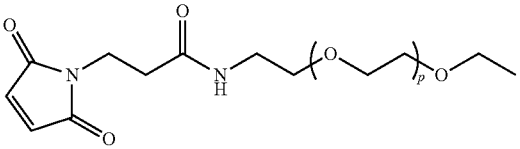

wherein p is 1 to 12.

In more preferred embodiments of the present invention, the polymer has 9 arms, m of R2 is 2-4, R9 is

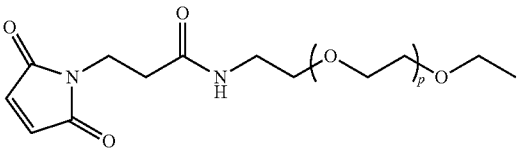

and p is 4 to 15. Still more preferably, m is 4 and p is 12.

When a polymer is to be conjugated via a cysteine (or other specified residue), the polymer can be linked directly or indirectly to the residue (e.g., with an intervening initiator, and or spacer or the like).

Dual antagonists can be incorporated into a pharmaceutical composition with a pharmaceutically acceptable excipient. Pharmaceutical compositions adapted for oral administration may be presented as discrete units such as capsules, as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions can be adapted for nasal administration wherein the excipient is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the excipient is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-400 mOsm/kg water.

The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The dual antagonists and pharmaceutical compositions containing them may be administered in an effective regime for treating or prophylaxis of a patient's disease including, for instance, administration by oral, intravitreal, intravenous, subcutaneous, intramuscular, intraosseous, intranasal, topical, intraperitoneal, and intralesional administration. Parenteral infusions include intramuscular, intravenous, intraarterial, intraperitoneal, or subcutaneous administration or routes among others. In therapy or as a prophylactic, the active agent may be administered to an individual as an injectable composition, for example as a sterile aqueous dispersion, preferably isotonic or substantially isotonic.

For administration to mammals, and particularly humans, it is expected that the dosage of the active agent is from 0.01 mg/kg body weight, typically around 1 mg/kg. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited.

This dosage may be repeated as often as appropriate (e.g., weekly, fortnightly, monthly, quarterly). If side effects develop the amount and/or frequency of the dosage can be reduced, in accordance with normal clinical practice. In one embodiment, the pharmaceutical composition may be administered once every one to thirty days.

The dual antagonists and pharmaceutical compositions of the invention can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

The dual antagonists and pharmaceutical compositions disclosed herein can be used for treatment or prophylaxis of disease, particularly the ocular diseases or conditions described herein. Although both antagonist modalities within the dual antagonist are believed to contribute to efficacy as discussed above and shown in Example 40 an understsanding of mechanism is not required for practice of the invention. Preferably, a dual antagonist is more effective than an equimolar concentration of each antagonist administered alone, or a 1:1 combination of the antagonists administered as separate molecules.

So used, the conjugates are typically formulated for and administered by ocular, intraocular, and/or intravitreal injection, and/or juxtascleral injection, and/or subretinal injection and/or subtenon injection, and/or superchoroidal injection and/or topical administration in the form of eye drops and/or ointment. Such dual antagonists and compositions can be delivered by a variety of methods, e.g. intravitreally as a device and/or a depot that allows for slow release of the compound into the vitreous, including those described in references such as Intraocular Drug Delivery, Jaffe, Ashton, and Pearson, editors, Taylor & Francis (March 2006). In one example, a device may be in the form of a minipump and/or a matrix and/or a passive diffusion system and/or encapsulated cells that release the compound for a prolonged period of time (Intraocular Drug Delivery, Jaffe, Ashton, and Pearson, editors, Taylor & Francis (March 2006).

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered.

Therapeutic dual agonists and related conjugates according to the present invention generally are placed into a container having a sterile access port, for example, an intravenous solution bag or vial having a stopper pierceable by a hypodermic injection needle. Such compositions may also be supplied in the form of pre-filled syringes.

A "stable" formulation is one in which the protein or protein conjugated to a polymer of other half-life extending moiety therein essentially retains its physical stability and/or chemical stability and/or biological activity upon storage. By "stable" is also meant a formulation which exhibits little or no signs of instability, including aggregation and/or deamidation. For example, in accordance with an aspect of the present invention, the formulations provided by the present invention may remain stable for at least two year, when stored as indicated at a temperature of 5-8° C.

Various analytical techniques for measuring protein stability are available in the art and are reviewed in Peptide and Protein Drug Delivery, 247-301 (Vincent Lee ed., New York, N.Y., 1991) and Jones, 1993 Adv. Drug Delivery Rev. 10: 29-90, for examples. Stability can be measured at a selected temperature for a selected time period. Storage of stable formulations is preferably for at least 6 months, more preferably 12 months, more preferably 12-18 months, and more preferably for 2 or more years.

A protein, such as an antibody or fragment thereof, "retains its physical stability" in a pharmaceutical formulation if it shows no signs of aggregation, precipitation, deamidation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

A protein-polymer conjugate "retains its chemical stability" the chemical bond between the protein and the polymer is maintained intact, e.g., it is not hydrolyzed or otherwise disrupted. The protein part of the conjugate retains its chemical stability as described above.

By "isotonic" is meant that the formulation of interest has essentially the same osmotic pressure as human blood or the vitreous for intravitreal injections. Isotonic formulations will generally have an osmotic pressure from about 250 to 400 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range of preferably from about 3.0 to about 8.0; for example from about 4.5 to 8; or about pH 6 to about 7.5; or about 6.0 to about 7.0, or about 6.5-7.0, or about pH 7.0 to about 7.5; or about 7.1 to about 7.4. A pH of any point in between the above ranges is also contemplated.

"PBS" phosphate buffered saline, Tris based buffers and histidine based buffers are particularly preferred buffers for the instantly invented dual antagonists. In the case of OG1448, PBS is particularly preferred. More preferably, in the case of OG1448, the PBS buffer has a pH of 7-8 and the concentration of OG1448 is from about 10 mg/ml to about 100 mg/ml. Still more preferably, the OG1448 is from about 25 to about 65 mg/ml and the pH is about 7.4. In the most preferred embodiments of the present invention, the concentration of OG1448 is 50 mg/ml to 60 mg/ml.

In preferred embodiments of the present invention, the PBS buffer is made up of at least $Na_2HPO_4$, $KH_2PO_4$ and NaCl adjusted so as to provide the appropriate pH. In particularly preferred embodiments of the present invention, the buffer may contain other pharmaceutical excipients such as KCl and other salts, detergents and/or preservatives so as to provide a stable storage solution.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkyl-benzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In accordance with an aspect of the present invention, formulations of dual PDGF/VEGF antagonists according to the present invention to be safe for human use or for animal testing must have sufficiently low levels of endotoxin. "Endotoxin" is lipopolysaccharide (LPS) derived from the cell membrane of Gram-negative bacteria. Endotoxin is composed of a hydrophilic polysaccharide moiety covalently linked to a hydrophobic lipid moiety (lipid A). Raetz C R, Ulevitch R J, Wright S D, Sibley C H, Ding A, Nathan C F. 1991. Gram-negative endotoxin: an extraordinary lipid with profound effects on eukaryotic signal transduction. FASEB J. 5(12):2652-2660. Lipid A is responsible for most of the biological activities of endotoxin, i.e., its toxicity. Endotoxins are shed in large amount upon bacterial cell death as well as during growth and division. They are highly heat-stable and are not destroyed under regular sterilizing conditions. Extreme treatments with heat or pH, e.g., 180-250° C. and over 0.1 M of acid or base must be used (Petsch D, Anspach F. 2000. Endotoxin removal from protein solutions. J Biotechnol. 76: 97-119). Such conditions of course would be highly detrimental to biological drugs.

In the biotech and pharmaceutical industries, it is possible to find endotoxin during both production processes and in final products. As bacteria can grow in nutrient poor media, including water, saline and buffers, endotoxins are prevalent unless precautions are taken. Endotoxin injection into an animal or human causes a wide variety of pathophysiological effects, including endotoxin shock, tissue injury and even death. Ogikubo Y, Ogikubo Y, Norimatsu M, Noda K, Takahashi J, Inotsume M, Tsuchiya M, Tamura Y. 2004. Evaluation of the bacterial endotoxin test for quantifications of endotoxin contamination of porcine vaccines. Biologics 32:88-93.

Pyrogenic reactions and shock are induced in mammals upon intravenous injection of endotoxin at low concentrations (1 ng/mL) (Fiske J M, Ross A, VanDerMeid R K, McMichael J C, Arumugham. 2001. Method for reducing endotoxin in *Moraxella catarrhalis* UspA2 protein preparations. J Chrom B. 753:269-278). The maximum level of endotoxin for intravenous applications of pharmaceutical and biologic product is set to 5 endotoxin units (EU) per kg of body weight per hour by all pharmacopoeias (Daneshiam M, Guenther A, Wendel A, Hartung T, Von Aulock S. 2006. In vitro pyrogen test for toxic or immunomodulatory drugs. J Immunol Method 313:169-175). EU is a measurement of the biological activity of an endotoxin. For example, 100 pg of the standard endotoxin EC-5 and 120 pg of endotoxin from *Escherichia coli* O111:B4 have activity of 1 EU (Hirayama C, Sakata M. 2002. Chromatographic removal of endotoxin from protein solutions by polymer particles. J Chrom B 781:419-432). Meeting this threshold level has always been a challenge in biological research and pharmaceutical industry (Berthold W, Walter J. 1994. Protein Purification: Aspects of Processes for Pharmaceutical Products. Biologicals 22:135-150; Petsch D, Anspach F B. 2000. Endotoxin removal from protein solutions. J Biotech 76:97-119).

The presence of endotoxin in drugs to be delivered via intravitreal injection is of particular concern. Intravitreal injection of drug (penicillin) was first performed in 1945 by Rycroft. Rycroft B W. 1945. Penicillin and the control of deep intra-ocular infection. British J Ophthalmol 29 (2): 57-87. The vitreous is a chamber where high level of drug can be introduced and maintained for relatively long periods of time. The concentration of drug that can be achieved via intravitreal injection far exceeds what can be generated by topical administration or by systemic administration (e.g. intravenous).

One of the most dangerous complications potentially arising from intravitreal injections is endophthalmitis. Endophthalmitis falls into two classes: infectious and sterile. Infectious endophthalmitis is generally cause by bacteria, fungi or parasites. The symptoms of infectious endophthalmitis include severe pain, loss of vision, and redness of the conjunctiva and the underlying episclera. Infectious endophthalmitis requires urgent diagnosis and treatment. Possible treatments include intravitreal injection of antibiotics and pars plana vitrectomy in some cases. Enucleation may be called for to remove a blind and painful eye. See, e.g., Christy N E, Sommer A. 1979. Antibiotic prophylaxis of postoperative endophthalmitis. Ann Ophthalmol 11 (8): 1261-1265.

Sterile endophthalmitis in contrast does not involve an infectious agent and can be defined as the acute intraocular inflammation of the vitreous cavity that resolves without the need of intravitreal antibiotics and/or vitreoretinal surgery. If a vitreous microbiological study has been done, it needs to be negative culture proven to sustain a diagnosis of sterile endophthalmitis. Marticorena J, Romano V, Gomez-Ulla F. 2012 "Sterile Endophthalmitis after Intravitreal Injections" Med Inflam. 928123.

It has been observed that intravitreal injection of biological drugs contaminated with endotoxin can result in sterile endophthalmitis. Marticorena, et al. Bevacizumab (Avastin) is approved by the Food and Drug Administration for the treatment of glioblastoma and of metastatic colorectal cancer, advanced nonsquamous non-small-cell lung cancer and metastatic kidney cancer. Bevacizumab is also widely used off label as a treatment for wet AMD. Bevacizumab comes from the manufacturer as a 100 mg/4 ml. This solution cannot be directly used for intravitreal injection and must be compounded by a pharmacist. Clusters of sterile endophthalmitis have been observed and are theorized to be cause by inadvertent contamination of bevacizumab by endotoxin by the compounding pharmacist.

Given the dire clinical results of intravitreal injection of endotoxin, the total amount of endotoxin that can be given to a patient via intravitreal dosing is highly limited. In accordance with an aspect of the present invention, a solution having a dual VEGF/PDGF antagonist according to the present invention is provided having an endotoxin level that does not exceed 5.0 EU/ml. More preferably, the endotoxin level does not exceed 1.0 EU/ml. Still more preferably, the endotoxin level does not exceed 0.5 EU/ml. Still more preferably, the endotoxin level does not exceed 0.2 EU/ml. In still more preferred embodiments, the endotoxin level does not exceed 0.1, 0.09, 0.08, 0.07, 0.06, 0.05, 0.04, 0.03, 0.02 or 0.01 EU/ml.

Two commonly used FDA-approved tests for the presence of endotoxin are the rabbit pyrogen test and Limulus Amoebodyte Lysate (LAL) assay (Hoffman S, et al. 2005. International validation of novel pyrogen tests based on human monocytoid cells J. Immunol. Methods 298:161-173; Ding J L, Ho B A. 2001. New era in pyrogen testing. Biotech. 19:277-281). The rabbit pyrogen test was developed in the 1920s and involves monitoring the temperature rise in a rabbit injected with a test solution. However, use of the rabbit pyrogen test has greatly diminished over the years due to expense and long turnaround time. Much more common is the LAL test. LAL is derived from the blood of a horseshoe crab and clots upon exposure to endotoxin.

One of the simplest LAL assays is the LAL gel-clot assay. Essentially, the LAL clotting assay is combined with a serial dilution of the sample in question. Formation of the gel is proportional to the amount of endotoxin in the sample. Serial dilutions are prepared from the sample and each dilution assayed for its ability to form LAL gel. At some point a negative reaction is contained. The amount of endotoxin in the original sample can be estimated from the dilution assay.

Other LAL tests have also been developed, including the turbidimetric LAL assay (Ong K G, Lelan J M, Zeng K F, Barrett G, Aourob M, Grimes C A. 2006. A rapid highly sensitive endotoxin detection system. Biosensors and Bioelectronics 21:2270-2274) and the chromogenic LAL assay (Haishima Y, Hasegawa C, Yagami T, Tsuchiya T, Matsuda R, Hayashi y. 2003, Estimation of uncertainty in kinetic-colorimetric assay of bacterial endotoxins. J Pharm Biomed Analysis. 32:495-503). The turbidimetric and chromogenic assays are much more sensitive and quantitative than the simple gel-clot dilution assay.

The present invention provides a method of reducing the amount of endotoxin in a composition having a dual VEGF/PDGF antagonist, the method having the steps of contacting the composition with an affinity chromatography resin that binds to the dual VEGF/PDGF antagonist; eluting the dual VEGF/PDGF antagonist from the affinity chromatography resin to form an affinity chromatography eluent having the antagonist; contacting the affinity chromatography eluent with an ion-exchange resin that binds the dual VEGF/PDGF antagonist; and eluting the dual VEGF/PDGF antagonist from the ion-exchange resin, wherein the dual VEGF/PDGF antagonist eluted from the ion-exchange resin is substantially free from endotoxin.

The above method for reducing the amount of endotoxin, or other method or process recited herein, can be performed in the order described in the steps above or it can optionally be performed by varying the order of the steps or even repeating one or more of the steps. In one embodiment, the method of reducing the amount of endotoxin in a composition is performed in the order of the described steps. In some embodiments, the affinity chromatography resin contacting, washing and eluting steps are repeated in the same order more than one time before contacting the affinity chromatography eluent with the ion exchange resin. The method can also include a filtering step using, for example, a 0.1 micron, 0.22 micron, or 0.44 micron filter, that can be performed on either one or more of the eluents removed after each resin binding step.

In certain instances, the steps of contacting the composition with affinity chromatography resin, washing and eluting the antibody from the affinity chromatography resin can be repeated more than one time before contacting the first eluent with an ion-exchange resin. In one embodiment, the affinity chromatography resin comprises a recombinant Protein A ("rProteinA") resin. One example of a suitable recombinant Protein A resin is rProteinA Sepharose FF® resin (Amersham, Piscataway, N.J.). In another embodiment, a suitable affinity chromatography resin would comprise a protein G chromatography resin. In other embodiments, a suitable affinity chromatography resin comprises a mixed Protein A/Protein G resin. In other embodiments, a suitable affinity chromatography resin comprises a hydrophobic charge induction resin that comprises a 4-mercaptoethylpyridine ligand such as a MEP HyperCel® resin (BioSepra, Cergy, Saint Christophe, France).

In some embodiments, it is preferred that the ion exchange resin comprises an anion-exchange resin. As will be known by the person skilled in the art, ion exchangers may be based on various materials with respect to the matrix as well as to the attached charged groups. For example, the following matrices may be used, in which the materials mentioned may be more or less cross-linked: MacroCap Q (GE Healthcare Biosciences, Piscataway, N.J.), agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange resin, the charged groups, which are covalently attached to the matrix, may, for example, be diethylaminoethyl, quaternary aminoethyl, and/or quaternary ammonium. It is preferred that the anion-exchange resin comprises a quaternary amine group. An exemplarily anion-exchange resin that has a quaternary amine group for binding the anti-M-CSF antibody is a Q Sepharose® resin (Amersham, Piscataway, N.J.).

In other aspects, if the endotoxin levels are higher than desired after subjecting the composition to the aforementioned anion-exchange chromatography step, the composition may in the alternative be subjected to a cation exchange resin. In accordance with this aspect of the present invention, any endotoxin in the composition should have a differential binding to the ion-exchange resin than the protein in question to allow purification of the protein from the endotoxin. In this regard, endotoxin is negatively charged and will generally bind to an anion exchange resin. If both the protein and the endotoxin bind to the anion exchange resin, purification of one from the other may be effectuated by using a salt gradient to elute the two into different fractions. The relative binding of the protein to a particular resin may also be effected by changing the pH of the buffer relative to the pI of the protein. In a preferred aspect of the present invention, cation-exchange chromatography is the sole ion-exchange chromatography employed.

In accordance with another aspect of the present invention, if the endotoxin levels are too high after the anion exchange resin, the composition may be further subjected to a second ion-exchange step, for example, by contacting the compositions with a cation exchange resin and followed by a wash step, then elution from the ion-exchange resin. In preferred embodiments, the cation exchange resin comprises a sulfonic group for binding. Exemplary cation exchange resins are SP Sepharose® resin FF (Amersham, Piscataway, N.J.) Poros XS (CEX) (Life Technology, Grand Island, N.Y.).

In accordance with an aspect of the invention, after the solution of dual PDGF/VEGF antagonist protein is produced having the specified level of endotoxin, there are a number of steps prior to final formulation of the protein. In some embodiments of the present invention, a half-life extending moiety is conjugated to the protein. The conjugate is then formulated into a final drug formulation which is injected into the patients. In some embodiments, the conjugate is again purified on an ion-exchange resin which can preferably be a cation-exchange resin. In other embodiments, the protein is formulated. In all cases, normal laboratory procedures must be employed to prevent the introduction of endotoxin contaminants into the protein sample or into the protein-polymer conjugate.

EXAMPLES

Example 1. Protein Sequence of PDGFRβ-GS10-Anti-VEGF-A Light Chain/Anti-VEGF-A Heavy Chain (Wild Type Fc)

A PDGFR-β trap-anti-VEGF-A light chain/anti-VEGF-A heavy chain was constructed having the sequence set forth below in FIGS. 7A, B. PDGFR-GS10-anti-VEGF-A light chain amino acids 1-282 correspond to 33 to 314 of human PDGFR-β (UniProtKB/Swiss-Prot: P09619.1), followed by the linker sequence GGGGSGGGGS and the bevacizumab light chain sequence. Optionally, no linker need be used between the PDGFR-β segment and the anti-VEGF segment. Alternatively, the linker may be the GGGGS motif x1, x2 (as noted above), x3, x4, etc. such that the activity of the two proteins is optimized. Other linker motifs known to those of skill in the art may also be used in accordance with the present invention, including G, GG, GGGS and GGGES x1, x2, x3, x4, etc. The linker may be combinations of the above. The sequence of FIG. 7A is set forth in SEQ ID NO. 19. FIG. 7B shows the bevacizumab heavy chain sequence (SEQ ID NO. 2). The bevacizumab light chain optionally has an M4L mutation (Kabat numbering). The bevacizumab heavy chain optionally has one or more of the following mutations: T28D, N31H, H97Y, S100aT (Kabat numbering), L234A, L235A, G237A, Q347C and L443C EU numbering).

Example 2. Protein Sequence of PDGFRβ-GG-Anti-VEGF-A Light Chain/Anti-VEGF-A Heavy Chain (Wild Type Fc)

Another PDGFR-β trap-anti-VEGF-A light chain/anti-VEGF-A heavy chain was constructed having the sequence set forth below in FIGS. 8A, B. FIG. 8A amino acids 1-282 correspond to 33 to 314 of human PDGFR-β (UniProtKB/Swiss-Prot: P09619.1), followed by the linker sequence GG and the bevacizumab light chain sequence. Alternatively, the linker may be the GGGGS motif x1, x2, x3, x4, etc. such that the activity of the two proteins is optimized. Other linker motifs may also be used in accordance with the present invention, including G, GG (as noted above), GGGS and GGGES x1, x2, x3, x4, etc. The linker may be combinations of the above. The protein sequence of FIG. 8A is set forth in SEQ ID NO. 3. FIG. 8B shows bevacizumab heavy chain sequence (SEQ ID NO. 2). The bevacizumab light chain of FIG. 8A optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 3. Protein Sequence of PDGFRβ-GS10-Anti-VEGF-A Heavy Chain (Wild Type Fc)/Anti-VEGF-A Light Chain Another PDGFR-β trap-anti-VEGF-A heavy chain (wild type Fc)/anti-VEGF-A light chain was constructed having the sequence set forth in FIGS. 9A, B. FIG. 9A amino acids 1-282 correspond to 33 to 314 of human PDGFR-β (UniProtKB/Swiss-Prot: P09619.1), followed by the linker sequence GGGGSGGGGS and the bevacizumab heavy chain sequence, optionally having Q347C or L443C (EU numbering). Alternatively, the linker may be the GGGGS motif x1, x2 (as noted above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 9A is set forth in SEQ ID NO. 4. The protein of FIG. 9B is the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 4. Protein Sequence of PDGFRβ-GG-Anti-VEGF-A Heavy Chain (Wild Type Fc)/Anti-VEGF-A Light Chain Another PDGFR-β trap-anti-VEGF-A heavy chain (wild type Fc)/anti-VEGF-A light chain was constructed having the sequence set forth below in FIGS. 10A, 10B. FIG. 10A amino acids 1-282 correspond to 33 to 314 of human PDGFR-β (UniProtKB/Swiss-Prot: P09619.1), followed by the linker sequence GG and the bevacizumab heavy chain sequence, optionally having Q347C or L443C. Alternatively, the linker may be the GGGGS motif x1, x2, x3, x4, etc. such that the activity of the two proteins is optimized. Other linker motifs may also be used in accordance with the present invention, including G, GG (as noted above), GGGS and GGGES x1, x2, x3, x4, etc. The linker may be combinations of the above. The protein sequence of FIG. 10A is set forth in SEQ ID NO. 6. The protein of FIG. 10B is the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 5. Protein Sequence of Anti-VEGF-A Heavy Chain (Wild Type Fc)-G521-PDGFRβ/Anti-VEGF-A Light Chain A PDGFR-β trap-anti-VEGF-A antibody construct was constructed with the anti-VEGF-A heavy chain being upstream or N-terminal to the PDGFR-β trap having the sequence set forth below in FIGS. 11A, B. FIG. 11A amino acids 1-451 correspond to the bevacizumab heavy chain sequence, optionally having Q347C or L443C, followed by linker sequence GGGGSGGGGSGGGGSGGGGSG. Alternatively, the linker may be the GGGGS motif x1, x2 (as noted above), x3, x4, etc. such that the activity of the two proteins is optimized. Other linker motifs also be used in accordance with the present invention, including G, GG, GGGS and GGGES x1, x2, x3, x4, etc. The linker may be combinations of the above. The linker is followed by amino acid sequences 33 to 314 of human PDGFR-β (UniProtKB/Swiss-Prot: P09619.1). The protein sequence of FIG. 11A is set forth in SEQ ID NO. 7. FIG. 11B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 6. Protein Sequence of PDGFRβ-GS10-Anti-VEGF-A Heavy Chain (Q347C)/Anti-VEGF-A Light Chain (TAF347)

Another PDGFR-β trap-anti-VEGF-A heavy chain (Q347C)/anti-VEGF-A light chain was constructed having the sequence set forth below in FIGS. 12A, B. FIG. 12A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Optionally, no linker need be used between the PDGFR-β segment and the anti-VEGF segment. The linker may be combinations of the above. Joined to the carboxyl terminus of the serine residue of the linker is the bevacizumab heavy chain with the following amino acid: T28D, N31H, H97Y, S100aT (Kabat numbering), L234A, L235A, G237A and Q347C (EU numbering). The protein sequence of FIG. 12A is set forth in SEQ ID NO. 8. The protein of FIG. 12B is ranibizumab light chain (bevacizumab w/ M4L) (SEQ ID NO. 12).

Example 7. Protein Sequence of PDGFRβ-GS10-Anti-VEGF-A Heavy Chain (L443C)/Anti-VEGF-A Light Chain Another PDGFR-β trap-anti-VEGF-A heavy chain (L443C))/anti-VEGF-A light chain was constructed having the sequence set forth below in FIGS. 13A, B. FIG. 13A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Joined to the carboxyl terminus of the serine residue of the linker is the bevacizumab heavy chain with the following amino acid: T28D, N31H, H97Y, S100aT (Kabat numbering), L234A, L235A, G237A and L443C (EU numbering). The TAF443 light chain is the same as bevacizumab except for a M4L change (Kabat numbering). The protein sequence of FIG. 13A is set forth in SEQ ID NO. 9. FIG. 13B shows the ranibizumab light chain (bevacizumab w/ M4L) (SEQ ID NO. 12).

Example 8. Protein Sequence of PDGFRβ-GS10-Anti-VEGF-A Light Chain/Anti-VEGF-A Fab A PDGFR-β trap-anti-VEGF-A light chain/anti-VEGF-A Fab was constructed having the sequence set forth below in FIGS. 14A, B. FIG. 14A amino acids 1-282 correspond to 33 to 314 of human PDGFR-β (UniProtKB/Swiss-Prot: P09619.1), followed by the linker sequence GGGGSGGGGS and the bevacizumab light chain sequence. Optionally, no linker need be used between the PDGFR-β segment and the anti-VEGF segment. Alternatively, the linker may be the GGGGS motif x1, x2 (as noted above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 14A is set forth in SEQ ID NO. 1. The protein of FIG. 14B is the bevacizumab Fab (SEQ ID NO. 21). The bevacizumab light chain of FIG. 14A optionally has an M4L mutation. The bevacizumab Fab of the second protein optionally has one or more of the following mutations: T28D, N31H, H97Y, and S100aT. The bevacizumab Fab of the second chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 9. Protein Sequence of PDGFRβ-GG-Anti-VEGF-A Light Chain/Anti-VEGF-A Fab A PDGFR-β trap-anti-VEGF-A light chain/anti-VEGF-A Fab was constructed having the sequence set forth below in FIGS. 15A, B. FIG. 15A amino acids 1-282 correspond to 33 to 314 of human PDGFR-β (UniProtKB/Swiss-Prot: P09619.1), followed by the linker sequence GG and the bevacizumab light chain sequence. Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG (as above), GGGS and GGGES x1, x2, x3, x4, etc. The linker may be combinations of the above. The protein sequence of FIG. 15A is set forth in SEQ ID NO. 3. FIG. 15B shows the heavy chain of bevacizumab Fab (SEQ ID NO. 21). The bevacizumab light chain of FIG. 15A optionally has an M4L mutation (Kabat numbering). The bevacizumab Fab of FIG. 15B optionally has one or more of the following mutations: T28D, N31H, H97Y, and S100aT (Kabat numbering). The bevacizumab Fab of FIG. 15B optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 10. Protein Sequence of PDGFRβ-GS10-Anti-VEGF-A Fab/Anti-VEGF-A Light Chain Another PDGFR-β trap-anti-VEGF-A Fab/anti-VEGF-A light chain was constructed having the sequence set forth below in FIGS. 16A, B. FIG. 16A amino acids 1-282 correspond to 33 to 314 of human PDGFR-β (UniProtKB/Swiss-Prot: P09619.1), followed by the linker sequence GGGGSGGGGS and the bevacizumab Fab sequence. Optionally, no linker need be used between the PDGFR-β segment and the anti-VEGF segment. Alternatively, the linker may be the GGGGS motif x1, x2 (as above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 16A is set forth in SEQ ID NO. 22. FIG. 16B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 11. Protein Sequence of PDGFRβ-GG-Anti-VEGF-A Fab/Anti-VEGF-A Light Chain Another PDGFR-β trap-anti-VEGF-A Fab/anti-VEGF-A light chain was constructed having the sequence set forth below in FIGS. 17A, B. FIG. 17A amino acids 1-282 correspond to 33 to 314 of human PDGFR-β (UniProtKB/Swiss-Prot: P09619.1), followed by the linker sequence GGGGSGGGGS and the bevacizumab Fab sequence. Optionally, no linker need be used between the PDGFR-β segment and the anti-VEGF segment. Alternatively, the linker may be the GGGGS motif x1, x2 (as above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 17A is set forth in SEQ ID NO. 23. FIG. 17B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The bevacizumab Fab heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 12. Protein Sequence of Anti-VEGF-A Fab-G521-PDGFRβ/Anti-VEGF-A Light Chain A PDGFR-β trap-anti-VEGF-A antibody construct was constructed with the anti-VEGF-A heavy chain being upstream or N-terminal to the PDGFR-β trap having the sequence set forth below in FIGS. 18A, B. FIG. 18A amino acids 1-231 correspond to the bevacizumab Fab followed by linker sequence GGGGSGGGGSGGGGSGGGGSG. Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The linker is followed by amino acid sequences 33 to 314 of human PDGFR-β (UniProtKB/Swiss-Prot: P09619.1). The protein sequence of FIG. 18A is set forth in SEQ ID NO. 24. FIG. 18B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT. The protein of FIG. 18A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 18B.

Example 13. Protein Sequence of PDGFRβ-GS10-Anti-VEGF-A Fab/Anti-VEGF-A Light Chain Another PDGFR-β trap-anti-VEGF-A Fab/anti-VEGF-A light chain was constructed having the sequence set forth below in FIGS. 19A, B. FIG. 19A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Optionally, no linker need be used between the PDGFR-β segment and the anti-VEGF segment. Alternatively, the linker may be the GGGGS motif x1, x2 (as above), x3, x4, etc. such that the activity of the two proteins is optimized.

Other linker motifs may also be used in accordance with the present invention, including G, GG, GGGS and GGGES x1, x2, x3, x4, etc. The linker may be combinations of the above. Joined to the carboxyl terminus of the serine residue of the linker is the bevacizumab Fab having the mutations T28D, N31H, H97Y, and S100aT (Kabat numbering). The protein sequence of FIG. 19A is set forth in SEQ ID NO. 25. The protein of FIG. 19B is the ranibizumab light chain (bevacizumab w/ M4L) (SEQ ID NO. 12). The protein of FIG. 19A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 19B.

Example 14. Protein Sequence of PDGFRβ-Anti-VEGF-A Fab/Anti-VEGF-A Light Chain (1a)

Another PDGFR-β trap-anti-VEGF-A Fab/anti-VEGF-A light chain was constructed having the sequence set forth in FIGS. 20A, B. FIG. 20A amino acids 1-283 correspond to 32 to 314 of human PDGFR-β (UniProtKB/Swiss-Prot: P09619.1), followed by the bevacizumab heavy chain. The protein sequence of FIG. 20A is set forth in SEQ ID NO. 26. The protein of FIG. 20B is the bevacizumab light chain sequence (SEQ ID NO. 5). As set forth in this example, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The bevacizumab light chain optionally has an M4L mutation. The bevacizumab heavy chain optionally has one or more of the following mutations: T28D, N31H, H97Y, S100aT (Kabat numbering), Q347C and L443C (EU numbering).

Example 15. Protein Sequence of PDGFR-β (D2-D3)-Anti-VEGF-A Heavy Chain/Anti-VEGF-A Light Chain (1b)

Another PDGFR-β trap (D2-D3)-anti-VEGF-A heavy chain/anti-VEGF-A light chain was constructed having the sequence set forth below in FIG. 21A, B. FIG. 21A amino acids 1-190 correspond to 125 to 314 of human PDGFR-β (UniProtKB/Swiss-Prot: P09619.1), followed by the bevacizumab heavy chain. The protein sequence of FIG. 21A is set forth in SEQ ID NO. 27. As set forth in this example, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. FIG. 21B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), Q347C and L443C (Eu numbering).

Example 16. Protein Sequence of PDGFR-β (D2-D3)-Anti-VEGF-A Fab/Anti-VEGF-A Light Chain (2b)

Another PDGFR-β trap (D2-D3)-anti-VEGF-A Fab/anti-VEGF-A light chain was constructed having the sequence set forth in FIGS. 22A, B. FIG. 22A amino acids 1-190 correspond to 125 to 314 of human PDGFR-β (UniProtKB/Swiss-Prot: P09619.1), followed by the bevacizumab Fab. As set forth in this example, no linker need be used between the PDGFR-β segment and the anti-VEGF segment. Alternatively, the linker may be the GGGGS motif x1, x2, x3, x4, etc. such that the activity of the two proteins is optimized. The GGGGSGGGGS linker is particularly preferred. Other linker motifs may also be used in accordance with the present invention, including G, GG, GGGS and GGGES x1, x2, x3, x4, etc. The linker may be combinations of the above. The sequence of FIG. 22A is set forth in SEQ ID NO. 28. FIG. 22B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The bevacizumab Fab of FIG. 22A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 22B.

Example 17. Protein Sequence of PDGFR-β (D2-D3)-Anti-VEGF-A Fab/Anti-VEGF-A Light Chain (2b')

Another PDGFR-β trap (D2-D3)-6×GS-anti-VEGF-A Fab/anti-VEGF-A light chain was constructed having the sequence set forth below in FIGS. 23A, B. FIG. 23A amino acids 1-190 correspond to 125 to 314 of human PDGFR-β (UniProtKB/Swiss-Prot: P09619.1), followed by the linker GGGSGGGGSGGGGSGGGGSGGGGSGGGGS and then by bevacizumab Fab. Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs known to those of skill in the art may also be used in accordance with the present invention, including G, GG, GGGS and GGGES x1, x2, x3, x4, etc. The linker may be combinations of the above. The protein sequence of FIG. 23A is set forth in SEQ ID NO. 29. FIG. 23B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The bevacizumab Fab heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 18. Protein Sequence of PDGFR-β (D2-D3)-Anti-VEGF-A Fab/Anti-VEGF-A Light Chain (2b')

Another anti-VEGF-A Fab-6×GS-PDGFR-β trap (D2-D3)/anti-VEGF-A light chain was constructed having the sequence set forth below in FIGS. 24A, B. FIG. 24A amino acids 1-190 correspond to 125 to 314 of human PDGFR-β (UniProtKB/Swiss-Prot: P09619.1), followed by the linker GGGSGGGGSGGGGSGGGGSGGGGSGGGGS and then by bevacizumab Fab. Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The sequence of FIG. 24A is set forth in SEQ ID NO. 29. FIG. 24B shows the bevacizumab light chain sequence (SEQ ID NO. 5). The bevacizumab light chain of FIG. 24B optionally has an M4L mutation. The bevacizumab heavy chain of the first protein optionally has one or more of the following mutations: T28D, N31H, H97Y, and S100aT (Kabat numbering). The bevacizumab Fab of FIG. 24A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 19. Protein Sequence of Anti-VEGF-A Fab-6×GS-PDGFR-β (D2-D3)/Anti-VEGF-A Light Chain (3)

Another anti-VEGF-A Fab-6×GS-PDGFR-β (D2-D3)/anti-VEGF-A light chain was constructed having the sequence set forth below in FIGS. 25A, B. FIG. 25A amino acids 1-231 correspond to bevacizumab Fab, followed by the linker GGGSGGGGSGGGGSGGGGSGGGGSGGGGS and then 125 to 314 of human PDGFR-β (UniProtKB/Swiss-Prot: P09619.1). Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The sequence of FIG. 25A is set forth in SEQ ID NO. 30. FIG. 25B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The PDGFR-β of FIG. 25A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 20. Production of Dual PDGFR/VEGF Antagonist Protein

The TAF443 heavy and light chains were cloned into expression plasmids and transfected into CHO cells. Cells were grown up in appropriate media and harvested. TAF443 was purified as follows. 10 L culture medium from CHO cells expressing SEQ ID NOS. 31 and 32 were adjusted with 5% (v/v) 1.1 M HEPES, 0.22 M EDTA, pH 6.7 or 10% 0.55 M Hepes, 0.11M EDTA, 5.5% Triton X-100, pH 6.7, and loaded onto a 167/400 ml Protein A column (2-run) packed with Mab Select Sure resin equilibrated in 50 mM Tris, 150 mM NaCl, pH 7.5 (5-CV). The column was washed with 50 mM Tris, 150 mM NaCl, pH 7.5 (2-CV), 50 mM Tris, 0.5M $CaCl_2$, pH 7.5 (5-CV), and then 10 mM Tris, 10 mM NaCl, pH 7.5 (3-CV) before the protein was eluted using 150 mM Glycine, 40 mM NaCl, pH 3.5 (4-CV). Fractions were pooled, adjusted to pH 3.5 using 2M Glycine, pH 2.7, and then neutralized to pH 7 using 2M HEPES, pH 8.0. The Protein A pool was loaded onto a 274 ml TMAE column equilibrated in 50 mM Hepes, 65 mM NaCl, pH 7.0 (5-CV). The column was washed with 50 mM Hepes, 65 mM NaCl, pH 7.0 (3-CV), and then eluted with 50 mM Tris, 200 mM NaCl, pH 7.5 (5-CV). The elution fractions were pooled and buffer exchanged in a 1150 mL Sephadex G-25 Coarse column equilibrated with PBS-CMF, pH 7.2. The pool was filtered, concentrated to >5 mg/ml via 30 k MWCO VivaFlow200. The concentrated protein was filtered through a 0.22 um filter, and then characterized by SDS-PAGE, analytical SEC, O.D.280/320, end toxin LAL assay, Protein A ELISA, IEF, and Freeze/Thaw Analysis.

The table below summarizes the properties of an example batch of purified TAF443.

| TAF443 Purified Lot Characteristics | |
| --- | --- |
| Concentration (UV) | 5.69 mg/ml |
| Purity (SEC) | 98.6% |
| MW (SDS-PAGE) | ~200 kDa (NR) |
| pI (IEF) | 4.2-4.5 |
| Endotoxin (LAL) | 0.1 EU/mg |
| Protein A (Elisa) | <10 ng/ml |
| Final Yield | ~700 mg/L (CM) |

Example 21. TAF Bi-Functional Molecule Stability at High Concentration in Representative Formulations The TAF bi-functionals were concentrated to 50-85 mg/ml in a series of standard formulation buffers ranging from pH 4.5 to 7.5, in the presence of excipients such as sucrose. Aliquots of these samples were stored at room temperature (RT) and 4° C. over a period of 6 weeks, and sampled at time zero and after each subsequent week to measure the percentage of aggregated material by analytical SEC. The effect of pH on aggregation of TAF443 can be seen in the following table.

| % Aggregates Observed in TAF Solution at various pHs over Time | | | | |
| --- | --- | --- | --- | --- |
| | Tris pH 7.5 | His pH 6.0 | His pH 5.5 | Lac pH 4.5 |
| Time 0 | <1 | <1 | <1 | <2 |
| Day 4 | <1 | <1 | <1 | ~3 |
| Week 1 | <1 | <1 | <1 | ~4 |
| Week 2 | <1 | <1 | ~2 | ~6 |
| Week 4 | <1 | <1 | ~3 | ~10 |
| Week 6 | <1 | <1 | ~3 | ~10 |

Example 22. Transfection of Constructs into CHO Cells

DNA constructs for TAFwt, TAF443 and TAF347 were transfected into CHO-K1 SV SSI: 3 pools/construct. The normal 3 weeks of recovery was observed in most of the cell lines. However, TAFwt and TAF347 cell lines lagged approximately 1 week behind the other cell lines. Once the pools were established, day 4 for most and day 3 for TAFwt and TAF347, conditioned media samples were run on Octet. 3-day conditioned media for TAFwt and TAF347 showed about 7 mg/ml by Octet. 4-day conditioned media showed about 21 mg/ml for TAF443. Small differences were observed between pools and the pools were used to make pools of pools which were carried forward for protein generation.

Example 23. SEC-MALS of Proteins

The PDGFR segment of TAF has 7 putative glycosylation sites. The protein appears to be heavily glycosylated from SEC-MALS measurements:

| Construct | Protein (kDa) | Sugar (kDa) | Total (kDa) |
|---|---|---|---|
| TAFwt | 184 | 63 | 247 |
| TAF334 | 182 | 62 | 244 |
| TAF443 | 187 | 63 | 250 |

The samples run on SEC-MALS were all greater than 98% pure. The molecular weights measured were reasonable. Some high molecular weight material was observed, probably a tri- to pentamer (data not shown).

Example 24. Thermal Stability of TAF Proteins

Thermal stability profiles were run of TAFwt, TAF443 and TAF347 in PBS, pH 7.2. Each protein had three peaks (data not shown). The relative positions of the peaks are set forth in the table below:

| Sample | $T_m1$ (° C.) | $T_m2$ (° C.) | $T_m3$ (° C.) |
|---|---|---|---|
| TAFwt | 58.1 ± 0.1 | 71.9 ± 0.1 | 83.2 ± 0.1 |
| TAF347 | 58.2 ± 0.1 | 71.9 ± 0.1 | 81.7 ± 0.1 |
| TAF443 | 58.2 ± 0.1 | 71.9 ± 0.1 | 84.4 ± 0.1 |

The stabilities of the proteins over the temperature range are very similar. It is noted however that there are some small changes in $T_m3$. $T_m3$ likely corresponds to the CH3 domain of the antibody domain of the three TAF proteins and the changes reflect the Cys mutations. The low overall stability of the TAF proteins is likely due to unfolding of the PDGFR segment of the proteins.

Example 25. TAF Forced Aggregation

The percentage of aggregates in a solution of the three TAF proteins as a function of heat was examined (data not shown). Solutions of each of the proteins (TAFwt, TAF347 and TAF443) started to show aggregates starting around 54° C. The percentage of aggregates for each of the proteins increased sharply as the temperature was increased. At 64° C., roughly 40% of each of the TAF proteins constituted aggregates. It is noted that the aggregation starts to occur at the lowest Tm, seemingly corresponding to the unfolding of the PDGFR portion of the protein.

Example 26. TAF443 Thermal Stability as a Function of pH

The thermal stability of TAF443 was examined at various pHs as set forth in the table below. In non PBS buffers, 4 thermal denaturation peaks are seen:

| Buffer | $T_m1$(° C.) | $T_m2$(° C.) | $T_m3$(° C.) | $T_m4$(° C.) |
|---|---|---|---|---|
| Tris pH 7.5 | 57 | 67 | 74 | 85.9 |
| His pH 6.0 | 53.3 | 62.9 | 75.4 | 84.9 |
| Succinate | 55.9 | 66.7 | 74.9 | 85.8 |
| Lucentis buffer, pH 4.8 | 53.9 | 61.3 | 75.1 | 82.9 |
| PBS pH 7.2 | 58.2 | 71.9 | | 84.4 |

As can be seen, there is a weak pH dependence. Notably, the $T_m2$ and $T_m3$ domain (presumably $C_H2$, $F_{ab}$) overlap in PBS, but not in other buffers.

Example 27. Affinity of Dual PDGF/VEGF Antagonist Proteins and Conjugates to Targets Surface plasmon resonance (SPR) was used to characterize the binding kinetics of recombinant human PDGF-BB (PeproTech, 100-14B) to TAF-WT, TAF-347, TAF-443, TAF443-6A250K, and TAF443-3A250K dual PDGF/VEGF antagonist variants. Initially, an anti-human IgG antibody (GE Healthcare, BR-1008-39) was covalently amine coupled onto all four flow cells of a CM5 carboxymethylated dextran coated sensorchip to a density of about 10,000 resonance units (RUs) following the manufacturer's protocol. Each PDGF/VEGF variant was captured to a level of approximately 150 RUs. The running and sample buffer for the PDGF analysis was HBS-EP+ 300 mM NaCl (10 mM 4-(2-hydroxyethyl)-1-piperazineethanesulfonic acid (HEPES) pH 7.4, 300 mM NaCl, 3 mM ethylenediaminetetraacetic acid (EDTA), 0.05% (v/v) Tween-20). A 2-fold serial dilution series of PDGF-BB ranging in concentration from 1 nM to 0.125 nM was injected at a flow rate of 100 µL/minute for a 110 second association with dissociations that varied from 300 to 2700 seconds. The surface was then regenerated with a 30 second pulse of 3M $MgCl_2$, a 30 second pulse of an ionic regeneration buffer (0.46M KSCN, 1.83 M MgCl2, 0.92 M urea, and 1.83 M guanidine-HCl pH7.4, Andersson et al., Analytical Chemistry, 1999) and then equilibrated with a 30 second pulse of HBS-EP+ 300 mM NaCl running buffer.

Similarly, SPR was used to determine the binding affinities of recombinant human VEGF121 (PeproTech, 100-20A) against the TAF-WT, TAF-347, and TAF-443 dual PDGF/VEGF antagonist variants. The running and sample buffer for the VEGF analysis was HBS-EP+ with a final concentration of 150 mM NaCl. A 2-fold dilution series of VEGF121 ranging in concentration from 100 nM to 12.5 nM was injected at a flow rate of 50 uL/minute for about a 50 second association with dissociations that varied from 300 to 3600 seconds. The surface was then regenerated with a 30 second pulse of 3M $MgCl_2$, a 30 second pulse of ionic regeneration buffer (0.46M KSCN, 1.83 M MgCl2, 0.92 M urea, and 1.83 M guanidine-HCl pH7.4, Andersson et al., Analytical Chemistry, 1999), and then equilibrated with a 30 second pulse of HBS-EP+ 150 mM NaCl running buffer.

All SPR assays were performed at 25° C. with a data collection rate of 1 Hz using a Biacore T200 instrument (GE Healthcare). The resulting PDGF and VEGF sensorgrams were double referenced using both a control surface and buffer injections. The rate constants were determined by fitting the data to a 1:1 Langmuir model with Biacore T200 evaluation software v2.0 and the equation $K_D = k_d/k_a$.

| | Biacore Affinity to PDGF-BB | | | | | | |
|---|---|---|---|---|---|---|---|
| Analyte | Ligand | ka(1/Ms) | kd(1/2) | t1/2 (min) | Rmax (RU) | Chi2/Rmax | KD (pM)* |
| PDGF-A* | TAF-WT | 7.97E+07 | 8.01E−05 | 144.28 | 15.16 | 0.16% | 1.01 |
| PDGF-B* | TAF-WT | 8.01E+07 | 9.19E−05 | 125.68 | 15.15 | 0.20% | 1.15 |

-continued

| | | | | | | | |
|---|---|---|---|---|---|---|---|
| PDGF-C* | TAF-WT | 8.65E+07 | 1.03E−04 | 111.94 | 15.32 | 0.15% | 1.19 |
| | | | | | | AVG +/− STDEV | 1.1 ± 0.1 |
| PDGF-A* | TAF-347C | 4.15E+07 | 8.41E−05 | 137.33 | 13.99 | 0.86% | 2.03 |
| PDGF-B* | TAF-347C | 5.82E+07 | 7.87E−05 | 146.79 | 13.08 | 1.05% | 1.35 |
| | | | | | | AVG +/− STDEV | 1.7 ± 0.3 |
| PDGF-A* | TAF-443C | 3.22E+07 | 4.96E−05 | 233.15 | 13.15 | 0.81% | 1.54 |
| PDGF-B* | TAF-443C | 5.62E+07 | 8.76E−05 | 131.89 | 12.19 | 0.96% | 1.56 |
| | | | | | | AVG +/− STDEV | 1.55 ± 0.01 |
| PDGF-A* | R3643-6A (TAF443-6A250K) | 7.60E+07 | 9.46E−05 | 122.09 | 8.11 | 0.415 | 1.25 |
| PDGF-B* | R3643-6A (TAF443-6A250K) | 5.62E+07 | 5.85E−05 | 197.55 | 8.33 | 0.30% | 1.04 |
| PDGF-C* | R3643-6A (TAF443-6A250K) | 3.48E+07 | 5.13E−05 | 225.41 | 8.45 | 0.80% | 1.47 |
| | | | | | | AVG +/− STDEV | 1.3 ± 0.2 |
| PDGF-A* | R3644-3A (TAF443-3A250K) | 5.76E+07 | 5.92−E05 | 195.04 | 8.15 | 0.31% | 1.03 |
| PDGF-B* | R3644-3A (TAF443-3A250K) | 2.86E+07 | 4.96E−05 | 233.05 | 8.52 | 0.60% | 1.73 |
| PDGF-C* | R3644-3A 3A250K) | 4.71E+07 | 7.52E−05 | 153.56 | 8.15 | 0.49% | 1.60 |
| | | | | | | AVG +/− STDEV | 1.5 ± 0.4 |

*A, B, and C refer to separate runs or measurements concerning the same analyte PDGF-BB Biacore Affinity to VEGP121

| Analyte* | Ligand | ka(1/Ms) | kd (1/s) | T1/2 (min) | Rmax (RU) | Chi2/Rmax | KD (pM) |
|---|---|---|---|---|---|---|---|
| VEGF-A | TAF-WT | 1.14E+05 | 2.01E−05 | 573.89 | 29.4 | 0.17% | 176.60 |
| VEGF-B | TAF-WT | 6.85E+05 | 5.89E−05 | 196.00 | 13.90 | 0.16% | 86.03 |
| VEGF-C | TAF-WT | 1.40E+05 | 2.96E−05 | 390.68 | 27.36 | 0.17% | 212.00 |
| VEGF-D | TAF-WT | 1.55E+05 | 2.69E−05 | 429.78 | 24.92 | 0.23% | 173.00 |
| | | | | | | AVG/STD DEV | 161.96 ± 53.46 |
| VEGF-A | TAF347 | 1.37E+05 | 3.83E−05 | 301.55 | 26.57 | 0.87% | 280.30 |
| VEGF-B | TAF347 | 1.42E+05 | 2.92E−05 | 446.21 | 24.56 | 0.35% | 182.40 |
| | | | | | | AVG | 231.35 ± 48.95 |
| VEGF-A | TAF443 | 1.46E+05 | 3.20E−05 | 361.01 | 25.87 | 0.75% | 219.30 |
| VEGF-B | TAF443 | 1.35E+05 | 3.10E−05 | 372.18 | 25.47 | 0.31 | 229.70 |
| | | | | | | AVG | 224.5 ± 5.2 |

*A, B, C, D, refer to different runs of the same analyte (VEGF121).

Example 28. Decapping of TAF443 Prior to Maleimide Conjugation

The TAF443 Cysteine residue is typically "capped" or oxidized by chemicals in the cell culture media and is not available for conjugation. In this regard, purified TAF443 (OG1321) is subjected to a decapping (i.e. reducing) procedure to remove the cap and enable the free (i.e. those not involved in Cys-Cys disulfide bonds) cysteine residue to be conjugated to the maleimide functionality of a polymer. Decapping is done by mixing TAF protein with a 30× molar excess for 1 hour at 25° C. of the reducing agent TCEP (3,3',3"-Phosphanetriyltripropanoic acid). The reduction reaction with TCEP is monitored by SDS-PAGE. Undenatured TAF runs as a single band at about 250 kDa (about 40 kDa of this weight is carbohydrate). When fully denatured the single 250 kDa band is converted into bands corresponding to the light and heavy chains. Following denaturation, the TAF protein was washed by UFdF using a Pellion XL Ultrafiltration Cassette with 20 mM Tris pH7.5, 150 mM NaCl, 0.5 mM TCEP buffer to remove the cap. The TCEP reagent was then removed in the same UFdF setup with 20 mM Tris pH7.5, 150 mM NaCl. Reduced TAF was allowed to refold using air (ambient Oxygen) which was again followed by SDS-PAGE as an assay.

A detailed procedure for decapping is as follows:

500 mg of OG1321 was thawed from −80° C. at 4° C. overnight, and warmed up in the 25° C. water bath before mixing with TCEP at 30× molar excess. The reaction was incubated in the 25° C. water bath for 1 hour. Samples were taken out at 15, 30, and 60 minutes to run on SDS-PAGE in order to evaluate the reduction completeness. A UFdF cassette with 10 kD MWCO was used to carry out buffer exchange. First buffer exchange step was done with 20 mM Tris pH7.5, 100 mM NaCl, 0.5 mM TCEP for ~100× to thoroughly remove the cap. A second buffer exchange step was done with 20 mM Tris pH7.5, 100 mM NaCl for ~1000× for TCEP remove prior to air refolding. The final TCEP concentration in the sample was ~0.5 μM. Samples were taken out from both buffer exchange steps for both SDS-PAGE and SEC analyses to evaluate the protein reoxidation status and protein aggregation. After the second buffer exchange step, the OG1321 was concentrated to ~2 mg/ml, 0.22 μm filtered, and allowed to re-oxidize with air at 4° C. Samples were taken out for SDS-PAGE and SEC analyses at different time points to evaluate the re-oxidation status. Re-oxidized OG1321 was 0.22 μm filtered and further concentrated. Continued to concentrate the sample with VIVACELL 100 30 k MWCO spin concentrators to 4-6 mg/ml and sterile filtered the sample. Quantified by OD280.

Example 29. Conjugation of TAF443 to Biopolymer

TAF443 which is also called OG1321 was conjugated to polymer OG1802 (see below) after decapping using a 15× excess of polymer in pH 7.5 Tris buffer to produce OG1448, media and absent reduction is not available to react with maleimide. Step B: reduced TAF is then conjugated to OG1802. Step C: conjugated TAF (OG1448) is then separated from unconjugated TAF and polymer via chromatography. These three general steps are broken down into seven smaller steps in the following table:

| General Step | Description | IPC Assays | Target Range |
|---|---|---|---|
| A | Step 1: To reduce OG1321 using tris (2-carboxyethyl) phosphine (TCEP). 30x molar of TCEP at 25° C. for 1 hour. | Non-reducing SDS-PAGE | >95% reduction |
|  | Step 2: To remove TCEP reducing agent and cap groups using UF/DF. First, wash with 0.5 mM TCEP in Tris pH 7.5 for a 100-fold volume exchange factor; followed by a 2$^{nd}$ wash with Tris buffer pH 7.5 for 1,000 fold volume exchange factor to remove the TCEP, targeting final TCEP level lower than 0.5 μM. | Non-reducing SDS-PAGE. | Band shift upon removal of the reducing agent. |
|  | Step 3: To refold protein to ensure the native disulfide pairs are fully oxidized while the internal cysteine residues remain reduced. | Non-reducing SDS-PAGE<br><br>UV/Vis for protein | Band upshift upon oxidation of the native disulfide pairs.<br><br>Final protein concentration at 6-8 mg/ml. |
| B | Step 4: To conjugate OG1321 protein to OG1802 biopolymer. Conjugate by mixing the oxidized OG1321 with OG1802. The process requires 15x molar of biopolymer to decapped protein and constant mixing. Low temperature at 2-8° C. for 20 hours and overlay the reaction with nitrogen gas to minimize oxidation. | Non-reducing SDS-PAGE<br>Analytical AE-HPLC | <20% full length band remains.<br><20% unreacted protein at OD 280 nm. |
| C | Step 5: To separate OG1448 conjugate from the unreacted OG1321 protein, unreacted OG1802 biopolymer, protein aggregates and other process contaminants. Purify OG1448 using MacroCap Q (AEX). The chromatography is performed at pH 7.5 in 20 mM Tris buffer and eluted using a NaCl gradient. A pool is made by combining fractions. | Analytical AE-HPLC for unreacted polymer and unreacted protein<br><br>Non-reducing SDS PAGE | <5% unreacted protein at OD 180 nm:<br><15% unreacted polymer at OD 220 nm.<br><5% unreacted protein |
|  | Step 6: To concentrate the OG1448 and to exchange the chromatography buffers for the formulation buffers. The pooled fractions from the previous step are diafiltered and then concentrated by UF/DF to achieve the target OG1448. | UV/Vis for protein concentration | OG1448 at 50 mg/ml |
|  | Step 7: To remove bioburden from the final product and to dispense into storage containers. The UF/DF final pool is 0.2 μm filtered into sterile containers, and pH and conductivity of the final filtrate is established. The drug substance is stored at −20° C. | UV/Vis for protein concentration<br>pH, Conductivity | OG1448 at 50 mg/ml<br>pH 7.2-7.5 | shown in FIG. 26, showing the chemical structure of OG1448 which is TAF443 conjugated to biopolymer OG1802. TAF443 is on the extreme right hand of the molecule shown in the figure, conjugated via the cysteine 443 residue to the 5 member ring. Conjugation was monitored by SDS-PAGE and driven to near completion. Conjugate was purified via anion exchange chromatography and buffer exchanged into the formulation buffer by UF/DF.

In general, there are three steps involved in the synthesis of OG1448 from components OG1802 and OG1321. Step A: OG1321 much be reduced or decapped to free up the sulfhydryl groups at cysteine position 443. Although the cysteine position at 443 of the heavy chain of TAF is not believed to be involved in cysteine-cysteine disulfide pairing, this cysteine is typically capped by components of the

Example 30. Purification of OG1448 Via Anion Exchange (Macrocap Q)

After conjugation of TAF443 to OG1802 as described above, OG1448 was purified as follows: After conjugation of TAF443 to OG1802 as described above, OG1448 was purified as follows: 2×400 ml of Macrocap Q columns were packed according to ~3:1 ratio of resin:conjugate. The columns were flushed with 5M of NaCl and equilibrated with 20 mM Tris pH7.5, 20 mM NaCl (equilibration buffer) by syphoning. The conjugation reaction mixture was diluted with 20 mM Tris pH7.5 and loaded on the columns. The columns were then chased with the equilibration buffer, and washed with 20 mM Tris pH7.5, 50 mM NaCl (Wash 1) and then 20 mM Tris pH7.5, 100 mM NaCl (Wash 2). Elution was done with 20 mM Tris pH7.5, with step gradient of 150 mM, 200 mM, 220 mM, 250 mM, 300 mM, and 500 mM NaCl. All the column flow-through, washes, and elution were collected in clean bottles for SDS-PAGE and AEX analyses. Elution fractions containing the conjugate were pooled and concentrated using Pellicon XL TFF cassette with 30 kD MWCO and PES membrane. The concentrated pool was then buffer exchanged against 1×PBS pH7.4 buffer for ~100× using the same TFF cassette and transferred to the VIVACELL 100 spin concentrators to further concentrate until the targeted concentration (~30 mg/ml) was achieved. The final conjugate was filtered through a 0.2 μm PES syringe filter for lot release.

Example 31. Reduction of Bacterial Endotoxin

To reduce levels of endotoxin in the final protein (OG1321) or conjugate (OG1448), purification procedures may be employed for either protein or conjugate which utilize cation exchanges in place of anion exchanges. For example, in the above procedure for purifying OG1321, the anion exchange TMAE resin is employed. In place of TMAE resin, the cation exchange resin CEX may be used. However, in order to use CEX residue the pH of the solution containing the protein in question must be reduced to below the protein's pI. For OG1321, the pH of the protein solution after the protein A column, is reduced to pH 3.5. The OG1321 is bound to the Poros XS column at pH5. Then, Porox XS (CEX) can be used to bind and elute the OG1321.

Example 32. Route 1 Synthesis of OG1802

Figure 27:
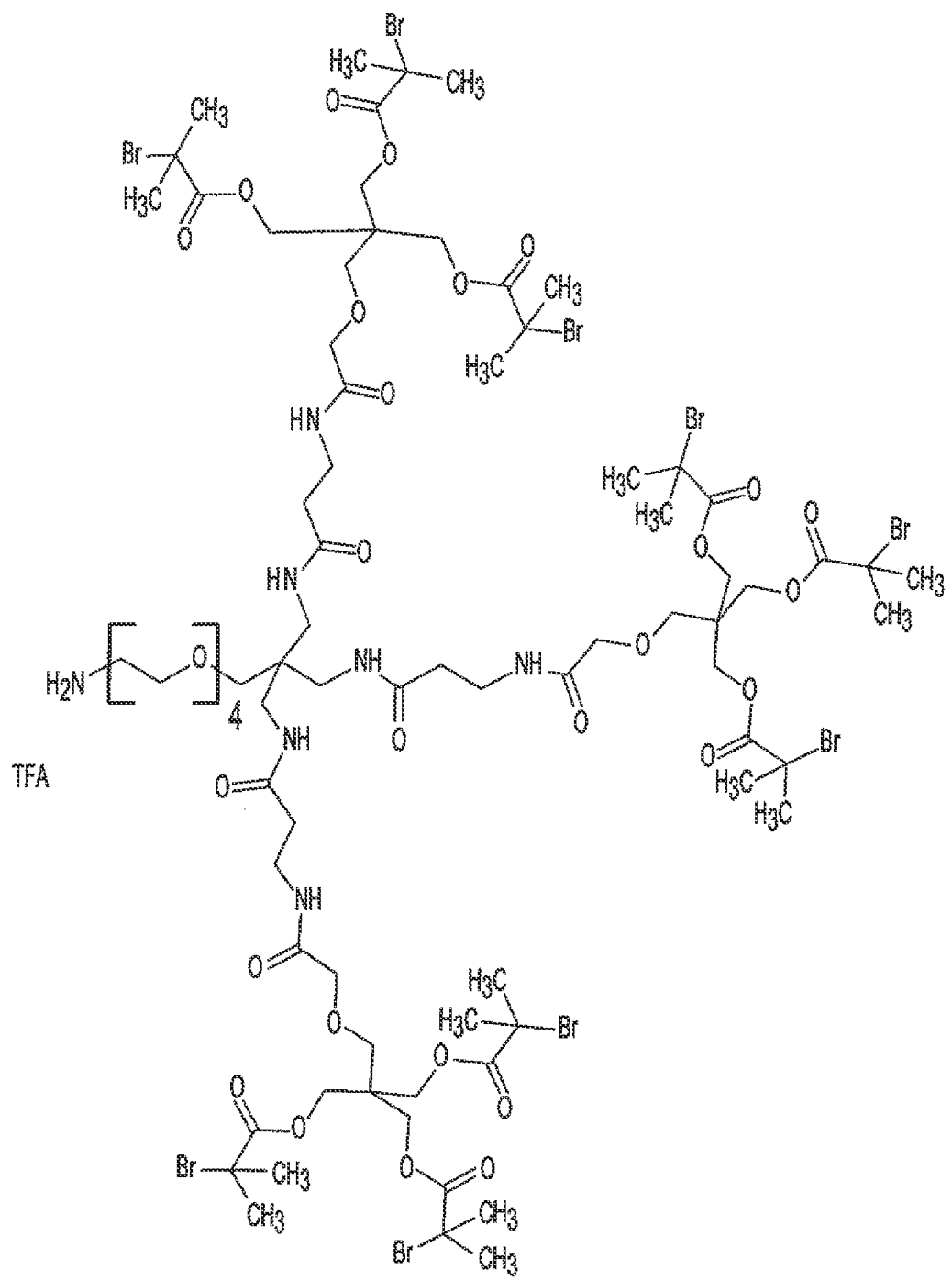
FIG. 27 shows Compound L.

A first route for the synthesis of OG1802 is as follows. First, TFA/amine salt initiator (Compound L) having the structure shown in FIG. 27 was synthesized as follows.

Figure 28:
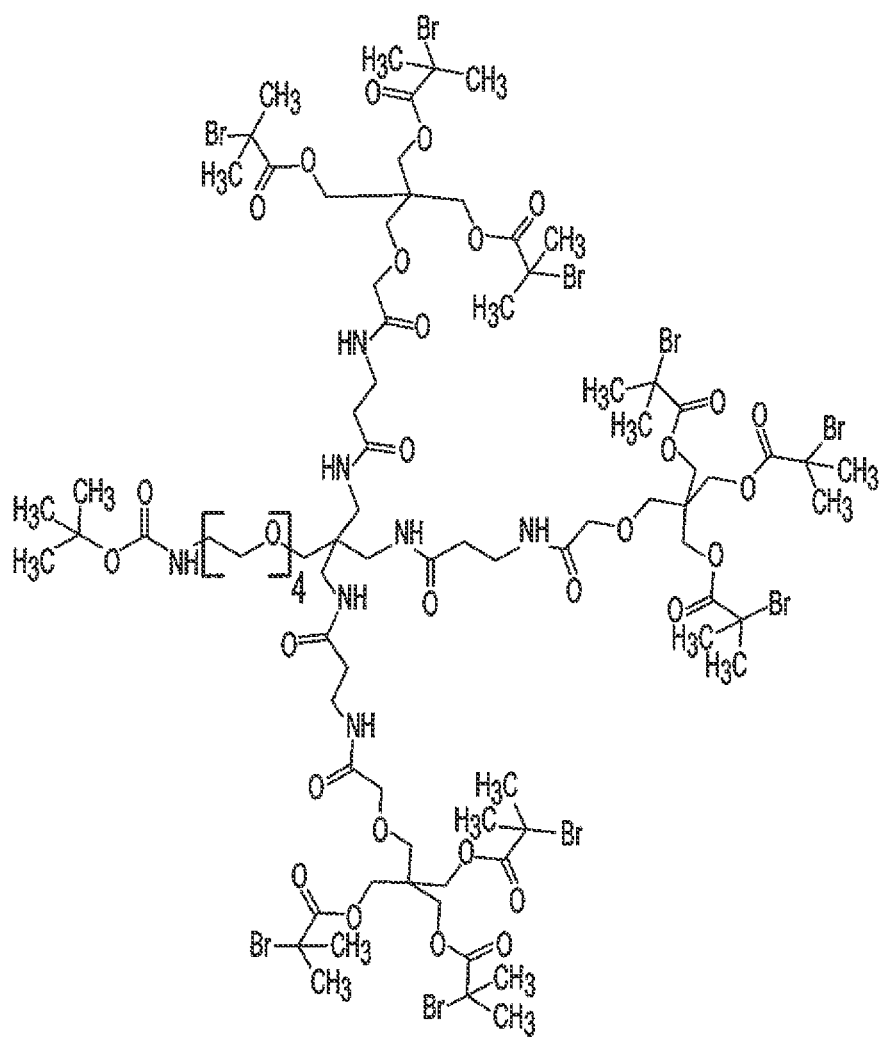
FIG. 28 shows Compound K.

First, Compound K, having the structure shown in FIG. 28 was synthesized as follows. Into a 200 mL round bottom flask under nitrogen was placed Compound J (OG1563) (1.9 g, 2.67 mmol, 3.3 equiv)

Compound J

Figure 38:
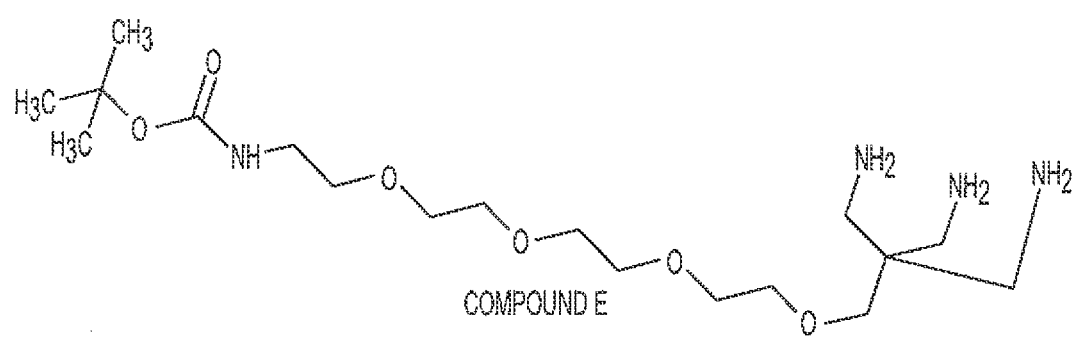
FIG. 38 shows Compound E.
Figure 39:
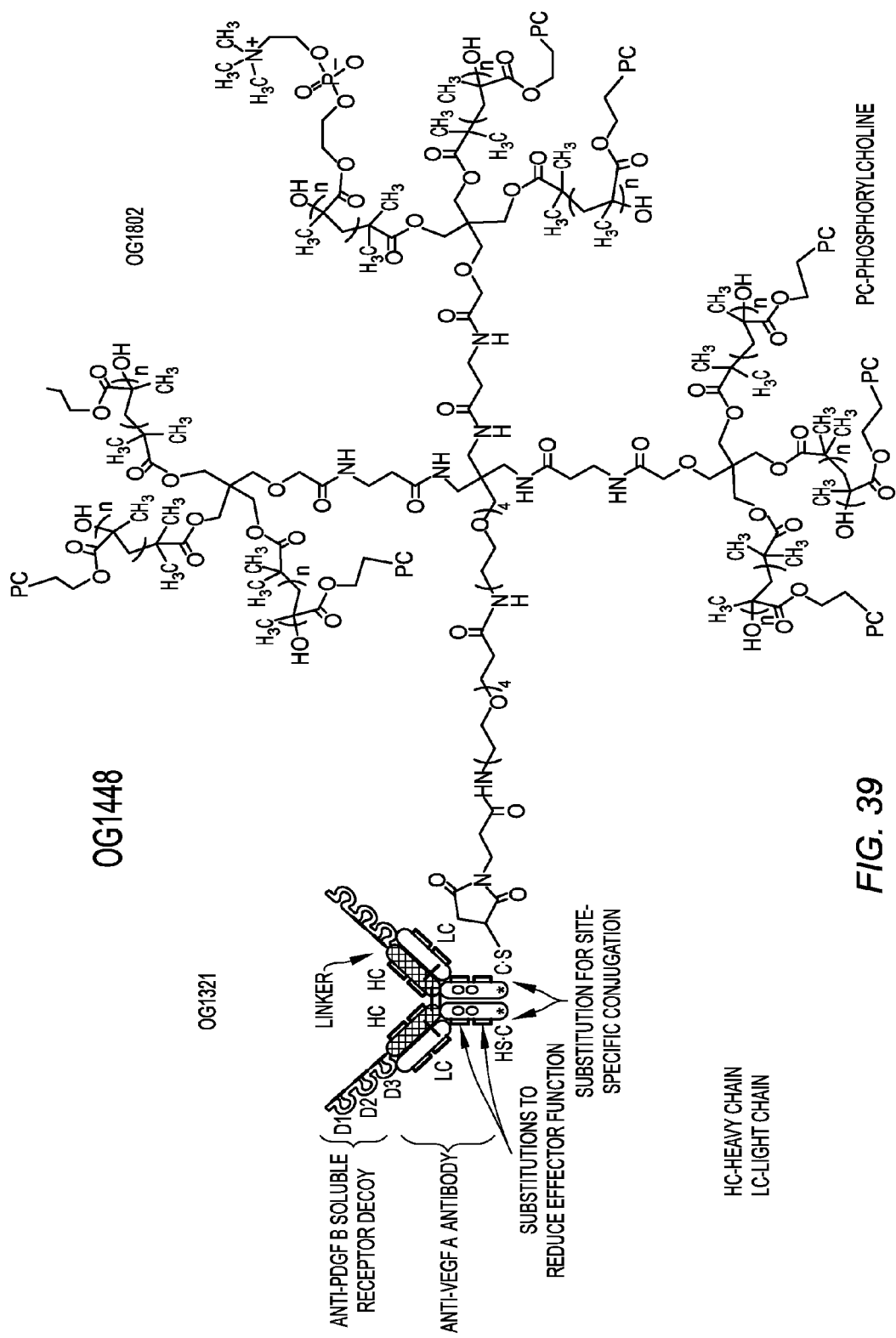
FIG. 39 depicts OG1448.

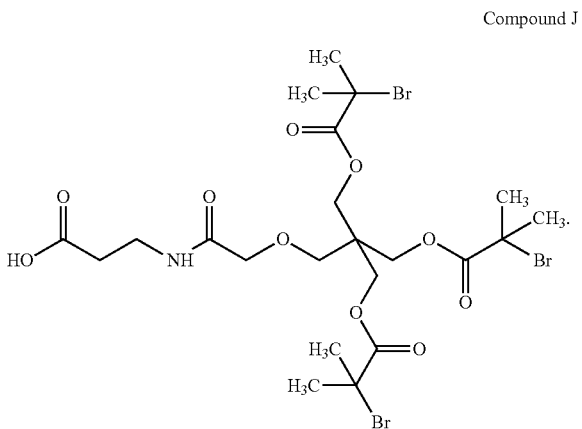 [SMILES: CC(C)(Br)C(=O)OCC(COCC(=O)NCCC(=O)O)(COC(=O)C(C)(C)Br)COC(=O)C(C)(C)Br]

and Compound E (0.525 g, 0.81 mmol, 1.0 equiv) (see FIG. 38) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): □□=1.36 (s, 9H, OC CH3), 1.90 (s, 54H, CC(CH3)2Br), 2.31 (t, J=7.2 Hz, 6H, C CH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, O=CCH2O), 4.27 (s, 18H, C CH2OC=O), 6.74 (br t, 1H, CH2NHC=O), 7.69 (t, J=6.8 Hz, 3H, CH2NHC=O), 7.84 (t, J=6.0 Hz, 3H, CH2 NHC=O). LC-MS (ES, m/z): [(M+2H-boc)/2]+ Calcd for (C84H136Br9N7O33+2H-Boc)/2=1196.6. Found 1196.6.

Next Compound L (FIG. 27) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): □□=1.90 (s, 54H, CC (CH3)2Br), 2.31 (t, J=7.2 Hz, 6H, CCH2CH2NH), 2.97-3.0 (m, 8H, CCH2NH and OCH2CH2NH), 3.17 (s, 2H, O CH2C), 3.3 (q, 6H, CH2CH2NHC=O), 3.4-3.59 (m, 20H, CH2), 3.87 (s, 6H, O=CCH2O), 4.27 (s, 18H, C CH2OC=O), 7.69-7.84 (m, 9H, both CH2NHC=O and NH3+).

LC-MS (ES, m/z): [(M+2H)/2]+ Calcd for (C84H136Br9N7O33+2H)/2=1196.6. Found 1197.4.

Next, compound L was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stirring), The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous.

After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. The table below sets forth polymer data for polymer employing compound L as an initiator.

| Theor. MW (kDa) | Polymer ID No. | Initiator | Mn (kDa) | Mp (kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 29) to the 750 kDa polymer referred to above to provide OG1802. Into a 20 mL vial was placed Polymer R3707 (750 kDa polymer made using L as initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH ~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2x~2 mL each tube) and this combined with the retentate. The retentate solution was filtered through a syringe filter (Acrodisc Supor, PN 4612), frozen and placed on a lyophilizer. This resulted in 485 mgs as a white powder.

Example 33. Biacore Binding Studies of TAF (OG1448 and OG1321)

The binding affinity of OG1448 (and OG1321) to its intended targets was evaluated via Biacore assay. Binding studies were performed at 25° C. and 37° C. using BioRad Proteon XPR36 and Biacore 2000 optical biosensors equipped with GLM (Proteon) and CM4 (Biacore) sensor chips and equilibrated with running buffer (10 mM HEPES, 150 mM NaCl, 0.005% Tween-20, 0.2 mg/ml BSA). OG1448, OG1321, bevacizumab, aflibercept and anti-PDGF were immobilized to the sensor surface via amine-coupling.

Binding of the coupled proteins to the ligands was determined by standard methodology. For example, rhVEGFA-165 was tested for binding in a three-fold dilution series starting at 52 nM. rhVEGFA-165 was injected across the surface for five minutes and then the dissociation phase was monitored for >1000 seconds as the surfaces were washed with buffer. The rhVEGFA-165/OG1448 complex appeared quite stable, as indicated by the apparently flat response during the wash phase (>300 seconds) (data not shown). The dissociation phase for the 52 nM rhVEGFA-165 was monitored for more than 2 hours. No decrease in the binding response over time was observed.

Similarly, rhPDGF-BB was tested for binding in a three-fold series starting at 11.4 nM. For the rhPDGF-BB/OG1448 interactions, the rate constants were too fast to be reported with confidence because of mass transport effects. The following $K_D$ constants were observed:

| | $K_D$ (pM) | | | | |
|---|---|---|---|---|---|
| | OG1321 | OG1448 | Bevacizumab | Aflibercept | Anti-PDGF |
| rhVEGFA-165 (25° C.) | 9.8 ± 0.1 | 5.1 ± 0.1 | 9.6 ± 0.8 | 1.56 ± 0.2 | |
| rhPDGF-BB (25° C.) | 14 ± 3 | 17 ± 2 | | | 107 ± 3 |

Example 34. TAF—a Competitive Inhibitor of rhVEGFA-165 Binding to rhVEGFR

As a measure of its potential potency on anti-VEGF activity, binding activity of TAF (OG1448 and OG1321) to VEGFA-165 was evaluated in a competitive binding assay where TAF, at different concentrations, was competing with immobilized rhVEGFR for binding of rhVEGF. rhVEGFA-165 bound by the immobilized VEGFR was determined by ELISA (data not shown).

Human VEGFR1/Fc was coated onto the bottom of 96-well ELISA plates at 1.0 µg/mL. Various concentrations of TAF (OG1448 and OG1321), ranging from 0.39 to 200 nM, were incubated with 0.1 nM of biotinylated VEGFA-165 for 30 min before adding to the ELISA plates. Biotinylated-rhVEGFA-165 bound to VEGFR1 was detected by streptavidin-HRP and followed by development with HRP substrates. Ranibizumab (Lucentis) and bevacizumab (Avastin) were similarly tested for competitive binding inhibition of VEGFA-165 to VEGFR1.

OG1321, OG1448, ranibizumab and bevacizumab showed similar $IC_{50}$s in inhibiting the binding of VEGF-165 to rhVEGFR suggesting similar potential potency in anti-VEGF activity. These results suggest that TAF (both OG1448 and OG1321) can be as potent as the approved agents ranibizumab and bevacizumab, hence, suitable for treating neovascular (i.e., wet) AMD.

| | $IC_{50}$(nM) | | | |
|---|---|---|---|---|
| | OG1321 | OG1448 | Ranibizumab | Bevacizumab |
| Competitive binding to rhVEGFA-165 (vs VEGFR) | 12.5 ± 1.2* | 8.5 ± 1.1* | 12.5 ± 1.2* | 10.7 ± 0.9* |

*Mean and SD of at least three trials.

Example 35. OG1448—a Competitive Inhibitor of rhVEGFA-165 Binding to rhVEGFR in the Presence of rhPDGF-BB To evaluate whether OG1448 can bind rhVEGFA-165 in the presence of rhPDGF-BB, i.e., whether rhPDGF-BB binding to the receptor decoy of TAF inhibits the ability of TAF to bind to rhVEGFA-165, a similar binding study to Example 27 was conducted but in the presence of various concentrations of rhPDGF-BB.

Human VEGFR1/Fc was coated onto the bottom of 96 well ELISA plates at 1.0 μg/mL. Various concentrations of OG1448 were incubated with 0.1 nM of rhVEGFA-165 plus rhPDGF-BB at 0.4, 1.2 and 2.0 nM, respectively, for 30 minutes before adding to the ELISA plates. rhVEGFA-165 binding to rhVEGFR1 was detected by biotinylated anti-VEGFA antibody, 0.4 μg/mL, followed with streptavidin HRP and HRP substrate. OG1448 was found to have an IC50 (nM) of 10.1. This is quite comparable to the IC50 observed without rhPDGF-BB from example 28. The value for OG1321 was not determined in this assay but is expected to be similar to OG1448.

Example 36. TAF—a Competitive Inhibitor of rhPDGF-BB Binding to rhPDGFR

As a measure of its potential potency of anti-PDGF activity, the binding activity of TAF (OG1448 and OG1321) to rhPDGF-BB was evaluated in a competitive binding assay where TAF, at different concentrations, was competing with immobilized PDGFR for binding of rhPDGFBB. rhPDGF-BB bound to immobilized PDGFR was determined by ELISA assay.

Human PDGFR/Fc was coated onto the bottom of 96-well ELISA plates at 0.4 μg/mL. Various concentrations of OG1448 and OG1321, ranging from 1 pM to 20 nM, were incubated with 0.2 nM of rhPDGF-BB for 30 minutes before adding to the ELISA plates. rhPDGF-BB bound to rhPDGFR was detected by biotinylated anti-PDGFBB antibody, 0.4 μg/mL, followed with streptavidin-HRP and HRP substrate.

OG1448, OG1321 and a reference anti-PDGF antibody showed similar IC50s in inhibiting rhPDGFBB binding to PDGFR, as shown in the following table, suggesting highly potent anti-PDGF activity.

| | IC50 (pM) | | |
|---|---|---|---|
| | OG1321 | OG1448 | Anti-PDGFBB |
| Competitive Binding to rhPDGFBB (vs rhPDGFR) | 46 ± 21* | 54 ± 21 | 66 |

*Mean and SD of at least 3 trials.

Example 37. OG1448—a Competitive Inhibitor of rhPDGF-BB Binding to rhPDGFR in the Presence of rhVEGFA-165

To evaluate whether OG1448 can bind rhPDGF-BB in the presence of rhVEGFA-165, a similar competitive inhibition of binding study towards PDGF (as Example 29) was performed in the presence and absence of rhVEGFA-165.

Human PDGFRb/Fc was coated onto the bottom of 96-well ELISA plates at 0.4 μg/mL. Various concentrations of OG1448 were incubated with 0.2 nM of PDGFBB and with 0.2 nM of PDGFRb plus rhVEGFA-165 at 0.2 nM, 0.6 nM and 1.0 nM, respectively, for 30 minutes before adding to the ELISA plates. PDGF-BB bind to PDGFRb was detected by biotinylated anti-PEGFBB antibody, 0.4 μg/mL, followed by streptavidin HRP and HRP substrate. The IC50 (pM) in the presence of rhVEGFA-165 (25) was comparable to the figure derived in Example 29. The figure for OG1321 in the presence of rhVEGFA-165 was not determined but is expected to be similar.

Example 38. Inhibition of VEGF-Induced Proliferation of Primary Human Retinal Microvascular Endothelial Cells (HRMVEC)

Endothelial cell proliferation is a crucial step in angiogenesis and hence in the pathogenesis of neovascular AMD. The ability of OG1448 to antagonize the proliferating action of VEGF on primary human retinal microvascular endothelial cells can be a measure of its bioactivity in treating neovascular AMD.

HRMVECs were stimulated with 1.3 nM of rhVEGF165-A for 3 days in the presence of various concentrations of TAF (OG1448 and OG1321) and reference drugs. Cell proliferation was measured by WST-1 cell proliferation detection reagent. Results are shown in the table below:

| | IC50 (nM) | | | | |
|---|---|---|---|---|---|
| | OG1321 | OG1448 | Ranibizumab | Bevacizumab | Aflibercept |
| Inhibition of VEGF induced proliferation of HRMVECs | 0.43 ± 0.05* | 0.49 ± 0.05* | 0.98 ± 1.21* | 0.81 ± 0.32* | 0.55 ± 0.08* |

*Mean and SD of at least 3 trials.

OG1448 and OG1321 demonstrated an IC50 in this assay comparable to other approved anti-VEGF therapies. These data show that TAF (both OG1448 and OG1321) has at least comparable potency to inhibit VEGF-mediated retinal microvascular endothelial cell proliferation activity as ranibizumab, bevacizumab and aflibercept.

Example 39. Inhibition of PDGF-Induced Proliferation of Primary Human Brain Vascular Pericytes (HBVP)

Pericyte migration and proliferation are crucial events in angiogenesis and hence play important roles in the pathogenesis of neovascular AMD. The ability of TAF (OG1448 and OG1321) to antagonize the proliferating action of PDGF on human brain pericytes can be a measure of its effectiveness in treating neovascular AMD.

HBVPs were stimulated with 2.0 nM of PDGFBB for 3 days in the presence of various concentrations of TAF (OG1449 and OG1321) and a reference anti-PDGF-BB antibody (R&D Systems, Catalog # AB-220-NA). Cell proliferation was measured by WST-1 cell proliferation detection reagent.

| | IC50 (nM) | | |
|---|---|---|---|
| | OG1321 | OG1448 | Anti-PDGF |
| Inhibition of PDGF induced proliferation of HPVPs | 5.0 ± 2.0* | 2.9 ± 1.4 | 5.4 |

*Mean and SD of at least 3 trials.

From the various experiments above comparing OG1321 (TAF443) to OG1448 (TAF443 polymer conjugate), it can be seen that conjugation to the HEMA-PC biopolymer does not negatively impact protein activity.

OG1448 and OG1321 show a comparable IC50 to the anti-PDGF antibody.

Example 40. Inhibition of Sprouting in Co-Culture of Human Retinal Microvascular Endothelial Cells (HRMVEC) and Human Mesenchymal Pericytes (HMPs)

To mimic in vivo conditions where endothelial cells and pericytes coexist in blood vessels and proliferate and migrate together during angiogenesis, events crucial in neovascular AMD, a three dimensional co-culture of HRMVECs and HMPs was established with the goal of evaluating the ability of OG1448 to inhibit angiogenesis in this complex model.

Vehicle, Avastin, an anti-PDGF-BB antibody (same as above), Avastin in combination with the anti-PDGF-BB antibody and OG1448 were added to the co-cultures on day 7. On day 14, immunohistochemical staining of CD31 (endothelial cells) and aSMA (pericytes) was used to quantify the lengths of sprouts emanating from established endothelial cell spheroids as compared across the experimental groups.

Figure 40:
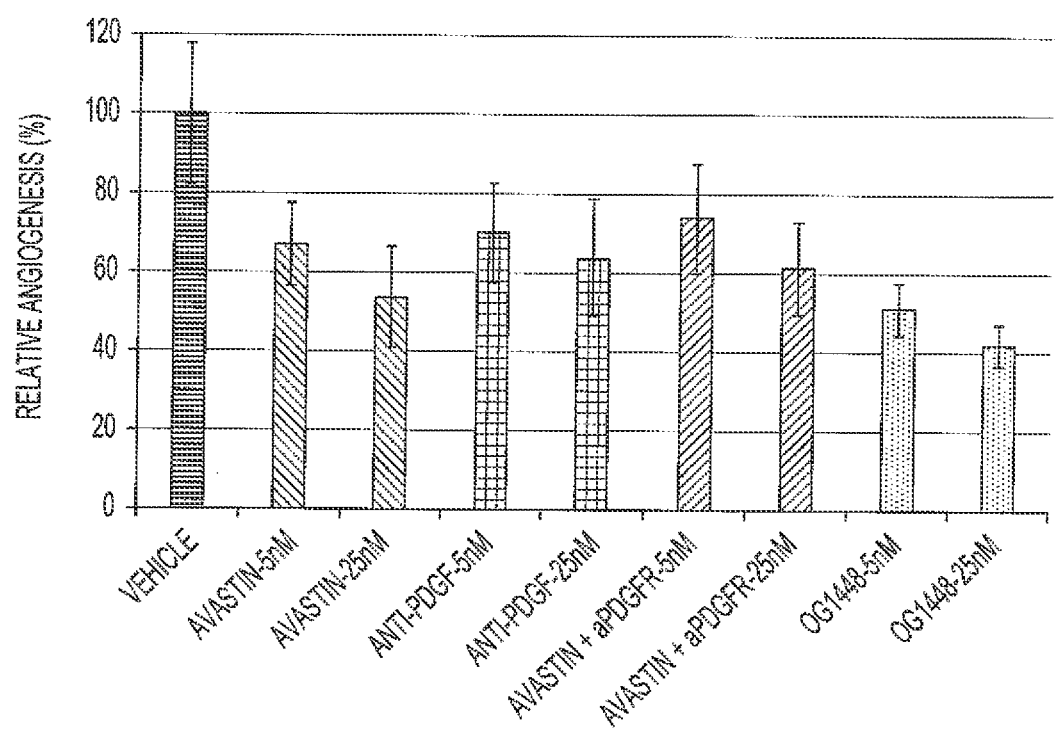
FIG. 40 shows relative angiogenesis using OG1448, Avastin, and an anti-PDGF-BB antibody and various combinations thereof.

OG1448 was more effective in inhibiting endothelial/pericyte sprouting in HRMVEC-HMP co-culture than Avastin alone or anti-PDGF alone at two different concentrations. Moreover, OG1448 was also more effective in inhibiting sprouting then a combination of Avastin and the anti-PDGF-BB antibody. This demonstrates that OG1448 is synergistic relative to Avastin and an anti-PDGF-BB antibody. The results are shown in the table below and in FIG. 40.

| Drug | Mean Total Sprout Length (pix) | S.D. (pix) | Relative Angiogenesis % | S.D. % |
|---|---|---|---|---|
| Vehicle | 6999 | 1266 | 100 | 18 |
| Avastin-5 nM | 4700 | 722 | 67 | 10 |
| Avastin-25 nM | 3763 | 909 | 54 | 13 |
| Anti-PDGF-5 nM | 4924 | 884 | 70 | 13 |
| Anti-PDGF-25 nM | 4461 | 1051 | 64 | 15 |
| Avastin + anti-PDGF-5 nM | 5197 | 948 | 74 | 14 |
| Avastin + anti-PDGF-25 nM | 4287 | 822 | 61 | 12 |
| OG1448-5 nM | 3584 | 478 | 51 | 7 |
| OG1448-25 nM | 2933 | 360 | 42 | 5 |

Example 41. Efficacy of OG1448 on Inhibition of Laser-Induced Choroidal Neovascularization in Cynomolgus Monkeys The in vivo efficacy of OG1448 was evaluated using the laser-induced choroidal neovascularization (CNV) model in cynomolgus monkeys, a well-recognized primate model of CNV. See, e.g., Nork T M, Dubielzig R R, Christian B J, et al. 2011. Prevention of experimental choroidal neovascularization and resolution of active lesions by VEGF trap in nonhuman primates. Arch Ophthalmol. 129: 1042-1052; Lloyd R L, Harris J, Wadhwa S, Chambers W. 2008. Food and Drug Administration approval process for ophthalmic drugs in the U.S. Curr Opin Ophthalmol. 19:190-194, both of which are hereby incorporated by reference. In this model, laser lesions are placed in the chorioretinal complex in the macula of the monkey eye with evidence of Bruch's membrane breakage. Choroidal neovascularization is developed in two to three weeks. At various time points, fluorescein angiography is used to evaluate the clinically relevant lesions (Grade IV) which show fluorescein leakage beyond the primary lesion. This CNV model has been used extensively for the study of CNV lesions and used as a benchmark for all currently approved treatment for neovascular AMD. In this model, all approved anti-VEGF agents for neovascular AMD are effective in inhibiting the leakage from the clinically relevant Grade IV lesions. The study was conducted at Covance, Madison, Wis.

In summary, a dose-related response to a single intravitreal injection of OG1448 at 0.5 or 2.4 mg/eye (calculated based on protein content) was observed in the animals in which CNV lesions were allowed to develop for 14 days before treatment and evaluated at subsequent time points using fluorescein angiography focusing on the clinically relevant Grade IV lesions on the retina/choroid. At 0.5 mg/eye, the beneficial effect on the Grade IV lesions was noticeable (p=0.019; generalized estimating equation [GEE] model; 0.5 mg treatment Group 7 vs PBS injected placebo Group 5). At 2.4 mg/eye OG1448, a dose (in molar equivalence) within the therapeutic dose of bevacizumab or aflibercept, was highly effective (75% reduction in Grade IV-CNV like lesions on Day 43 from Day 15 versus 27% reduction in the PBS-treated group) (p=0.0007; GEE model; 2.4 mg treatment Group 9 vs PBS injected placebo Group 5) in ameliorating the leakage of Grade IV-CNV lesions.

OG1448 shows effectiveness in inhibiting the leakage from the clinically relevant Grade IV lesion in this benchmark CNV model.

The groups and study design are shown in the following table. The study included groups for tolerability (Groups 1 thorough 4) however for purposes of this patent application only the groups for pharmacological activity and a control group treated with phosphate buffered saline (PBS) injection are shown.

| Group | No. of Females | Dose-Route | Dose Level mg/left eye/dose | mg/right eye/dose | mg/kg/dose | Dose Concentration (mg/ml) |
|---|---|---|---|---|---|---|
| 5 | 6 | Intra-vitreous[a] | 0 | 0 | NA | 0 |
| 6 | 6 | Intra-vitreous[a] | 0.24 | 0.24 | NA | 5.9 |
| 7 | 6 | Intra-vitreous[b] | 0.51 | 0.51 | NA | 10.2 |
| 9 | 6 | Intra-vitreous[b] | 2.40 | 2.40 | NA | 26.6 |

NA = not applicable
[a] = at days 1, 15, and 29 (a total of 3 doses); laser on day 8 of the dosing phase.
[b] = once; laser treatment on 15 days prior to injection Two treatment regimens were evaluated. In the prevention regimen, OG1448 was given intravitreally three times bilaterally at 0.24 mg/eye/dose (dose content was based on protein content; Group 6) or PBS (Group 5) on days 1, 15 and 29 with laser treatment on day 8 of the dosing phase. Fluorescein angiograms on days 15, 21, 30, 37 and 43 of laser treatment (days 22, 28, 37, 44 and 50 of the dosing phase) were used for evaluation of the clinically relevant Grade IV lesions.

In the treatment regimen (Groups 7 [0.5 mg], 8 [0.5 mg] and 9 [2.4 mg]), OG1448 was administered intravitreally to both eyes of 6 animals at doses of 0.5 mg (Groups 7 and 9) or 2.4 mg/eye (Group 9) 15 days after laser induction when CNV lesions were established. Fluorescein angiograms obtained at Days 15, 21, 30, 37 and 43 of laser treatment were used for evaluation of the clinically relevant Grade IV lesions.

Figure 41:
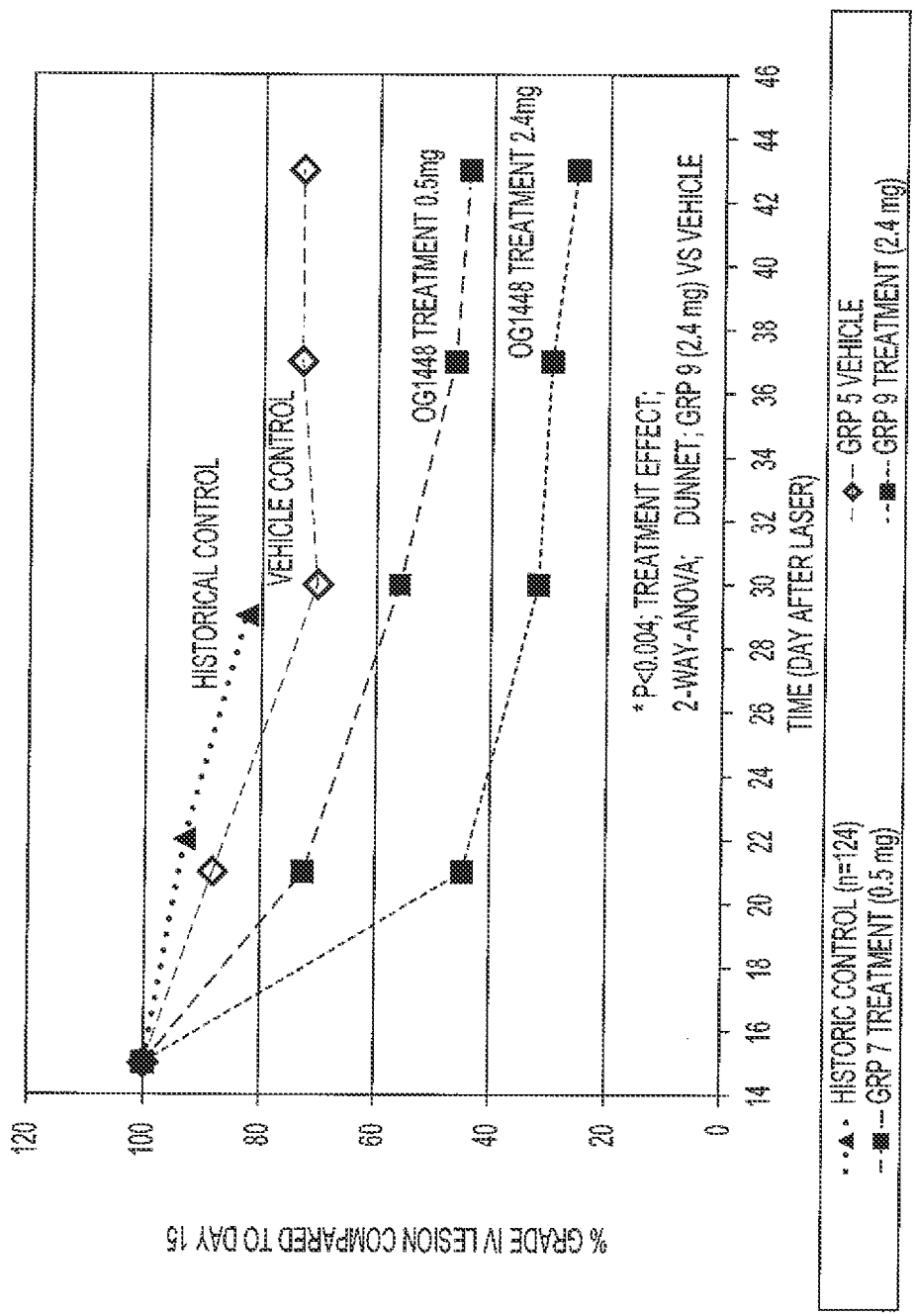
FIG. 41 shows the % grade IV lesions compared to day in the CNV monkey model for the compounds indicated.

Using generalized estimating equation (Gee) models (Halekoh, U & Yan J (2006) The R Package geepack for Generalized Estimating Equations Journal of Statistical Software 15, 2, pp 1-11), a dose-related response to OG1448 was observed in the intervention regimen. At 0.5 mg/eye, the effect was notable as shown by the difference in the percent change in Grade IV lesions as compared to the vehicle control (0.5 mg treatment Group 7 vs PBS injected placebo Group 5; p=0.019, GEE). With 2.4 mg/eye OG1448 (a dose in molar equivalence within the therapeutic dose of bevacizumab or aflibercept) a 75% reduction in percent change in Grade IV lesions (2.4 mg treatment Group 9 vs PBS injected placebo Group 5; p=0.0007, GEE) was observed on day 43 as compared to a 27% reduction in CNV in the PBS control group. The data from the various experiments in the monkey CNV model are shown in FIG. 41.

OG1448 shows dose dependent effectiveness in inhibiting the leakage from the clinically relevant Grade IV lesion in this CNV model. These results are consistent with the studies described above showing activity of OG1448 against VEGF-mediated angiogenic activities.

Example 42. Tissue Distribution and Pharmacokinetics

A tissue distribution and pharmacokinetic study using $^{125}$I-OG1448 was conducted using male New Zealand Red White F1 Cross pigmented rabbits. In summary, this study showed a vitreal half-life of 16.1 days for OG1448 in rabbits, approximately three times that reported for aflibercept (4.5 days) and 5 times that of ranibizumab (2.9 days) (Bakri S J, Snyder M R, Reid J M et al. 2007. Pharmacokinetics of Intravitreal Ranibizumab [Lucentis]. Ophthalmology 114:2179-2182) with little plasma exposure (approximately 0.2% of that of vitreous exposure) and a plasma half-life of 6.5 days (aflibercept reported 6.5 days) (Struble C, Koehler-Stec E, Zimmer E, and Tu W. 2008. Pharmacokinetics and ocular tissue penetration of VEGF Trap after intravitreal injections in rabbits. EVER; Portorz, Slovenia).

The purpose of this study was to assess the ocular distribution and pharmacokinetics of non-radiolabeled test articles and radiolabeled test articles following an intravitreal or intravenous dose administration to male New Zealand Red White F1 rabbits. Treatment groups and the study design are shown in the table below:

| Groups and Study Design (Covance study) | | | | | |
|---|---|---|---|---|---|
| Group | # of males | Dose Route | Test Article | Dose (mg) | Sample Collected |
| 1 | 14 | IVT | $^{125}$I-OG1448 | 0.25/eye (OU) | Blood, ocular tissues |
| 2 | 2 | IV | $^{125}$I-OG1448 | 0.25/animal | Blood |
| 3 | 6 | IVT | OG1448 | 0.25 (OD) | Blood, whole eyes for histology |
| 4 | 6 | IVT | OG1448 | 0.25 (OD) | Blood, vitreous humor |

IVT: intravitreal;
IV: intravenous;
OU: Both eyes;
OD: right eye

PK parameters were obtained based on radioanalysis. Clearance profiles from vitreous, retina and choroid were similar to one another. This pattern is consistent with other established CNV treatments such as ranibizumab or aflibercept. Set forth in the table below are pharmacokinetic parameters in different ocular tissues after single bilateral intravitreal injection of 0.25 mg $^{125}$I-OG1448.

| Matrix | $C_{MAX}$ (NG Eq./G) | $T_{1/2}$ (day) | $AUC_{0-\infty}$ (Day*NG EQ./G) | Exposure as % of vitreous exposure |
|---|---|---|---|---|
| Plasma | 494 | 6.48 | 3,790 | 0.189 |
| Aqueous humor | 5,250 | 11.6 | 68,800 | 3.423 |
| Choroid-RPE | 4,170 | 32.8 | 134,000 | 6.667 |
| Iris-ciliary body | 12,100 | 42.6 | 235,000 | 11.692 |
| Retina | 13,500 | 30.4 | 309,000 | 15.373 |
| Vitreous humor | 112,000 | 16.1 | 2,010,000 | 100.00 |

Figure 42:
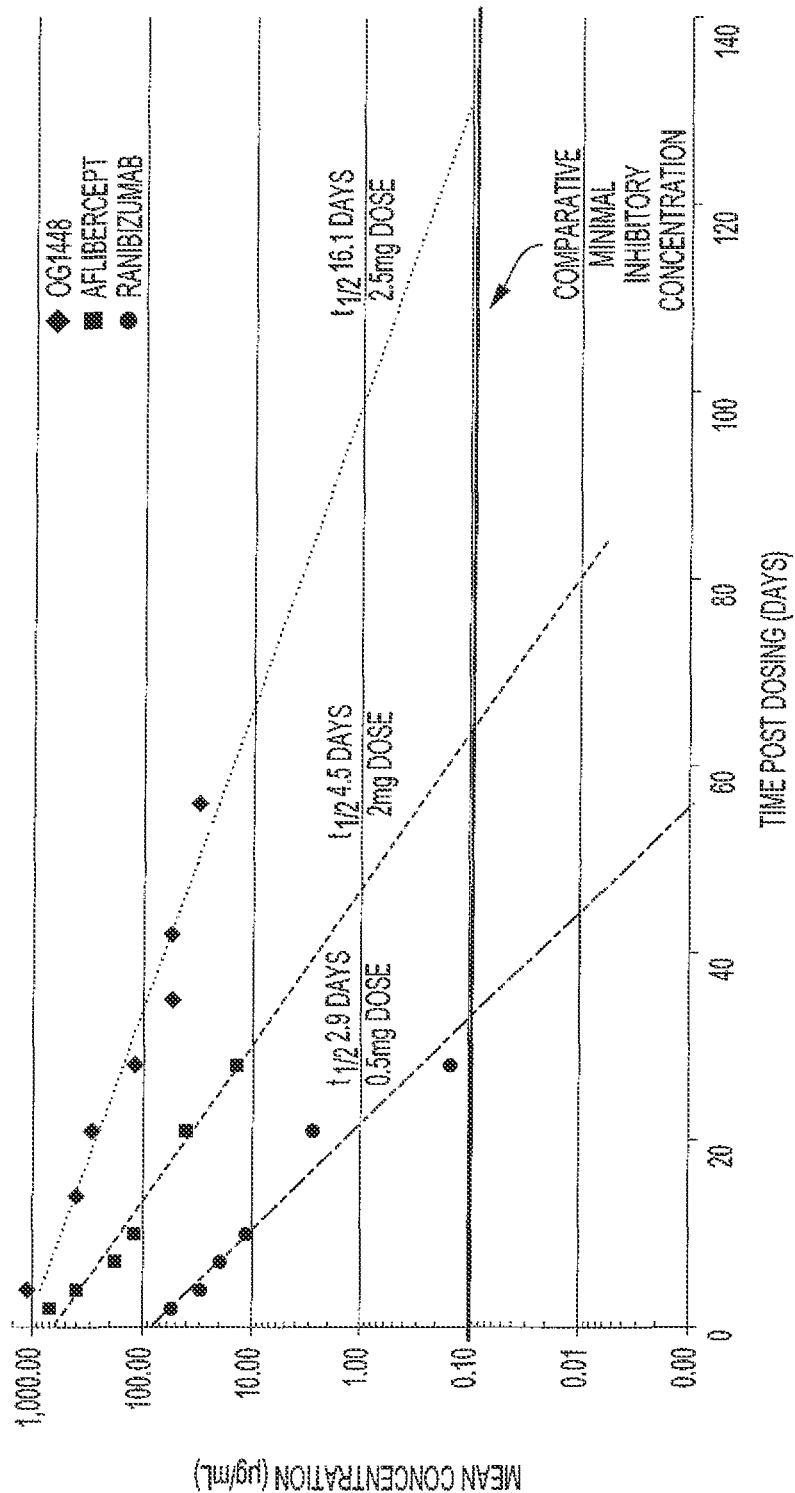
FIG. 42 shows OG1448 ocular pharmacokinetics versus aflibercept and ranibizumab in the rabbit vitreous.

The ocular tissue half-life of various VEGF inhibitors is compared with OG1448 in the table below and in FIG. 42, which suggests that OG1448 can stay above a pharmaceutically active minimal inhibitory concentration of 0.1 µg/ml for greater than 90 days, as opposed to 30 days for Lucentis and 50 days for Eylea:

| Ocular Tissue Elimination Half Life (Days) | | | |
|---|---|---|---|
| | Vitreous | Retina | Choroid |
| Pegaptinib[1] | 3.5 | — | — |
| Ranibizumab[1] | 2.9 | 2.9 | — |
| Aflibercept[1] | 4.5 | 5.5 | 4.8 |
| OG1448[2] | 16.1 | 30.5 | 32.9 |

[1]Based on publicly available data from 28-day rabbit studies: Drolet D W, Nelson J, Tucker C E, et al. 2000. Pharmacokinetics and safety of an anti-vascular endothelial growth factor Aptamer (NX 1828) following injection into the vitreous humor of rhesus monkeys. Pharm Res. 17: 1503-1510; Gaudreault J, Fei D, Beyer J C et al. 2007. Pharmacokinetics and retinal distribution of ranibizumab, a humanized antibody fragment directed against VEGF-A, following intravitreal administration in rabbits. Retina 27: 859-870; Bakri (2007), supra; Struble 2008, supra.
[2]Based on intravitreal injection of 250 µg in the rabbit eye.

The study showed a vitreal half-life of 16.1 days for OG1448 in rabbits, approximately three times the 4.5 day vitreal half-life reported for aflibercept and five times the vitreal half-life of ranibizumab (2.9 days) (Bakri 2007, supra) with low plasma exposure (approximately 0.2% of that of vitreous exposure); the plasma exposure is consistent to that of aflibercept (Sinapis C I, Routsias J G, Sinapis A I, et al. 2011. Pharmacokinetics of intravitreal bevacizumab [Avastin®] in rabbits. Clinical Ophthalmology 5:697-704).

Similar to the reported data for ranibizumab and aflibercept, the vitreal, retinal and choroidal clearance profiles are similar to one another.

Example 43. Toxicology

Two pilot non-GLP single dose ocular and systemic tolerability studies on OG1448 were conducted at Covance: (i) a single dose 57-day intravitreal or intravenous tolerability study in pigmented rabbits and (ii) a single dose tolerability study after intravitreal (58-day study) or intravenous (28-day study) administration in cynomolgus monkeys.

In brief, single dose intravitreal injection of 0.25 mg OG1448/dose/eye in rabbits was initially well tolerated but was associated with persistent anterior (mild to moderate conjunctival hyperemia, mild to moderate aqueous flare and cells) and posterior segment (mild to severe white vitreous cells, mild to moderate vitreous haze and presence of vitreous floaters, and multifocal grey-white subretinal inflammatory foci) inflammation which developed approximately two weeks postdose (or later). This inflammatory response improved with immune-suppressive and anti-inflammatory therapy. The time of onset post-dose and response to treatment are consistent with an immune-mediated response typical for intraocularly administered humanized biopharmaceuticals in animals.

In contrast, a single intravitreal dose at 0.24 or 1.4 mg OG1448/dose/eye was well tolerated in cynomolgus monkeys with no adverse finding or evidence of immune reactions ophthalmologically, clinically, and histopathologically.

In the efficacy study (discussed above), intravitreal injections of 0.24 mg/eye/dose for three times at 14 days apart or a single injection of 0.5 mg/eye/dose were well tolerated with at least 40 days of follow-up as shown on ocular examinations. No immune-related reactions were noted in the eyes of treated animals.

These studies demonstrate that OG1448 is well tolerated when administered intravitreally or intravenously at the doses evaluated.

Example 44. Single-Dose Tolerance in Cynomolgus Monkeys

The purpose of this part of the study was to evaluate tolerability of OG1448 after intravitreous or intravenous administration in cynomolgus monkeys.

Ocular and systemic tolerability groups and study design are shown in the table below:

| Group and Study Design | | | | | |
|---|---|---|---|---|---|
| | | | Dose Level[a,b] | | Dose Concentration (mg/ml) |
| Group | No. of females | Dose Route | μg/left eye/dose | mg/right eye/dose | mg/Kg/dose |
| 1 | 3 | IVT | 0 | 0.236 | NA | 5.9 |
| 2 | 3 | IVT | 0 | 1.36 | NA | 27.2 |
| 3 | 2 | IV | NA | NA | 0.235 | 9.4 |
| 4 | 2 | IV | NA | NA | 1.41 | 9.4 |

IVT = intravitreal;
IV = intravenous;
NA = not applicable
[a] The right eye of animals in Groups 1 and 2 received the test article via intravitreous injection. Animals in Groups 3 and 4 received the test article via colus intravenous injection.
[b] The left eye of animals in Groups 1 and 2 animals received vehicle control only (phosphate buffered saline, pH 74).

Ocular examinations by board certified veterinary ophthalmologists were performed across all four groups predose and (i) for intravitreal groups: on days 3, 8, 15, 29, 43 and 57, and (ii) for intravenous groups: on days 3, 8, 15, and 29. Animals were followed with clinical observations and clinical pathology on days 3, 8, 15, 29, 43 and 57 when applicable. Anatomic pathology was also performed—macroscopic observation during necropsy for all animals, and microscopic evaluations for ocular tissues for groups 1 and 2 (day 57) and for a standard list of systemic organs for groups 3 and 4 (day 29).

There were no adverse or toxicologically meaningful findings in any group. There were no findings in clinical observations and body weight in any group. There were no OG1448-related macroscopic or microscopic findings from anatomic pathology for any group (ocular tissues for intravitreally injected groups and standard list of organs/tissues for intravenously injected groups).

Ophthalmic findings for intravitreal administration groups were limited to injection-related events such as mild to moderate and transient presence of aqueous and/or vitreous cells and scars at the site of aqueous humor sampling.

Example 45. Synthesis of Polymer OG1786

Figure 30:
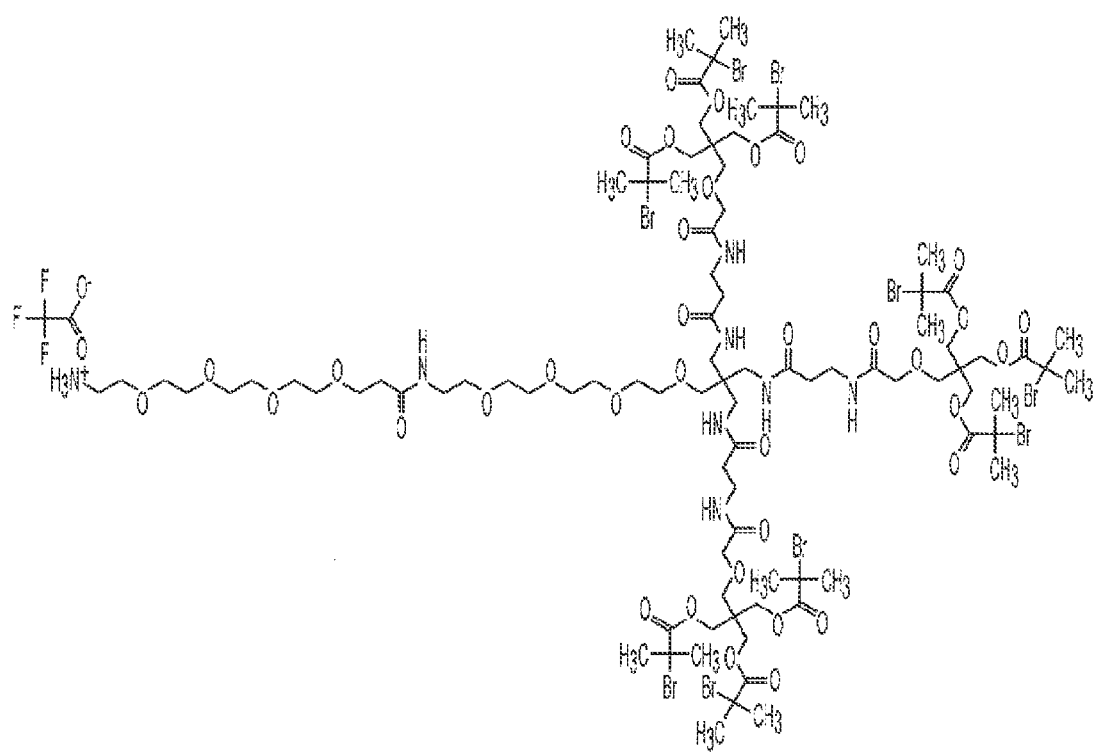
FIG. 30 shows OG1786.
Figure 31:
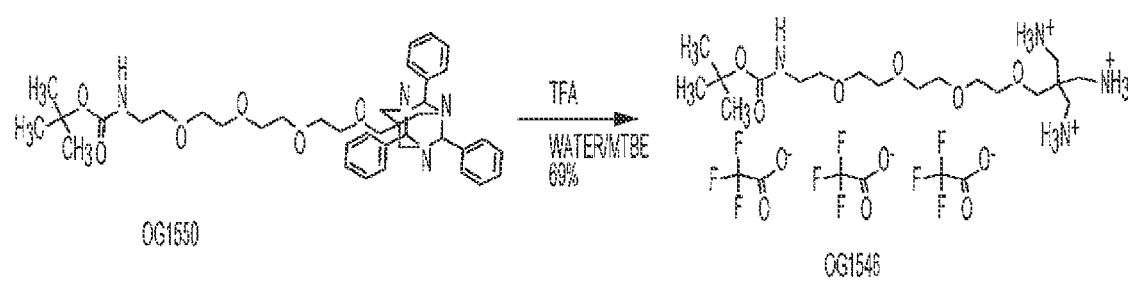
FIG. 31 shows the synthesis of OG1546 from OG1550.

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TFA) as shown in FIG. 30. OG1786 is prepared as follows. First, OG1550 is reacted with TFA (trifluoro acetic acid) to produce OG1546 as depicted in FIG. 31.

In a 1 L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH ~4, by pH paper).

The product was collected by lyophilization. 11.5 g white solid was obtained. This material is extremely hygroscopic, so best handled under nitrogen. The product was confirmed by LCMS.

Figure 32:
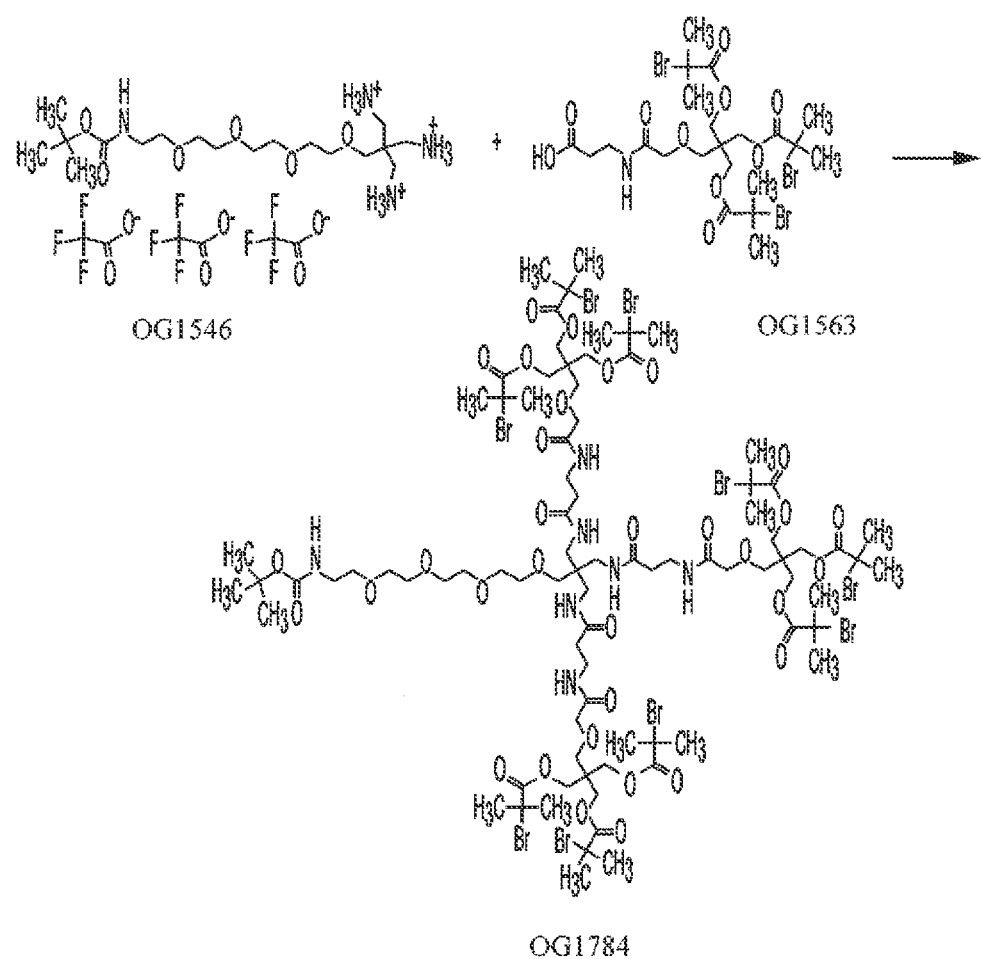
FIG. 32 shows the synthesis of OG1784 from OG1546 and OG1563.

The prepared OG1546 was then reacted with OG1563 to yield OG1784 (as depicted in FIG. 32).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH-3). The organic phase was washed with water/saturated sodium chloride (100 ml/25 ml), and the aqueous phase was AQ3 (pH-3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 µm, product number 02915-20). The filtrate was split into three equal portions and purified in three runs.

Loaded onto a RediSep Rf Gold C18 column (275 g, SN 69-2203-339, Lot#24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods.

| OG1784 lot | R5172 | R5228 |
|---|---|---|
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Figure 33:
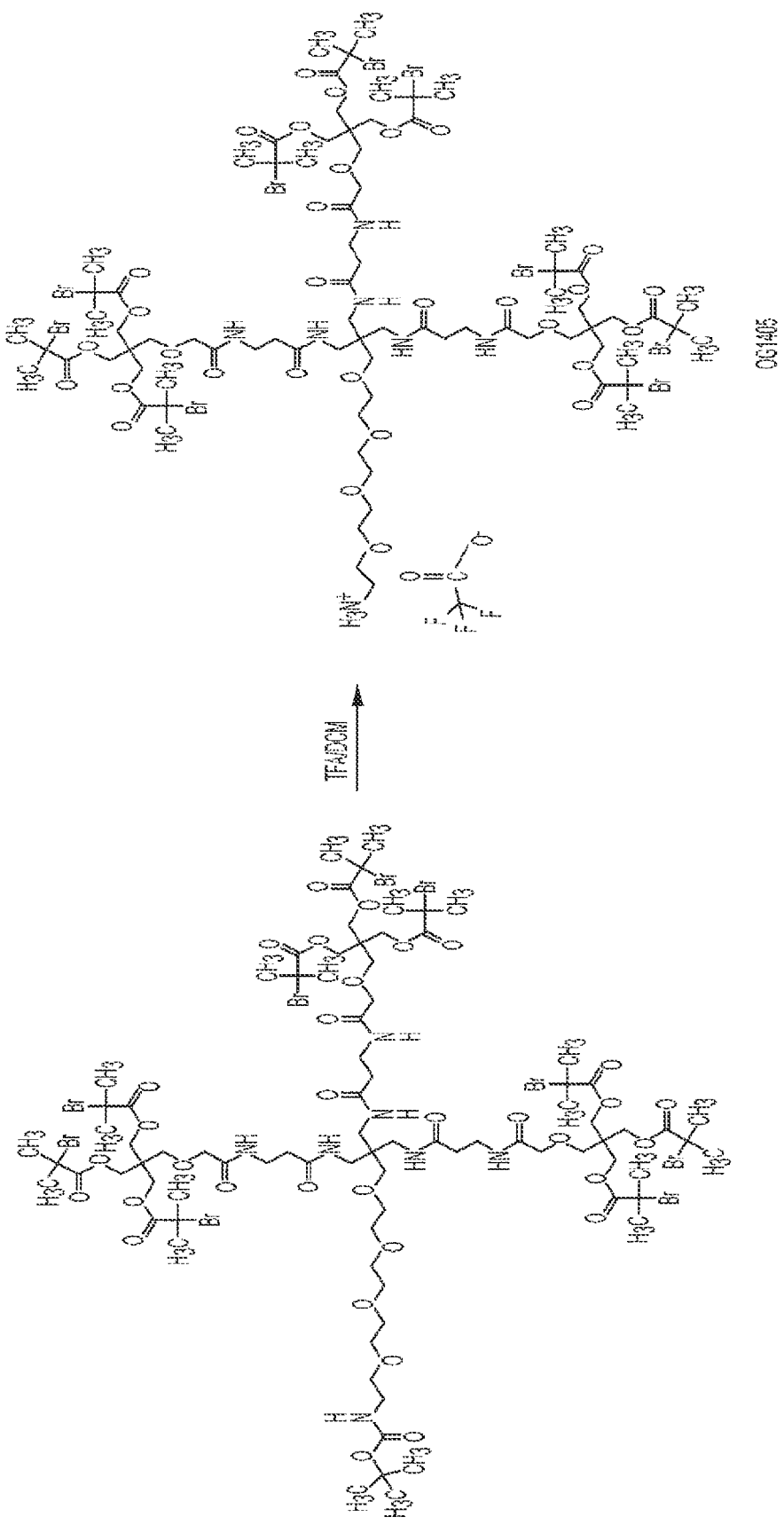
FIG. 33 shows the synthesis of OG1405 from OG1784.

Next OG1405 was prepared from OG1784 as depicted in FIG. 33. In a 500 ml round bottom flask equipped with a magnetic stir bar was added OG1784 (20.9 g), followed by dichloromethane (50 ml) then trifluoroacetic acid (20 ml). The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed.

Next, OG1405 was reacted with OG1402 to prepare OG1785 as set forth in FIG. 34. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml) and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 µm, product number 02915-20) and split into three equal portions, each of which were individually purified as follows.

Portions were loaded onto Redi-Sep Gold C18 column (275 g, SN—69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS: OG1785 was isolated as a foamy solid (R5329, 19.0 g, 83% yield, 95.1% purity (a/a 210 nm), stored under nitrogen at 4° C.

Next, the tert-butyloxycarbonyl protecting group on OG1785 was removed using trifluoroacetic acid (TFA) to produce OG1786 as depicted in FIG. 35.

Example 46. Synthesis of Polymer 1801

Compound OG1802 is conjugated to a sulfhydryl group of TAF443 to produce OG1448. Polymer OG1801 is made first from the initiator OG1786. OG1801 has an amine functionality, which is more stable (than maleimide) during polymer synthesis. To synthesize polymer OG1801, a modified version of ATRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL of DMF under room temperature to make 100 mg/mL stock solution; Sampled for initiator concentration and purity test; Added the initiator solution to the flask under Argon. The reaction solution became dark brown and started thickening over time; Sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, transferred all the fractions to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 47. Synthesis of Polymer OG1802

Starting materials and reagents needed in the reaction is calculated based on batch input of OG1801. The linker is 3-maleimidopropionic acid, NHS ester. Added 30 ml of 0.5 M sodium phosphate (in WFI, pH8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln; Added linker solution dropwise 815 uL per minute to the polymer sln with strong stirring. Took 5 min to added 4095 uL of linker solution. Reacted at room temperature for 30 min. Quenched reaction with 20 mL of 5% acetic acid to achieve a final pH of 5. Filtered the solution using 1 L vacuum filter (0.2 um).

OG1802 is then purified as follows: Milipore cross flow cassettes was used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 µM 1 L filter bottle. The polymer solution could be stored at 2-8° C. for up to 3 month before conjugation.

Example 48. Formulations of OG1448; Injectability 27.2 mg/ml and 44.5 mg/ml solutions of OG1448 were prepared using 1.7 mM $KH_2PO_4$; 5 mM $Na_2HPO_4$; 150 mM NaCl in sterile water for injection. The OG1448 conjugate was concentrated by a Millipore Pellicon XL TFF cartridge (catalog# PXBO30A50, EMD Millipore), 30 kD MWCO or VIVACELL 100 spin concentrator (catalog# VC1022, Sartorius), 30 kD MWCO, depending on the volume. The 27.2 mg/ml solution of TAF was injected intravitreally into the monkeys for the efficacy experiments described above through a 30 gauge (G) ½ inch needle. Excessive pressure was not required to push the OG1448 through the needle. The 44.5 mg/ml solution was tested for injectability in the laboratory and was also capable of being pushed through the needle without excessive pressure by a female operator.

Example 49. Storage Stability

An ongoing stability study was conducted using OG1448 reference lot R5606 at 44.5 mg/ml in PBS at pH 7.4 (as described above). Three temperatures were chosen for the study: room temperature (RT), 4° C. and −20° C. Sampling frequency is at 0, 14, 28, 91, 181 and 362 days. Samples were evaluated by SDS-PAGE and analytical AE-HPLC for unreacted and sequestered protein, and potential aggregates. It was observed (data not shown) that OG1448 demonstrates less than 5% protein impurity by AE-HPLC at all three temperatures up to six months, which is similar to the level at time 0. This study is ongoing.

Example 50. Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

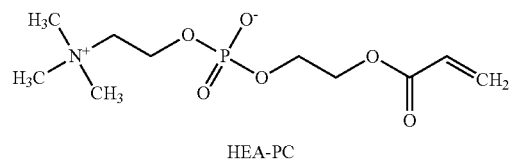 [SMILES: C=CC(=O)OCCOP(=O)([O-])OCC[N+](C)(C)C]

HEA-PC

HEA-PC was polymerized to the initiator shown in Example 23 as compound L.

| Reactant | Name | Amount | MW |
|---|---|---|---|
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-(dimethylamino)ethyl]amine (Me6TREN) | 2.73 mg | 230.39 |
| Solvent A | N,N-Dimethylformamide (DMF) | 21.85 µl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 µl of dry DMF and a 200 mg/ml solution of ligand by dissolving 4.6 mg of Me6TREN in 23 jut of dry DMF. Dispense 8.25 µl of the stock solution of initiator and 13.6 µl of the ligand into a tube. Degas at −78° C. for 5 mn then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at −78° C. Rinse the vial with 200 µl of methanol and add it inside the reactor at −78° C. and then 0.5 mL of distilled water then another 200 µl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 uL) was added. Another 2-3 ml of methanol was added and the catalyst was allowed to oxidize overnight at 4° C. Conversion determined by 1H NMR was estimated to be 94%.

The next day the polymer was dialyzed and subjected SEC/MALS analysis using Shodex SB806M_HQ column (7.8×300 mm) in 1×PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein, including TAF443.

Next, the maleimide Mal-PEG4-PFP (see Example 23 above) ester was snapped on to the HEA-PC polymer as shown in Example 23. The resulting maleimide functionalized HEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am-PC), having the following structure:

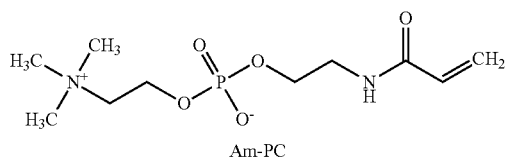 [SMILES: "Am-PC" ; C=CC(=O)NCCOP(=O)([O-])OCC[N+](C)(C)C]

Am-PC

The Am-PC was used for polymerization employing a 3 arm initiator (a TFA salt) having the structure:

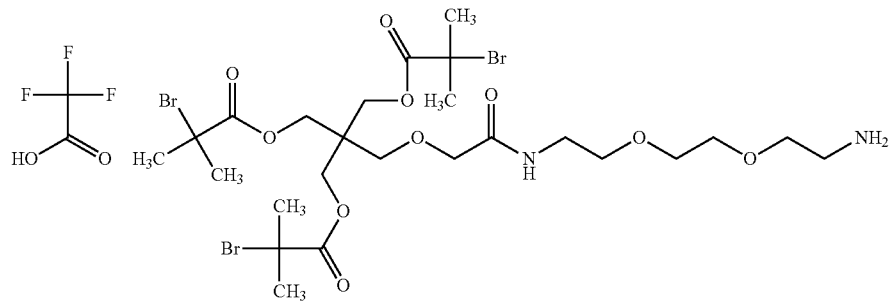

The synthesis of the Am-PC polymer was conducted as follows:

| Reactant | Name/Identity | Amount | MW |
|---|---|---|---|
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 230.39 |
| Solvent A | N,N-Dimethylformamide (DMF) | 31.7 µl | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 uL of dry DMF. Add 19.7 uL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 mn. Add 1 mg of CuBr. Prepared a stock solution of $CuBr_2$ at 200 mg/mL by dissolving 4 mg $CuBr_2$ in 20 µL of DMF. Add 0.5 g of monomer (AmPC) to 1 mL of methanol (slow dissolution/viscous solution), followed by 1 uL of the stock solution of $CuBr_2$. Add the monomer solution dropwise to the reaction mixture above. Rinse with 1 mL of water. Degas the reaction mixture thoroughly (freeze-thaw). Let the reaction proceed for 24 hours.

Afterwards the Am-PC polymer may be dialyzed. The molecular weight of the above polymer was determined by SEC/MALS: Mn is 215 kDa, Mp: 250 kDa, PDI is 1.17. Conversion was estimated by 1H NMR to be 94%. A maleimide functionality can be added to the Am-PC polymer as discussed above for HEMA-PC and HEA-PC. Maleimide functionalized Am-PC polymer can be conjugated to a protein, such as TAF443, as described above.

Example 51. Reverse Ellman's Assay for Calculating Free Maleimide in a Compound

After addition of the maleimide functionality to polymer OG1801 to form OG1802 (see above), an Ellman's assay is used to determine the amount of functional maleimide (i.e. conjugatable) in a sample. Thiol converts Ellman's reagent (DTNB) to TNB- then to TNB2- in water at neutral and alkaline pH, which gives off a yellow color (measured at 412 nm). A standard curve is established with cysteine. Since the maleimide reacts with thiol, this assay actually measures the thiol (cysteine) left. The inhibition is calculated as the (original thiol—thiol left after maleimide polymer addition)/ (original thiol) and is expressed as a percentage.

Reagents Employed in Assay: A standard curve was prepared using the cysteine from 62.5 µM to 2 µM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 µM of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

SEQUENCES

```
                                                                      SEQ ID NO. 1
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGSGGG  GSDIQMTQSP SSLSASVGDR VTITCSASQD

321 ISNYLNWYQQ KPGKAPKVLI YFTSSLHSGV PSRFSGSGSG TDFTLTISSL QPEDFATYYC QQYSTVPWTF GQGTKVEIKR

401 TVAAPSVFIF PPSDEQLKSG TASVVCLLNN FYPREAKVQW KVDNALQSGN SQESVTEQDS KDSTYSLSST LTLSKADYEK

481 HKVYACEVTH QGLSSPVTKS FNRGEC

SEQ ID NO. 2
  1 EVQLVESGGG LVQPGGSLRL SCAASGYTFT NYGMNWVRQA PGKGLEWVGW INTYTGEPTY AADFKRRFTF SLDTSKSTAY

81 LQMNSLRAED TAVYYCAKYP HYYGSSHWYF DVWGQGTLVT VSSASTKGPS VFPLAPSSKS TSGGTAALGC LVKDYFPEPV

161 TVSWNSGALT SGVHTFPAVL QSSGLYSLSS VVTVPSSSLG TQTYICNVNH KPSNTKVDKK VEPKSCDKTH TCPPCPAPEL

241 LGGPSVFLFP PKPKDTLMIS RTPEVTCVVV DVSHEDPEVK FNWYVDGVEV HNAKTKPREE QYNSTYRVVS VLTVLHQDWL

321 NGKEYKCKVS NKALPAPIEK TISKAKGQPR EPQVYTLPPS REEMTKNQVS LTCLVKGFYP SDIAVEWESN GQPENNYKTT

401 PPVLDSDGSF FLYSKLTVDK SRWQQGNVFS CSVMHEALHN HYTQKSLSLS PGK

SEQ ID NO. 3
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGDIQMTQ SPSSLSASVG DRVTITCSAS QDISNYLNWY

321 QQKPGKAPKV LIYFTSSLHS GVPSRFSGSG SGTDFTLTIS SLQPEDFATY YCQQYSTVPW TFGQGTKVEI KRTVAAPSVF

401 IFPPSDEQLK SGTASVVCLL NNFYPREAKV QWKVDNALQS GNSQESVTEQ DSKDSTYSLS STLTLSKADY EKHKVYACEV

481 THQGLSSPVT KSFNRGEC

SEQ ID NO. 4
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGSGGG  GSEVQLVESG GGLVQPGGSL RLSCAASGYT

321 FTNYGMNWVR QAPGKGLEWV GWINTYTGEP TYAADFKRRF TFSLDTSKST AYLQMNSLRA EDTAVYYCAK YPHYYGSSHW

401 YFDVWGQGTL VTVSSASTKG PSVFPLAPSS KSTSGGTAAL GCLVKDYFPE PVTVSWNSGA LTSGVHTFPA VLQSSGLYSL

481 SSVVTVPSSS LGTQTYICNV NHKPSNTKVD KKVEPKSCDK THTCPPCPAP ELLGGPSVFL FPPKPKDTLM ISRTPEVTCV

561 VVDVSHEDPE VKFNWYVDGV EVHNAKTKPR EEQYNSTYRV VSVLTVLHQD WLNGKEYKCK VSNKALPAPI EKTISKAKGQ

641 PREPQVYTLP PSREEMTKNQ VSLTCLVKGF YPSDIAVEWE SNGQPENNYK TTPPVLDSDG SFFLYSKLTV DKSRWQQGNV

721 FSCSVMHEAL HNHYTQKSLS LSPGK
```

```
                                                              SEQ ID NO. 5
  1 DIQMTQSPSS LSASVGDRVT ITCSASQDIS NYLNWYQQKP GKAPKVLIYF TSSLHSGVPS RFSGSGSGTD FTLTISSLQP

81 EDFATYYCQQ YSTVPWTFGQ GTKVEIKRTV AAPSVFIFPP SDEQLKSGTA SVVCLLNNFY PREAKVQWKV DNALQSGNSQ

161 ESVTEQDSKD STYSLSSTLT LSKADYEKHK VYACEVTHQG LSSPVTKSFN RGEC
                                                              SEQ ID NO. 6
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGEVQLVE SGGGLVQPGG SLRLSCAASG YTFTNYGMNW

321 VRQAPGKGLE WVGWINTYTG EPTYAADFKR RFTFSLDTSK STAYLQMNSL RAEDTAVYYC AKYPHYYGSS HWYFDVWGQG

401 TLVTVSSAST KGPSVFPLAP SSKSTSGGTA ALGCLVKDYF PEPVTVSWNS GALTSGVHTF PAVLQSSGLY SLSSVVTVPS

481 SSLGTQTYIC NVNHKPSNTK VDKKVEPKSC DKTHTCPPCP APELLGGPSV FLFPPKPKDT LMISRTPEVT CVVVDVSHED

561 PEVKFNWYVD GVEVHNAKTK PREEQYNSTY RVVSVLTVLH QDWLNGKEYK CKVSNKALPA PIEKTISKAK GQPREPQVYT

641 LPPSREEMTK NQVSLTCLVK GFYPSDIAVE WESNGQPENN YKTTPPVLDS DGSFFLYSKL TVDKSRWQQG NVFSCSVMHE

721 ALHNHYTQKS LSLSPGK
                                                              SEQ ID NO. 7
  1 EVQLVESGGG LVQPGGSLRL SCAASGYTFT NYGMNWVRQA PGKGLEWVGW INTYTGEPTY AADFKRRFTF SLDTSKSTAY

81 LQMNSLRAED TAVYYCAKYP HYYGSSHWYF DVWGQGTLVT VSSASTKGPS VFPLAPSSKS TSGGTAALGC LVKDYFPEPV

161 TVSWNSGALT SGVHTFPAVL QSSGLYSLSS VVTVPSSSLG TQTYICNVNH KPSNTKVDKK VEPKSCDKTH TCPPCPAPEL

241 LGGPSVFLFP PKPKDTLMIS RTPEVTCVVV DVSHEDPEVK FNWYVDGVEV HNAKTKPREE QYNSTYRVVS VLTVLHQDWL

321 NGKEYKCKVS NKALPAPIEK TISKAKGQPR EPQVYTLPPS REEMTKNQVS LTCLVKGFYP SDIAVEWESN GQPENNYKTT

401 PPVLDSDGSF FLYSKLTVDK SRWQQGNVFS CSVMHEALHN HYTQKSLSLS PGGGGGSGGG GSGGGGSGGG GSGLVVTPPG

481 PELVLNVSST FVLTCSGSAP VVWERMSQEP PQEMAKAQDG TFSSVLTLTN LTGLDTGEYF CTHNDSRGLE TDERKRLYIF

561 VPDPTVGFLP NDAEELFIFL TEITEITIPC RVTDPQLVVT LHEKKGDVAL PVPYDHQRGF SGIFEDRSYI CKTTIGDREV

641 DSDAYYVYRL QVSSINVSVN AVQTVVRQGE NITLMCIVIG NEVVNFEWTY PRKESGRLVE PVTDFLLDMP YHIRSILHIP

721 SAELEDSGTY TCNVTESVND HQDEKAINIT VVESG
                                                              SEQ ID NO. 8
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGSGGG GSEVQLVESG GGLVQPGGSL RLSCAASGYD

321 FTHYGMNWVR QAPGKGLEWV GWINTYTGEP TYAADFKRRF TFSLDTSKST AYLQMNSLRA EDTAVYYCAK YPYYGTSHW

401 YFDVWGQGTL VTVSSASTKG PSVFPLAPSS KSTSGGTAAL GCLVKDYFPE PVTVSWNSGA LTSGVHTFPA VLQSSGLYSL

481 SSVVTVPSSS LGTQTYICNV NHKPSNTKVD KKVEPKSCDK THTCPPCPAP EAAGAPSVFL FPPKPKDTLM ISRTPEVTCV

561 VVDVSHEDPE VKFNWYVDGV EVHNAKTKPR EEQYNSTYRV VSVLTVLHQD WLNGKEYKCK VSNKALPAPI EKTISKAKGQ

641 PREPCVYTLP PSREEMTKNQ VSLTCLVKGF YPSDIAVEWE SNGQPENNYK TTPPVLDSDG SFFLYSKLTV DKSRWQQGNV

721 FSCSVMHEAL HNHYTQKSLS LSPGK
                                                              SEQ ID NO. 9
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGSGGG GSEVQLVESG GGLVQPGGSL RLSCAASGYD

321 FTHYGMNWVR QAPGKGLEWV GWINTYTGEP TYAADFKRRF TFSLDTSKST AYLQMNSLRA EDTAVYYCAK YPYYGTSHW
```

```
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THTCPPCPAP EAAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPQVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS CSPGK
```

SEQ ID NO. 10
```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC
```

SEQ ID NO. 11
```
  1 MRLPGAMPAL ALKGELLLLS LLLLLEPQIS QGLVVTPPGP ELVLNVSSTF VLTCSGSAPV VWERMSQEPP QEMAKAQDGT
 81 FSSVLTLTNL TGLDTGEYFC THNDSRGLET DERKRLYIFV PDPTVGFLPN DAEELFIFLT EITEITIPCR VTDPQLVVTL
161 HEKKGDVALP VPYDHQRGFS GIFEDRSYIC KTTIGDREVD SDAYYVYRLQ VSSINVSVNA VQTVVRQGEN ITLMCIVIGN
241 EVVNFEWTYP RKESGRLVEP VTDFLLDMPY HIRSILHIPS AELEDSGTYT CNVTESVNDH QDEKAINITV VESGYVRLLG
321 EVGTLQFAEL HRSRTLQVVF EAYPPPTVLW FKDNRTLGDS SAGEIALSTR NVSETRYVSE LTLVRVKVAE AGHYTMRAFH
401 EDAEVQLSFQ LQINVPVRVL ELSESHPDSG EQTVRCRGRG MPQPNIIWSA CRDLKRCPRE LPPTLLGNSS EEESQLETNV
481 TYWEEEQEFE VVSTLRLQHV DRPLSVRCTL RNAVGQDTQE VIVVPHSLPF KVVVISAILA LVVLTIISLI ILIMLWQKKP
561 RYEIRWKVIE SVSSDGHEYI YVDPMQLPYD STWELPRDQL VLGRTLGSGA FGQVVEATAH GLSHSQATMK VAVKMLKSTA
641 RSSEKQALMS ELKIMSHLGP HLNVVNLLGA CTKGGPIYII TEYCRYGDLV DYLHRNKHTF LQHHSDKRRP PSAELYSNAL
721 PVGLPLPSHV SLTGESDGGY MDMSKDESVD YVPMLDMKGD VKYADIESSN YMAPYDNYVP SAPERTCRAT LINESPVLSY
801 MDLVGFSYQV ANGMEFLASK NCVHRDLAAR NVLICEGKLV KICDFGLARD IMRDSNYISK GSTFLPLKWM APESIFNSLY
881 TTLSDVWSFG ILLWEIFTLG GTPYPELPMN EQFYNAIKRG YRMAQPAHAS DEIYEIMQKC WEEKFEIRPP FSQLVLLLER
961 LLGEGYKKKY QQVDEEFLRS DHPAILRSQA RLPGFHGLRS PLDTSSVLYT AVQPNEGDND YIIPLPDPKP EVADEGPLEG
1041 SPSLASSTLN EVNTSSTISC DSPLEPQDEP EPEPQLELQV EPEPELEQLP DSGCPAPRAE AEDSFL
```

SEQ ID NO. 12
```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC
```

SEQ ID NO. 13
```
  1 EVQLVESGGG LVQPGGSLRL SCAASGYDFT HYGMNWVRQA PGKGLEWVGW INTYTGEPTY AADFKRRFTF SLDTSKSTAY
 81 LQMNSLRAED TAVYYCAKYP YYYGTSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH L
```

SEQ ID NO. 14
```
  1 MVSYWDTGVL LCALLSCLLL TGSSSGSKLK DPELSLKGTQ HIMQAGQTLH LQCRGEAAHK WSLPEMVSKE SERLSITKSA
 81 CGRNGKQFCS TLTLNTAQAN HTGFYSCKYL AVPTSKKKET ESAIYIFISD TGRPFVEMYS EIPEIIHMTE GRELVIPCRV
161 TSPNITVTLK KFPLDTLIPD GKRIIWDSRK GFIISNATYK EIGLLTCEAT VNGHLYKTNY LTHRQTNTII DVQISTPRPV
241 KLLRGHTLVL NCTATTPLNT RVQMTWSYPD EKNKRASVRR RIDQSNSHAN IFYSVLTIDK MQNKDKGLYT CRVRSGPSFK
321 SVNTSVHIYD KAFITVKHRK QQVLETVAGK RSYRLSMKVK AFPSPEVVWL KDGLPATEKS ARYLTRGYSL IIKDVTEEDA
401 GNYTILLSIK QSNVFKNLTA TLIVNVKPQI YEKAVSSFPD PALYPLGSRQ ILTCTAYGIP QPTIKWFWHP CNHNHSEARC
481 DFCSNNEESF ILDADSNMGN RIESITQRMA IIEGKNKMAS TLVVADSRIS GIYICIASNK VGTVGRNISF YITDVPNGFH
561 VNLEKMPTEG EDLKLSCTVN KFLYRDVTWI LLRTVNNRTM HYSISKQKMA ITKEHSITLN LTIMNVSLQD SGTYACRARN
641 VYTGEEILQK KEITIRDQEA PYLLRNLSDH TVAISSSTTL DCHANGVPEP QITWFKNNHK IQQEPGIILG PGSSTLFIER
721 VTEEDEGVYH CKATNQKGSV ESSAYLTVQG TSDKSNLELI TLTCTCVAAT LFWLLLTLFI RKMKRSSSEI KTDYLSIIMD
```

```
 801 PDEVPLDEQC ERLPYDASKW EFARERLKLG KSLGRGAFGK VVQASAFGIK KSPTCRTVAV KMLKEGATAS EYKALMTELK

881 ILTHIGHHLN VVNLLGACTK QGGPLMVIVE YCKYGNLSNY LKSKRDLFFL NKDAALHMEP KKEKMEPGLE QGKKPRLDSV

961 TSSESFASSG FQEDKSLSDV EEEEDSDGFY KEPITMEDLI SYSFQVARGM EFLSSRKCIH RDLAARNILL SENNVVKICD

1041 FGLARDIYKN PDYVRKGDTR LPLKWMAPES IFDKIYSTKS DVWSYGVLLW EIFSLGGSPY PGVQMDEDFC SRLREGMRMR

1121 APEYSTPEIY QIMLDCWHRD PKERPRFAEL VEKLGDLLQA NVQQDGKDYI PINAILTGNS GFTYSTPAFS EDFFKESISA

1201 PKFNSGSSDD VRYVNAFKFM SLERIKTFEE LLPNATSMFD DYQGDSSTLL ASPMLKRFTW TDSKPKASLK IDLRVTSKSK

1281 ESGLSDVSRP SFCHSSCGHV SEGKRRFTYD HAELERKIAC CSPPPDYNSV VLYSTPPI
```

```
                                                                                    SEQ ID NO. 15
   1 MQSKVLLAVA LWLCVETRAA SVGLPSVSLD LPRLSIQKDI LTIKANTTLQ ITCRGQRDLD WLWPNNQSGS EQRVEVTECS

81 DGLFCKTLTI PKVIGNDTGA YKCFYRETDL ASVIYVYVQD YRSPFIASVS DQHGVVYITE NKNKTVVIPC LGSISNLNVS

161 LCARYPEKRF VPDGNRISWD SKKGFTIPSY MISYAGMVFC EAKINDESYQ SIMYIVVVG YRIYDVVLSP SHGIELSVGE

241 KLVLNCTART ELNVGIDFNW EYPSSKHQHK KLVNRDLKTQ SGSEMKKFLS TLTIDGVTRS DQGLYTCAAS SGLMTKKNST

321 FVRVHEKPFV AFGSGMESLV EATVGERVRI PAKYLGYPPP EIKWYKNGIP LESNHTIKAG HVLTIMEVSE RDTGNYTVIL

401 TNPISKEKQS HVVSLVVYVP PQIGEKSLIS PVDSYQYGTT QTLTCTVYAI PPPHHIHWYW QLEEECANEP SQAVSVTNPY

481 PCEEWRSVED FQGGNKIEVN KNQFALIEGK NKTVSTLVIQ AANVSALYKC EAVNKVGRGE RVISFHVTRG PEITLQPDMQ

561 PTEQESVSLW CTADRSTFEN LTWYKLGPQP LPIHVGELPT PVCKNLDTLW KLNATMFSNS TNDILIMELK NASLQDQGDY

641 VCLAQDRKTK KRHCVVRQLT VLERVAPTIT GNLENQTTSI GESIEVSCTA SGNPPPQIMW FKDNETLVED SGIVLKDGNR

721 NLTIRRVRKE DEGLYTCQAC SVLGCAKVEA FFIIEGAQEK TNLEIIILVG TAVIAMFFWL LLVIILRTVK RANGGELKTG

801 YLSIVMDPDE LPLDEHCERL PYDASKWEFP RDRLKLGKPL GRGAFGQVIE ADAFGIDKTA TCRTVAVKML KEGATHSEHR

881 ALMSELKILI HIGHHLNVVN LLGACTKPGG PLMVIVEFCK FGNLSTYLRS KRNEFVPYKT KGARFRQGKD YVGAIPVDLK

961 RRLDSITSSQ SSASSGFVEE KSLSDVEEEE APEDLYKDFL TLEHLICYSF QVAKGMEFLA SRKCIHRDLA ARNILLSEKN

1041 VVKICDFGLA RDIYKDPDYV RKGDARLPLK WMAPETIFDR VYTIQSDVWS FGVLLWEIFS LGASPYPGVK IDEEFCRRLK

1121 EGTRMRAPDY TTPEMYQTML DCWHGEPSQR PTFSELVEHL GNLLQANAQQ DGKDYIVLPI SETLSMEEDS GLSLPTSPVS

1201 CMEEEEVCDP KFHYDNTAGI SQYLQNSKRK SRPVSVKTFE DIPLEEPEVK VIPDDNQTDS GMVLASEELK TLEDRTKLSP

1281 SFGGMVPSKS RESVASEGSN QTSGYQSGYH SDDTDTTVYS SEEAELLKLI EIGVQTGSTA QILQPDSGTT LSSPPV
```

```
                                                                                    SEQ ID NO. 16
   1 MQRGAALCLR LWLCLGLLDG LVSGYSMTPP TLNITEESHV IDTGDSLSIS CRGQHPLEWA WPGAQEAPAT GDKDSEDTGV

81 VRDCEGTDAR PYCKVLLLHE VHANDTGSYV CYYKYIKARI EGTTAASSYV FVRDFEQPFI NKPDTLLVNR KDAMWVPCLV

161 SIPGLNVTLR SQSSVLWPDG QEVVWDDRRG MLVSTPLLHD ALYLQCETTW GDQDFLSNPF LVHITGNELY DIQLLPRKSL

241 ELLVGEKLVL NCTVWAEFNS GVTFDWDYPG KQAERGKWVP ERRSQQTHTE LSSILTIHNV SQHDLGSYVC KANNGIQRFR

321 ESTEVIVHEN PFISVEWLKG PILEATAGDE LVKLPVKLAA YPPPEFQWYK DGKALSGRHS PHALVLKEVT EASTGTYTLA

401 LWNSAAGLRR NISLELVVNV PPQIHEKEAS SPSIYSRHSR QALTCTAYGV PLPLSIQWHW RPWTPCKMFA QRSLRRRQQQ

481 DLMPQCRDWR AVTTQDAVNP IESLDTWTEF VEGKNKTVSK LVIQNANVSA MYKCVVSNKV GQDERLIYFY VTTIPDGFTI

561 ESKPSEELLE GQPVLLSCQA DSYKYEHLRW YRLNLSTLHD AHGNPLLLDC KNVHLFATPL AASLEEVAPG ARHATLSLSI

641 PRVAPEHEGH YVCEVQDRRS HDKHCHKKYL SVQALEAPRL TQNLTDLLVN VSDSLEMQCL VAGAHAPSIV WYKDERLLEE

721 KSGVDLADSN QKLSIQRVRE EDAGRYLCSV CNAKGCVNSS ASVAVEGSED KGSMEIVILV GTGVIAVFFW VLLLLIFCNM

801 RRPAHADIKT GYLSIIMDPG EVPLEEQCEY LSYDASQWEF PRERLHLGRV LGYGAFGKVV EASAFGIHKG SSCDTVAVKM

881 LKEGATASEH RALMSELKIL IHIGNHLNVV NLLGACTKPQ GPLMVIVEFC KYGNLSNFLR AKRDAFSPCA EKSPEQRGRF

961 RAMVELARLD RRRPGSSDRV LFARFSKTEG GARRASPDQE AEDLWLSPLT MEDLVCYSFQ VARGMEFLAS RKCIHRDLAA

1041 RNILLSESDV VKICDFGLAR DIYKDPDYVR KGSARLPLKW MAPESIFDKV YTTQSDVWSF GVLLWEIFSL GASPYPGVQI

1121 NEEFCQRLRD GTRMRAPELA TPAIRRIMLN CWSGDPKARP AFSELVEILG DLLQGRGLQE EEEVCMAPRS QQSSEEGSFS

1201 QVSTMALHIA QADAEDSPPS LQRHSLAARY YNWVSFPGCL ARGAETRGSS RMKTFEEFPM TPTTYKGSVD NQTDSGMVLA
```

```
1281 SEEFEQIESR HRQESGFSCK GPGQNVAVTR AHPDSQGRRR RPERGARGGQ VFYNSEYGEL SEPSEEDHCS PSARVTFFTD
1361 NSY
```

SEQ ID NO. 17
```
   1 ASTKGPSVFP LAPSSKSTSG GTAALGCLVK DYFPEPVTVS WNSGALTSGV HTFPAVLQSS GLYSLSSVVT VPSSSLGTQT
  81 YICNVNHKPS NTKVDKKVEP KSCDKTHTCP PCPAPELLGG PSVFLFPPKP KDTLMISRTP EVTCVVVDVS HEDPEVKFNW
 161 YVDGVEVHNA KTKPREEQYN STYRVVSVLT VLHQDWLNGK EYKCKVSNKA LPAPIEKTIS KAKGQPREPQ VYTLPPSRDE
 241 LTKNQVSLTC LVKGFYPSDI AVEWESNGQP ENNYKTTPPV LDSDGSFFLY SKLTVDKSRW QQGNVFSCSV MHEALHNHYT
 321 QKSLSLSPGK
```

SEQ ID NO. 18
```
   1 TVAAPSVFIF PPSDEQLKSG TASVVCLLNN FYPREAKVQW KVDNALQSGN SQESVTEQDS KDSTYSLSST LTLSKADYEK
  81 HKVYACEVTH QGLSSPVTKS FNRGEC
```

SEQ ID NO. 19
```
   1 LVVTPPGPEL VLNVSSTFVL TCSGSAPVVW ERMSQEPPQE MAKAQDGTFS SVLTLTNLTG LDTGEYFCTH NDSRGLETDE
  81 RKRLYIFVPD PTVGFLPNDA EELFIFLTEI TEITIPCRVT DPQLVVTLHE KKGDVALPVP YDHQRGFSGI FEDRSYICKT
 161 TIGDREVDSD AYYVYRLQVS SINVSVNAVQ TVVRQGENIT LMCIVIGNEV VNFEWTYPRK ESGRLVEPVT DFLLDMPYHI
 241 RSILHIPSAE LEDSGTYTCN VTESVNDHQD EKAINITVVE SGGGGGSGGG GSDIQMTQSP SSLSASVGDR VTITCSASQD
 321 ISNYLNWYQQ KPGKAPKVLI YFTSSLHSGV PSRFSGSGSG TDFTLTISSL QPEDFATYYC QQYSTVPWTF GQGTKVEIKR
 401 TVAAPSVFIF PPSDEQLKSG TASVVCLLNN FYPREAKVQW KVDNALQSGN SQESVTEQDS KDSTYSLSST LTLSKADYEK
 481 HKVYACEVTH QGLSSPVTKS FNRGEC
```

SEQ ID NO. 21
```
   1 EVQLVESGGG LVQPGGSLRL SCAASGYTFT NYGMNWVRQA PGKGLEWVGW INTYTGEPTY AADFKRRFTF SLDTSKSTAY
  81 LQMNSLRAED TAVYYCAKYP HYYGSSHWYF DVWGQGTLVT VSSASTKGPS VFPLAPSSKS TSGGTAALGC LVKDYFPEPV
 161 TVSWNSGALT SGVHTFPAVL QSSGLYSLSS VVTVPSSSLG TQTYICNVNH KPSNTKVDKK VEPKSCDKTH T
```

SEQ ID NO. 22
```
   1 LVVTPPGPEL VLNVSSTFVL TCSGSAPVVW ERMSQEPPQE MAKAQDGTFS SVLTLTNLTG LDTGEYFCTH NDSRGLETDE
  81 RKRLYIFVPD PTVGFLPNDA EELFIFLTEI TEITIPCRVT DPQLVVTLHE KKGDVALPVP YDHQRGFSGI FEDRSYICKT
 161 TIGDREVDSD AYYVYRLQVS SINVSVNAVQ TVVRQGENIT LMCIVIGNEV VNFEWTYPRK ESGRLVEPVT DFLLDMPYHI
 241 RSILHIPSAE LEDSGTYTCN VTESVNDHQD EKAINITVVE SGGGGGSGGG GSEVQLVESG GGLVQPGGSL RLSCAASGYT
 321 FTNYGMNWVR QAPGKGLEWV GWINTYTGEP TYAADFKRRF TFSLDTSKST AYLQMNSLRA EDTAVYYCAK YPHYYGSSHW
 401 YFDVWGQGTL VTVSSASTKG PSVFPLAPSS KSTSGGTAAL GCLVKDYFPE PVTVSWNSGA LTSGVHTFPA VLQSSGLYSL
 481 SSVVTVPSSS LGTQTYICNV NHKPSNTKVD KKVEPKSCDK THT
```

SEQ ID NO. 23
```
   1 LVVTPPGPEL VLNVSSTFVL TCSGSAPVVW ERMSQEPPQE MAKAQDGTFS SVLTLTNLTG LDTGEYFCTH NDSRGLETDE
  81 RKRLYIFVPD PTVGFLPNDA EELFIFLTEI TEITIPCRVT DPQLVVTLHE KKGDVALPVP YDHQRGFSGI FEDRSYICKT
 161 TIGDREVDSD AYYVYRLQVS SINVSVNAVQ TVVRQGENIT LMCIVIGNEV VNFEWTYPRK ESGRLVEPVT DFLLDMPYHI
 241 RSILHIPSAE LEDSGTYTCN VTESVNDHQD EKAINITVVE SGGGEVQLVE SGGGLVQPGG SLRLSCAASG YTFTNYGMNW
 321 VRQAPGKGLE WVGWINTYTG EPTYAADFKR RFTFSLDTSK STAYLQMNSL RAEDTAVYYC AKYPHYYGSS HWYFDVWGQG
 401 TLVTVSSAST KGPSVFPLAP SSKSTSGGTA ALGCLVKDYF PEPVTVSWNS GALTSGVHTF PAVLQSSGLY SLSSVVTVPS
 481 SSLGTQTYIC NVNHKPSNTK VDKKVEPKSC DKTHT
```

SEQ ID NO. 24
```
   1 EVQLVESGGG LVQPGGSLRL SCAASGYTFT NYGMNWVRQA PGKGLEWVGW INTYTGEPTY AADFKRRFTF SLDTSKSTAY
  81 LQMNSLRAED TAVYYCAKYP HYYGSSHWYF DVWGQGTLVT VSSASTKGPS VFPLAPSSKS TSGGTAALGC LVKDYFPEPV
 161 TVSWNSGALT SGVHTFPAVL QSSGLYSLSS VVTVPSSSLG TQTYICNVNH KPSNTKVDKK VEPKSCDKTH TGGGGGSGGG
 241 GSGGGGSGGG GSGLVVTPPG PELVLNVSST FVLTCSGSAP VVWERMSQEP PQEMAKAQDG TFSSVLTLTN LTGLDTGEYF
```

-continued

```
321 CTHNDSRGLE TDERKRLYIF VPDPTVGFLP NDAEELFIFL TEITEITIPC RVTDPQLVVT LHEKKGDVAL PVPYDHQRGF
401 SGIFEDRSYI CKTTIGDREV DSDAYYVYRL QVSSINVSVN AVQTVVRQGE NITLMCIVIG NEVVNFEWTY PRKESGRLVE
481 PVTDFLLDMP YHIRSILHIP SAELEDSGTY TCNVTESVND HQDEKAINIT VVESG
```

SEQ ID NO. 25
```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGGSGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THL
```

SEQ ID NO. 26
```
  1 LVVTPPGPE LVLNVSSTFV LTCSGSAPVV WERMSQEPPQ EMAKAQDGTF SSVLTLTNLT GLDTGEYFCT HNDSRGLETD
 80 ERKRLYIFVP DPTVGFLPND AEELFIFLTE ITEITIPCRV TDPQLVVTLH EKKGDVALPV PYDHQRGFSG IFEDRSYICK
160 TTIGDREVDS DAYYVYRLQV SSINVSVNAV QTVVRQGENI TLMCIVIGNE VVNFEWTYPR KESGRLVEPV TDFLLDMPYH
240 IRSILHIPSA ELEDSGTYTC NVTESVNDHQ DEKAINITVV ESGEVQLVES GGGLVQPGGS LRLSCAASGY TFTNYGMNWV
320 RQAPGKGLEW VGWINTYTGE PTYAADFKRR FTFSLDTSKS TAYLQMNSLR AEDTAVYYCA KYPHYYGSSH WYFDVWGQGT
400 LVTVSSASTK GPSVFPLAPS SKSTSGGTAA LGCLVKDYFP EPVTVSWNSG ALTSGVHTFP AVLQSSGLYS LSSVVTVPSS
480 SLGTQTYICN VNHKPSNTKV DKKVEPKSCD KTHTCPPCPA PELLGGPSVF LFPPKPKDTL MISRTPEVTC VVVDVSHEDP
560 EVKFNWYVDG VEVHNAKTKP REEQYNSTYR VVSVLTVLHQ DWLNGKEYKC KVSNKALPAP IEKTISKAKG QPREPQVYTL
640 PPSREEMTKN QVSLTCLVKG FYPSDIAVEW ESNGQPENNY KTTPPVLDSD GSFFLYSKLT VDKSRWQQGN VFSCSVMHEA
720 LHNHYTQKSL SLSPGK
```

SEQ ID NO. 27
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH TCPPCPAPEL LGGPSVFLFP PKPKDTLMIS RTPEVTCVVV DVSHEDPEVK FNWYVDGVEV
481 HNAKTKPREE QYNSTYRVVS VLTVLHQDWL NGKEYKCKVS NKALPAPIEK TISKAKGQPR EPQVYTLPPS REEMTKNQVS
561 LTCLVKGFYP SDIAVEWESN GQPENNYKTT PPVLDSDGSF FLYSKLTVDK SRWQQGNVFS CSVMHEALHN HYTQKSLSLS
641 PGK
```

SEQ ID NO. 28
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH T
```

SEQ ID NO. 29
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG GGGSGGGGSG GGGSGGGGSG GGGSGGGGSE VQLVESGGGL VQPGGSLRLS
```

```
241 CAASGYTFTN YGMNWVRQAP GKGLEWVGWI NTYTGEPTYA ADFKRRFTFS LDTSKSTAYL QMNSLRAEDT AVYYCAKYPH

321 YYGSSHWYFD VWGQGTLVTV SSASTKGPSV FPLAPSSKST SGGTAALGCL VKDYFPEPVT VSWNSGALTS GVHTFPAVLQ

401 SSGLYSLSSV VTVPSSSLGT QTYICNVNHK PSNTKVDKKV EPKSCDKTHT
```

```
                                                                                      SEQ ID NO. 30
  1 EVQLVESGGG LVQPGGSRL  SCAASGYTFT NYGMNWVRQA PGKGLEWVGW INTYTGEPTY AADFKRRFTF SLDTSKSTAY

81 LQMNSLRAED TAVYYCAKYP HYYGSSHWYF DVWGQGTLVT VSSASTKGPS VFPLAPSSKS TSGGTAALGC LVKDYFPEPV

161 TVSWNSGALT SGVHTFPAVL QSSGLYSLSS VVTVPSSSLG TQTYICNVNH KPSNTKVDKK VEPKSCDKTH TGGGSGGGGS

241 GGGGSGGGGS GGGGSGGGGS VGFLPNDAEE LFIFLTEITE ITIPCRVTDP QLVVTLHEKK GDVALPVPYD HQRGFSGIFE

321 DRSYICKTTI GDREVDSDAY YVYRLQVSSI NVSVNAVQTV VRQGENITLM CIVIGNEVVN FEWTYPRKES GRLVEPVTDF

401 LLDMPYHIRS ILHIPSAELE DSGTYTCNVT ESVNDHQDEK AINITVVESG
```

SEQ ID NO: 31 Nucleic acid encoding heavy chain anti-VEGF-PDGFR fusion

```
GACGGATCGGGAGATCTCCCGATCCCCTATGGTGCACTCTCAGTACAATCTGCTCTGATGCCGCA
TAGTTAAGCCAGTATCTGCTCCCTGCTTGTGTGTTGGAGGTCGCTGAGTAGTGCGCGAGCAAAT
TTAAGCTACAACAAGGCAAGGCTTGACCGACAATTGCATGAAGAATCTGCTTAGGGTTAGGCGTT
TTGCGCTGCTTCGCGATGTACGGGCCAGATATACGCGTTGACATTGATTATTGACTAGTTATTAA
TAGTAATCAATTACGGGGTCATTAGTTCATAGCCCATATATGGAGTTCCGCGTTACATAACTTAC
GGTAAATGGCCCGCCTGGCTGACCGCCCAACGACCCCCGCCCATTGACGTCAATAATGACGTATG
TTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCAGTACA
TCTACGTATTAGTCATCGCTATTACCATGGTGATGCGGTTTTGGCAGTACATCAATGGGCGTGGA
TAGCGGTTTGACTCACGGGGATTTCCAAGTCTCCACCCCATTGACGTCAATGGGAGTTTGTTTTG
GCACCAAAATCAACGGGACTTTCCAAAATGTCGTAACAACTCCGCCCCATTGACGCAAATGGGCG
GTAGGCGTGTACGGTGGGAGGTCTATATAAGCAGAGCTCTCTGGCTAACTAGAGAACCCACTGCT
TACTGGCTTATCGAAATTAATACGACTCACTATAGGGAGACCCAAGCTGGCTAGCGTTTAAACTT
AAGCTTGGTACCGAGCTCGGATCCACTAGTCCAGTGTGGTGGAATTCTGCAGATATCCAGCACAG
TGGCGGCCGCCatgaaagctgtggtgctggccgtggctctggtcttcctgacagggagccaggct
ctggtcgtcacaccccggggccagagcttgtcctcaatgtctccagcaccttcgttctgacctg
ctcgggttcagctccggtggtgtgggaacggatgtcccaggagcccccacaggaaatggccaagg
cccaggatggcaccttctccagcgtgctcacactgaccaacctcactgggctagacacgggagaa
tactttgcacccacaatgactccgtggactggagaccgatgagcggaaacggctctacatctt
tgtgccagatccaccgtgggcttcctccctaatgatgccgaggaactattcatctttctcacgg
aaataactgagatcaccattccatgccgagtaacagaccacagctggtggtgacactgcacgag
aagaaaggggacgttgcactgcctgtccctatgatcaccaacgtggcttttctggtatctttga
ggacagaagctacatctgcaaaaccaccattggggacagggaggtggattctgatgcctactatg
tctacagactccaggtgtcatccatcaacgtctctgtgaacgcagtgcagactgtggtccgccag
ggtgagaacatcaccctcatgtgcattgtgatcgggaatgaggtggtcaacttcgagtggacata
cccccgcaaagaaagtgggcggctggtggagccggtgactgacttcctcttggatatgccttacc
acatccgctccatcctgcacatccccagtgccgagttagaagactcggggacctacacctgcaat
gtgacggagagtgtgaatgaccatcaggatgaaaaggccatcaacatcaccgtggttgagagcgg
cggtggtggcggctccggtggaggcggaagcgaggtgcagctggtggaatccggcggaggcctgg
```

-continued

```
tccagcctggcggatccctgagactgtcctgtgccgcctccggctacgacttcacccattacggc
atgaactgggtccgacaggcccctggcaagggcctggaatgggtcggatggatcaacacctacac
cggcgagcccacctacgccgccgacttcaagcggcggttcaccttctccctggacacctccaagt
ccaccgcctacctgcagatgaactccctgcgggccgaggacaccgccgtgtactactgcgccaag
tacccctactactacggcacctcccactggtacttcgacgtgtggggccagggcaccctggtcac
cgtgtcctccgcctctaccaagggcccctccgtgttccctctggccccctccagcaagtccacct
ctggcggcaccgccgctctgggctgcctggtcaaggactacttccccgagccgtgaccgtgtcc
tggaactctggcgccctgacctccggcgtgcacacctttccagccgtgctgcagtcctccggcct
gtactccctgtcctccgtcgtgaccgtgccctccagctctctgggcacccagacctacatctgca
acgtgaaccacaagccctccaacaccaaggtggacaagaaggtggaacccaagtcctgcgacaag
acccacacctgtccccctgccctgccctgaagcagccggtgcacccagcgtgttcctgttccc
cccaaagcccaaggacaccctgatgatctcccggaccccgaagtgacctgcgtggtggtggacg
tgtcccacgaggaccctgaagtgaagttcaattggtacgtggacggcgtggaagtgcacaatgcc
aagaccaagccagagaggaacagtacaactccacctaccgggtggtgtccgtgctgaccgtgct
gcatcaggactggctgaacggcaaagagtacaagtgcaaggtctccaacaaggccctgcctgccc
ccatcgaaaagaccatctccaaggccaagggccagccccgcgagcctcaggtgtacacactgcca
cccagccgggaagagatgaccaagaaccaggtctccctgacctgtctggtcaagggcttctaccc
ctccgatatcgccgtcgaatgggagtccaacggccagcccgagaacaactacaagaccacccccc
ctgtgctggactccgacggctcattcttcctgtactccaagctgaccgtggacaagtcccggtgg
cagcagggcaacgtgttctcctgctccgtgatgcacgaggccctgcacaaccactacacccagaa
gtccctgtcctgcagccccggcaagtgataaTCTAGAGGGCCCGTTTAAACCCGCTGATCAGCCT
CGACTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAGACAATA
GCAGGCATGCTGGGGATGCGGTGGGCTCTATGGCTTCTGAGGCGGAAAGAACCAGCTGGGGCTCT
AGGGGGTATCCCCACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCG
CCACGTTCGCCGGCTTTCCCCGTCAAGCTCTAAATCGGGGGCTCCCTTTAGGGTTCCGATTTAGT
GCTTTACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGTTCC
AAACTGGAACAACACTCAACCCTATCTCGGTCTATTCTTTTGATTTATAAGGGATTTTGCCGATT
TCGGCCTATTGGTTAAAAAATGAGCTGATTTAACAAAAATTTAACGCGAATTAATTCTGTGGAAT
GTGTGTCAGTTAGGGTGTGGAAAGTCCCCAGGCTCCCCAGCAGGCAGAAGTATGCAAAGCATGCA
TCTCAATTAGTCAGCAACCAGGTGTGGAAAGTCCCCAGGCTCCCCAGCAGGCAGAAGTATGCAAA
GCATGCATCTCAATTAGTCAGCAACCATAGTCCCGCCCCTAACTCCGCCCATCCCGCCCCTAACT
CCGCCCAGTTCCGCCCATTCTCCGCCCCATGGCTGACTAATTTTTTTATTTATGCAGAGGCCGA
GGCCGCCTCTGCCTCTGAGCTATTCCAGAAGTAGTGAGGAGGCTTTTTTGGAGGCCTAGGCTTTT
GCAAAAAGCTCCCGGGAGCTTGTATATCCATTTTCGGATCTGATCAAGAGACAGGATGAGGATCG
TTTCGCATGATTGAACAAGATGGATTGCACGCAGGTTCTCCGGCCGCTTGGGTGGAGAGGCTATT
CGGCTATGACTGGGCACAACAGACAATCGGCTGCTCTGATGCCGCCGTGTTCCGGCTGTCAGCGC
```

-continued

```
AGGGGCGCCCGGTTCTTTTTGTCAAGACCGACCTGTCCGGTGCCCTGAATGAACTGCAGGACGAG
GCAGCGCGGCTATCGTGGCTGGCCACGACGGGCGTTCCTTGCGCAGCTGTGCTCGACGTTGTCAC
TGAAGCGGGAAGGGACTGGCTGCTATTGGGCGAAGTGCCGGGGCAGGATCTCCTGTCATCTCACC
TTGCTCCTGCCGAGAAAGTATCCATCATGGCTGATGCAATGCGGCGGCTGCATACGCTTGATCCG
GCTACCTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACTGTTCG
CCAGGCTCAAGGCGCGCATGCCCGACGGCGAGGATCTCGTCGTGACCCATGGCGATGCCTGCTTG
CCGAATATCATGGTGGAAAATGGCCGCTTTTCTGGATTCATCGACTGTGGCCGGCTGGGTGTGGC
GGACCGCTATCAGGACATAGCGTTGGCTACCCGTGATATTGCTGAAGAGCTTGGCGGCGAATGGG
CTGACCGCTTCCTCGTGCTTTACGGTATCGCCGCTCCCGATTCGCAGCGCATCGCCTTCTATCGC
CTTCTTGACGAGTTCTTCTGAGCGGGACTCTGGGGTTCGAAATGACCGACCAAGCGACGCCCAAC
CTGCCATCACGAGATTTCGATTCCACCGCCGCCTTCTATGAAAGGTTGGGCTTCGGAATCGTTTT
CCGGGACGCCGGCTGGATGATCCTCCAGCGCGGGGATCTCATGCTGGAGTTCTTCGCCCACCCCA
ACTTGTTTATTGCAGCTTATAATGGTTACAAATAAAGCAATAGCATCACAAATTTCACAAATAAA
GCATTTTTTCACTGCATTCTAGTTGTGGTTTGTCCAAACTCATCAATGTATCTTATCATGTCTG
TATACCGTCGACCTCTAGCTAGAGCTTGGCGTAATCATGGTCATAGCTGTTTCCTGTGTGAAATT
GTTATCCGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCTG
AAGCCAGTTACCTTCGGAAAAAGAGTTGGTAGCTCTTGATCCGGCAAACAAACCACCGCTGGTAG
CGGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGGTATGGCTTCATTCAG
CTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCA
```

GCACTGCATAATTCTCTTACTGTCATGCCATCCGTAAGATGCTTTTCTGTGACTGGTGAGTACTC

AACCAAGTCATTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTTCTTCGGGGCGA

AAACTCTCAAGGATCTTACCGCTGTTGAGATCCAGTTCGATGTAACCCACTCGTGCACCCAACTG

ATCTTCAGCATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAGAAAAATAA

ACAAATAGGGGTTCCGCGCACATTTCCCCGAAAAGTGCCACCTGACGTC

SEQ ID NO: 32: Light chain encoding anti-VEGF light chain
GACGGATCGGGAGATCTCCCGATCCCCTATGGTGCACTCTCAGTACAATCTGCTCTGATGCCGCA

TAGTTAAGCCAGTATCTGCTCCCTGCTTGTGTGTTGGAGGTCGCTGAGTAGTGCGCGAGCAAAAT

TTAAGCTACAACAAGGCAAGGCTTGACCGACAATTGCATGAAGAATCTGCTTAGGGTTAGGCGTT

TTGCGCTGCTTCGCGATGTACGGGCCAGATATACGCGTTGACATTGATTATTGACTAGTTATTAA

TAGTAATCAATTACGGGGTCATTAGTTCATAGCCCATATATGGAGTTCCGCGTTACATAACTTAC

GGTAAATGGCCCGCCTGGCTGACCGCCCAACGACCCCCGCCCATTGACGTCAATAATGACGTATG

TTCCCATAGTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTCAATGACGG

TAAATGGCCCGCCTGGCATTATGCCCAGTACATGACCTTATGGGACTTTCCTACTTGGCAGTACA

TCTACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTTTTG

GCACCAAAATCAACGGGACTTTCCAAAATGTCGTAACAACTCCGCCCCATTGACGCAAATGGGCG

GTAGGCGTGTACGGTGGGAGGTCTATATAAGCAGAGCTCTCTGGCTAACTAGAGAACCCACTGCT

TACTGGCTTATCGAAATTAATACGACTCACTATAGGGAGACCCAAGCTGGCTAGCGTTTAAACTT

AAGCTTGGTACCGAGCTCGGATCCACTAGTCCAGTGTGGTGGAATTCTGCAGATATCCAGCACAG

TGGCGGCCGCCatgggatggagctgtatcatcctcttcttggtggcaacagctacaggcgtgcac tccgacatccagctgacccagtccccctccagcctgtccgcctctgtgggcgacagagtgaccat cacctgttccgccagccaggacatctccaactacctgaactggtatcagcagaagcccggcaagg cccccaaggtgctgatctacttcacctcctccctgcactccggcgtgccctccagattctccggc tctggctccggcaccgactttaccctgaccatctccagcctgcagcccgaggacttcgccaccta ctactgccagcagtactccaccgtgccctggaccttcggccagggcaccaaggtggaaatcaagc ggaccgtggccgctccctccgtgttcatcttcccaccctccgacgagcagctgaagtccggaacc gcctccgtcgtgtgcctgctgaacaacttctaccccgcgaggccaaggtgcagtggaaggtgga caacgccctgcagagcggcaactcccaggaatccgtcaccgagcaggactccaaggacagcacct actccctgtccagcaccctgaccctgtccaaggccgactacgagaagcacaaggtgtacgcctgc gaagtgacccaccagggcctcagctcccagtgaccaagtccttcaacccgggcgagtgctagta aTCTAGAGGGCCCGTTTAAACCCGCTGATCAGCCTCGACTGTGCCTTCTAGTTGCCAGCCATCTG

TTGTTTGCCCCTCCCCCGTGCCTTCCTTGACCCTGGAAGGTGCCACTCCCACTGTCCTTTCCTAA

TAAAATGAGGAAATTGCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGGATGCGGTGGGCTCTA

TGGCTTCTGAGGCGGAAAGAACCAGCTGGGGCTCTAGGGGGTATCCCCACGCGCCCTGTAGCGGC

GCATTAAGCGCGGCGGGTGTGGTGGTTACGCGCAGCGTGACCGCTACACTTGCCAGCGCCCTAGC

-continued

```
GCCCGCTCCTTTCGCTTTCTTCCCTTCCTTTCTCGCCACGTTCGCCGGCTTTCCCCGTCAAGCTC
TAAATCGGGGCTCCCTTTAGGGTTCCGATTTAGTGCTTTACGGCACCTCGACCCCAAAAAACTT
GATTAGGGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTATCTCGG
TCTATTCTTTTGATTTATAAGGGATTTTGCCGATTTCGGCCTATTGGTTAAAAAATGAGCTGATT
TAACAAAAATTTAACGCGAATTAATTCTGTGGAATGTGTGTCAGTTAGGGTGTGGAAAGTCCCCA
GGCTCCCCAGCAGGCAGAAGTATGCAAAGCATGCATCTCAATTAGTCAGCAACCAGGTGTGGAAA
GTCCCCAGGCTCCCCAGCAGGCAGAAGTATGCAAAGCATGCATCTCAATTAGTCAGCAACCATAG
TCCCGCCCCTAACTCCGCCCATCCCGCCCCTAACTCCGCCCAGTTCCGCCCATTCTCCGCCCCAT
GGCTGACTAATTTTTTTTATTTATGCAGAGGCCGAGGCCGCCTCTGCCTCTGAGCTATTCCAGAA
GTAGTGAGGAGGCTTTTTTGGAGGCCTAGGCTTTTGCAAAAAGCTCCCGGGAGCTTGTATATCCA
TTTTCGGATCTGATCAAGAGACAGGATGAGGATCGTTTCGCATGATTGAACAAGATGGATTGCAC
GCAGGTTCTCCGGCCGCTTGGGTGGAGAGGCTATTCGGCTATGACTGGGCACAACAGACAATCGG
CTGCTCTGATGCCGCCGTGTTCCGGCTGTCAGCGCAGGGGCGCCCGGTTCTTTTTGTCAAGACCG
ACCTGTCCGGTGCCCTGAATGAACTGCAGGACGAGGCAGCGCGGCTATCGTGGCTGGCCACGACG
GGCGTTCCTTGCGCAGCTGTGCTCGACGTTGTCACTGAAGCGGGAAGGGACTGGCTGCTATTGGG
CGAAGTGCCGGGGCAGGATCTCCTGTCATCTCACCTTGCTCCTGCCGAGAAAGTATCCATCATGG
CTGATGCAATGCGGCGGCTGCATACGCTTGATCCGGCTACCTGCCCATTCGACCACCAAGCGAAA
CATCGCATCGAGCGAGCACGTACTCGGATGGAAGCCGGTCTTGTCGATCAGGATGATCTGGACGA
AGAGCATCAGGGGCTCGCGCCAGCCGAACTGTTCGCCAGGCTCAAGGCGCGCATGCCCGACGGCG
AGGATCTCGTCGTGACCCATGGCGATGCCTGCTTGCCGAATATCATGGTGGAAAATGGCCGCTTT
TCTGGATTCATCGACTGTGGCCGGCTGGGTGTGGCGGACCGCTATCAGGACATAGCGTTGGCTAC
CCGTGATATTGCTGAAGAGCTTGGCGGCGAATGGGCTGACCGCTTCCTCGTGCTTTACGGTATCG
CCGCTCCCGATTCGCAGCGCATCGCCTTCTATCGCCTTCTTGACGAGTTCTTCTGAGCGGGACTC
TGGGGTTCGAAATGACCGACCAAGCGACGCCCAACCTGCCATCACGAGATTTCGATTCCACCGCC
GCCTTCTATGAAAGGTTGGGCTTCGGAATCGTTTTCCGGGACGCCGGCTGGATGATCCTCCAGCG
CGGGGATCTCATGCTGGAGTTCTTCGCCCACCCCAACTTGTTTATTGCAGCTTATAATGGTTACA
AATAAAGCAATAGCATCACAAATTTCACAAATAAAGCATTTTTTTCACTGCATTCTAGTTGTGGT
TTGTCCAAACTCATCAATGTATCTTATCATGTCTGTATACCGTCGACCTCTAGCTAGAGCTTGGC
GTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACA
GAATCAGGGGATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTAT
```

-continued

```
CGTCTTGAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACGGCTACA
CTAGAAGAACAGTATTTGGTATCTGCGCTCTGCTGAAGCCAGTTACCTTCGGAAAAAGAGTTGGT
AGCTCTTGATCCGGCAAACAAACCACCGCTGGTAGCGGTTTTTTTGTTTGCAAGCAGCAGATTAC
GCGCAGAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGCTGCAATG
ATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGTG
GTGTCACGCTCGTCGTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGT
TTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCG
AAAAGTGCCACCTGACGTC
```

---

SEQUENCE LISTING

<160> NUMBER OF SEQ ID NOS: 56

<210> SEQ ID NO 1
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95
```

```
Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
            210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
            275                 280                 285

Gly Gly Gly Ser Asp Ile Gln Met Thr Gln Ser Pro Ser Ser Leu Ser
            290                 295                 300

Ala Ser Val Gly Asp Arg Val Thr Ile Thr Cys Ser Ala Ser Gln Asp
305                 310                 315                 320

Ile Ser Asn Tyr Leu Asn Trp Tyr Gln Gln Lys Pro Gly Lys Ala Pro
                325                 330                 335

Lys Val Leu Ile Tyr Phe Thr Ser Ser Leu His Ser Gly Val Pro Ser
            340                 345                 350

Arg Phe Ser Gly Ser Gly Ser Gly Thr Asp Phe Thr Leu Thr Ile Ser
            355                 360                 365

Ser Leu Gln Pro Glu Asp Phe Ala Thr Tyr Tyr Cys Gln Gln Tyr Ser
            370                 375                 380

Thr Val Pro Trp Thr Phe Gly Gln Gly Thr Lys Val Glu Ile Lys Arg
385                 390                 395                 400

Thr Val Ala Ala Pro Ser Val Phe Ile Phe Pro Pro Ser Asp Glu Gln
                405                 410                 415

Leu Lys Ser Gly Thr Ala Ser Val Val Cys Leu Leu Asn Asn Phe Tyr
            420                 425                 430

Pro Arg Glu Ala Lys Val Gln Trp Lys Val Asp Asn Ala Leu Gln Ser
            435                 440                 445

Gly Asn Ser Gln Glu Ser Val Thr Glu Gln Asp Ser Lys Asp Ser Thr
            450                 455                 460

Tyr Ser Leu Ser Ser Thr Leu Thr Leu Ser Lys Ala Asp Tyr Glu Lys
465                 470                 475                 480

His Lys Val Tyr Ala Cys Glu Val Thr His Gln Gly Leu Ser Ser Pro
                485                 490                 495

Val Thr Lys Ser Phe Asn Arg Gly Glu Cys
            500                 505
```

```
<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

-continued

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 3
<211> LENGTH: 498
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
        50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
                100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
        130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
        210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys

```
            260                 265                 270
Ala Ile Asn Ile Thr Val Val Glu Ser Gly Gly Gly Asp Ile Gln Met
            275                 280                 285

Thr Gln Ser Pro Ser Ser Leu Ser Ala Ser Val Gly Asp Arg Val Thr
        290                 295                 300

Ile Thr Cys Ser Ala Ser Gln Asp Ile Ser Asn Tyr Leu Asn Trp Tyr
305                 310                 315                 320

Gln Gln Lys Pro Gly Lys Ala Pro Lys Val Leu Ile Tyr Phe Thr Ser
                325                 330                 335

Ser Leu His Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Gln Gln Tyr Ser Thr Val Pro Trp Thr Phe Gly Gln
370                 375                 380

Gly Thr Lys Val Glu Ile Lys Arg Thr Val Ala Ala Pro Ser Val Phe
385                 390                 395                 400

Ile Phe Pro Pro Ser Asp Glu Gln Leu Lys Ser Gly Thr Ala Ser Val
                405                 410                 415

Val Cys Leu Leu Asn Asn Phe Tyr Pro Arg Glu Ala Lys Val Gln Trp
            420                 425                 430

Lys Val Asp Asn Ala Leu Gln Ser Gly Asn Ser Gln Glu Ser Val Thr
        435                 440                 445

Glu Gln Asp Ser Lys Asp Ser Thr Tyr Ser Leu Ser Ser Thr Leu Thr
    450                 455                 460

Leu Ser Lys Ala Asp Tyr Glu Lys His Lys Val Tyr Ala Cys Glu Val
465                 470                 475                 480

Thr His Gln Gly Leu Ser Ser Pro Val Thr Lys Ser Phe Asn Arg Gly
                485                 490                 495

Glu Cys

<210> SEQ ID NO 4
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
```

-continued

```
            115                 120                 125
His Glu Lys Lys Gly Asp Val Ala Leu Pro Val Pro Tyr Asp His Gln
130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                    165                 170                 175

Leu Gln Val Ser Ser Ile Asn Val Ser Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                    245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Gly Gly Gly Ser Gly
            275                 280                 285

Gly Gly Gly Ser Glu Val Gln Leu Val Glu Ser Gly Gly Gly Leu Val
290                 295                 300

Gln Pro Gly Gly Ser Leu Arg Leu Ser Cys Ala Ala Ser Gly Tyr Thr
305                 310                 315                 320

Phe Thr Asn Tyr Gly Met Asn Trp Val Arg Gln Ala Pro Gly Lys Gly
                    325                 330                 335

Leu Glu Trp Val Gly Trp Ile Asn Thr Tyr Thr Gly Glu Pro Thr Tyr
                340                 345                 350

Ala Ala Asp Phe Lys Arg Arg Phe Thr Phe Ser Leu Asp Thr Ser Lys
            355                 360                 365

Ser Thr Ala Tyr Leu Gln Met Asn Ser Leu Arg Ala Glu Asp Thr Ala
370                 375                 380

Val Tyr Tyr Cys Ala Lys Tyr Pro His Tyr Tyr Gly Ser Ser His Trp
385                 390                 395                 400

Tyr Phe Asp Val Trp Gly Gln Gly Thr Leu Val Thr Val Ser Ser Ala
                    405                 410                 415

Ser Thr Lys Gly Pro Ser Val Phe Pro Leu Ala Pro Ser Ser Lys Ser
                420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                    485                 490                 495

Ile Cys Asn Val Asn His Lys Pro Ser Asn Thr Lys Val Asp Lys Lys
                500                 505                 510

Val Glu Pro Lys Ser Cys Asp Lys Thr His Thr Cys Pro Pro Cys Pro
            515                 520                 525

Ala Pro Glu Leu Leu Gly Gly Pro Ser Val Phe Leu Phe Pro Pro Lys
530                 535                 540
```

```
Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 6
<211> LENGTH: 737
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
        50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Val Gln Leu
        275                 280                 285
```

-continued

Val Glu Ser Gly Gly Gly Leu Val Gln Pro Gly Gly Ser Leu Arg Leu
290                 295                 300

Ser Cys Ala Ala Ser Gly Tyr Thr Phe Thr Asn Tyr Gly Met Asn Trp
305                 310                 315                 320

Val Arg Gln Ala Pro Gly Lys Gly Leu Glu Trp Val Gly Trp Ile Asn
            325                 330                 335

Thr Tyr Thr Gly Glu Pro Thr Tyr Ala Ala Asp Phe Lys Arg Arg Phe
            340                 345                 350

Thr Phe Ser Leu Asp Thr Ser Lys Ser Thr Ala Tyr Leu Gln Met Asn
            355                 360                 365

Ser Leu Arg Ala Glu Asp Thr Ala Val Tyr Tyr Cys Ala Lys Tyr Pro
370                 375                 380

His Tyr Gly Ser Ser His Trp Tyr Phe Asp Val Trp Gly Gln Gly
385                 390                 395                 400

Thr Leu Val Thr Val Ser Ser Ala Ser Thr Lys Gly Pro Ser Val Phe
            405                 410                 415

Pro Leu Ala Pro Ser Ser Lys Ser Thr Ser Gly Gly Thr Ala Ala Leu
            420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
            485                 490                 495

Ser Asn Thr Lys Val Asp Lys Lys Val Glu Pro Lys Ser Cys Asp Lys
            500                 505                 510

Thr His Thr Cys Pro Pro Cys Pro Ala Pro Glu Leu Leu Gly Gly Pro
            515                 520                 525

Ser Val Phe Leu Phe Pro Pro Lys Pro Lys Asp Thr Leu Met Ile Ser
530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
            565                 570                 575

Ala Lys Thr Lys Pro Arg Glu Glu Gln Tyr Asn Ser Thr Tyr Arg Val
            580                 585                 590

Val Ser Val Leu Thr Val Leu His Gln Asp Trp Leu Asn Gly Lys Glu
            595                 600                 605

Tyr Lys Cys Lys Val Ser Asn Lys Ala Leu Pro Ala Pro Ile Glu Lys
610                 615                 620

Thr Ile Ser Lys Ala Lys Gly Gln Pro Arg Glu Pro Gln Val Tyr Thr
625                 630                 635                 640

Leu Pro Pro Ser Arg Glu Glu Met Thr Lys Asn Gln Val Ser Leu Thr
            645                 650                 655

Cys Leu Val Lys Gly Phe Tyr Pro Ser Asp Ile Ala Val Glu Trp Glu
            660                 665                 670

Ser Asn Gly Gln Pro Glu Asn Asn Tyr Lys Thr Thr Pro Pro Val Leu
            675                 680                 685

Asp Ser Asp Gly Ser Phe Phe Leu Tyr Ser Lys Leu Thr Val Asp Lys
690                 695                 700

Ser Arg Trp Gln Gln Gly Asn Val Phe Ser Cys Ser Val Met His Glu

Ala Leu His Asn His Tyr Thr Gln Lys Ser Leu Ser Leu Ser Pro Gly
705                 710                 715                 720

Lys
        725                 730                 735

<210> SEQ ID NO 7
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala

```
                   325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
Leu Ser Pro Gly Gly Gly Gly Ser Gly Gly Gly Gly Ser Gly Gly
                450                 455                 460
Gly Gly Ser Gly Gly Gly Gly Ser Gly Leu Val Val Thr Pro Pro Gly
465                 470                 475                 480
Pro Glu Leu Val Leu Asn Val Ser Ser Thr Phe Val Leu Thr Cys Ser
                485                 490                 495
Gly Ser Ala Pro Val Val Trp Glu Arg Met Ser Gln Glu Pro Pro Gln
                500                 505                 510
Glu Met Ala Lys Ala Gln Asp Gly Thr Phe Ser Ser Val Leu Thr Leu
                515                 520                 525
Thr Asn Leu Thr Gly Leu Asp Thr Gly Glu Tyr Phe Cys Thr His Asn
                530                 535                 540
Asp Ser Arg Gly Leu Glu Thr Asp Glu Arg Lys Arg Leu Tyr Ile Phe
545                 550                 555                 560
Val Pro Asp Pro Thr Val Gly Phe Leu Pro Asn Asp Ala Glu Glu Leu
                565                 570                 575
Phe Ile Phe Leu Thr Glu Ile Thr Glu Ile Thr Ile Pro Cys Arg Val
                580                 585                 590
Thr Asp Pro Gln Leu Val Val Thr Leu His Glu Lys Lys Gly Asp Val
                595                 600                 605
Ala Leu Pro Val Pro Tyr Asp His Gln Arg Gly Phe Ser Gly Ile Phe
                610                 615                 620
Glu Asp Arg Ser Tyr Ile Cys Lys Thr Thr Ile Gly Asp Arg Glu Val
625                 630                 635                 640
Asp Ser Asp Ala Tyr Tyr Val Tyr Arg Leu Gln Val Ser Ser Ile Asn
                645                 650                 655
Val Ser Val Asn Ala Val Gln Thr Val Val Arg Gln Gly Glu Asn Ile
                660                 665                 670
Thr Leu Met Cys Ile Val Ile Gly Asn Glu Val Val Asn Phe Glu Trp
                675                 680                 685
Thr Tyr Pro Arg Lys Glu Ser Gly Arg Leu Val Glu Pro Val Thr Asp
                690                 695                 700
Phe Leu Leu Asp Met Pro Tyr His Ile Arg Ser Ile Leu His Ile Pro
705                 710                 715                 720
Ser Ala Glu Leu Glu Asp Ser Gly Thr Tyr Thr Cys Asn Val Thr Glu
                725                 730                 735
Ser Val Asn Asp His Gln Asp Glu Lys Ala Ile Asn Ile Thr Val Val
                740                 745                 750
```

```
Glu Ser Gly
        755

<210> SEQ ID NO 8
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
    115                 120                 125

His Glu Lys Lys Gly Asp Val Ala Leu Pro Val Pro Tyr Asp His Gln
130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Leu Val
    290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
```

```
                340             345             350
Ala Ala Asp Phe Lys Arg Arg Phe Thr Phe Ser Leu Asp Thr Ser Lys
            355                 360                 365

Ser Thr Ala Tyr Leu Gln Met Asn Ser Leu Arg Ala Glu Asp Thr Ala
        370                 375                 380

Val Tyr Tyr Cys Ala Lys Tyr Pro Tyr Tyr Gly Thr Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
        435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Thr Cys Pro Pro Cys Pro
        515                 520                 525

Ala Pro Glu Ala Ala Gly Ala Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Cys Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 9
```

<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Gly Leu Val
    290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
        355                 360                 365

Ser Thr Ala Tyr Leu Gln Met Asn Ser Leu Arg Ala Glu Asp Thr Ala
```

370                 375                 380
Val Tyr Tyr Cys Ala Lys Tyr Pro Tyr Tyr Gly Thr Ser His Trp
385                 390                 395                 400

Tyr Phe Asp Val Trp Gly Gln Gly Thr Leu Val Thr Val Ser Ser Ala
            405                 410                 415

Ser Thr Lys Gly Pro Ser Val Phe Pro Leu Ala Pro Ser Ser Lys Ser
        420                 425                 430

Thr Ser Gly Gly Thr Ala Ala Leu Gly Cys Leu Val Lys Asp Tyr Phe
    435                 440                 445

Pro Glu Pro Val Thr Val Ser Trp Asn Ser Gly Ala Leu Thr Ser Gly
450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
            485                 490                 495

Ile Cys Asn Val Asn His Lys Pro Ser Asn Thr Lys Val Asp Lys Lys
        500                 505                 510

Val Glu Pro Lys Ser Cys Asp Lys Thr His Thr Cys Pro Pro Cys Pro
    515                 520                 525

Ala Pro Glu Ala Ala Gly Ala Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
        580                 585                 590

Gln Tyr Asn Ser Thr Tyr Arg Val Val Ser Val Leu Thr Val Leu His
    595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
            645                 650                 655

Thr Lys Asn Gln Val Ser Leu Thr Cys Leu Val Lys Gly Phe Tyr Pro
        660                 665                 670

Ser Asp Ile Ala Val Glu Trp Glu Ser Asn Gly Gln Pro Glu Asn Asn
    675                 680                 685

Tyr Lys Thr Thr Pro Pro Val Leu Asp Ser Asp Gly Ser Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
            725                 730                 735

Lys Ser Leu Ser Cys Ser Pro Gly Lys
        740                 745

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

```
<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 11
<211> LENGTH: 1106
<212> TYPE: PRT
<213> ORGANISM: Homo sapiens

<400> SEQUENCE: 11

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
                20                  25                  30

Leu Val Val Thr Pro Pro Gly Pro Glu Leu Val Leu Asn Val Ser Ser
            35                  40                  45

Thr Phe Val Leu Thr Cys Ser Gly Ser Ala Pro Val Val Trp Glu Arg
50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
130                 135                 140
```

```
Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
            165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560
```

-continued

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
            805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
            885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Glu Lys
            930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu

```
                      980                 985                 990
Pro Gly Phe His Gly Leu Arg Ser  Pro Leu Asp Thr Ser  Ser Val Leu
              995                 1000                1005

Tyr Thr  Ala Val Gln Pro Asn  Glu Gly Asp Asn Asp  Tyr Ile Ile
    1010                 1015                1020

Pro Leu  Pro Asp Pro Lys Pro  Glu Val Ala Asp Glu  Gly Pro Leu
    1025                 1030                1035

Glu Gly  Ser Pro Ser Leu Ala  Ser Ser Thr Leu Asn  Glu Val Asn
    1040                 1045                1050

Thr Ser  Ser Thr Ile Ser Cys  Asp Ser Pro Leu Glu  Pro Gln Asp
    1055                 1060                1065

Glu Pro  Glu Pro Glu Pro Gln  Leu Glu Leu Gln Val  Glu Pro Glu
    1070                 1075                1080

Pro Glu  Leu Glu Gln Leu Pro  Asp Ser Gly Cys Pro  Ala Pro Arg
    1085                 1090                1095

Ala Glu  Ala Glu Asp Ser Phe  Leu
    1100                 1105

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 13
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 14
<211> LENGTH: 1338
<212> TYPE: PRT
<213> ORGANISM: Homo sapiens

<400> SEQUENCE: 14

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80
```

```
Cys Gly Arg Asn Gly Lys Gln Phe Cys Ser Thr Leu Thr Leu Asn Thr
                85                  90                  95
Ala Gln Ala Asn His Thr Gly Phe Tyr Ser Cys Lys Tyr Leu Ala Val
            100                 105                 110
Pro Thr Ser Lys Lys Lys Glu Thr Glu Ser Ala Ile Tyr Ile Phe Ile
        115                 120                 125
Ser Asp Thr Gly Arg Pro Phe Val Glu Met Tyr Ser Glu Ile Pro Glu
130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
```

```
                500                 505                 510
Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925
```

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

-continued

Pro Pro Asp Tyr Asn Ser Val Val Leu Tyr Ser Thr Pro Pro Ile
    1325                1330                1335

<210> SEQ ID NO 15
<211> LENGTH: 1356
<212> TYPE: PRT
<213> ORGANISM: Homo sapiens

<400> SEQUENCE: 15

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

```
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
                420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu Ile Ile Ile Leu
            755                 760                 765
Val Gly Thr Ala Val Ile Ala Met Phe Phe Trp Leu Leu Leu Val Ile
    770                 775                 780
```

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
        820                 825                 830

Arg Leu Lys Leu Gly Lys Pro Leu Gly Arg Gly Ala Phe Gly Gln Val
    835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
        900                 905                 910

Met Val Ile Val Glu Phe Cys Lys Phe Gly Asn Leu Ser Thr Tyr Leu
    915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Glu Ala Pro
        980                 985                 990

Glu Asp Leu Tyr Lys Asp Phe Leu Thr Leu Glu His Leu Ile Cys Tyr
    995                 1000                1005

Ser Phe Gln Val Ala Lys Gly Met Glu Phe Leu Ala Ser Arg Lys
1010                1015                1020

Cys Ile His Arg Asp Leu Ala Ala Arg Asn Ile Leu Leu Ser Glu
1025                1030                1035

Lys Asn Val Val Lys Ile Cys Asp Phe Gly Leu Ala Arg Asp Ile
1040                1045                1050

Tyr Lys Asp Pro Asp Tyr Val Arg Lys Gly Asp Ala Arg Leu Pro
1055                1060                1065

Leu Lys Trp Met Ala Pro Glu Thr Ile Phe Asp Arg Val Tyr Thr
1070                1075                1080

Ile Gln Ser Asp Val Trp Ser Phe Gly Val Leu Leu Trp Glu Ile
1085                1090                1095

Phe Ser Leu Gly Ala Ser Pro Tyr Pro Gly Val Lys Ile Asp Glu
1100                1105                1110

Glu Phe Cys Arg Arg Leu Lys Glu Gly Thr Arg Met Arg Ala Pro
1115                1120                1125

Asp Tyr Thr Thr Pro Glu Met Tyr Gln Thr Met Leu Asp Cys Trp
1130                1135                1140

His Gly Glu Pro Ser Gln Arg Pro Thr Phe Ser Glu Leu Val Glu
1145                1150                1155

His Leu Gly Asn Leu Leu Gln Ala Asn Ala Gln Gln Asp Gly Lys
1160                1165                1170

Asp Tyr Ile Val Leu Pro Ile Ser Glu Thr Leu Ser Met Glu Glu
1175                1180                1185

Asp Ser Gly Leu Ser Leu Pro Thr Ser Pro Val Ser Cys Met Glu

-continued

```
                1190                1195                1200
Glu Glu Glu Val Cys Asp Pro Lys Phe His Tyr Asp Asn Thr Ala
    1205                1210                1215
Gly Ile Ser Gln Tyr Leu Gln Asn Ser Lys Arg Lys Ser Arg Pro
    1220                1225                1230
Val Ser Val Lys Thr Phe Glu Asp Ile Pro Leu Glu Pro Glu
    1235                1240                1245
Val Lys Val Ile Pro Asp Asp Asn Gln Thr Asp Ser Gly Met Val
    1250                1255                1260
Leu Ala Ser Glu Glu Leu Lys Thr Leu Glu Asp Arg Thr Lys Leu
    1265                1270                1275
Ser Pro Ser Phe Gly Gly Met Val Pro Ser Lys Ser Arg Glu Ser
    1280                1285                1290
Val Ala Ser Glu Gly Ser Asn Gln Thr Ser Gly Tyr Gln Ser Gly
    1295                1300                1305
Tyr His Ser Asp Asp Thr Asp Thr Thr Val Tyr Ser Ser Glu Glu
    1310                1315                1320
Ala Glu Leu Leu Lys Leu Ile Glu Ile Gly Val Gln Thr Gly Ser
    1325                1330                1335
Thr Ala Gln Ile Leu Gln Pro Asp Ser Gly Thr Thr Leu Ser Ser
    1340                1345                1350
Pro Pro Val
    1355

<210> SEQ ID NO 16
<211> LENGTH: 1363
<212> TYPE: PRT
<213> ORGANISM: Homo sapiens

<400> SEQUENCE: 16

Met Gln Arg Gly Ala Ala Leu Cys Leu Arg Leu Trp Leu Cys Leu Gly
1               5                   10                  15
Leu Leu Asp Gly Leu Val Ser Gly Tyr Ser Met Thr Pro Pro Thr Leu
                20                  25                  30
Asn Ile Thr Glu Glu Ser His Val Ile Asp Thr Gly Asp Ser Leu Ser
            35                  40                  45
Ile Ser Cys Arg Gly Gln His Pro Leu Glu Trp Ala Trp Pro Gly Ala
        50                  55                  60
Gln Glu Ala Pro Ala Thr Gly Asp Lys Asp Ser Glu Asp Thr Gly Val
65                  70                  75                  80
Val Arg Asp Cys Glu Gly Thr Asp Ala Arg Pro Tyr Cys Lys Val Leu
                85                  90                  95
Leu Leu His Glu Val His Ala Asn Asp Thr Gly Ser Tyr Val Cys Tyr
            100                 105                 110
Tyr Lys Tyr Ile Lys Ala Arg Ile Glu Gly Thr Thr Ala Ala Ser Ser
        115                 120                 125
Tyr Val Phe Val Arg Asp Phe Glu Gln Pro Phe Ile Asn Lys Pro Asp
    130                 135                 140
Thr Leu Leu Val Asn Arg Lys Asp Ala Met Trp Val Pro Cys Leu Val
145                 150                 155                 160
Ser Ile Pro Gly Leu Asn Val Thr Leu Arg Ser Gln Ser Ser Val Leu
                165                 170                 175
Trp Pro Asp Gly Gln Glu Val Val Trp Asp Asp Arg Arg Gly Met Leu
            180                 185                 190
```

-continued

```
Val Ser Thr Pro Leu Leu His Asp Ala Leu Tyr Leu Gln Cys Glu Thr
        195                 200                 205
Thr Trp Gly Asp Gln Asp Phe Leu Ser Asn Pro Phe Leu Val His Ile
210                 215                 220
Thr Gly Asn Glu Leu Tyr Asp Ile Gln Leu Leu Pro Arg Lys Ser Leu
225                 230                 235                 240
Glu Leu Leu Val Gly Glu Lys Leu Val Leu Asn Cys Thr Val Trp Ala
                245                 250                 255
Glu Phe Asn Ser Gly Val Thr Phe Asp Trp Asp Tyr Pro Gly Lys Gln
            260                 265                 270
Ala Glu Arg Gly Lys Trp Val Pro Glu Arg Arg Ser Gln Gln Thr His
        275                 280                 285
Thr Glu Leu Ser Ser Ile Leu Thr Ile His Asn Val Ser Gln His Asp
    290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Pro Glu Phe Gln Trp
        355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Gln Ile His Glu Lys Glu Ala Ser Ser Pro
            420                 425                 430
Ser Ile Tyr Ser Arg His Ser Arg Gln Ala Leu Thr Cys Thr Ala Tyr
        435                 440                 445
Gly Val Pro Leu Pro Leu Ser Ile Gln Trp His Trp Arg Pro Trp Thr
    450                 455                 460
Pro Cys Lys Met Phe Ala Gln Arg Ser Leu Arg Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
            500                 505                 510
Gly Lys Asn Lys Thr Val Ser Lys Leu Val Ile Gln Asn Ala Asn Val
        515                 520                 525
Ser Ala Met Tyr Lys Cys Val Val Ser Asn Lys Val Gly Gln Asp Glu
    530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
```

```
            610                 615                 620
Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Val Ala Gly Ala
        690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
                740                 745                 750

Ala Lys Gly Cys Val Asn Ser Ser Ala Ser Val Ala Val Glu Gly Ser
            755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
                820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
        850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                965                 970                 975

Ser Asp Arg Val Leu Phe Ala Arg Phe Ser Lys Thr Glu Gly Gly Ala
                980                 985                 990

Arg Arg Ala Ser Pro Asp Gln Glu Ala Glu Asp Leu Trp Leu Ser Pro
            995                1000                1005

Leu Thr Met Glu Asp Leu Val Cys Tyr Ser Phe Gln Val Ala Arg
        1010                1015                1020

Gly Met Glu Phe Leu Ala Ser Arg Lys Cys Ile His Arg Asp Leu
        1025                1030                1035
```

Ala Ala Arg Asn Ile Leu Leu Ser Glu Ser Asp Val Val Lys Ile
1040                1045                1050

Cys Asp Phe Gly Leu Ala Arg Asp Ile Tyr Lys Asp Pro Asp Tyr
1055                1060                1065

Val Arg Lys Gly Ser Ala Arg Leu Pro Leu Lys Trp Met Ala Pro
1070                1075                1080

Glu Ser Ile Phe Asp Lys Val Tyr Thr Thr Gln Ser Asp Val Trp
1085                1090                1095

Ser Phe Gly Val Leu Leu Trp Glu Ile Phe Ser Leu Gly Ala Ser
1100                1105                1110

Pro Tyr Pro Gly Val Gln Ile Asn Glu Glu Phe Cys Gln Arg Leu
1115                1120                1125

Arg Asp Gly Thr Arg Met Arg Ala Pro Glu Leu Ala Thr Pro Ala
1130                1135                1140

Ile Arg Arg Ile Met Leu Asn Cys Trp Ser Gly Asp Pro Lys Ala
1145                1150                1155

Arg Pro Ala Phe Ser Glu Leu Val Glu Ile Leu Gly Asp Leu Leu
1160                1165                1170

Gln Gly Arg Gly Leu Gln Glu Glu Glu Val Cys Met Ala Pro
1175                1180                1185

Arg Ser Ser Gln Ser Ser Glu Glu Gly Ser Phe Ser Gln Val Ser
1190                1195                1200

Thr Met Ala Leu His Ile Ala Gln Ala Asp Ala Glu Asp Ser Pro
1205                1210                1215

Pro Ser Leu Gln Arg His Ser Leu Ala Ala Arg Tyr Tyr Asn Trp
1220                1225                1230

Val Ser Phe Pro Gly Cys Leu Ala Arg Gly Ala Glu Thr Arg Gly
1235                1240                1245

Ser Ser Arg Met Lys Thr Phe Glu Glu Phe Pro Met Thr Pro Thr
1250                1255                1260

Thr Tyr Lys Gly Ser Val Asp Asn Gln Thr Asp Ser Gly Met Val
1265                1270                1275

Leu Ala Ser Glu Glu Phe Glu Gln Ile Glu Ser Arg His Arg Gln
1280                1285                1290

Glu Ser Gly Phe Ser Cys Lys Gly Pro Gly Gln Asn Val Ala Val
1295                1300                1305

Thr Arg Ala His Pro Asp Ser Gln Gly Arg Arg Arg Arg Pro Glu
1310                1315                1320

Arg Gly Ala Arg Gly Gly Gln Val Phe Tyr Asn Ser Glu Tyr Gly
1325                1330                1335

Glu Leu Ser Glu Pro Ser Glu Glu Asp His Cys Ser Pro Ser Ala
1340                1345                1350

Arg Val Thr Phe Phe Thr Asp Asn Ser Tyr
1355                1360

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

-continued

```
                     20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 106
<212> TYPE: PRT
<213> ORGANISM: Homo sapiens

<400> SEQUENCE: 18

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60
```

```
Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

<210> SEQ ID NO 19
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Leu Val Val Thr Pro Gly Pro Glu Leu Val Leu Asn Val Ser Ser
 1               5                  10                  15

Thr Phe Val Leu Thr Cys Ser Gly Ser Ala Pro Val Val Trp Glu Arg
                 20                  25                  30

Met Ser Gln Glu Pro Pro Gln Glu Met Ala Lys Ala Gln Asp Gly Thr
             35                  40                  45

Phe Ser Ser Val Leu Thr Leu Thr Asn Leu Thr Gly Leu Asp Thr Gly
         50                  55                  60

Glu Tyr Phe Cys Thr His Asn Asp Ser Arg Gly Leu Glu Thr Asp Glu
 65                  70                  75                  80

Arg Lys Arg Leu Tyr Ile Phe Val Pro Asp Pro Thr Val Gly Phe Leu
                 85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
        130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
        210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Gly Gly Gly Ser Gly
            275                 280                 285

Gly Gly Gly Ser Asp Ile Gln Met Thr Gln Ser Pro Ser Ser Leu Ser
        290                 295                 300

Ala Ser Val Gly Asp Arg Val Thr Ile Thr Cys Ser Ala Ser Gln Asp
305                 310                 315                 320
```

```
Ile Ser Asn Tyr Leu Asn Trp Tyr Gln Gln Lys Pro Gly Lys Ala Pro
            325                 330                 335

Lys Val Leu Ile Tyr Phe Thr Ser Ser Leu His Ser Gly Val Pro Ser
            340                 345                 350

Arg Phe Ser Gly Ser Gly Ser Gly Thr Asp Phe Thr Leu Thr Ile Ser
            355                 360                 365

Ser Leu Gln Pro Glu Asp Phe Ala Thr Tyr Tyr Cys Gln Gln Tyr Ser
        370                 375                 380

Thr Val Pro Trp Thr Phe Gly Gln Gly Thr Lys Val Glu Ile Lys Arg
385                 390                 395                 400

Thr Val Ala Ala Pro Ser Val Phe Ile Phe Pro Pro Ser Asp Glu Gln
            405                 410                 415

Leu Lys Ser Gly Thr Ala Ser Val Val Cys Leu Leu Asn Asn Phe Tyr
            420                 425                 430

Pro Arg Glu Ala Lys Val Gln Trp Lys Val Asp Asn Ala Leu Gln Ser
        435                 440                 445

Gly Asn Ser Gln Glu Ser Val Thr Glu Gln Asp Ser Lys Asp Ser Thr
    450                 455                 460

Tyr Ser Leu Ser Ser Thr Leu Thr Leu Ser Lys Ala Asp Tyr Glu Lys
465                 470                 475                 480

His Lys Val Tyr Ala Cys Glu Val Thr His Gln Gly Leu Ser Ser Pro
            485                 490                 495

Val Thr Lys Ser Phe Asn Arg Gly Glu Cys
            500                 505

<210> SEQ ID NO 20
<211> LENGTH: 498
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
            85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
```

165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
        210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Asp Ile Gln Met
        275                 280                 285

Thr Gln Ser Pro Ser Ser Leu Ser Ala Ser Val Gly Asp Arg Val Thr
        290                 295                 300

Ile Thr Cys Ser Ala Ser Gln Asp Ile Ser Asn Tyr Leu Asn Trp Tyr
305                 310                 315                 320

Gln Gln Lys Pro Gly Lys Ala Pro Lys Val Leu Ile Tyr Phe Thr Ser
                325                 330                 335

Ser Leu His Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Gln Gln Tyr Ser Thr Val Pro Trp Thr Phe Gly Gln
        370                 375                 380

Gly Thr Lys Val Glu Ile Lys Arg Thr Val Ala Ala Pro Ser Val Phe
385                 390                 395                 400

Ile Phe Pro Pro Ser Asp Glu Gln Leu Lys Ser Gly Thr Ala Ser Val
                405                 410                 415

Val Cys Leu Leu Asn Asn Phe Tyr Pro Arg Glu Ala Lys Val Gln Trp
            420                 425                 430

Lys Val Asp Asn Ala Leu Gln Ser Gly Asn Ser Gln Glu Ser Val Thr
        435                 440                 445

Glu Gln Asp Ser Lys Asp Ser Thr Tyr Ser Leu Ser Ser Thr Leu Thr
        450                 455                 460

Leu Ser Lys Ala Asp Tyr Glu Lys His Lys Val Tyr Ala Cys Glu Val
465                 470                 475                 480

Thr His Gln Gly Leu Ser Ser Pro Val Thr Lys Ser Phe Asn Arg Gly
                485                 490                 495

Glu Cys

<210> SEQ ID NO 21
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr

```
                  20                  25                  30
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
        50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
            210                 215                 220
Ser Cys Asp Lys Thr His Thr
225                 230

<210> SEQ ID NO 22
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140
```

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
            165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Leu Val
    290                 295                 300

Gln Pro Gly Gly Ser Leu Arg Leu Ser Cys Ala Ala Ser Gly Tyr Thr
305                 310                 315                 320

Phe Thr Asn Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
        355                 360                 365

Ser Thr Ala Tyr Leu Gln Met Asn Ser Leu Arg Ala Glu Asp Thr Ala
    370                 375                 380

Val Tyr Tyr Cys Ala Lys Tyr Pro His Tyr Tyr Gly Ser Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
        435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Thr
        515                 520

<210> SEQ ID NO 23
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Glu Val Gln Leu
        275                 280                 285

Val Glu Ser Gly Gly Leu Val Gln Pro Gly Gly Ser Leu Arg Leu
    290                 295                 300

Ser Cys Ala Ala Ser Gly Tyr Thr Phe Thr Asn Tyr Gly Met Asn Trp
305                 310                 315                 320

Val Arg Gln Ala Pro Gly Lys Gly Leu Glu Trp Val Gly Trp Ile Asn
                325                 330                 335

Thr Tyr Thr Gly Glu Pro Thr Tyr Ala Ala Asp Phe Lys Arg Arg Phe
            340                 345                 350

Thr Phe Ser Leu Asp Thr Ser Lys Ser Thr Ala Tyr Leu Gln Met Asn
        355                 360                 365

Ser Leu Arg Ala Glu Asp Thr Ala Val Tyr Tyr Cys Ala Lys Tyr Pro
    370                 375                 380

His Tyr Tyr Gly Ser Ser His Trp Tyr Phe Asp Val Trp Gly Gln Gly
385                 390                 395                 400

```
Thr Leu Val Thr Val Ser Ser Ala Ser Thr Lys Gly Pro Ser Val Phe
                405                 410                 415
Pro Leu Ala Pro Ser Ser Lys Ser Thr Ser Gly Gly Thr Ala Ala Leu
            420                 425                 430
Gly Cys Leu Val Lys Asp Tyr Phe Pro Glu Pro Val Thr Val Ser Trp
        435                 440                 445
Asn Ser Gly Ala Leu Thr Ser Gly Val His Thr Phe Pro Ala Val Leu
    450                 455                 460
Gln Ser Ser Gly Leu Tyr Ser Leu Ser Ser Val Val Thr Val Pro Ser
465                 470                 475                 480
Ser Ser Leu Gly Thr Gln Thr Tyr Ile Cys Asn Val Asn His Lys Pro
                485                 490                 495
Ser Asn Thr Lys Val Asp Lys Lys Val Glu Pro Lys Ser Cys Asp Lys
            500                 505                 510
Thr His Thr
        515

<210> SEQ ID NO 24
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Gly Gly Gly Gly Ser Gly Gly Gly
225                 230                 235                 240
```

Gly Ser Gly Gly Gly Ser Gly Gly Gly Ser Gly Leu Val Val
            245                 250                 255

Thr Pro Pro Gly Pro Glu Leu Val Leu Asn Val Ser Ser Thr Phe Val
            260                 265                 270

Leu Thr Cys Ser Gly Ser Ala Pro Val Val Trp Glu Arg Met Ser Gln
        275                 280                 285

Glu Pro Pro Gln Glu Met Ala Lys Ala Gln Asp Gly Thr Phe Ser Ser
290                 295                 300

Val Leu Thr Leu Thr Asn Leu Thr Gly Leu Asp Thr Gly Glu Tyr Phe
305                 310                 315                 320

Cys Thr His Asn Asp Ser Arg Gly Leu Glu Thr Asp Glu Arg Lys Arg
                325                 330                 335

Leu Tyr Ile Phe Val Pro Asp Pro Thr Val Gly Phe Leu Pro Asn Asp
            340                 345                 350

Ala Glu Glu Leu Phe Ile Phe Leu Thr Glu Ile Thr Glu Ile Thr Ile
        355                 360                 365

Pro Cys Arg Val Thr Asp Pro Gln Leu Val Val Thr Leu His Glu Lys
    370                 375                 380

Lys Gly Asp Val Ala Leu Pro Val Pro Tyr Asp His Gln Arg Gly Phe
385                 390                 395                 400

Ser Gly Ile Phe Glu Asp Arg Ser Tyr Ile Cys Lys Thr Thr Ile Gly
            405                 410                 415

Asp Arg Glu Val Asp Ser Asp Ala Tyr Tyr Val Tyr Arg Leu Gln Val
        420                 425                 430

Ser Ser Ile Asn Val Ser Val Asn Ala Val Gln Thr Val Val Arg Gln
    435                 440                 445

Gly Glu Asn Ile Thr Leu Met Cys Ile Val Ile Gly Asn Glu Val Val
450                 455                 460

Asn Phe Glu Trp Thr Tyr Pro Arg Lys Glu Ser Gly Arg Leu Val Glu
465                 470                 475                 480

Pro Val Thr Asp Phe Leu Leu Asp Met Pro Tyr His Ile Arg Ser Ile
            485                 490                 495

Leu His Ile Pro Ser Ala Glu Leu Glu Asp Ser Gly Thr Tyr Thr Cys
        500                 505                 510

Asn Val Thr Glu Ser Val Asn Asp His Gln Asp Glu Lys Ala Ile Asn
    515                 520                 525

Ile Thr Val Val Glu Ser Gly
    530                 535

<210> SEQ ID NO 25
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly

```
                    50                  55                  60
Glu Tyr Phe Cys Thr His Asn Asp Ser Arg Gly Leu Glu Thr Asp Glu
 65                      70                  75                  80

Arg Lys Arg Leu Tyr Ile Phe Val Pro Asp Pro Thr Val Gly Phe Leu
                     85                  90                  95

Pro Asn Asp Ala Glu Glu Leu Phe Ile Phe Leu Thr Glu Ile Thr Glu
                100                 105                 110

Ile Thr Ile Pro Cys Arg Val Thr Asp Pro Gln Leu Val Val Thr Leu
                115                 120                 125

His Glu Lys Lys Gly Asp Val Ala Leu Pro Val Pro Tyr Asp His Gln
            130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Gly Gly Gly Ser Gly
                275                 280                 285

Gly Gly Gly Ser Glu Val Gln Leu Val Glu Ser Gly Gly Gly Leu Val
            290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
                340                 345                 350

Ala Ala Asp Phe Lys Arg Arg Phe Thr Phe Ser Leu Asp Thr Ser Lys
                355                 360                 365

Ser Thr Ala Tyr Leu Gln Met Asn Ser Leu Arg Ala Glu Asp Thr Ala
            370                 375                 380

Val Tyr Tyr Cys Ala Lys Tyr Pro Tyr Tyr Gly Thr Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
                420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
            450                 455                 460

Val His Thr Phe Pro Ala Val Leu Gln Ser Ser Gly Leu Tyr Ser Leu
465                 470                 475                 480
```

```
Ser Ser Val Val Thr Val Pro Ser Ser Leu Gly Thr Gln Thr Tyr
            485                 490                 495

Ile Cys Asn Val Asn His Lys Pro Ser Asn Thr Lys Val Asp Lys Lys
                500                 505                 510

Val Glu Pro Lys Ser Cys Asp Lys Thr His Leu
        515                 520

<210> SEQ ID NO 26
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
        50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Tyr Thr Phe Thr Asn Tyr Gly Met Asn Trp Val Arg
```

-continued

```
        305                 310                 315                 320
        Gln Ala Pro Gly Lys Gly Leu Glu Trp Val Gly Trp Ile Asn Thr Tyr
                        325                 330                 335
        Thr Gly Glu Pro Thr Tyr Ala Ala Asp Phe Lys Arg Arg Phe Thr Phe
                        340                 345                 350
        Ser Leu Asp Thr Ser Lys Ser Thr Ala Tyr Leu Gln Met Asn Ser Leu
                        355                 360                 365
        Arg Ala Glu Asp Thr Ala Val Tyr Tyr Cys Ala Lys Tyr Pro His Tyr
                        370                 375                 380
        Tyr Gly Ser Ser His Trp Tyr Phe Asp Val Trp Gly Gln Gly Thr Leu
        385                 390                 395                 400
        Val Thr Val Ser Ser Ala Ser Thr Lys Gly Pro Ser Val Phe Pro Leu
                        405                 410                 415
        Ala Pro Ser Ser Lys Ser Thr Ser Gly Gly Thr Ala Ala Leu Gly Cys
                        420                 425                 430
        Leu Val Lys Asp Tyr Phe Pro Glu Pro Val Thr Val Ser Trp Asn Ser
                        435                 440                 445
        Gly Ala Leu Thr Ser Gly Val His Thr Phe Pro Ala Val Leu Gln Ser
                        450                 455                 460
        Ser Gly Leu Tyr Ser Leu Ser Ser Val Val Thr Val Pro Ser Ser Ser
        465                 470                 475                 480
        Leu Gly Thr Gln Thr Tyr Ile Cys Asn Val Asn His Lys Pro Ser Asn
                        485                 490                 495
        Thr Lys Val Asp Lys Lys Val Glu Pro Lys Ser Cys Asp Lys Thr His
                        500                 505                 510
        Thr Cys Pro Pro Cys Pro Ala Pro Glu Leu Leu Gly Gly Pro Ser Val
                        515                 520                 525
        Phe Leu Phe Pro Pro Lys Pro Lys Asp Thr Leu Met Ile Ser Arg Thr
                        530                 535                 540
        Pro Glu Val Thr Cys Val Val Val Asp Val Ser His Glu Asp Pro Glu
        545                 550                 555                 560
        Val Lys Phe Asn Trp Tyr Val Asp Gly Val Glu Val His Asn Ala Lys
                        565                 570                 575
        Thr Lys Pro Arg Glu Glu Gln Tyr Asn Ser Thr Tyr Arg Val Val Ser
                        580                 585                 590
        Val Leu Thr Val Leu His Gln Asp Trp Leu Asn Gly Lys Glu Tyr Lys
                        595                 600                 605
        Cys Lys Val Ser Asn Lys Ala Leu Pro Ala Pro Ile Glu Lys Thr Ile
                        610                 615                 620
        Ser Lys Ala Lys Gly Gln Pro Arg Glu Pro Gln Val Tyr Thr Leu Pro
        625                 630                 635                 640
        Pro Ser Arg Glu Glu Met Thr Lys Asn Gln Val Ser Leu Thr Cys Leu
                        645                 650                 655
        Val Lys Gly Phe Tyr Pro Ser Asp Ile Ala Val Glu Trp Glu Ser Asn
                        660                 665                 670
        Gly Gln Pro Glu Asn Asn Tyr Lys Thr Thr Pro Pro Val Leu Asp Ser
                        675                 680                 685
        Asp Gly Ser Phe Phe Leu Tyr Ser Lys Leu Thr Val Asp Lys Ser Arg
                        690                 695                 700
        Trp Gln Gln Gly Asn Val Phe Ser Cys Ser Val Met His Glu Ala Leu
        705                 710                 715                 720
        His Asn His Tyr Thr Gln Lys Ser Leu Ser Leu Ser Pro Gly Lys
                        725                 730                 735
```

<210> SEQ ID NO 27
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Val Gly Phe Leu Pro Asn Asp Ala Glu Glu Leu Phe Ile Phe Leu Thr
1               5                   10                  15

Glu Ile Thr Glu Ile Thr Ile Pro Cys Arg Val Thr Asp Pro Gln Leu
            20                  25                  30

Val Val Thr Leu His Glu Lys Lys Gly Asp Val Ala Leu Pro Val Pro
        35                  40                  45

Tyr Asp His Gln Arg Gly Phe Ser Gly Ile Phe Glu Asp Arg Ser Tyr
50                  55                  60

Ile Cys Lys Thr Thr Ile Gly Asp Arg Glu Val Asp Ser Asp Ala Tyr
65                  70                  75                  80

Tyr Val Tyr Arg Leu Gln Val Ser Ser Ile Asn Val Ser Val Asn Ala
                85                  90                  95

Val Gln Thr Val Val Arg Gln Gly Glu Asn Ile Thr Leu Met Cys Ile
            100                 105                 110

Val Ile Gly Asn Glu Val Val Asn Phe Glu Trp Thr Tyr Pro Arg Lys
        115                 120                 125

Glu Ser Gly Arg Leu Val Glu Pro Val Thr Asp Phe Leu Leu Asp Met
130                 135                 140

Pro Tyr His Ile Arg Ser Ile Leu His Ile Pro Ser Ala Glu Leu Glu
145                 150                 155                 160

Asp Ser Gly Thr Tyr Thr Cys Asn Val Thr Glu Ser Val Asn Asp His
                165                 170                 175

Gln Asp Glu Lys Ala Ile Asn Ile Thr Val Val Glu Ser Gly Glu Val
            180                 185                 190

Gln Leu Val Glu Ser Gly Gly Gly Leu Val Gln Pro Gly Gly Ser Leu
        195                 200                 205

Arg Leu Ser Cys Ala Ala Ser Gly Tyr Thr Phe Thr Asn Tyr Gly Met
210                 215                 220

Asn Trp Val Arg Gln Ala Pro Gly Lys Gly Leu Glu Trp Val Gly Trp
225                 230                 235                 240

Ile Asn Thr Tyr Thr Gly Glu Pro Thr Tyr Ala Ala Asp Phe Lys Arg
                245                 250                 255

Arg Phe Thr Phe Ser Leu Asp Thr Ser Lys Ser Thr Ala Tyr Leu Gln
            260                 265                 270

Met Asn Ser Leu Arg Ala Glu Asp Thr Ala Val Tyr Tyr Cys Ala Lys
        275                 280                 285

Tyr Pro His Tyr Tyr Gly Ser Ser His Trp Tyr Phe Asp Val Trp Gly
290                 295                 300

Gln Gly Thr Leu Val Thr Val Ser Ser Ala Ser Thr Lys Gly Pro Ser
305                 310                 315                 320

Val Phe Pro Leu Ala Pro Ser Ser Lys Ser Thr Ser Gly Gly Thr Ala
                325                 330                 335

Ala Leu Gly Cys Leu Val Lys Asp Tyr Phe Pro Glu Pro Val Thr Val
            340                 345                 350

Ser Trp Asn Ser Gly Ala Leu Thr Ser Gly Val His Thr Phe Pro Ala
```

-continued

```
                355                 360                 365
Val Leu Gln Ser Ser Gly Leu Tyr Ser Leu Ser Ser Val Val Thr Val
        370                 375                 380
Pro Ser Ser Leu Gly Thr Gln Thr Tyr Ile Cys Asn Val Asn His
385                 390                 395                 400
Lys Pro Ser Asn Thr Lys Val Asp Lys Lys Val Glu Pro Lys Ser Cys
                405                 410                 415
Asp Lys Thr His Thr Cys Pro Pro Cys Pro Ala Pro Glu Leu Leu Gly
            420                 425                 430
Gly Pro Ser Val Phe Leu Phe Pro Pro Lys Pro Lys Asp Thr Leu Met
        435                 440                 445
Ile Ser Arg Thr Pro Glu Val Thr Cys Val Val Val Asp Val Ser His
        450                 455                 460
Glu Asp Pro Glu Val Lys Phe Asn Trp Tyr Val Asp Gly Val Glu Val
465                 470                 475                 480
His Asn Ala Lys Thr Lys Pro Arg Glu Glu Gln Tyr Asn Ser Thr Tyr
                485                 490                 495
Arg Val Val Ser Val Leu Thr Val Leu His Gln Asp Trp Leu Asn Gly
            500                 505                 510
Lys Glu Tyr Lys Cys Lys Val Ser Asn Lys Ala Leu Pro Ala Pro Ile
        515                 520                 525
Glu Lys Thr Ile Ser Lys Ala Lys Gly Gln Pro Arg Glu Pro Gln Val
        530                 535                 540
Tyr Thr Leu Pro Pro Ser Arg Glu Glu Met Thr Lys Asn Gln Val Ser
545                 550                 555                 560
Leu Thr Cys Leu Val Lys Gly Phe Tyr Pro Ser Asp Ile Ala Val Glu
                565                 570                 575
Trp Glu Ser Asn Gly Gln Pro Glu Asn Asn Tyr Lys Thr Thr Pro Pro
            580                 585                 590
Val Leu Asp Ser Asp Gly Ser Phe Phe Leu Tyr Ser Lys Leu Thr Val
        595                 600                 605
Asp Lys Ser Arg Trp Gln Gln Gly Asn Val Phe Ser Cys Ser Val Met
        610                 615                 620
His Glu Ala Leu His Asn His Tyr Thr Gln Lys Ser Leu Ser Leu Ser
625                 630                 635                 640
Pro Gly Lys

<210> SEQ ID NO 28
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Gly Phe Leu Pro Asn Asp Ala Glu Glu Leu Phe Ile Phe Leu Thr
1               5                   10                  15
Glu Ile Thr Glu Ile Thr Ile Pro Cys Arg Val Thr Asp Pro Gln Leu
                20                  25                  30
Val Val Thr Leu His Glu Lys Lys Gly Asp Val Ala Leu Pro Val Pro
            35                  40                  45
Tyr Asp His Gln Arg Gly Phe Ser Gly Ile Phe Glu Asp Arg Ser Tyr
        50                  55                  60
Ile Cys Lys Thr Thr Ile Gly Asp Arg Glu Val Asp Ser Asp Ala Tyr
```

```
                65                  70                  75                  80
        Tyr Val Tyr Arg Leu Gln Val Ser Ser Ile Asn Val Ser Val Asn Ala
                        85                  90                  95
        Val Gln Thr Val Val Arg Gln Gly Glu Asn Ile Thr Leu Met Cys Ile
                        100                 105                 110
        Val Ile Gly Asn Glu Val Val Asn Phe Glu Trp Thr Tyr Pro Arg Lys
                        115                 120                 125
        Glu Ser Gly Arg Leu Val Glu Pro Val Thr Asp Phe Leu Leu Asp Met
                        130                 135                 140
        Pro Tyr His Ile Arg Ser Ile Leu His Ile Pro Ser Ala Glu Leu Glu
        145                 150                 155                 160
        Asp Ser Gly Thr Tyr Thr Cys Asn Val Thr Glu Ser Val Asn Asp His
                        165                 170                 175
        Gln Asp Glu Lys Ala Ile Asn Ile Thr Val Val Glu Ser Gly Glu Val
                        180                 185                 190
        Gln Leu Val Glu Ser Gly Gly Gly Leu Val Gln Pro Gly Gly Ser Leu
                        195                 200                 205
        Arg Leu Ser Cys Ala Ala Ser Gly Tyr Thr Phe Thr Asn Tyr Gly Met
                        210                 215                 220
        Asn Trp Val Arg Gln Ala Pro Gly Lys Gly Leu Glu Trp Val Gly Trp
        225                 230                 235                 240
        Ile Asn Thr Tyr Thr Gly Glu Pro Thr Tyr Ala Ala Asp Phe Lys Arg
                        245                 250                 255
        Arg Phe Thr Phe Ser Leu Asp Thr Ser Lys Ser Thr Ala Tyr Leu Gln
                        260                 265                 270
        Met Asn Ser Leu Arg Ala Glu Asp Thr Ala Val Tyr Tyr Cys Ala Lys
                        275                 280                 285
        Tyr Pro His Tyr Tyr Gly Ser Ser His Trp Tyr Phe Asp Val Trp Gly
                        290                 295                 300
        Gln Gly Thr Leu Val Thr Val Ser Ser Ala Ser Thr Lys Gly Pro Ser
        305                 310                 315                 320
        Val Phe Pro Leu Ala Pro Ser Ser Lys Ser Thr Ser Gly Gly Thr Ala
                        325                 330                 335
        Ala Leu Gly Cys Leu Val Lys Asp Tyr Phe Pro Glu Pro Val Thr Val
                        340                 345                 350
        Ser Trp Asn Ser Gly Ala Leu Thr Ser Gly Val His Thr Phe Pro Ala
                        355                 360                 365
        Val Leu Gln Ser Ser Gly Leu Tyr Ser Leu Ser Ser Val Val Thr Val
                        370                 375                 380
        Pro Ser Ser Ser Leu Gly Thr Gln Thr Tyr Ile Cys Asn Val Asn His
        385                 390                 395                 400
        Lys Pro Ser Asn Thr Lys Val Asp Lys Val Glu Pro Lys Ser Cys
                        405                 410                 415
        Asp Lys Thr His Thr
                        420

<210> SEQ ID NO 29
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

-continued

```
Val Gly Phe Leu Pro Asn Asp Ala Glu Glu Leu Phe Ile Phe Leu Thr
1               5                   10                  15
Glu Ile Thr Glu Ile Thr Ile Pro Cys Arg Val Thr Asp Pro Gln Leu
            20                  25                  30
Val Val Thr Leu His Glu Lys Lys Gly Asp Val Ala Leu Pro Val Pro
                35                  40                  45
Tyr Asp His Gln Arg Gly Phe Ser Gly Ile Phe Glu Asp Arg Ser Tyr
50                      55                  60
Ile Cys Lys Thr Thr Ile Gly Asp Arg Glu Val Asp Ser Asp Ala Tyr
65                  70                  75                  80
Tyr Val Tyr Arg Leu Gln Val Ser Ser Ile Asn Val Ser Val Asn Ala
                85                  90                  95
Val Gln Thr Val Val Arg Gln Gly Glu Asn Ile Thr Leu Met Cys Ile
            100                 105                 110
Val Ile Gly Asn Glu Val Val Asn Phe Glu Trp Thr Tyr Pro Arg Lys
        115                 120                 125
Glu Ser Gly Arg Leu Val Glu Pro Val Thr Asp Phe Leu Leu Asp Met
    130                 135                 140
Pro Tyr His Ile Arg Ser Ile Leu His Ile Pro Ser Ala Glu Leu Glu
145                 150                 155                 160
Asp Ser Gly Thr Tyr Thr Cys Asn Val Thr Glu Ser Val Asn Asp His
                165                 170                 175
Gln Asp Glu Lys Ala Ile Asn Ile Thr Val Val Glu Ser Gly Gly Gly
            180                 185                 190
Gly Ser Gly Gly Gly Gly Ser Gly Gly Gly Gly Ser Gly Gly Gly Gly
        195                 200                 205
Ser Gly Gly Gly Gly Ser Gly Gly Gly Ser Glu Val Gln Leu Val
    210                 215                 220
Glu Ser Gly Gly Gly Leu Val Gln Pro Gly Gly Ser Leu Arg Leu Ser
225                 230                 235                 240
Cys Ala Ala Ser Gly Tyr Thr Phe Thr Asn Tyr Gly Met Asn Trp Val
                245                 250                 255
Arg Gln Ala Pro Gly Lys Gly Leu Glu Trp Val Gly Trp Ile Asn Thr
            260                 265                 270
Tyr Thr Gly Glu Pro Thr Tyr Ala Ala Asp Phe Lys Arg Arg Phe Thr
        275                 280                 285
Phe Ser Leu Asp Thr Ser Lys Ser Thr Ala Tyr Leu Gln Met Asn Ser
    290                 295                 300
Leu Arg Ala Glu Asp Thr Ala Val Tyr Tyr Cys Ala Lys Tyr Pro His
305                 310                 315                 320
Tyr Tyr Gly Ser Ser His Trp Tyr Phe Asp Val Trp Gly Gln Gly Thr
                325                 330                 335
Leu Val Thr Val Ser Ser Ala Ser Thr Lys Gly Pro Ser Val Phe Pro
            340                 345                 350
Leu Ala Pro Ser Ser Lys Ser Thr Ser Gly Gly Thr Ala Ala Leu Gly
        355                 360                 365
Cys Leu Val Lys Asp Tyr Phe Pro Glu Pro Val Thr Val Ser Trp Asn
    370                 375                 380
Ser Gly Ala Leu Thr Ser Gly Val His Thr Phe Pro Ala Val Leu Gln
385                 390                 395                 400
Ser Ser Gly Leu Tyr Ser Leu Ser Ser Val Val Thr Val Pro Ser Ser
                405                 410                 415
Ser Leu Gly Thr Gln Thr Tyr Ile Cys Asn Val Asn His Lys Pro Ser
```

```
                    420                 425                 430
Asn Thr Lys Val Asp Lys Lys Val Glu Pro Lys Ser Cys Asp Lys Thr
            435                 440                 445

His Thr
    450

<210> SEQ ID NO 30
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Ser Gly Gly Gly Gly Ser
225                 230                 235                 240

Gly Gly Gly Gly Ser Gly Gly Gly Ser Gly Gly Gly Gly Ser Gly
                245                 250                 255

Gly Gly Gly Ser Val Gly Phe Leu Pro Asn Asp Ala Glu Glu Leu Phe
            260                 265                 270

Ile Phe Leu Thr Glu Ile Thr Glu Ile Thr Ile Pro Cys Arg Val Thr
        275                 280                 285

Asp Pro Gln Leu Val Val Thr Leu His Glu Lys Lys Gly Asp Val Ala
    290                 295                 300

Leu Pro Val Pro Tyr Asp His Gln Arg Gly Phe Ser Gly Ile Phe Glu
305                 310                 315                 320
```

```
Asp Arg Ser Tyr Ile Cys Lys Thr Thr Ile Gly Asp Arg Glu Val Asp
            325                 330                 335

Ser Asp Ala Tyr Tyr Val Tyr Arg Leu Gln Val Ser Ser Ile Asn Val
        340                 345                 350

Ser Val Asn Ala Val Gln Thr Val Arg Gln Gly Glu Asn Ile Thr
    355                 360                 365

Leu Met Cys Ile Val Ile Gly Asn Glu Val Val Asn Phe Glu Trp Thr
370                 375                 380

Tyr Pro Arg Lys Glu Ser Gly Arg Leu Val Glu Pro Val Thr Asp Phe
385                 390                 395                 400

Leu Leu Asp Met Pro Tyr His Ile Arg Ser Ile Leu His Ile Pro Ser
                405                 410                 415

Ala Glu Leu Glu Asp Ser Gly Thr Tyr Thr Cys Asn Val Thr Glu Ser
            420                 425                 430

Val Asn Asp His Gln Asp Glu Lys Ala Ile Asn Ile Thr Val Val Glu
        435                 440                 445

Ser Gly
    450

<210> SEQ ID NO 31
<211> LENGTH: 7719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgccatga agctgtggt gctggccgtg gctctggtct   1020
tcctgacagg gagccaggct ctggtcgtca caccccggg gccagagctt gtcctcaatg   1080
tctccagcac cttcgttctg acctgctcgg gttcagctcc ggtggtgtgg aacggatgt   1140 cccaggagcc cccacaggaa atggccaagg cccaggatgg caccttctcc agcgtgctca   1200
cactgaccaa cctcactggg ctagacacgg agaatactt ttgcacccac aatgactccc   1260
```

```
gtggactgga gaccgatgag cggaaacggc tctacatctt tgtgccagat cccaccgtgg    1320
gcttcctccc taatgatgcc gaggaactat tcatctttct cacggaaata actgagatca    1380
ccattccatg ccgagtaaca gacccacagc tggtggtgac actgcacgag aagaaaggg    1440 acgttgcact gcctgtcccc tatgatcacc aacgtggctt ttctggtatc tttgaggaca    1500
gaagctacat ctgcaaaacc accattgggg acagggaggt ggattctgat gcctactatg    1560
tctacagact ccaggtgtca tccatcaacg tctctgtgaa cgcagtgcag actgtggtcc    1620
gccagggtga aacatcacc ctcatgtgca ttgtgatcgg aatgaggtg gtcaacttcg     1680 agtggacata ccccgcaaa gaaagtgggc ggctggtgga gccggtgact gacttcctct    1740
tggatatgcc ttaccacatc cgctccatcc tgcacatccc cagtgccgag ttagaagact    1800
cggggaccta cacctgcaat gtgacggaga gtgtgaatga ccatcaggat gaaaaggcca    1860
tcaacatcac cgtggttgag agcggcggtg gtggcggctc cggtggaggc ggaagcgagg    1920
tgcagctggt ggaatccggc ggaggcctgg tccagcctgg cggatccctg agactgtcct    1980
gtgccgcctc cggctacgac ttcacccatt acggcatgaa ctgggtccga caggcccctg    2040
gcaagggcct ggaatgggtc ggatggatca acacctacac cggcgagccc acctacgccg    2100
ccgacttcaa gcggcggttc accttctccc tggacacctc caagtccacc gcctacctgc    2160
agatgaactc cctgcgggcc gaggacaccg ccgtgtacta ctgcgccaag tacccctact    2220
actacggcac ctcccactgg tacttcgacg tgtggggcca gggcaccctg gtcaccgtgt    2280
cctccgcctc taccaagggc ccctccgtgt tccctctggc ccctccagc aagtccacct    2340 ctggcggcac cgccgctctg ggctgcctgg tcaaggacta cttccccgag cccgtgaccg    2400
tgtcctggaa ctctggcgcc ctgacctccg gcgtgcacac cttccagcc gtgctgcagt    2460 cctccggcct gtactccctg cctccgtcg tgaccgtgcc ctccagctct ctgggcaccc    2520
agacctacat ctgcaacgtg aaccacaagc cctccaacac caaggtggac aagaaggtgg    2580
aacccaagtc ctgcgacaag acccacacct gtccccctg ccctgcccct gaagcagccg    2640
gtgcacccag cgtgttcctg ttccccccaa agcccaagga cacctgatg atctcccgga    2700 cccccgaagt gacctgcgtg gtggtggacg tgtcccacga ggaccctgaa gtgaagttca    2760
attggtacgt ggacggcgtg gaagtgcaca atgccaagac caagcccaga gaggaacagt    2820
acaactccac ctaccgggtg gtgtccgtgc tgaccgtgct gcatcaggac tggctgaacg    2880
gcaaagagta caagtgcaag gtctccaaca aggccctgcc tgcccccatc gaaaagacca    2940
tctccaaggc caagggccag ccccgcgagc ctcaggtgta cacactgcca cccagccggg    3000
aagagatgac caagaaccag gtctccctga cctgtctggt caagggcttc taccctccg    3060 atatcgccgt cgaatgggag tccaacggcc agcccgagaa caactacaag accccccc    3120 ctgtgctgga ctccgacggc tcattcttcc tgtactccaa gctgaccgtg gacaagtccc    3180
ggtggcagca gggcaacgtg ttctcctgct ccgtgatgca cgaggccctg cacaaccact    3240
acacccagaa gtccctgtcc tgcagcccg gcaagtgata atctagaggg cccgtttaaa    3300
cccgctgatc agcctcgact gtgccttcta gttgccagcc atctgttgtt tgcccctccc    3360
ccgtgccttc cttgacctg gaaggtgcca ctcccactgt cctttcctaa taaaatgagg    3420
aaattgcatc gcattgtctg agtaggtgtc attctattct ggggggtggg gtggggcagg    3480
acagcaaggg ggaggattgg gaagacaata gcaggcatgc tggggatgcg gtgggctcta    3540
tggcttctga ggcggaaaga accagctggg gctctagggg gtatccccac gcgccctgta    3600
```

```
gcggcgcatt aagcgcggcg ggtgtggtgg ttacgcgcag cgtgaccgct acacttgcca    3660
gcgccctagc gcccgctcct ttcgcttcct tcccttcctt tctcgccacg ttcgccggct    3720
ttccccgtca agctctaaat cggggctcc  ctttagggtt ccgatttagt gctttacggc    3780
acctcgaccc caaaaaactt gattagggtg atggttcacg tagtgggcca tcgccctgat    3840
agacggtttt tcgcccttg acgttggagt ccacgttctt taatagtgga ctcttgttcc    3900
aaactggaac aacactcaac cctatctcgg tctattcttt tgatttataa gggattttgc    3960
cgatttcggc ctattggtta aaaatgagc tgatttaaca aaatttaac gcgaattaat    4020 tctgtggaat gtgtgtcagt tagggtgtgg aaagtcccca ggctcccag caggcagaag    4080 tatgcaaagc atgcatctca attagtcagc aaccaggtgt ggaaagtccc caggctcccc    4140
agcaggcaga agtatgcaaa gcatgcatct caattagtca gcaaccatag tcccgcccct    4200
aactccgccc atcccgcccc taactccgcc cagttccgcc cattctccgc cccatggctg    4260
actaattttt tttatttatg cagaggccga ggccgcctct gcctctgagc tattccagaa    4320
gtagtgagga ggcttttttg gaggcctagg cttttgcaaa aagctcccgg gagcttgtat    4380
atccattttc ggatctgatc aagagacagg atgaggatcg tttcgcatga ttgaacaaga    4440
tggattgcac gcaggttctc cggccgcttg ggtggagagg ctattcggct atgactgggc    4500
acaacagaca atcggctgct ctgatgccgc cgtgttccgg ctgtcagcgc aggggcgccc    4560 ggttctttt  gtcaagaccg acctgtccgg tgccctgaat gaactgcagg acgaggcagc    4620
gcggctatcg tggctggcca cgacgggcgt tccttgcgca gctgtgctcg acgttgtcac    4680
tgaagcggga agggactggc tgctattggg cgaagtgccg gggcaggatc tcctgtcatc    4740
tcaccttgct cctgccgaga aagtatccat catggctgat gcaatgcggc ggctgcatac    4800
gcttgatccg gctacctgcc cattcgacca ccaagcgaaa catcgcatcg agcgagcacg    4860
tactcggatg aagccggtc  ttgtcgatca ggatgatctg gacgaagagc atcaggggct    4920
cgcgccagcc gaactgttcg ccaggctcaa ggcgcgcatg cccgacggcg aggatctcgt    4980
cgtgacccat ggcgatgcct gcttgccgaa tatcatggtg gaaaatggcc gcttttctgg    5040
attcatcgac tgtggccggc tgggtgtggc ggaccgctat caggacatag cgttggctac    5100
ccgtgatatt gctgaagagc ttggcggcga atgggctgac cgcttcctcg tgctttacgg    5160
tatcgccgct cccgattcgc agcgcatcgc cttctatcgc cttcttgacg agttcttctg    5220
agcgggactc tggggttcga aatgaccgac caagcgacgc ccaacctgcc atcacgagat    5280
ttcgattcca ccgccgcctt ctatgaaagg ttgggcttcg gaatcgtttt ccggacgcc     5340 ggctggatga tcctccagcg cggggatctc atgctggagt tcttcgccca ccccaacttg    5400
tttattgcag cttataatgg ttacaaataa agcaatagca tcacaaattt cacaaataaa    5460 gcatttttt  cactgcattc tagttgtggt ttgtccaaac tcatcaatgt atcttatcat    5520
gtctgtatac cgtcgacctc tagctagagc ttggcgtaat catggtcata gctgtttcct    5580
gtgtgaaatt gttatccgct cacaattcca cacaacatac gagccggaag cataaagtgt    5640
aaagcctggg gtgcctaatg agtgagctaa ctcacattaa ttgcgttgcg ctcactgccc    5700
gctttccagt cgggaaacct gtcgtgccag ctgcattaat gaatcggcca acgcgcgggg    5760
agaggcggtt tgcgtattgg gcgctcttcc gcttcctcgc tcactgactc gctgcgctcg    5820
gtcgttcggc tgcggcgagc ggtatcagct cactcaaagg cggtaatacg ttatccaca    5880 gaatcagggg ataacgcagg aaagaacatg tgagcaaaag gccagcaaaa ggccaggaac    5940
cgtaaaaagg ccgcgttgct ggcgtttttc cataggctcc gcccccctga cgagcatcac    6000
```

```
aaaaatcgac gctcaagtca gaggtggcga aacccgacag gactataaag ataccaggcg      6060 tttcccctg gaagctccct cgtgcgctct cctgttccga ccctgccgct taccggatac       6120
ctgtccgcct ttctcccttc gggaagcgtg gcgctttctc atagctcacg ctgtaggtat      6180
ctcagttcgg tgtaggtcgt tcgctccaag ctgggctgtg tgcacgaacc ccccgttcag      6240
cccgaccgct gcgccttatc cggtaactat cgtcttgagt ccaacccggt aagacacgac      6300
ttatcgccac tggcagcagc cactggtaac aggattagca gagcgaggta tgtaggcggt      6360
gctacagagt tcttgaagtg gtggcctaac tacggctaca ctagaagaac agtatttggt      6420
atctgcgctc tgctgaagcc agttaccttc ggaaaaagag ttggtagctc ttgatccggc      6480
aaacaaacca ccgctggtag cggtttttt gtttgcaagc agcagattac gcgcagaaaa       6540
aaaggatctc aagaagatcc tttgatcttt tctacggggt ctgacgctca gtggaacgaa      6600
aactcacgtt aagggatttt ggtcatgaga ttatcaaaaa ggatcttcac ctagatcctt      6660
ttaaattaaa aatgaagttt taaatcaatc taaagtatat atgagtaaac ttggtctgac      6720
agttaccaat gcttaatcag tgaggcacct atctcagcga tctgtctatt tcgttcatcc      6780
atagttgcct gactccccgt cgtgtagata actacgatac gggagggctt accatctggc      6840
cccagtgctg caatgatacc gcgagaccca cgctcaccgg ctccagattt atcagcaata      6900
aaccagccag ccggaagggc cgagcgcaga agtggtcctg caactttatc cgcctccatc      6960
cagtctatta attgttgccg ggaagctaga gtaagtagtt cgccagttaa tagtttgcgc      7020
aacgttgttg ccattgctac aggcatcgtg gtgtcacgct cgtcgtttgg tatggcttca      7080
ttcagctccg gttcccaacg atcaaggcga gttacatgat cccccatgtt gtgcaaaaaa      7140
gcggttagct ccttcggtcc tccgatcgtt gtcagaagta agttggccgc agtgttatca      7200
ctcatggtta tggcagcact gcataattct cttactgtca tgccatccgt aagatgcttt      7260
tctgtgactg gtgagtactc aaccaagtca ttctgagaat agtgtatgcg gcgaccgagt      7320
tgctcttgcc cggcgtcaat acgggataat accgcgccac atagcagaac tttaaaagtg      7380
ctcatcattg gaaaacgttc ttcggggcga aaactctcaa ggatcttacc gctgttgaga      7440
tccagttcga tgtaacccac tcgtgcaccc aactgatctt cagcatcttt tactttcacc      7500
agcgtttctg ggtgagcaaa aacaggaagg caaaatgccg caaaaaaggg aataagggcg      7560
acacggaaat gttgaatact catactcttc ctttttcaat attattgaag catttatcag      7620
ggttattgtc tcatgagcgg atacatattt gaatgtattt agaaaaataa acaaataggg      7680
gttccgcgca catttccccg aaaagtgcca cctgacgtc                             7719
```

<210> SEQ ID NO 32
<211> LENGTH: 6129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
```

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgccatgg gatggagctg tatcatcctc ttcttggtgg   1020
caacagctac aggcgtgcac tccgacatcc agctgaccca gtccccctcc agcctgtccg   1080
cctctgtggg cgacagagtg accatcacct gttccgccag ccaggacatc tccaactacc   1140
tgaactggta tcagcagaag cccggcaagg cccccaaggt gctgatctac ttcacctcct   1200
ccctgcactc cggcgtgccc tccagattct ccggctctgg ctccggcacc gactttaccc   1260
tgaccatctc agcctgcag cccgaggact cgccaccta ctactgccag cagtactcca   1320
ccgtgccctg gaccttcggc cagggcacca aggtggaaat caagcggacc gtggccgctc   1380
cctccgtgtt catcttccca ccctccgacg agcagctgaa gtccggaacc gcctccgtcg   1440
tgtgcctgct gaacaacttc taccccgcg aggccaaggt gcagtggaag gtggacaacg   1500
ccctgcagag cggcaactcc caggaatccg tcaccgagca ggactccaag gacagcacct   1560
actccctgtc cagcaccctg accctgtcca aggccgacta cgagaagcac aaggtgtacg   1620
cctgcgaagt gacccaccag ggcctcagct cccagtgac caagtccttc aaccggggcg   1680
agtgctagta atctagaggg cccgtttaaa cccgctgatc agcctcgact gtgccttcta   1740
gttgccagcc atctgttgtt tgcccctccc ccgtgccttc cttgaccctg gaaggtgcca   1800
ctcccactgt cctttcctaa taaaatgagg aaattgcatc gcattgtctg agtaggtgtc   1860
attctattct ggggggtggg gtggggcagg acagcaaggg ggaggattgg gaagacaata   1920
gcaggcatgc tggggatgcg gtgggctcta tggcttctga ggcggaaaga accagctggg   1980
gctctagggg gtatccccac gcgccctgta gcggcgcatt aagcgcggcg ggtgtggtgg   2040
ttacgcgcag cgtgaccgct acacttgcca gcgccctagc gcccgctcct ttcgctttct   2100
tcccttcctt tctcgccacg ttcgccggct ttccccgtca gctctaaat cggggctcc   2160
ctttagggtt ccgatttagt gctttacggc acctcgaccc caaaaaactt gattagggtg   2220
atggttcacg tagtgggcca tcgccctgat agacggtttt tcgccctttg acgttggagt   2280
ccacgttctt taatagtgga ctcttgttcc aaactggaac aacactcaac cctatctcgg   2340
tctattcttt tgatttataa gggattttgc cgatttcggc ctattggtta aaaaatgagc   2400
tgatttaaca aaaatttaac gcgaattaat tctgtggaat gtgtgtcagt tagggtgtgg   2460
aaagtcccca ggctccccag caggcagaag tatgcaaagc atgcatctca attagtcagc   2520
aaccaggtgt ggaaagtccc caggctcccc agcaggcaga agtatgcaaa gcatgcatct   2580
caattagtca gcaaccatag tcccgcccct aactccgccc atcccgcccc taactccgcc   2640
```

```
cagttccgcc cattctccgc cccatggctg actaatttttt tttatttatg cagaggccga    2700
ggccgcctct gcctctgagc tattccagaa gtagtgagga ggcttttttg gaggcctagg    2760
cttttgcaaa aagctcccgg gagcttgtat atccattttc ggatctgatc aagagacagg    2820
atgaggatcg tttcgcatga ttgaacaaga tggattgcac gcaggttctc cggccgcttg    2880
ggtggagagg ctattcggct atgactgggc acaacagaca atcggctgct ctgatgccgc    2940
cgtgttccgg ctgtcagcgc aggggcgccc ggttcttttt gtcaagaccg acctgtccgg    3000
tgccctgaat gaactgcagg acgaggcagc gcggctatcg tggctggcca cgacgggcgt    3060
tccttgcgca gctgtgctcg acgttgtcac tgaagcggga agggactggc tgctattggg    3120
cgaagtgccg gggcaggatc tcctgtcatc tcaccttgct cctgccgaga agtatccat    3180 catggctgat gcaatgcggc ggctgcatac gcttgatccg gctacctgcc cattcgacca    3240
ccaagcgaaa catcgcatcg agcgagcacg tactcggatg aagccggtc ttgtcgatca    3300 ggatgatctg gacgaagagc atcagggggct cgcgccagcc gaactgttcg ccaggctcaa    3360
ggcgcgcatg cccgacggcg aggatctcgt cgtgacccat ggcgatgcct gcttgccgaa    3420
tatcatggtg gaaaatggcc gcttttctgg attcatcgac tgtggccggc tgggtgtggc    3480
ggaccgctat caggacatag cgttggctac ccgtgatatt gctgaagagc ttggcggcga    3540
atgggctgac cgcttcctcg tgctttacgg tatcgccgct cccgattcgc agcgcatcgc    3600
cttctatcgc cttcttgacg agttcttctg agcgggactc tggggttcga atgaccgac    3660 caagcgacgc ccaacctgcc atcacgagat ttcgattcca ccgccgcctt ctatgaaagg    3720
ttgggcttcg gaatcgtttt ccgggacgcc ggctggatga tcctccagcg cggggatctc    3780
atgctggagt tcttcgccca ccccaacttg tttattgcag cttataatgg ttacaaataa    3840
agcaatagca tcacaaattt cacaaataaa gcatttttttt cactgcattc tagttgtggt    3900
ttgtccaaac tcatcaatgt atcttatcat gtctgtatac cgtcgacctc tagctagagc    3960
ttggcgtaat catggtcata gctgtttcct gtgtgaaatt gttatccgct cacaattcca    4020
cacaacatac gagccggaag cataaagtgt aaagcctggg gtgcctaatg agtgagctaa    4080
ctcacattaa ttgcgttgcg ctcactgccc gctttccagt cgggaaacct gtcgtgccag    4140
ctgcattaat gaatcggcca acgcgcgggg agaggcggtt tgcgtattgg gcgctcttcc    4200
gcttcctcgc tcactgactc gctgcgctcg gtcgttcggc tgcggcgagc ggtatcagct    4260
cactcaaagg cggtaatacg gttatccaca gaatcagggg ataacgcagg aaagaacatg    4320
tgagcaaaag gccagcaaaa ggccaggaac cgtaaaaagg ccgcgttgct ggcgtttttc    4380
cataggctcc gcccccctga cgagcatcac aaaaatcgac gctcaagtca gaggtggcga    4440
aacccgacag gactataaag ataccaggcg tttccccctg gaagctccct cgtgcgctct    4500
cctgttccga ccctgccgct taccggatac ctgtccgcct ttctcccttc gggaagcgtg    4560
gcgctttctc atagctcacg ctgtaggtat ctcagttcgg tgtaggtcgt tcgctccaag    4620
ctgggctgtg tgcacgaacc ccccgttcag cccgaccgct gcgccttatc cggtaactat    4680
cgtcttgagt ccaacccggt aagacacgac ttatcgccac tggcagcagc cactggtaac    4740
aggattagca gagcgaggta tgtaggcggt gctacagagt tcttgaagtg gtggcctaac    4800
tacggctaca ctagaagaac agtatttggt atctgcgctc tgctgaagcc agttaccttc    4860
ggaaaaagag ttggtagctc ttgatccggc aaacaaacca ccgctggtag cggttttttt    4920
gtttgcaagc agcagattac gcgcagaaaa aaaggatctc aagaagatcc tttgatcttt    4980
tctacggggt ctgacgctca gtggaacgaa aactcacgtt aagggatttt ggtcatgaga    5040
```

```
ttatcaaaaa ggatcttcac ctagatcctt ttaaattaaa aatgaagttt taaatcaatc    5100
taaagtatat atgagtaaac ttggtctgac agttaccaat gcttaatcag tgaggcacct    5160
atctcagcga tctgtctatt tcgttcatcc atagttgcct gactcccgt cgtgtagata     5220 actacgatac gggagggctt accatctggc cccagtgctg caatgatacc gcgagaccca    5280
cgctcaccgg ctccagattt atcagcaata aaccagccag ccggaagggc cgagcgcaga    5340
agtggtcctg caactttatc cgcctccatc cagtctatta attgttgccg ggaagctaga    5400
gtaagtagtt cgccagttaa tagtttgcgc aacgttgttg ccattgctac aggcatcgtg    5460
gtgtcacgct cgtcgtttgg tatggcttca ttcagctccg gttcccaacg atcaaggcga    5520
gttacatgat cccccatgtt gtgcaaaaaa gcggttagct ccttcggtcc tccgatcgtt    5580
gtcagaagta agttggccgc agtgttatca ctcatggtta tggcagcact gcataattct    5640
cttactgtca tgccatccgt aagatgcttt tctgtgactg gtgagtactc aaccaagtca    5700
ttctgagaat agtgtatgcg gcgaccgagt tgctcttgcc cggcgtcaat acgggataat    5760
accgcgccac atagcagaac tttaaaagtg ctcatcattg gaaaacgttc ttcggggcga    5820
aaactctcaa ggatcttacc gctgttgaga tccagttcga tgtaacccac tcgtgcaccc    5880
aactgatctt cagcatcttt tactttcacc agcgtttctg ggtgagcaaa aacaggaagg    5940
caaaatgccg caaaaaaggg aataagggcg acacggaaat gttgaatact catactcttc    6000 cttttcaat attattgaag catttatcag ggttattgtc tcatgagcgg atacatattt     6060
gaatgtattt agaaaaataa acaaataggg gttccgcgca catttccccg aaaagtgcca    6120
cctgacgtc                                                            6129
```

<210> SEQ ID NO 33
<211> LENGTH: 1106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160
```

-continued

His Glu Lys Lys Gly Asp Val Ala Leu Pro Val Pro Tyr Asp His Gln
              165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

-continued

His Glu Tyr Ile Tyr Val Asp Pro Met Gln Leu Pro Tyr Asp Ser Thr
                580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
        610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
                660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Lys
    930                 935                 940            Lys

Phe Glu Ile Arg Pro Pro Phe Ser Gln Leu Val Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser  Pro Leu Asp Thr Ser  Ser Val Leu

-continued

```
             995                1000                1005
Tyr Thr Ala Val Gln Pro Asn Glu Gly Asp Asn Asp Tyr Ile Ile
    1010                1015                1020

Pro Leu Pro Asp Pro Lys Pro Glu Val Ala Asp Glu Gly Pro Leu
    1025                1030                1035

Glu Gly Ser Pro Ser Leu Ala Ser Ser Thr Leu Asn Glu Val Asn
    1040                1045                1050

Thr Ser Ser Thr Ile Ser Cys Asp Ser Pro Leu Glu Pro Gln Asp
    1055                1060                1065

Glu Pro Glu Pro Glu Pro Gln Leu Glu Leu Gln Val Glu Pro Glu
    1070                1075                1080

Pro Glu Leu Glu Gln Leu Pro Asp Ser Gly Cys Pro Ala Pro Arg
    1085                1090                1095

Ala Glu Ala Glu Asp Ser Phe Leu
    1100                1105

<210> SEQ ID NO 34
<211> LENGTH: 1338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Val Ser Tyr Trp Asp Thr Gly Val Leu Leu Cys Ala Leu Leu
1               5                  10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
                35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
                115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

-continued

```
Lys Leu Leu Arg Gly His Thr Leu Val Leu Asn Cys Thr Ala Thr Thr
            245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
            290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
            610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
```

```
                660                 665                 670
Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
            770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
            930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
        1010                1015                1020

Ala Ala Arg Asn Ile Leu Leu Ser Glu Asn Asn Val Val Lys Ile
        1025                1030                1035

Cys Asp Phe Gly Leu Ala Arg Asp Ile Tyr Lys Asn Pro Asp Tyr
        1040                1045                1050

Val Arg Lys Gly Asp Thr Arg Leu Pro Leu Lys Trp Met Ala Pro
        1055                1060                1065

Glu Ser Ile Phe Asp Lys Ile Tyr Ser Thr Lys Ser Asp Val Trp
        1070                1075                1080
```

```
Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 35
<211> LENGTH: 1356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
```

```
                   85                  90                  95
Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
            130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
            210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
            290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
            355                 360                 365

Ile Pro Leu Glu Ser Asn His Thr Ile Lys Ala Gly His Val Leu Thr
            370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
            450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510
```

```
Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
        530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
        770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
        850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925
```

-continued

```
Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
```

```
                1325                1330                1335
        Thr Ala Gln Ile Leu Gln Pro Asp Ser Gly Thr Thr Leu Ser Ser
            1340                1345                1350
        Pro Pro Val
            1355

<210> SEQ ID NO 36
<211> LENGTH: 1363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320
```

```
Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Glu Phe Gln Trp
        355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
            405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
```

```
            740                 745                 750
Ala Lys Gly Cys Val Asn Ser Ser Ala Ser Val Ala Val Glu Gly Ser
                755                 760                 765

Glu Asp Lys Gly Ser Met Glu Ile Val Ile Leu Val Gly Thr Gly Val
        770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
                820                 825                 830

Tyr Asp Ala Ser Gln Trp Glu Phe Pro Arg Glu Arg Leu His Leu Gly
                835                 840                 845

Arg Val Leu Gly Tyr Gly Ala Phe Gly Lys Val Val Glu Ala Ser Ala
                850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
                915                 920                 925

Phe Cys Lys Tyr Gly Asn Leu Ser Asn Phe Leu Arg Ala Lys Arg Asp
                930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                965                 970                 975

Ser Asp Arg Val Leu Phe Ala Arg Phe Ser Lys Thr Glu Gly Gly Ala
                980                 985                 990

Arg Arg Ala Ser Pro Asp Gln Glu  Ala Glu Asp Leu Trp Leu Ser Pro
                995                 1000                1005

Leu Thr Met Glu Asp Leu Val  Cys Tyr Ser Phe Gln  Val Ala Arg
        1010                1015                1020

Gly Met Glu Phe Leu Ala Ser Arg Lys Cys Ile His  Arg Asp Leu
        1025                1030                1035

Ala Ala Arg Asn Ile Leu Leu  Ser Glu Ser Asp Val  Val Lys Ile
        1040                1045                1050

Cys Asp Phe Gly Leu Ala Arg  Asp Ile Tyr Lys Asp  Pro Asp Tyr
        1055                1060                1065

Val Arg Lys Gly Ser Ala Arg  Leu Pro Leu Lys Trp  Met Ala Pro
        1070                1075                1080

Glu Ser Ile Phe Asp Lys Val  Tyr Thr Thr Gln Ser  Asp Val Trp
        1085                1090                1095

Ser Phe Gly Val Leu Leu Trp  Glu Ile Phe Ser Leu  Gly Ala Ser
        1100                1105                1110

Pro Tyr Pro Gly Val Gln Ile  Asn Glu Glu Phe Cys  Gln Arg Leu
        1115                1120                1125

Arg Asp Gly Thr Arg Met Arg  Ala Pro Glu Leu Ala  Thr Pro Ala
        1130                1135                1140

Ile Arg Arg Ile Met Leu Asn  Cys Trp Ser Gly Asp  Pro Lys Ala
        1145                1150                1155
```

Arg Pro Ala Phe Ser Glu Leu Val Glu Ile Leu Gly Asp Leu Leu
        1160                1165                1170

Gln Gly Arg Gly Leu Gln Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Glu Asp His Cys Ser Pro Ser Ala
    1340                1345                1350

Arg Val Thr Phe Phe Thr Asp Asn Ser Tyr
    1355                1360

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser
1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Ser
1

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 39

Gly Gly Gly Glu Ser
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser Gly Gly Gly Gly Ser
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Gly Ser Gly Gly Gly Gly Ser Gly Gly Gly Gly Ser Gly
1               5                   10                  15

Gly Gly Gly Ser Gly
            20

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Asp Phe Thr His Tyr Gly Met Asn
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ile Asn Thr Tyr Thr Gly Glu Pro Thr Tyr Ala Ala Asp Phe Lys
1               5                   10                  15

Arg

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Pro Tyr Tyr Tyr Gly Thr Ser His Trp Tyr Phe Asp Val
```

```
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ala Ser Gln Asp Ile Ser Asn Tyr Leu Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Thr Ser Ser Leu His Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Ser Thr Val Pro Trp Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Tyr Thr Phe Thr Asn Tyr Gly Met Asn
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Pro His Tyr Tyr Gly Ser Ser His Trp Tyr Phe Asp Val
1               5                   10

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: misc_feature
<222> LOCATION: (1)..(20)
<223> OTHER INFORMATION: This sequence may encompass 1-4 'Gly-Gly-Gly-
      Gly-Ser' repeating units

<400> SEQUENCE: 50

Gly Gly Gly Gly Ser Gly Gly Gly Ser Gly Gly Gly Gly Ser Gly
1               5                   10                  15

Gly Gly Gly Ser
            20

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: This sequence may encompass 1-4 'Gly'
      residues

<400> SEQUENCE: 51

Gly Gly Gly Gly
1

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This sequence may encompass 1-4 'Gly-Gly'
      repeating units

<400> SEQUENCE: 52

Gly Gly Gly Gly Gly Gly Gly Gly
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This sequence may encompass 1-4 'Gly-Gly-Gly-
      Ser' repeating units

<400> SEQUENCE: 53

Gly Gly Gly Ser Gly Gly Gly Ser Gly Gly Gly Ser Gly Gly Gly Ser
1               5                   10                  15

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<221> NAME/KEY: misc_feature
<222> LOCATION: (1)..(20)
<223> OTHER INFORMATION: This sequence may encompass 1-4 'Gly-Gly-Gly-
      Glu-Ser' repeating units

<400> SEQUENCE: 54

Gly Gly Gly Glu Ser Gly Gly Glu Ser Gly Gly Gly Glu Ser Gly
1               5                   10                  15

Gly Gly Glu Ser
            20

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Gly Gly Cys
1               5

<210> SEQ ID NO 56
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Ser Gly Gly Gly Gly Ser Gly Gly Gly Ser Gly Gly
1               5                   10                  15

Gly Gly Ser Gly Gly Gly Gly Ser Gly Gly Gly Gly Ser
            20                  25
```

What is claimed:

1. A conjugate comprising (1) a fusion protein comprising a VEGF antagonist linked to a PDGF antagonist, wherein the VEGF antagonist is an anti-VEGF antibody and the PDGF antagonist is a PDGFR extracellular trap segment, wherein the PDGFR extracellular trap segment comprises domains D1-D3 of PDGFR-β; and (2) a phosphorylcholine containing polymer, wherein the polymer is covalently bonded to the fusion protein.

2. The conjugate of claim 1, wherein the polymer comprises 2-(methacryloyloxy)ethyl (2-(trimethylammonio) ethyl) phosphate (MPC) monomers.

3. The conjugate of claim 2, wherein the polymer has a peak molecular weight between 300,000 and 1,750,000 Daltons as measured by size exclusion chromatography multi angle light scattering (hereinafter "SEC-MALS").

4. The conjugate of claim 3, wherein the polymer has a peak molecular weight between 500,000 and 1,000,000 Daltons as measured by SEC-MALS.

5. The conjugate of claim 4, wherein the polymer has a peak molecular weight between 600,000 to 800,000 Daltons as measured by SEC-MALS.

6. The conjugate of claim 3, wherein the polymer has 3 or more arms.

7. The conjugate of claim 6, wherein the polymer has 3, 4, 5, 6, 7, 8, 9, 10, 11 or 12 arms.

8. The conjugate of claim 7, wherein the polymer has 9 arms.

9. The conjugate of claim 1, wherein the anti-VEGF antibody comprises a heavy chain and a light chain, and the heavy chain is fused via a linker to the C-terminus of the PDGFR extracellular trap segment.

10. The conjugate of claim 9, wherein the anti-VEGF antibody is an IgG.

11. The conjugate of claim 10, wherein the polymer is covalently bonded to a sulfhydryl group from a cysteine residue on the heavy chain the anti-VEGF IgG.

12. The conjugate of claim 10, wherein the fusion protein comprises a tetramer consisting of two identical pairs of polypeptide chains, each pair consisting of a fusion polypeptide complexed to the light chain, wherein the amino acid sequence of the fusion polypeptide is set forth in SEQ ID NO: 9 and the amino acid sequence of the light chain is set forth in SEQ ID NO: 10, and wherein the polymer (i) comprises 2-(methacryloyloxy)ethyl (2-(trimethylammonio) ethyl) phosphate (MPC) monomers, and (ii) has a peak molecular weight between 600,000 to 800,000 Daltons as measured by SEC-MALS.

13. The conjugate of claim 12, wherein the polymer is covalently bonded to the sulfhydryl group on the cysteine residue at position 741 of SEQ ID NO: 9.

14. The conjugate of claim 13, wherein the fusion protein, consists of a tetramer.

15. The conjugate of claim 9, wherein the linker comprises the amino acid sequence GG, or comprises the amino acid sequence as set forth in SEQ ID NO: 40 or SEQ ID NO: 41.

16. The conjugate of claim 15, wherein the linker comprises the amino acid sequence as set forth in SEQ ID NO: 40.

17. The conjugate of claim 16, wherein the heavy chain of the anti-VEGF antibody comprises three complementarity determining regions (CDRs) comprising the amino acid sequences as set forth in SEQ ID NO: 42, SEQ ID NO: 43, and SEQ ID NO: 44, respectively.

18. The conjugate of claim 17, wherein the light chain of the anti-VEGF comprises three CDRs comprising the amino acid sequences as set forth in SEQ ID NO: 45, SEQ ID NO: 46 and SEQ ID NO: 47, respectively.

19. The conjugate of claim 18, wherein the isotype of the heavy chain is IgG1, and the isotype of the light chain is kappa.

20. The conjugate of claim 19, wherein the heavy chain constant domain has the amino acid sequence as set forth in SEQ ID NO: 17, and the light chain constant domain has the amino acid sequence as set forth in SEQ ID NO: 18.

21. The conjugate of claim 19, wherein the heavy chain constant domain has the amino acid sequence as set forth in SEQ ID NO: 17 except for the presence of one or more mutations to reduce effector function.

22. The conjugate of claim 21, wherein the mutations are to one or more of the following amino acid positions (EU numbering): E233, L234, L235, G236, G237, A327, A330, and P331.

23. The conjugate of claim 22, wherein the mutations are selected from the group consisting of E233P, L234V, L234A, L235A, G237A, A3270, A330S and P331 S.

24. The conjugate of claim 23, wherein the mutations are: L234A, L235A and G237A.

25. The conjugate of claim 19, wherein the heavy chain constant domain has the amino acid sequence as set forth in SEQ ID NO: 17 except for the presence of mutations L234A, L235A and G237A and a cysteine residue added by recombinant DNA technology.

26. The conjugate of claim 25, wherein the cysteine residue is selected from the group consisting of Q347C and L443C (EU numbering).

27. The conjugate of claim 26, wherein the cysteine residue is L443C.

28. The conjugate of claim 1, wherein the PDGFR extracellular trap segment comprises an amino acid sequence as set forth in amino acids 33-314 of SEQ ID NO: 11.

29. The conjugate of claim 1, wherein the anti-VEGF antibody is an anti-VEGF-A antibody.

30. A liquid pharmaceutical composition comprising:
the conjugate of claim 1 and a pharmaceutically acceptable excipient, wherein the composition has an endotoxin level less than 0.2 EU/ml.

31. A method for the treatment or delaying the onset of a disease in a patient in need thereof, said method comprising administering to the patient an effective amount of the conjugate of claim 1,
wherein the disease is a neovascular disorder.

32. The method of claim 31, wherein the neovascular disorder is subretinal fibrosis.

33. The method of claim 31, wherein the neovascular disorder is an ocular neovascular disorder.

34. The method of claim 33, wherein the ocular neovascular disorder is wet age related macular degeneration.

\* \* \* \* \*